(12) United States Patent
Krainer et al.

(10) Patent No.: US 9,976,143 B2
(45) Date of Patent: May 22, 2018

(54) TARGETED AUGMENTATION OF NUCLEAR GENE OUTPUT

(71) Applicant: Cold Spring Harbor Laboratory, Cold Spring Harbor, NY (US)

(72) Inventors: Adrian Krainer, Huntington Station, NY (US); Isabel Aznarez, Queens, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days. days.

(21) Appl. No.: 14/874,420

(22) Filed: Oct. 3, 2015

(65) Prior Publication Data

US 2016/0298121 A1 Oct. 13, 2016

Related U.S. Application Data

(60) Provisional application No. 62/059,847, filed on Oct. 3, 2014.

(51) Int. Cl.
| | |
|---|---|
| *A61K 48/00* | (2006.01) |
| *C12N 15/113* | (2010.01) |
| *C07K 14/805* | (2006.01) |
| *C07K 14/47* | (2006.01) |
| *C12Q 1/68* | (2018.01) |
| *C12N 15/11* | (2006.01) |

(52) U.S. Cl.
CPC .......... *C12N 15/1137* (2013.01); *C07K 14/47* (2013.01); *C07K 14/4702* (2013.01); *C07K 14/4736* (2013.01); *C07K 14/805* (2013.01); *C12N 15/111* (2013.01); *C12Q 1/6883* (2013.01); *C12N 15/113* (2013.01); *C12N 2310/11* (2013.01); *C12N 2310/315* (2013.01); *C12N 2310/3341* (2013.01); *C12N 2320/11* (2013.01); *C12N 2320/33* (2013.01); *C12Q 2600/136* (2013.01); *C12Q 2600/158* (2013.01); *C12Y 101/01205* (2013.01); *C12Y 304/24087* (2013.01)

(58) Field of Classification Search
CPC .................................................. A61K 48/00
See application file for complete search history.

(56) References Cited

U.S. PATENT DOCUMENTS

| | | | |
|---|---|---|---|
| 4,866,042 A | 9/1989 | Neuwelt | |
| 5,151,510 A | 9/1992 | Stec et al. | |
| 5,656,612 A | 8/1997 | Monia | |
| 5,665,593 A | 9/1997 | Kole et al. | |
| 5,914,396 A | 6/1999 | Cook et al. | |
| 5,916,808 A | 6/1999 | Kole et al. | |
| 5,976,879 A | 11/1999 | Kole et al. | |
| 6,166,197 A | 12/2000 | Cook et al. | |
| 6,210,892 B1 | 4/2001 | Bennett et al. | |
| 6,294,520 B1 | 9/2001 | Naito | |
| 6,451,991 B1 | 9/2002 | Martin et al. | |
| 6,632,427 B1 | 10/2003 | Finiels et al. | |
| 6,677,445 B1 | 1/2004 | Innis et al. | |
| 6,756,523 B1 | 6/2004 | Kahn et al. | |
| 6,846,921 B2 | 1/2005 | Innis et al. | |
| 6,936,589 B2 | 8/2005 | Naito | |
| 6,963,589 B1 | 11/2005 | Sugata et al. | |
| 7,015,315 B1 | 3/2006 | Cook et al. | |
| 7,101,993 B1 | 9/2006 | Cook et al. | |
| 7,432,249 B2 | 10/2008 | Crooke | |
| 7,432,250 B2 | 10/2008 | Crooke | |
| 8,067,569 B2 | 11/2011 | Iversen et al. | |
| 8,124,745 B2 | 2/2012 | Allerson et al. | |
| 8,258,109 B2 | 9/2012 | Bennett et al. | |
| 8,436,163 B2 | 5/2013 | Iversen et al. | |
| 8,450,467 B2 | 5/2013 | Manoharan et al. | |
| 8,637,478 B2 | 1/2014 | Bennett | |
| 8,846,885 B2 | 9/2014 | Hirai et al. | |
| 8,895,722 B2 | 11/2014 | Iversen et al. | |
| 9,193,969 B2 | 11/2015 | Montefeltro et al. | |
| 9,714,422 B2 | 7/2017 | Vorechovsky et al. | |
| 2004/0063129 A1 | 4/2004 | Gaarde et al. | |
| 2004/0219515 A1 | 11/2004 | Bentwich | |
| 2005/0221354 A1 | 10/2005 | Mounts | |
| 2005/0233327 A1 | 10/2005 | Welch et al. | |
| 2006/0134670 A1 | 6/2006 | Piu | |
| 2007/0009899 A1 | 1/2007 | Mounts | |
| 2007/0087376 A1 | 4/2007 | Potashkin | |
| 2007/0249538 A1 | 10/2007 | Sazani et al. | |
| 2008/0269123 A1 | 10/2008 | Li et al. | |
| 2009/0186846 A1* | 7/2009 | Chabot .................. | A61K 48/00 514/44 R |
| 2009/0264353 A1 | 10/2009 | Orum et al. | |
| 2010/0166784 A1 | 7/2010 | Murphy et al. | |

(Continued)

FOREIGN PATENT DOCUMENTS

| | | |
|---|---|---|
| CN | 103667438 A | 3/2014 |
| EP | 0549615 A1 | 7/1993 |

(Continued)

OTHER PUBLICATIONS

Nishida et al. Journal of Human Genetics 2015, 60,327-333.*
Melhuish et al. BMC Molecular Biology 2006:7, 1-10.*
Aartsma-Rus, et al. Antisense-mediated exon skipping: a versatile tool with therapeutic and research applications. RNA. Oct. 2007;13(10):1609-24. Epub Aug. 7, 2007.
Altschul SF et al. Basic local alignment search tool. J. Mol. Biol., vol. 215, No. 3, pp. 403-410, (Oct. 5, 1990).
Aly, et al. Extreme genetic risk for type 1A diabetes. Proc Natl Acad Sci U S A. Sep. 19, 2006;103(38):14074-9. Epub Sep. 11, 2006.
Amarnath, S. et al. The PDL1-PD1 Axis Converts Human TH1 Cells into Regulatory T Cells. Science Translational Medicine, vol. 3, No. 111, pp. 1-13. (Nov. 30, 2011).
Au, K.S. et al. Molecular Genetic Basis of Tuberous Sclerosis Complex: From Bench to Bedside. Journal of Child Neurology. vol. 19, No. 9 (Sep. 2004).

(Continued)

*Primary Examiner* — Brian A Whiteman
(74) *Attorney, Agent, or Firm* — Wilson Sonsini Goodrich & Rosati

(57) ABSTRACT

Provided herein are methods and compositions for increasing production of a target protein or functional RNA by a cell.

42 Claims, 45 Drawing Sheets

(56) References Cited

U.S. PATENT DOCUMENTS

| | | | |
|---|---|---|---|
| 2011/0124591 A1* | 5/2011 | Bennett | A61K 31/7115 514/43 |
| 2011/0229891 A1 | 9/2011 | Michaud et al. | |
| 2012/0190728 A1 | 7/2012 | Bennett et al. | |
| 2013/0109850 A1 | 5/2013 | Prakash et al. | |
| 2013/0253036 A1 | 9/2013 | Collard et al. | |
| 2013/0289092 A1 | 10/2013 | Rigo et al. | |
| 2014/0128449 A1 | 5/2014 | Liu et al. | |
| 2014/0186839 A1 | 7/2014 | Margulies et al. | |
| 2014/0194610 A1 | 7/2014 | Verdine et al. | |
| 2014/0235605 A1 | 8/2014 | Shiffman et al. | |
| 2014/0343127 A1 | 11/2014 | Kammler | |
| 2014/0349290 A1 | 11/2014 | Watnick et al. | |
| 2014/0378526 A1 | 12/2014 | Rossi et al. | |
| 2014/0378527 A1 | 12/2014 | Van Deutekom | |
| 2014/0378533 A1 | 12/2014 | Freier | |
| 2015/0004217 A1 | 1/2015 | Guild et al. | |
| 2015/0018540 A1 | 1/2015 | Prakash et al. | |
| 2015/0184153 A1 | 7/2015 | Freier et al. | |
| 2015/0337310 A1 | 11/2015 | Walker et al. | |
| 2016/0017322 A1 | 1/2016 | Vorechovsky et al. | |
| 2016/0244762 A1 | 8/2016 | Vorechovsky et al. | |
| 2017/0101641 A1 | 4/2017 | Vorechovsky | |

FOREIGN PATENT DOCUMENTS

| | | |
|---|---|---|
| EP | 2114981 B1 | 5/2013 |
| WO | WO-9402501 A1 | 2/1994 |
| WO | WO-9426887 A1 | 11/1994 |
| WO | WO-2006107846 A2 | 10/2006 |
| WO | WO2011057350 A1 * | 5/2011 |
| WO | WO-2011057350 A1 | 5/2011 |
| WO | WO-2014012081 A2 | 1/2014 |
| WO | WO-2014031575 A1 | 2/2014 |
| WO | WO-2014121287 A2 | 8/2014 |
| WO | WO-2014172698 A1 | 10/2014 |
| WO | WO-2015035091 A1 | 3/2015 |
| WO | WO-2015193651 A1 | 12/2015 |
| WO | WO-2016054615 A2 | 4/2016 |
| WO | WO-2016077837 A1 | 5/2016 |

OTHER PUBLICATIONS

Balagurumoorthy, et al. Hairpin and parallel quartet structures for telomeric sequences. Nucleic Acids Res. Aug. 11, 1992;20(15):4061-7.

Balkwill, et al. Repression of translation of human estrogen receptor alpha by G-quadruplex formation. Biochemistry. Dec. 8, 2009;48(48):11487-95. doi: 10.1021/bi901420k.

Barratt, et al. Remapping the insulin gene/IDDM2 locus in type 1 diabetes. Diabetes. Jul. 2004;53(7):1884-9.

Battistini et al. A new CACNA1A gene mutation in acetazolamide-responsive familial hemiplegic migraine and ataxia. Neurology, vol. 53, No. 1, pp. 38-43 (Jul. 13, 1999).

Baughan, et al. Delivery of bifunctional RNAs that target an intronic repressor and increase SMN levels in an animal model of spinal muscular atrophy. Hum Mol Genet. May 1, 2009;18(9):1600-11. doi: 10.1093/hmg/ddp076. Epub Feb. 19, 2009.

Beaudoin, et al. 5'-UTR G-quadruplex structures acting as translational repressors. Nucleic Acids Res. Nov. 2010;38(20):7022-36. doi: 10.1093/nar/gkq557. Epub Jun. 22, 2010.

Berge, SM et al. Pharmaceutical Salts Journal of Pharmaceutical Sciences, vol. 66, No. 1, pp. 1-19 (1977).

Berger, W. et al. The molecular basis of human retinal and vitreoretinal diseases. Progress in Retinal and Eye Research. vol. 29, pp. 335-375 (2010).

Bicknell, et al. Introns in UTRs: why we should stop ignoring them. Bioessays. Dec. 2012;34(12):1025-34. doi: 10.1002/bies.201200073. Epub Oct. 26, 2012.

Blencowe, Benjamin. Reflections for the 20th anniversary issue of RNA journal. RNA Journal, vol. 21, No. 4, pp. 573-575 (2015).

Boothby, T. et al. Removal of Retained Introns Regulates Translation in the Rapidly Developing Gametophyte of Marsilea vestita. Developmental Cell vol. 24, pp. 517-529, (Mar. 11, 2013).

Booy, et al. The RNA helicase RHAU (DHX36) unwinds a G4-quadruplex in human telomerase RNA and promotes the formation of the P1 helix template boundary. Nucleic Acids Res. May 2012;40(9):4110-24. doi: 10.1093/nar/gkr1306. Epub Jan. 11, 2012.

Boutz, et al. Detained introns are a novel, widespread class of post-transcriptionally spliced introns. Genes Dev. Jan. 1, 2015;29(1):63-80. doi: 10.1101/gad.247361.114.

Braunschweig, et al. Widespread intron retention in mammals functionally tunes transcriptomes. Widespread intron retention in mammals functionally tunes transcriptomes. Genome Res. Nov. 2014;24(11):1774-86. doi: 10.1101/gr.177790.114. Epub Sep. 25, 2014.

Buchman, et al. Comparison of intron-dependent and intron-independent gene expression. Mol Cell Biol. Oct. 1988;8(10):4395-405.

Buckley, P.T. et al. Cytoplasmic intron retention, function, splicing, and the sentinel RNA hypothesis. WIREs RNA, vol. 5, pp. 223-2330 (Mar./Apr. 2014).

Bugaut, et al. 5'-UTR RNA G-quadruplexes: translation regulation and targeting. Nucleic Acids Res. Jun. 2012;40(11):4727-41. doi: 10.1093/nar/gks068. Epub Feb. 20, 2012.

Bugaut, et al. An RNA hairpin to G-quadruplex conformational transition. J Am Chem Soc. Dec. 12, 2012;134(49):19953-6. doi: 10.1021/ja308665g. Epub Nov. 29, 2012.

Buratti, et al. DBASS3 and DBASS5: databases of aberrant 3'- and 5'-splice sites. Nucleic Acids Res. Jan. 2011;39(Database issue):D86-91. doi: 10.1093/nar/gkq887. Epub Oct. 6, 2010.

Buratti, et al. RNA folding affects the recruitment of SR proteins by mouse and human polypurinic enhancer elements in the fibronectin EDA exon. Mol Cell Biol. Feb. 2004;24(3):1387-400.

Callis, et al. Introns increase gene expression in cultured maize cells. Genes Dev. Dec. 1987;1(10):1183-200.

Cavaloc, et al. The splicing factors 9G8 and SRp20 transactivate splicing through different and specific enhancers. RNA. Mar. 1999;5(3):468-83.

Cazzola, et al. Translational pathophysiology: a novel molecular mechanism of human disease. Blood. Jun. 1, 2000;95(11):3280-8.

Collie, et al. The application of DNA and RNA G-quadruplexes to therapeutic medicines. Chem Soc Rev. Dec. 2011;40(12):5867-92. doi: 10.1039/c1cs15067g. Epub Jul. 25, 2011.

Creacy, et al. G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. Dec. 12, 2008;283(50):34626-34. doi: 10.1074/jbc.M806277200. Epub Oct. 7, 2008.

Culler, et al. Functional selection and systematic analysis of intronic splicing elements identify active sequence motifs and associated splicing factors. Nucleic Acids Res. Aug. 2010;38(15):5152-65. doi: 10.1093/nar/gkq248. Epub Apr. 12, 2010.

Davies, et al. A genome-wide search for human type 1 diabetes susceptibility genes. Nature. Sep. 8, 1994;371(6493):130-6.

Decorsiere, et al. Essential role for the interaction between hnRNP H/F and a G quadruplex in maintaining p53 pre-mRNA 3'-end processing and function during DNA damage. Genes Dev. Feb. 1, 2011;25(3):220-5. doi: 10.1101/gad.607011.

Deere, J. et al. Antisense Phosphorodiamidate Morpholino Oligomer Length and Target Position Effects on Gene-Specific Inhibitionin *Escherichia coli.* Antimicrobial Agents Andchemotherapy, vol. 49, No. 1, p. 249-255(Jan. 2005).

Derecka, et al. Occurrence of a quadruplex motif in a unique insert within exon C of the bovine estrogen receptor alpha gene (ESR1). Biochemistry. Sep. 7, 2010;49(35):7625-33. doi: 10.1021/bi100804f.

Dias, N. et al. Antisense oligonucleotides: basic concepts and mechanisms Mol. Cancer Ther. vol. 1, pp. 347-355, (Mar. 2002).

Didiot, et al. The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.

(56) References Cited

OTHER PUBLICATIONS

Ding, H. et al. DeliveringPD-1 inhibitory signal concomitant with blocking ICOS co-stimulation suppresses lupus-like syndrome in autoimmune BXSB mice. Clinical Immunology, vol. 118, pp. 258-267, (2006).
Dominski, et al. Restoration of correct splicing in thalassemic pre-mRNA by antisense oligonucleotides. Proc Natl Acad Sci U S A. Sep. 15, 1993;90(18):8673-7.
Du, et al. Correction of prototypic ATM splicing mutations and aberrant ATM function with antisense morpholino oligonucleotides. Proc Natl Acad Sci U S A. Apr. 3, 2007;104(14):6007-12. Epub Mar. 26, 2007.
Ducros et al. Recurrence of the T666M calcium channel CACNA1A gene mutation in familial hemiplegic migraine with progressive cerebellar ataxia. Am J Hum Genet. vol. 64, No. 1, pp. 89-98 (Jan. 1999).
Duryagina R, et al. Overexpression of Jagged-1 and its intracellular domain in human mesenchymal stromal cells differentially affect the interaction with hematopoietic stem and progenitor cells. Stem Cells Dev. vol. 22, No. 20, pp. 2736-2750 (2013).
Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.
Emerick, et al. Multivariate analysis and visualization of splicing correlations in single-gene transcriptomes. BMC Bioinformatics. Jan. 18, 2007;8:16.
Fededa, et al. A polar mechanism coordinates different regions of alternative splicing within a single gene. Mol Cell. Aug. 5, 2005;19(3):393-404.
Fletcher, Sue et al. Antisense suppression of donor splice site mutations in the dystrophin gene transcript. Molecular Genetics & Genomic Medicine, vol. 1, No. 3, pp. 162-173, Jun. 13, 2013.
Fred, et al. The human insulin mRNA is partly translated via a cap- and eIF4A-independent mechanism. Biochem Biophys Res Commun. Sep. 9, 2011;412(4):693-8. doi: 10.1016/j.bbrc.2011.08.030. Epub Aug. 16, 2011.
Friedman, KJ et al. Correction of aberrant splicing of the cystic fibrosis transmembrane conductance regulator (CFTR) gene by antisense oligonucleotides. J. Biol. Chem. Dec. 17, 1999;274(51):36193-36199.
Friend, KL et al. Detection of a novel missense mutation and second recurrent mutation in the CACNA1A gene in individuals with EA-2 and FHM. Hum Genet. vol. 105(3):261-5 (Sep. 1999).
Furukawa & Kish 2008, Gene Reviews Pagon Ra et al. eds. Univ. of WA Seattle, NCBI Bookshelf ID NBK1437.
Galante, et al. Detection and evaluation of intron retention events in the human transcriptome. RNA. May 2004;10(5):757-65.
Garner, et al. Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.
Geary et al. Absolute Bioavailability of 29-O-(2-Methoxyethyl)-Modified Antisense Oligonucleotides following Intraduodenal Instillation in Rats. J Pharmacol Exp Ther. vol. 296, No. 3, pp. 898-904 (Mar. 2001).
Geary, RS, et al., Pharmacokinetic properties of 2'-O-(2-methoxyethyl)-modified oligonucleotide analogs in rats. J Pharmacal Exp Ther. vol. 296, No. 3, pp. 890-897 (Mar. 2001).
Gianchecchi, E. et al. Recent insights into the role of the PD-1/PD-L1 pathway in immunological tolerance and autoimmunity Autoimmunity Reviews vol. 12, pp. 1091-1100, (2013).
Gohring, J. et al. Imaging of Endogenous Messenger RNA Splice Variants in Living Cells Reveals Nuclear Retention of Transcripts Inaccessible to Nonsense-Mediated Decay in *Arabidopsis*. The Plant Cell. vol. 26, pp. 754-764.(Feb. 2014).
Gomez, et al. Telomerase downregulation induced by the G-quadruplex ligand 12459 in A549 cells is mediated by hTERT RNA alternative splicing. Nucleic Acids Res. Jan. 16, 2004;32(1):371-9. Print 2004.

Goyenvalle, et al. Therapeutic approaches to muscular dystrophy. Hum Mol Genet. Apr. 15, 2011;20(R1):R69-78. doi: 10.1093/hmg/ddr105. Epub Mar. 24, 2011.
Hai, et al. A G-tract element in apoptotic agents-induced alternative splicing. Nucleic Acids Res. Jun. 2008;36(10):3320-31. doi: 10.1093/nar/gkn207. Epub Apr. 24, 2008.
Hamdan, F. et al. Mutations in SYNGAP1 in Autosomal Nonsyndromic Mental Retardation. The New England Journal of Medicine. N. Engl. Med. vol. 360, No. 6, pp. 599, (Feb. 5, 2009).
Hargous, et al. Molecular basis of RNA recognition and TAP binding by the SR proteins SRp20 and 9G8. EMBO J. Nov. 1, 2006;25(21):5126-37. Epub Oct. 12, 2006.
Hegele, et al. Dynamic protein-protein interaction wiring of the human spliceosome. Mol Cell. Feb. 24, 2012;45(4):567-80. doi: 10.1016/j.molcel.2011.12.034.
Heyn, P. et al. Introns and gene expression: Cellular constraints, transcriptional regulation, and evolutionary consequences. Bioessays vol. 37, pp. 148-154 (2014).
Hirata et al. Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand. J. Immunology vol. 174 pp. 1888-1897 (2005).
Hua, et al. Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.
Hunt, et al. Negligible impact of rare autoimmune-locus coding-region variants on missing heritability. Nature. Jun. 13, 2013;498(7453):232-5. doi: 10.1038/nature12170. Epub May 22, 2013.
International Application No. PCT/GB2015/051756 International Search Report and Written Opinion dated Nov. 30, 2015.
International Application No. PCT/US2015/53896 International Search Report and Written Opinion dated Mar. 3, 2016.
Iwamoto, et al. Transcription-dependent nucleolar cap localization and possible nuclear function of DExH RNA helicase RHAU. Exp Cell Res. Apr. 1, 2008;314(6):1378-91. doi: 10.1016/j.yexcr.2008.01.006. Epub Jan. 16, 2008.
Jarver, P. et al., A Chemical View of Oligonucleotides for Exon Skipping and Related Drug Applications, Nucleic Acid Therapeutics vol. 24, No. (1), pp. 37-47, (2014).
Jurkiewicz, D. et al. Spectrum of JAG1 gene mutations in Polish patients with Alagille syndrome. J. Appl. Genetics vol. 55, pp. 329-336, (2014).
Katsani, K.R. et al. Functional Genomics Evidence Unearths New Moonlighting Roles of Outer Ring Coat Nucleoporins. Scientific Reports. vol. 4, No. 4655 (Apr. 11, 2014).
Ke, et al. Quantitative evaluation of all hexamers as exonic splicing elements. Genome Res. Aug. 2011;21(8):1360-74. doi: 10.1101/gr.119628.110. Epub Jun. 9, 2011.
Keir, M.E. et al. PD-1 and Its Ligands in Tolerance and Immunity. Annu. Rev. Immunol. vol. 26, pp. 677-704 (2008).
Kikin, et al. QGRS Mapper: a web-based server for predicting G-quadruplexes in nucleotide sequences. Nucleic Acids Res. Jul. 1, 2006;34(Web Server issue):W676-82.
Kole, et al. RNA therapeutics: beyond RNA interference and antisense oligonucleotides. Nat Rev Drug Discov. Jan. 20, 2012;11(2):125-40. doi: 10.1038/nrd3625.
Kralovicova, et al. Allele-specific recognition of the 3' splice site of INS intron 1. Hum Genet. Oct. 2010;128(4):383-400. doi: 10.1007/s00439-010-0860-1. Epub Jul. 14, 2010.
Kralovicova, et al. Compensatory signals associated with the activation of human GC 5' splice sites. Nucleic Acids Res. Sep. 1, 2011;39(16):7077-91. doi: 10.1093/nar/gkr306. Epub May 23, 2011.
Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.

(56) References Cited

OTHER PUBLICATIONS

Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.

Kralovicova, et al. Phenotypic consequences of branch point substitutions. Hum Mutat. Aug. 2006;27(8):803-13.

Kralovicova, et al. Position-dependent repression and promotion of DQB1 intron 3 splicing by GGGG motifs. J Immunol. Feb. 15, 2006;176(4):2381-8.

Kralovicova, et al. Variants in the human insulin gene that affect pre-mRNA splicing: is—23Hphl a functional single nucleotide polymorphism at IDDM2? Diabetes. Jan. 2006;55(1):260-4.

LaPlanche et al. Phosphorothioate-modified oligodeoxyribonucleotides. III. NMR and UV spectroscoptc studies of thRp-Rp,Sp-Sp, anRp-Sduplexes, [d(GGsAATTCC)]2, derived from diastereomeriO-ethyl phosphorothioates Nucleic Acids Res. vol. 14, No. 22, pp. 9081-9093 (Nov. 25, 1986).

Le Hir, et al. How introns influence and enhance eukaryotic gene expression. Trends Biochem Sci. Apr. 2003;28(4):215-20.

Lee, E.S. et al. The Consensus 5' Splice Site Motif Inhibits mRNA Nuclear Export. PLoS One vol. 10, No. 3, p. e0122743 (Mar. 31, 2015).

Lei, et al. Identification of splicing silencers and enhancers in sense Alus: a role for pseudoacceptors in splice site repression. Mol Cell Biol. Aug. 2005;25(16):6912-20.

Li et al. PD-L1—Driven Tolerance Protects Neurogenin3-Induced Islet Neogenesis to Reverse Established Type 1 Diabetes in NOD Mice. Diabetes vol. 64, pp. 529-540 (Feb. 2015; epub Oct. 20, 2014).

Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.

Lu, F. Conditional JAG1 Mutation Shows the Developing Heart Is More Sensitive Than Developing Liver to JAG1 Dosage. Am. J. Hum. Genet. vol. 72, pp. 1065-1070 (2003).

Ludecke et al. Recessively inherited L-DOPA-responsive parkinsonism in infancy caused by a point mutation (L205P) in the tyrosine hydroxylase gene Hum. Mol. Genet. vol. 5, pp. 1023-1028, (1996).

Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.

Mansouri, S. et al. Epstein-Barr Virus EBNA1 Protein Regulates Viral Latency through Effects on let-7 MicroRNA and Dicer. Journal of Virology, vol. 88, No. 19, pp. 11166-11177, (Oct. 2014).

Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.

Marquez, Y. et al. Unmasking alternative splicing inside protein-coding exons defines exitrons and their role inproteome plasticity. Genome vol. 25, pp. 995-1007 (2015).

Mayeda, et al. Surveying cis-acting sequences of pre-mRNA by adding antisense 2'-O-methyl oligoribonucleotides to a splicing reaction. J Biochem. Sep. 1990;108(3):399-405.

Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.

Miller at al. 1993-2015 GeneReviews Eds. Pagon RA et al. Seattle (WA); University of WA, Seattle Bookshelf ID NBK1318.

Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.

Mochizuki, T. et al. PKD2, a gene for polycystic kidney disease that encodes an integral membrane protein. Science vol. 272, pp. 1339-1342 (1996).

Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.

Mulley et al. A new molecular mechanism for severe myoclonic epilepsy of infancy: Exonic deletions in SCN1A.Neurol. vol. 67, pp. 1094-1095 (2006).

Mulley et al. SCN1A mutations and epilepsy. Hum. Muta. vol. 25, pp. 535-542 (2005).

Neidle, S. and Balasubramanian, S. (2006) Quadruplex Nucleic Acids. RSC Biomolecular Sciences, Cambridge, UK, table of contents and title page, pp. 1-12.

Nishi, M. et al. Insulin gene mutations and diabetes. Journal of Diabetes Investigation vol. 2 Issue 2 (Apr. 2011).

Nussinov. Conserved quartets near 5' intron junctions in primate nuclear pre-mRNA. J Theor Biol. Jul. 8, 1988;133(1):73-84.

Oda, T. et al. Identification and cloning of the human homolog (JAG) of the rat Jagged1 gene from the Alagille syndrome critical region at 20p12.Genomics vol. 43, No. 3, pp. 376-379 (1997).

Okazaki, T. et al. PD-1 and PD-1 ligands: from discovery to clinical application. International Immunology(The Japanese Society for Immunology), vol. 19, No. 7, pp. 813-824, (2007).

Pacheco, et al. Diversity of vertebrate splicing factor U2AF35: identification of alternatively spliced U2AF1 mRNAS. J Biol Chem. Jun. 25, 2004;279(26):27039-49. Epub Apr. 19, 2004.

Pacheco, et al. RNA interference knockdown of hU2AF35 impairs cell cycle progression and modulates alternative splicing of Cdc25 transcripts. Mol Biol Cell. Oct. 2006;17(10):4187-99. Epub Jul. 19, 2006.

Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.

Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.

Peng, et al. Functional importance of different patterns of correlation between adjacent cassette exons in human and mouse. BMC Genomics. Apr. 26, 2008;9:191. doi: 10.1186/1471-2164-9-191.

Penton, A.L. Notch signaling in human development and disease. Seminars in Cell & Developmental Biology. vol. 23, pp. 450-457 (2012).

Pugliese, et al. The insulin gene is transcribed in the human thymus and transcription levels correlated with allelic variation at the INS VNTR-IDDM2 susceptibility locus for type 1 diabetes. Nat Genet. Mar. 1997;15(3):293-7.

Ray, D. et al. A compendium of RNA-binding motifs for decoding gene regulation. Nature. vol. 499, No. 7457, pp. 172-177 (Jul. 11, 2013).

Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.

Reynolds, DM et al. Aberrant Splicing in the PKD2 Gene as a Cause of Polycystic Kidney Disease. Am. Soc. Nephrol. vol. 10, pp. 2342-2351 (1999).

Ritprajak et al. Keratinocyte-Associated B7-H1 Directly Regulates Cutaneous Effector CD8+ T Cell Responses. J Immunology vol. 184, pp. 4918-4925 (2010).

RNA 2-14 the Nineteenth Annual Meeting of the RNA Society. Quebec City, Canada. (Jun. 3-8, 2014), pp. 1-464.

Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.

Rosenbloom et al. The UCSC Genome Browser database: 2015 Update. Nucleic Acids Research 43, Database Issue doi:101093/nar/gku1177.

Ruskin, et al. A factor, U2AF, is required for U2 snRNP binding and splicing complex assembly. Cell. Jan. 29, 1988;52(2):207-19.

Sakabe, et al. Sequence features responsible for intron retention in human. BMC Genomics. Feb. 26, 2007;8:59.

(56) References Cited

OTHER PUBLICATIONS

Samatanga, et al. The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.
Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.
Sierakowska, H et al. Repair of thalassemic human beta-globin mRNA in mammalian cells by antisense oligonucleotides. Proc Natl Acad Sci U S A. Nov. 12, 1996;93(23):12840-4.
Singh, et al. An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.
Sirand-Pugnet, et al. An intronic (A/U)GGG repeat enhances the splicing of an alternative intron of the chicken beta-tropomyosin pre-mRNA. Nucleic Acids Res. Sep. 11, 1995;23(17):3501-7.
Skjevik et al. The N-Terminal Sequence of Tyrosine Hydroxylase Is a Conformationally Versatile Motif That Binds 14-3-3 Proteins and Membranes. J. Mol. Bio. vol. 426, pp. 150-168 (2014).
Smith, et al. Alternative pre-mRNA splicing: the logic of combinatorial control. Trends Biochem Sci. Aug. 2000;25(8):381-8.
Stead, et al. Global haplotype diversity in the human insulin gene region. Genome Res. Sep. 2003;13(9):2101-11.
Stec et al. Automated solid-phase synthesis, separation, and stereochemistry of phosphorothioate analogs of oligodeoxyribonucleotides J. Am. Chem. Soc., 1984, 106 (20), pp. 6077-6079 (1984).
Stein et al. Physicochemical properties of phosphorothioate oligodeoxynucleotides. Nucleic Acids Res. Apr. 25, 1988;16(8):3209-21.
Summerton, James. Morpholino Antisense Oligos: Applications in Biopharmaceutical Research Morpholinos constitute a radical redesign of DNA, providing decisive advantages over the more conventional oligo types used for modulating gene expression. Innovations in Pharmaceutical Technology Issue No. 17 (2005).
Swaans, RJM et al. Four novel mutations in the Tyrosine Hydroxylase gene in patients with infantile parkinsonism Annals of Human Genetic, vol. 64, No. 1, pp. 25-31, (Jan. 2000).
Tabrez, S. et al. A Synopsis of the Role of Tyrosine Hydroxylase in Parkinson's Disease. CNS & Neurological Disorders—Drug Targets vol. 11, No. 4 (2012).
Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.
Tilgner et al. Deep Sequencing of subcellular RNA factions shows splicing to be predominantly co-transcriptional in the human genome but inefficient for lncRNAs. Genome Research vol. 22, No. 9, pp. 1616-1625 (2012).
Torres, V.E. et al. Autosomal dominant polycystic kidney disease: the last 3 years. Kidney International vol. 76, pp. 149-168 (May 20, 2009).
Trabattoni, M. et al. Costimulatory Pathways in Multiple Disease Sclerosis: Distinctive Expression of PD-1 and PD-L1 in Patients with Different Patterns of Disease. J. Immunol. vol. 183, pp. 4984-4993 (2009).
Turnpenny, P.D. et al. Alagille syndrome: pathogenesis, diagnosis and management. European Journal of Human Genetics vol. 20, pp. 251-257 (2012).
Uhlmann, E. et al. Antisense oligonucleotides: a new therapeutic principle. Chemical Reviews vol. 90, No. 4, pp. 543-584 (Jun. 1990).
Vafiadis, et al. Insulin expression in human thymus is modulated by INS VNTR alleles at the IDDM2 locus. Nat Genet. Mar. 1997;15(3):289-92.
Verhaart, I.E.C. AON-Mediated Exon Skipping for Duchenne Muscular Dystrophy. Chapter 3. pp. 1-26 (Aug. 1, 2012).

Vieira, N. et al. Jagged 1Rescues the Duchenne Muscular Dystrophy Phenotype. Cell vol. 163, pp. 1204-1213 (Nov. 19, 2015).
Voelker, et al. A comprehensive computational characterization of conserved mammalian intronic sequences reveals conserved motifs associated with constitutive and alternative splicing. Genome Res. Jul. 2007;17(7):1023-33. Epub May 24, 2007.
Wahl, et al. The spliceosome: design principles of a dynamic RNP machine. Cell. Feb. 20, 2009;136(4):701-18. doi: 10.1016/j.cell.2009.02.009.
Wan et al. Synthesis, biophysical properties and biological activity of second generation antisense oligonucleotides containing chiral phosphorothioate linkages. Nucleic Acids Research, vol. 42, No. 22, pp. 13456-13468 (2014).
Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.
Wang et al. Human Adenovirus Type 36 Enhances Glucose Uptake in Diabetic and Nondiabetic Human Skeletal Muscle Cells Independent of Insulin Signaling. Diabetes vol. 57, pp. 1861-1869 (2008).
Wang, et al. Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.
Wang, et al. Regulation of insulin preRNA splicing by glucose. Proc Natl Acad Sci U S A. Apr. 29, 1997;94(9):4360-5.
Wieland, et al. RNA quadruplex-based modulation of gene expression. Chem Biol. Jul. 2007;14(7):757-63.
Xing, et al. The multiassembly problem: reconstructing multiple transcript isoforms from EST fragment mixtures. Genome Res. Mar. 2004;14(3):426-41. Epub Feb. 12, 2004.
Yang, Y. et al. Oligomerization of the polycystin-2 C-terminal tail and effects on its Ca2+binding properties. J. Bio. Chem. vol. 290, No. 16, pp. 10544-10554 (2015).
Yeo, et al. Discovery and analysis of evolutionarily conserved intronic splicing regulatory elements. PLoS Genet. May 25, 2007;3(5):e85. Epub Apr. 13, 2007.
Yoshida, et al. Frequent pathway mutations of splicing machinery in myelodysplasia. Nature. Sep. 11, 2011;478(7367):64-9. doi: 10.1038/nature10496.
Zhang, et al. Insulin as an autoantigen in NOD/human diabetes. Curr Opin Immunol. Feb. 2008;20(1):111-8. doi: 10.1016/j.coi.2007.11.005.
Zhang, et al. The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.
Zhang, J. et al. PowerBLAST: A New Network BLAST Application for Interactive or Automated Sequence Analysis and Annotation Genome Res., vol. 7, pp. 649-656, (1997).
Zon et al. Phosphorothioate oligonucleotides: chemistry, purification, analysis, scale-up and future directions. Anti-Cancer Drug Design vol. 6, No. 6, pp. 539-568 (1991).
Zon G. and Stec, W.J. (1991) In Eckstein, F. (ed.), Oligonucleotides and Analogues: A Practical Approach. Oxford University Press, Oxford, UK, pp. 87-108.
Bassi et al. A novel mutation in the ATP1A2 gene causes alternating hemiplegia of childhood. J. Med. Genet. 41:621-628 (2004).
Bravo-Gil, et al., Improving the management of Inherited Retinal Dystrophies by targeted sequencing of a population-specific gene panel, Scientific Reports, Apr. 1, 2016,6:23910, 10 pages.
Corallini et al. Transcriptional and Posttranscriptional Regulation of the CTNS Gene. Pediatric Research 70(2):130-135 (Aug. 2011).
Gonzalez-Santos, et al., Mutation in the splicing factor Hprp3p linked to retinitis pigmentosa impairs interactions within the U4/U6 snRNP pigmentosa impairs interactions within the U4/U6 snRNP complex, PubMed Central CANADA , Author Manuscript, Jul. 7, 2015, 29 pages.
Hua et al. Antisense masking of an hnRNP A1/A2 intronic splicing silencer corrects SMN2 splicing in transgenic mice. Am. J. Hum. Genet. 82:834-848 (Mar. 27, 2008).

(56) References Cited

OTHER PUBLICATIONS

International Application No. PCT/US16/66576 International Search Report and Written Opinion dated May 4, 2017.
International Application No. PCT/US16/66691 International Search Report and Written Opinion dated May 10, 2017.
International Application No. PCT/US16/66708 International Search Report and Written Opinion dated May 8, 2017.
International Application No. PCT/US16/66721 International Search Report and Written Opinion dated May 1, 2017.
International Application No. PCT/US2016/066564 International Search Report and Written Opinion dated May 4, 2017.
International search report and written opinion dated Jun. 5, 2017 for PCT Application No. US-2016/066684.
Kim et al. The role of synaptic GTPase-activating protein in neuronal development and synaptic plasticity. J. Neurosci. 23(4):1119-1124 (Feb. 15, 2003).
Luo et al. Palmitic Acid Suppresses Apolipoprotein M Gene Expression via the Pathway of PPARb/d in HepG2 Cells. Biochemical and Biophysical Research Communications, 445(1):203-207 (Feb. 2014).
Moskowitz, et al., Mutation in Scheie syndrome (MPS IS): a G-->A transition creates new splice site in intron 5 of one IDUA allele, Hum. Mutat. 2(2):141-144 (1993).
Precursor mRNA-Processing Factor 3, S. Cerevisiae, Homolog of; PRPF3m, Accessed on Mar. 18, 2017, 3 pages.
Soutar et al. Mechanisms of disease: genetic causes of familial hpercholesterolemia. Nat. Clin. Pract. Cardiovasc. Med. 4:214-255 (Apr. 1, 2007).
U.S. Appl. No. 14/741,071 Notice of Allowability dated May 12, 2017.
U.S. Appl. No. 15/148,303 Notice of Allowance dated Jun. 7, 2017.
Co-pending U.S. Appl. No. 15/619,984, filed Jun. 12, 2017.
Aizer AA, et al. Lack of reduction in racial disparities in cancer-specific mortality over a 20-year period. Cancer. 2014;120:1532-9.
Anders S. et al. Detecting differential usage of exons from RNA-seq data. Genome Res. 2012;22(10):2008-17. Epub Jun. 23, 2012.doi: gr.133744.111 [pii] 10.1101/gr.133744.111. PubMed PMID: 22722343.
Bakkenist CJ, Kastan MB. DNA damage activates ATM through intermolecular autophosphorylation and dimer dissociation. Nature. 2003;421(6922):499-506. doi: 10.1038/nature01368. PubMed PMID: 12556884.
Beli P, et al., Proteomic investigations reveal a role for RNA processing factor THRAP3 in the DNA damage response. Mol Cell. 2012;46(2):212-25. doi: 10.1016/j.molcel.2012.01.026. PubMed PMID: 22424773; PubMed Central PMCID: PMC3565437.
Bethke L, et al. Comprehensive analysis of the role of DNA repair gene polymorphisms on risk of glioma. Hum Mol Genet. 2008;17(6):800-5. Epub Dec. 1, 2007.doi: ddm351 [pii] 10.1093/hmg/ddm351. PubMed PMID: 18048407.
Blencowe BJ. Splicing regulation: the cell cycle connection. Curr Biol. 2003;13(4):R149-51. PubMed PMID: 12593819.
Bonnen, P.E., et al. Haplotypes at ATM identify coding-sequence variation and indicate a region of extensive linkage disequilibrium. Am J Hum Genet. 2000;67(6):1437-51. Epub Nov. 15, 2000.doi: S0002-9297(07)63213-3 [pii] 10.1086/316908. PubMed PMID: 11078475.
Brooks, A.N., et al. A pan-cancer analysis of transcriptome changes associated with somatic mutations in U2AF1 reveals commonly altered splicing events. PLoS One. 2014; 9(1):e87361. Epub Feb. 6, 2014.doi: 10.1371/journal.pone.0087361 PONE-D-13-26905 [pii]. PubMed PMID: 24498085.
Burns, CG, et al. Connections between pre-mRNA processing and regulation of the eukaryotic cell cycle. Front Horm Res. 1999; 25:59-82.
Chambers, A.L., et al. The INO80 chromatin remodeling complex prevents polyploidy and maintains normal chromatin structure at centromeres. Genes Dev. 2012; 26(23):2590-603. Epub Dec. 5, 2012.doi: 26/23/2590 [pii] 10.1101/gad.199976.112. PubMed PMID: 23207916.

Chen, M.S., et al. Chk1 kinase negatively regulates mitotic function of Cdc25A phosphatase through 14-3-3 binding. Mol Cell Biol. 2003; 23(21):7488-97. PubMed PMID: 14559997; PubMed Central PMCID: PMC207598.
Chen, T., et al. A functional single nucleotide polymorphism in promoter of ATM is associated with longevity. Mech Ageing Dev. 2010; 131:636-40.
Choi, HH, et al. CHK2 kinase promotes pre-mRNA splicing via phosphorylating CDK11p110. Oncogene. 2014; 33:108-15.
Colla, S., et al. Telomere dysfunction drives aberrant hematopoietic differentiation and myelodysplastic syndrome. Cancer Cell. 2015; 27(5):644-57. doi: 10.1016/j.ccell.2015.04.007. PubMed PMID: 25965571.
Consortium. TGP. An integrated map of genetic variation from 1,092 human genomes. Nature (London). 2012; 491:56-65.
Corey, S.J., et al. A non-classical translocation involving 17q12 (retinoic acid receptor alpha) in acute promyelocytic leukemia (APML) with atypical features. Leukemia. 1994; 8(8):1350-3. PubMed PMID: 8057672.
Corvelo, A., et al. Genome-wide association between branch point properties and alternative splicing. PLoS Comput Biol. 2010; 6(11):e1001016. Epub Dec. 3, 2010.doi: 10.1371/journal.pcbi.1001016. PubMed PMID: 21124863.
Scott, S.P., et al. Missense mutations but not allelic variants alter the function of ATM by dominant interference in patients with breast cancer. Proc Natl Acad Sci USA. 2002;99:925-30.
Coulombe-Huntington J., et al. Fine-Scale Variation and Genetic Determinants of Alternative Splicing across Individuals. PLoS Genet. 2009; 5(12):e1000766. Epub Dec. 17, 2009.doi: 10.1371/journal.pgen.1000766. PubMed PMID: 20011102.
Dedic, T. et al. Alagille Syndrome Mimicking Biliary Atresia in Early Infancy, PLOS OONE, 10(11):e0143939: pp. 1-7 (Nov. 20, 2015).
Divina, P. et al. Ab initio prediction of cryptic splice-site activation and exon skipping. Eur J Hum Genet. 2009; 17:759-65.
Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.
El Bougrini, J., et al. PML positively regulates interferon gamma signaling. Biochimie. 2011; 93(3):389-98. doi: 10.1016/j.biochi.2010.11.005. PubMed PMID: 21115099.
Fairbrother, W.G., et al. Predictive identification of exonic splicing enhancers in human genes. Science. 2002; 297(5583):1007-13. PubMed PMID: 12114529.
Ferreira, P.G., et al. Transcriptome characterization by RNA sequencing identifies a major molecular and clinical subdivision in chronic lymphocytic leukemia. Genome Res. 2014; 24:212-26.
Gibson, G. Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.
Gozani, O., et al. A potential role for U2AF-SAP 155 interactions in recruiting U2 snRNP to the branch site. Mol Cell Biol. 1998; 18(8):4752-60. PubMed PMID: 9671485.
Graveley, B.R. The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.
Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.
Guth, S., et al. Dual function for U2AF(35) in AG-dependent pre-mRNA splicing. Mol Cell Biol. 2001;21(22):7673-81. PubMed PMID: 11604503.
Hamdan, F. F. et al. De Novo SYNGAP1 Mutations in Nonsyndromic Intellectual Disability and Autism, Biol. Psychiatry, 69:898-901 (2011).
Hastings, M.L., et al. Control of pre-mRNA splicing by the general splicing factors PUF60 and U2AF. PLoS ONE. 2007;2:e538. PubMed PMID: 17579712.

(56) References Cited

OTHER PUBLICATIONS

He, Y.H., et al. Association of the insulin-like growth factor binding protein 3 (IGFBP-3) polymorphism with longevity in Chinese nonagenarians and centenarians. Aging (Milano). 2014;6:944-56.
Hernan, I. et al. Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.
Hishida, A. et al. Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.
*Homo sapiens* pre-mRNA processing factor 3 (PRPF3), mRNA, NCBI Reference Sequence: NM_004698.2 Accessed Apr. 6, 2017.
Hua, Y., et al. Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal.pbio.0050073. PubMed PMID: 17355180.
Huynh, K.D., et al. BCoR, a novel corepressor involved in BCL-6 repression. Genes Dev. 2000;14(14):1810-23. PubMed PMID: 10898795; PubMed Central PMCID: PMC316791.
International Application No. PCT/GB2015/051756 International Preliminary Report on Patentability, dated Dec. 26, 2016.
International Application No. PCT/GB2016/053136 International Search Report and Written Opinion dated Mar. 6, 2017.
International Application No. PCT/GB2016/053136 Partial International Search Report dated Jan. 19, 2017.
Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.
Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.
Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.
Kim, J. et al. The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12.118. PubMed PMID: 24389012.
Kim P., et al. ChimerDB 2.0—a knowledgebase for fusion genes updated. Nucleic Acids Res. 2009;38(Database issue):D81-5. Epub Nov. 13, 2009.doi: gkp982 [pii] 10.1093/nar/gkp982. PubMed PMID: 19906715.
Kralovicova, J. et al. Branch sites haplotypes that control alternative splicing. Hum Mol Genet. 2004;13:3189-202.
Kralovicova, J. et al. The role of short RNA loops in recognition of a single-hairpin exon derived from a mammalian-wide interspersed repeat. RNA Biol. 2015;12(1):54-69. doi: 10.1080/15476286.2015.1017207. PubMed PMID: 25826413.
Lee, J., et al. Metastasis of neuroendocrine tumors are characterized by increased cell proliferation and reduced expression of the ATM gene. PLoS ONE. 2012;7:e34456.
LeHir, H. et al. 5'-End RET Splicing: Absence of Variants in Normal Tissues and Intron Retention in Pheochromocytomas, Oncology 63:84-91 (2002).
Lemaire, M., et al. CDC25B phosphorylation by p38 and MK-2. Cell Cycle. 2006;5(15):1649-53. PubMed PMID: 16861915.
Liang, Xue-Hai et al., T ranslation efficiency of mRNAs is increased by antisense oligonucleotides targeting upstream open reading frames,Nature Biotechnology, 34(8):875-882 (Aug. 2016).
Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.
Litchfield, D.W., et al. Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.
Lo, YL et al. ATM Polymorphisms and risk of lung cancer among never smokers, Lung Cancer 69(2):148-154 (2010).
Magi-Galuzzi, C. et al. TMPRSS2-ERG gene fusion prevalence and class are significantly difference in prostate cancer of Caucasian, African-American and Japanese patients. The Prostate. 2011;71:489-97.
Matsuoka, S., et al. Ataxia telangiectasia-mutated phosphorylates Chk2 in vivo and in vitro. Proc Natl Acad Sci USA. 2000;97:10389-94.
Matsuoka, S., et al. ATM and ATR substrate analysis reveals extensive protein networks responsive to DNA damage. Science. 2007;316(5828):1160-6. Epub May 26, 2007.doi: 316/5828/1160 [pii] 10.1126/science.1140321. PubMed PMID: 17525332.
Melhuish, et al. The Tgif2 gene contains a retained intron within the coding sequence, BMC Molecular Biology 7(2);1-10 (2006).
Mendell, J.T., ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science.1074428 1074428 [pii]. PubMed PMID: 12228722.
Merendino, L., et al. Inhibition of msl-2 splicing by Sex-lethal reveals interaction between U2AF35 and the 3' splice site AG. Nature. 1999;402(6763):838-41. PubMed PMID: 10617208.
Mirey, G., et al. CDC25B phosphorylated by pEg3 localizes to the centrosome and the spindle poles at mitosis. Cell Cycle. 2005;4(6):806-11. PubMed PMID: 15908796.
Mitelman, F., et al. The impact of translocations and gene fusions on cancer causation. Nat Rev Cancer. 2007;7(4):233-45. Epub Mar. 16, 2007.doi: nrc2091 [pii] 10.1038/nrc2091. PubMed PMID: 17361217.
Montecucco, A., et al. Pre-mRNA processing factors meet the DNA damage response. Front Genet. 2013;4:102. doi: 10.3389/fgene.2013.00102. PubMed PMID: 23761808; PubMed Central PMCID: PMC3674313.
Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.
Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).
Nguyen, L.A., et al. Physical and functional link of the leukemia-associated factors AML1 and PML. Blood. 2005;105(1):292-300. doi: 10.1182/blood-2004-03-1185. PubMed PMID: 15331439.
Nishida, A. et al. Tissue- and Case-specific retention of intron 40 in mature dystrophin mRNA, Journal of Human Genetic 60;327-333 (2015).
Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.
Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.
Page-McCaw, P.S., et al. PUF60: a novel U2AF65-related splicing activity. RNA. 1999;5(12):1548-60. PubMed PMID: 10606266.
Passamonti, C. et al. A novel inherited SCN1A mutation associated with different neuropsychological phenotypes: Is there a common core deficit? Epilepsy & Behavior 43:89-92 (2015).
Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.
Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.
Pear, Warren S. New roles for Notch in tuberous sclerosis, Journal of Clinical Investigation, 120(1):84-87 (Jan. 4, 2010).

(56) References Cited

OTHER PUBLICATIONS

Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.

Perdiguero, E., et al. Regulation of Cdc25C activity during the meiotic G2/M transition. Cell Cycle. 2004;3(6):733-7. PubMed PMID: 15136768.

Piaceri, I., et al. Ataxia-telangiectasia mutated (ATM) genetic variant in Italian centenarians. Neurophysiology. 2013;34:573-5.

Przychodzen, B., et al. Patterns of missplicing due to somatic U2AF1 mutations in myeloid neoplasms. Blood. 2013;122:999-1006. Epub Jun. 19, 2013.doi: blood-2013-01-480970 [pii] 10.1182/blood-2013-01-480970. PubMed PMID: 23775717.

Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.

Romero, P.R., et al. Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas.0507916103. PubMed PMID: 16717195.

Ruchlemer, R., et al. Geography, ethnicity and roots in chronic lymphocytic leukemia. Leuk Lymphoma. 2013;54(6):1142-50. doi: 10.3109/10428194.2012.740670. PubMed PMID: 23121522.

Rudd, M.F., et al. Variants in the ATM-BRCA2-CHEK2 axis predispose to chronic lymphocytic leukemia. Blood. 2006;108(2):638-44. Epub Apr. 1, 2006.doi: 2005-12-5022 [pii] 10.1182/blood-2005-12-5022. PubMed PMID: 16574953.

Shao, C., et al. Mechanisms for U2AF to define 3' splice sites and regulate alternative splicing in the human genome. Nat Struct Mol Biol. 2014;doi: 10.1038/nsmb.2906.

Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.

Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.

Shiloh, Y., et al the ATM protein kinase: regulating the cellular response to genotoxic stress, and more. Nat Rev Mol Cell Biol. 2013;14(4):197-210. doi: 10.1038/nrm3546. PubMed PMID: 23486281.

Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.

Shirley, M.H., et al Incidence of haematological malignancies by ethnic group in England, Jul. 2001. Br J Haematol. 2013;163(4):465-77. doi: 10.1111/bjh.12562. PubMed PMID: 24033296.

Smith, C.W., et al. Scanning and competition between AGs are involved in 3' splice site selection in mammalian introns. Mol Cell Biol. 1993;13(8):4939-52. PubMed PMID: 8336728.

Smith, P.J., et al. An increased specificity score matrix for the prediction of SF2/ASF-specific exonic splicing enhancers. Hum Mol Genet. 2006;15(16):2490-508. PubMed PMID: 16825284.

Soo, R.A., et al. Ethnic differences in survival outcome in patients with advanced stage non-small cell lung cancer. J Thorac Oncol. 2011;6:1030-8.

Stamm, S. Regulation of alternative splicing by reversible protein phosphorylation. J Biol Chem. 2008;283(3):1223-7. PubMed PMID: 18024427.

Stankovic, T., et al. Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.

Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.

Sun, H., et al. Multiple splicing defects in an intronic false exon. Mol Cell Biol. 2000;20(17):6414-25. PubMed PMID: 10938119.

Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.

Taylor, A.M., et al. Ataxia telangiectasia: more variation at clinical and cellular levels. Clin Genet. 2015;87(3):199-208. doi: 10.1111/cge.12453. PubMed PMID: 25040471.

Taylor, A.M., et al. Leukemia and lymphoma in ataxia telangiectasia. Blood. 1996;87(2):423-38. PubMed PMID: 8555463.

Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).

Trapnell, C. et al. Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.

Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.

U.S. Appl. No. 14/741,071 Non-Final Office Action dated Dec. 1, 2016.

Wang, Z. et al. Systematic identification and analysis of exonic splicing silencers. Cell. 2004;119(6):831-45. PubMed PMID: 15607979.

Warf, M.B., et al. Role of RNA structure in regulating pre-mRNA splicing. Trends Biochem Sci. 2010;35(3):169-78. Epub Dec. 5, 2009.doi: S0968-0004(09)00196-0 [pii].

Wu, J.Y., et al. Specific interactions between proteins implicated in splice site selection and regulated alternative splicing. Cell. 1993;75(6)1 061-70. Epub Dec. 17, 1993.doi: 0092-8674(93)90316-I [pii]. PubMed PMID: 8261509.

Wu, S. et al. Functional recognition of the 3' splice site AG by the splicing factor U2AF35.Nature. 1999;402(6763):832-5. PubMed PMID: 10617206.

Wu, Y. et al. MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.

Xia, Y. et al. Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.

Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.

Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.

Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.

Yoshida, K., et al. Splicing factor mutations and cancer. Wiley Interdiscip Rev RNA. 2014;5(4):445-59. doi: 10.1002/wrna.1222. PubMed PMID: 24523246.

Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.

(56) References Cited

OTHER PUBLICATIONS

Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.

Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.

Zarnack K., et al. Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.

Zhang C., et al. RNA landscape of evolution for optimal exon and intron discrimination. Proc Natl Acad Sci USA. 2008;105(15):5797-802. Epub Apr. 9, 2008.doi: 0801692105 [pii] 10.1073/pnas.0801692105. PubMed PMID: 18391195.

Zhang, X.H., et al. Computational definition of sequence motifs governing constitutive exon splicing. Genes Dev. 2004;18:1241-50. PubMed PMID: 15145827.

Zorio, D.A., et al. Both subunits of U2AF recognize the 3' splice site in Caenorhabditis elegans. Nature. 1999;402(6763):835-8. PubMed PMID: 10617207.

Zuker, M. Mfold web server for nucleic acid folding and hybridization prediction. Nucleic Acids Res. 2003;31(13):3406-15. Epub Jun. 26, 2003. PubMed PMID: 12824337.

Goncharova et al. Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.

International Application No. PCT/US2015/053896 International Preliminary Report on Patentability dated Apr. 4, 2017.

International Application No. PCT/US2016/066414 International Search Report and Written Opinion dated Apr. 19, 2017.

International Application No. PCT/US2016/066417 International Search Report and Written Opinion dated Apr. 19, 2017.

International Application No. PCT/US2016/066705 International Search Report and Written Opinion dated Apr. 24, 2017.

Nomakuchi et al. Antisense-oligonucleotide-directed inhibition of nonsense-mediated mRNA decay. Nat. Biotechnol. 34(2):164-166 (Feb. 2016).

Sahashi et al. Pathological impact of SMN2 mis-splicing in adult SMA mice. EMBO Mol. Med. 5(10):1586-601 (Oct. 2013).

Sahashi et al. TSUNAMI: an antisense method to phenocopy splicing-associated diseases in animals. Genes Dev. 26(16):1874-1884 (Aug. 15, 2012).

Staropoli et al. Rescue of gene-expression changes in an induced mouse model of spinal muscular atrophy by an antisense oligonucleotide that promotes inclusion of SMN2 exon 7. Genomics 105:220-228 (2015).

Wu et al. AT-AC Pre-mRNA Splicing Mechanisms and Conservation of Minor Introns in Voltage-Gated Ion Channel Genes. Molecular and Cellular Biology 19(5): 3225-3236 (May 1999).

Zimrin et al. An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).

* cited by examiner

1. Nuclear RNA + probes incubation

2. RNase digestion of single stranded RNA

3. Denaturing PAGE electrophoresis

Western blot analysis

Western blot analysis

Hot RT-PCR analysis

1. ARPE-19
2. HeLa
3. U2OS

| PIR[1] | EXPERIMENT | SOURCE |
|---|---|---|
| 35.5 | hot RT-PCR | ARPE19[2] |
| 18 | hot RT-PCR | HeLa[3] |
| 26 | hot RT-PCR | U2OS[4] |
| 33 | RNAseq-ASOthera | ARPE-19 |

[1]Percent intron retention
[2]Retina epithelial
[3]Cervical carcinoma
[4]Osteosarcoma

SEQUENCE LISTING

<160> NUMBER OF SEQ ID NOS: 403

<210> SEQ ID NO 1
<211> LENGTH: 124
<212> TYPE: RNA
<213> ORGANISM: Homo sapiens

<400> SEQUENCE: 1
ugggcuacga acugaaggau gagaucgagc gcaaauucga caaguggcag gagccgccgc    60

-continued

```
cugugaagca ggugaagccg cugccugcgc cccuggaugg acagcggaag aagcgaggcg    120
gccg                                                                 124

<210> SEQ ID NO 2
<211> LENGTH: 84
<212> TYPE: RNA
<213> ORGANISM: Homo sapiens

<400> SEQUENCE: 2
gggcccuggg ggaccgguag gcaugggggu cauggagggg agaagccggc guccuccucc    60
cagccgacuc ccuggcgccg ccca                                           84

<210> SEQ ID NO 3
<211> LENGTH: 69
<212> TYPE: RNA
<213> ORGANISM: Homo sapiens

<400> SEQUENCE: 3
uaccgcaaga ugaaggagcg gcuggggcug acggagaucc ggaagcaggc caaccguaug    60
agcuucgga                                                            69

<210> SEQ ID NO 4
<211> LENGTH: 125
<212> TYPE: RNA
<213> ORGANISM: Homo sapiens

<400> SEQUENCE: 4
ucgaggagga cgccuaccag gaggaccugg gauucagccu gggccaccug ggcaagucgg    60
gcagugggcg ugugcggcag acacagguaa acgaggccac caaggccagg aucuccaaga    120
cgcug                                                                125

<210> SEQ ID NO 5
<211> LENGTH: 66
<212> TYPE: RNA
<213> ORGANISM: Homo sapiens

<400> SEQUENCE: 5
ggccagaccc aggugggggcu ggggaccgag ggacacaagg uggggggagc ccagaucgca    60
gccucc                                                               66

<210> SEQ ID NO 6
<211> LENGTH: 95
<212> TYPE: RNA
<213> ORGANISM: Homo sapiens

<400> SEQUENCE: 6
ggacccugca gaagcagagc gucguauaug gcgggaaguc caccauccgc gaccgcuccu    60
cgggcacggc cuccagcgug gccuucaccc cacuc                               95

<210> SEQ ID NO 7
<211> LENGTH: 27
<212> TYPE: RNA
<213> ORGANISM: Homo sapiens

<400> SEQUENCE: 7
aucuuaguau caauugguga aucauuc                                        27

<210> SEQ ID NO 8
```

<211> LENGTH: 3290
<212> TYPE: DNA
<213> ORGANISM: Homo sapiens

<400> SEQUENCE: 8

```
tattttcttt ctatgaaata taatagtatg cattgtaagt ataaaagaaa ttaaagcttt      60
ctataatttg aatttccaaa tgcagttatt caaacacctc atccaggcat attgcataga     120
attttatgag atatatatat ctcagattta ctttcaaatc aagtttaatc tcaaatcata     180
ctcctaattg gtgaacttca aaacttttct aaatatccac ttgagattat ataatacata     240
tatacatttg tgtatataca tacatatata cgtgagctgt ttttgctcac aacatttcta     300
tcaccaaatg tgtgagattt ttttctcacc caaatctatt cttcaactct ctggtgttct     360
acaattcaat tcaattctga cactaattac ccagagtcag catcagactc cacaggttca     420
agggctcagt cccacaaaaa tggtctcact gcagacacca gtcacaagtg tcaggtcccc     480
aggctacacc acacttccgt ctgacttgaa tacgaagttg ggggttccg atagtgcctc      540 ttccttacag tttgatccac tgccagaact actcacaaaa ctctgaaaaa tattctactt     600
actattatca gttcatcata aaagatacaa atgaacagcc agatgaagaa atattatata     660
gggtgaggtc cagaagagtc cctagcacag gggcttctgt ccctggggag ttggggtgca     720
ccaccttcct agcacttaga catgtttacc aactccaaag atctcccaac cttattgttg     780
aggggttttt atggggtttt cattatatag gcataattga ttaactcaat ttccaacccc     840
ctcccctccc tggatagagg gtggggctga agttccaag cttctactca agacttggtc      900
tttctggcaa ccagcttcca tcctaaatta gctaggtacc caccaagtat cacctcatta     960
gaacaaaaga tggtcccatc acccttatca cacatgaaat tcgaagggtt ttaggagctc    1020
tgtcccagga accagggaca aagaccaaat atctttcaat gataccatgt atgtatgtac    1080
ataacctcac aggaatcttt ataaaacaat tttgaaattc actcattatg agtgtgattt    1140
gaaatgagat actccaaaat gtaagcccga tatccaaatg tcaccagcct gtccctgcct    1200
actggtctcc ttccatacat atgcactttt tgcttgtcct tcctctcaga cttctaggat    1260 attcttttc tggtacactg attaggaatt gtttgcatga atcctgcct cagtgaaagt      1320 ggcagagctt cattctagga gatccaaggg aaagctttgc tttgaaacat ttattctagg    1380
ctgcaaatcc acaaccctag ttggccttcc attaaagtca ctaattcagc agtcccatat    1440
tcaatatgca ttactgttaa tatgttgcac catctccatt cccctgagag cttatatttt    1500 taattttaa attttatttt ttagagacag tgtctcactc tgtcacctac ttattataac     1560
ctcaaactcc tcggcccaag cagtcctctc accttagcct cccaagttgc caggactaca    1620
ggcatgcacc accatgtcca gctaattttt aaatttttg tagagacagg gttttctatg     1680
ttggccagat tggtattgaa ctcctggctt ccacgatacc ccgtctcagc ctcccaaaga    1740
actgggatta cagatgtgag ccactgcacc tggccagaga gcttatattc ttataggaat    1800
gggaagactg cctatgttat gtgttgctac ataatacatt acccccaaac ttagtgactt    1860
aaaacaaacg cttattatct ccatttctgt gggtcaataa tctaggcatg acttagctgg    1920
gccagagttt ctccaaagtc tgtgatcaag gtgtcagttg ggctgggcct gcagtcatct    1980
caaggctcca ctagaggagc attcactggc agacttattc aaatggctgt tggctgatcc    2040
tcgatggcta ttggcccctc tattggtttc ttgcccttgg gccctccat agtactgctt      2100 gctattcaca acatggcagc ttgctttgcc cagagcaggg actctgaggg aggcagggaa    2160
ataaagagca agagagaggt cacagtctta ttgtaatcta attctggaaa tgacagccca    2220
```

```
ttactttttgg catattattt tggttagaag caagacaaca gtagatctag cccacacacg    2280 agggaggag gatcacacaa ggaggtgaat accaggaggt ggggtcattg ggagccatct     2340
gagaggctgc ccaccacact gcctcaagta actagggaga ggtaaaagtt tatatgccag    2400
atgaccaaat attaaaatgt gtgttacaaa tagttcacga tgggctcagc tgtcagactt    2460
tacaaaggag ctatgggacc ttataaggac agttggaact ggctaggtat cacatagtgg    2520
tcttcaaaca ttttgcttg ccataacctc taaaataatt gggaaaaagt tgaatgtact     2580
tccatatctt aaagctgata atttaaaata ttatacattt aatagcagca cgggatttag    2640
tttttgttaa attgtatatg tgctccaaat agatttacca tcaaaacctg ttttgaattt    2700
aatattggga gaattcgcta gtttaatttt tggaaaataa agtataattg gcaaagctaa    2760
tcctcactgt tgaatctatc cgtcaaatca gatataattt ctatcagaaa gtctatatga    2820
cttgtcaaca taatacccat aaagtgaatc aaaaattatt attcattgaa cacatcatct    2880
cttatcaaat tcttgtgacc ttccttctgg ttgtataata gcctaaaaaa caaaaaaagg    2940
acaaaagcaa gtttccagaa agctgttctg acttgcctac ttctgaaaag tagtcctgta    3000
tggtgggttc tgaaaatgag gaaccaggac ttgcagagta ggcagttgct ggaggaagaa    3060
tgtgagctgc atgggaaaag acaggaggat ttacaaagag tgggtgttta attggggatg    3120
gaattaggta gttattctga tttttagatt tttcatatct tttatttggt ccaatgaagc    3180
agaaaattta aatgaagtta ttacctttgc ctgattttg acacacctca aactataact     3240
tgaggttgct aactatgaaa cactggcatt taatgattta aagtaaagaa              3290

<210> SEQ ID NO 9
<211> LENGTH: 139
<212> TYPE: RNA
<213> ORGANISM: Homo sapiens

<400> SEQUENCE: 9
cuucugagaa guuccagaaa auaaaucaga ugguauguaa cagcgaccgu gugcucaaaa     60
gaagugcuga aggaagcaac ccuccuaaac cacugaaaaa acuacgcuuu gauauugaag    120
gaucagauga agcagaugg                                                 139

<210> SEQ ID NO 10
<211> LENGTH: 89
<212> TYPE: RNA
<213> ORGANISM: Homo sapiens

<400> SEQUENCE: 10
auggugcauc ugacuccuga ggagaagucu gccguuacug cccuguggg caaggugaac      60 guggaugaag uugguggug aggcccuggg                                       89

<210> SEQ ID NO 11
<211> LENGTH: 110
<212> TYPE: DNA
<213> ORGANISM: Homo sapiens

<400> SEQUENCE: 11
tatcaaggtt acaagacagg tttaaggaga ccaatagaaa ctgggcatgt ggagacagag      60
aagactcttg ggtttctgat aggcactgac tctctctgcc tattggtcta                110

<210> SEQ ID NO 12
<211> LENGTH: 219
<212> TYPE: RNA
```

<213> ORGANISM: Homo sapiens

<400> SEQUENCE: 12

| cugcuggugg ucuacccuug gacccagagg uucuuugagu ccuuugggga ucuguccacu | 60 |
| ccugaugcug uuaugggcaa cccuaaggug aaggcucaug gcaagaaagu gcucggugcc | 120 |
| uuuagugaug gccuggcuca ccuggacaac ucaagggca ccuuugccac acugagugag | 180 |
| cugcacugug acaagcugca cguggauccu gagaacuuc | 219 |

<210> SEQ ID NO 13
<211> LENGTH: 142
<212> TYPE: RNA
<213> ORGANISM: Homo sapiens

<400> SEQUENCE: 13

| acacucgcuu cuggaacguc ugagguuauc aauaagcucc uagucagac gccauggguc | 60 |
| auuucacaga ggaggacaag gcuacuauca caagccugug gggcaaggug aauguggaag | 120 |
| augcuggagg agaaacccug gg | 142 |

<210> SEQ ID NO 14
<211> LENGTH: 102
<212> TYPE: DNA
<213> ORGANISM: Homo sapiens

<400> SEQUENCE: 14

| ctctggtgac caggacaagg gagggaagga aggaccctgt gcctggcaaa agtccaggtc | 60 |
| gcttctcagg atttgtggca ccttctgact gtcaaactgt tc | 102 |

<210> SEQ ID NO 15
<211> LENGTH: 219
<212> TYPE: RNA
<213> ORGANISM: Homo sapiens

<400> SEQUENCE: 15

| cuccugguug ucuacccaug gacccagagg uucuuugaca gcuuggcaa ccuguccucu | 60 |
| gccucugcca ucaugggcaa ccccaaaguc aaggcacaug gcaagaaggu gcugacuucc | 120 |
| uugggagaug ccacaaagca ccuggaugau ucaagggca ccuuugccca gcugagugaa | 180 |
| cugcacugug acaagcugca uguggauccu gagaacuuc | 219 |

<210> SEQ ID NO 16
<211> LENGTH: 860
<212> TYPE: DNA
<213> ORGANISM: Homo sapiens

<400> SEQUENCE: 16

| tccaggagat gtttcagccc tgttgccttt agtctcgagg caacttagac aacggagtat | 60 |
| tgatctgagc acagcaggt gtgagctgtt tgaagatact ggggttgggg gtgaagaaac | 120 |
| tgcagaggac taactgggct gagacccagt ggtaatgttt tagggcctaa ggagtgcctc | 180 |
| taaaaatcta gatggacaat tttgactttg agaaagaga ggtggaaatg aggaaaatga | 240 |
| cttttcttta ttagattcca gtagaaagaa ctttcatctt tccctcattt ttgttgtttt | 300 |
| aaaacatcta tctggaggca ggacaagtat ggtcgttaaa aagatgcagg cagaaggcat | 360 |
| atattggctc agtcaaagtg gggaactttg gtgccaaaac atacattgct aaggctattc | 420 |
| ctatatcagc tggacacata taaaatgctg ctaatgcttc attacaaact tatatccttt | 480 |
| aattccagat gggggcaaag tatgtccagg ggtgaggaac aattgaaaca tttgggctgg | 540 |

```
agtagatttt gaaagtcagc tctgtgtgtg tgtgtgtgtg tgcgcgcgcg cgtgtgtgtg      600
tgtgtgtcag cgtgtgtttc ttttaacgtc ttcagcctac aacatacagg gttcatggtg      660
gcaagaagat agcaagattt aaattatggc cagtgactag tgcttgaagg ggaacaacta      720
cctgcattta atgggaaggc aaaatctcag gctttgaggg aagttaacat aggcttgatt      780
ctgggtggaa gcttggtgtg tagttatctg gaggccaggc tggagctctc agctcactat      840
gggttcatct ttattgtctc                                                  860

<210> SEQ ID NO 17
<211> LENGTH: 125
<212> TYPE: RNA
<213> ORGANISM: Homo sapiens

<400> SEQUENCE: 17
uccugggaaa ugugcugguq accguuuugg caauccauuu cggcaaagaa uucaccccug       60
aggugcaggc uuccuggcag aagaugguga cugcaguggc cagugcccug uccuccagau      120
accac                                                                  125

<210> SEQ ID NO 18
<211> LENGTH: 182
<212> TYPE: RNA
<213> ORGANISM: Homo sapiens

<400> SEQUENCE: 18
aauuggaagc aaaugacauc acagcagguc agagaaaaag gguugagcgg caggcaccca       60
gaguaguagg ucuuuggcau uaggagcuug agcccagacg gcccuagcag ggaccccagc      120
gcccgagaga ccaugcagag gucgccucug gaaaaggcca gcguugucuc caaacuuuuu      180
uu                                                                     182

<210> SEQ ID NO 19
<211> LENGTH: 1000
<212> TYPE: DNA
<213> ORGANISM: Homo sapiens

<400> SEQUENCE: 19
aaggtggcca accgagcttc ggaaagacac gtgcccacga agaggaggg cgtgtgtatg        60 ggttgggttt ggggtaaagg aataagcagt ttttaaaaag atgcgctatc attcattgtt      120
ttgaaagaaa atgtgggtat tgtagaataa aacagaaagc attaagaaga gatggaagaa      180
tgaactgaag ctgattgaat agagagccac atctacttgc aactgaaaag ttagaatctc      240
aagactcaag tacgctacta tgcacttgtt ttatttcatt tttctaagaa actaaaaata      300
cttgttaata agtacctaag tatggtttat tggttttccc ccttcatgcc ttggacactt      360
gattgtcttc ttggcacata caggtgccat gcctgcatat agtaagtgct cagaaaacat      420
ttcttgactg aattcagcca acaaaaattt tggggtaggt agaaaatata tgcttaaagt      480
atttattgtt atgagactgg atatatctag tatttgtcac aggtaaatga ttcttcaaaa      540
attgaaagca aatttgttga aatatttatt ttgaaaaaag ttacttcaca agctataaat      600
tttaaaagcc ataggaatag ataccgaagt tatatccaac tgacatttaa taaattgtat      660
tcatagccta atgtgatgag ccacagaagc ttgcaaactt taatgagatt tttaaaata       720 gcatctaagt tcggaatctt aggcaaagtg ttgttagatg tagcacttca tatttgaagt      780
gttctttgga tattgcatct actttgttcc tgttattata ctggtgtgaa tgaatgaata      840
```

```
ggtactgctc tctcttggga cattacttga cacataatta cccaatgaat aagcatactg    900
aggtatcaaa aaagtcaaat atgttataaa tagctcatat atgtgtgtag gggggaagga    960
atttagcttt cacatctctc ttatgtttag ttctctgcat                         1000
```

<210> SEQ ID NO 20
<211> LENGTH: 107
<212> TYPE: RNA
<213> ORGANISM: Homo sapiens

<400> SEQUENCE: 20

```
uggaccagac caauuuugag gaaaggauac agacagcgcc uggaauuguc agacauauac     60
caaaucccuu cuguugauuc ugcugacaau cuaucugaaa aauugga                  107
```

<210> SEQ ID NO 21
<211> LENGTH: 1000
<212> TYPE: DNA
<213> ORGANISM: Homo sapiens

<400> SEQUENCE: 21

```
ttcatgtaca ttgtttagtt gaagagagaa attcatatta ttaattattt agagaagaga     60
aagcaaacat attataagtt taattcttat atttaaaaat aggagccaag tatggtggct    120
aatgcctgta atcccaacta tttggaggc caagatgaga ggattgcttg agaccaggag    180
tttgatacca gcctgggcaa catagcaaga tgttatctct acacaaaata aaaaagttag    240
ctgggaatgg tagtgcatgc ttgtattccc agctactcag gaggctgaag caggagggtt    300
acttgagccc aggagtttga ggttgcagtg agctatgatt gtgccactgc actccagctt    360
gggtgacaca gcaaaaccct ctctctctaa aaaaaaaaa aaaaaggaac atctcatttt    420
cacactgaaa tgttgactga atcattaaaa caataaaatc ataaagaaa aataatcagt    480 ttcctaagaa atgatttttt ttcctgaaaa atacacattt ggtttcagag aatttgtctt    540
attagagacc atgagatgga ttttgtgaaa actaaagtaa caccattatg aagtaaatcg    600
tgtatatttg cttcaaaac ctttatattt gaatacaaat gtactccctg ggaagtctta    660
aggtaatggc tactggttat caaacaaatg taaaaattgt atatttttga gtacctgtta    720
catgccaggt agaatatctc ctctcagcca ctctgagtgg aaagcatcat tatctctatt    780
ttacagaaaa gcaaactgag gctcagagag ataatatact ttgccagtta atgaatgatg    840
gagccatgat tccagctgag gtctgtattg ccttgctctc taggaatggt agtccccccc    900
ataaagaatc tctcagtttc cttttccaatc aaaaggttag gatccttttg attgccagtg    960
acagaaaccc aatttactag cttaagtaaa taaaaggaac                        1000
```

<210> SEQ ID NO 22
<211> LENGTH: 105
<212> TYPE: RNA
<213> ORGANISM: Homo sapiens

<400> SEQUENCE: 22

```
gaaugggaua gagagcuggc uucaaagaaa aauccuaaac ucauuaaugc ccuucggcga     60
uguuuuuucu ggagauuuau guucuaugga aucuuuuuau auuua                   105
```

<210> SEQ ID NO 23
<211> LENGTH: 1000
<212> TYPE: DNA
<213> ORGANISM: Homo sapiens

<400> SEQUENCE: 23

```
gatctcattt gtacattcat tatgtatcac ataactatat tcattttgt gattatgaaa      60 agactacgaa atctggtgaa taggtgtaaa aatataaagg atgaatccaa ctccaaacac     120
taagaaacca cctaaaactc tagtaaggat aagtaaaaat cctttggaac taaaatgtcc     180
tggaacacgg gtggcaattt acaatctcaa tgggctcagc aaaataaatt gcttgcttaa     240
aaaattattt tctgttatga ttccaaatca cattatctta ctagtacatg agattactgg     300
tgcctttatt ttgctgtatt caacaggaga gtgtcaggag acaatgtcag cagaattagg     360
tcaaatgcag ctaattacat atatgaatgt ttgtaatatt ttgaaatcat atctgcatgg     420
tgaattgttt caagaaaaaa cactaaaaat ttaaagtata gcagctttaa atactaaata     480
aataatacta aaaatttaaa gttctcttgc aatatatttt cttaatatct tacatctcat     540
cagtgtgaaa agttgcacat ctgaaaatcc aggctttgtg gtgtttaagt gccttgtatg     600
ttccccagtt gctgtccaat gtgactctga tttattattt tctacatcat gaaagcatta     660
tttgaatcct tggttgtaac ctataaaagg agacagattc aagacttgtt taatcttctt     720
gttaaagctg tgcacaatat ttgctttggg gcgtttactt atcatatgga ttgacttgtg     780
tttatattgg tctttatgcc tcagggagtt aaacagtgtc tcccagagaa atgccatttg     840
tgttacattg cttgaaaaat ttcagttcat acaccccat gaaaaataca tttaaaactt      900
atcttaacaa agatgagtac acttaggccc agaatgttct ctaatgctct tgataatttc     960
ctagaagaaa tttttctgac ttttgaaata atagatccat                          1000

<210> SEQ ID NO 24
<211> LENGTH: 212
<212> TYPE: RNA
<213> ORGANISM: Homo sapiens

<400> SEQUENCE: 24
aagucaccaa agcaguacag ccucucuuac ugggaagaau cauagcuucc uaugacccgg      60
auaacaagga ggaacgcucu aucgcgauuu aucuaggcau aggcuuaugc cuucucuuua     120
uugugaggac acugcuccua cacccagcca uuuuuggccu ucaucacauu ggaaugcaga     180
ugagaauagc uauguuuagu uugauuuaua ag                                   212

<210> SEQ ID NO 25
<211> LENGTH: 3141
<212> TYPE: DNA
<213> ORGANISM: Homo sapiens

<400> SEQUENCE: 25
acttccttgc acaggcccca tggcacatat attctgtatc gtacatgttt taatgtcata      60
aattaggtag tgagctggta caagtaaggg ataaatgctg aaattaattt aatatgccta     120
ttaaataaat ggcaggaata attaatgctc ttaattatcc ttgataattt aattgactta     180
aactgataat tattgagtat cttctgtaaa ctgcctctgt tgtagttttt tttttctcct     240
aatcatgtta tcattttttt ggaatccatg gtttcctgtt aagatgactc acacagccta     300
cataaaagta attgacaaaa tatcatctta tagtaaaatg ccacatatct ttatgttcag     360
caagaagagt ataatatatg attgttaatg ataacccaaa caacaaaaga tttcaccttta     420 actggttgtc ataagtagta gtatccaccg ccttattttg agttggattt ttatcatcct     480
atgagcccta caaattaaaa gttttttggaa cagcacgtgc attgaaccca taagaaccta     540
ctctgctttt ctgcatgtat tgtccagaca agagaccaaa ttgccgaggc atcatttagg     600
```

```
tgaattctaa ttaacattta gctaccttac aaccacaatt caaggttgtt tcaaaggcat    660
gtgcttgcat catcctgatt cactaccatg tgttactaac ttggatctgc aaagtcatta    720
taaaaagctg ttttgatgga cttatttgga tattgcttta cccttcttct ctcttttctt    780
ttatcaatgt aaaacatta tatgttaaat acttggcttt taagagcata gatctgaaat     840
ctgcctctag caaataaccc ataacacttc taagatatac ctgcaaggtc aattgtgttg    900
taaaaccttg ataaccatac tttattgttc aaaaaagcct tttatgaagg cagaagttaa    960 aaaaaaaaa caaaaaaac agagtccaca gttatcacct cagctacaat ctcatcagtt     1020
cacaagtacc agcaaaacat gtgataagtc aacaaatgtt ttatttcaat ctgaacattt    1080
tacgtaagtg aagactttgt tagatatcat ttggaatgtg aatctacac agttggcata    1140 tcagagaagg ttgaattcag tttaataaat gtttatagaa agtgcttgtt atcataatga    1200
taatagctca ggatgtgcat gacaagcttt taagcgattg ggtacactat ctcatttgat    1260
cttctgcaca actattaatg gtaggtacta ttatccctat cttatggata agtaaactaa    1320
gatttaaaaa gtacagaaca tggtgtgaac actgcttcaa aatttctaaa ataggtaaat    1380
cacgatctct aaactggagg gttgtccaac cactagggac aatagagtac tgatatttag    1440
tggtcagact gtaatgcggg aagagacagg catgggctaa acgggtgtag agatcaaata    1500
aggggcaggt tagtttgtaa acatgtccat atgtaacatt tagcacaaat acaggatata    1560
ggtgctttca gacccagctg cattgataaa aagttaggtg gtattgtatc tgtcttcctt    1620
tctcaatgtt gcatatctgt gttcttgccc agtttgcttc atctctctag ccacacttat    1680
tggcctacaa tggcatcatc accaaagaag gcaatcccat ctccgtgtgg ctttggtttg    1740
ctccctaaag taaaccttgt gtttactttt cccaggtctc atgctttccc atatctgacc    1800
tgttttgtcc tcatggccag gatatgtggg acctttccta caatgttcca aagtttgtaa    1860
tagagctctt ctctgctttg ttccaaattc tgcaacattt tacttaaat aatgaattta     1920 aatacaaaca aacttgagct tgcctatac ttttcaagaa tgcagagata actaaattaa     1980 taaaatatt cattgagtcc ttactgtgca cacagctcta tgttaagcct tgtgcagaac     2040
tcaaagtcac tcgagattaa gcctgttact aagttatgtg caatttagct cagtggattt    2100
cccccacttc atattgctct gataatgttt tggaattaac tgccttgatt ccttcttttc    2160
tctgcttgtc tatacactat ttattattct acaccatctc aaattctaac tcctcaagaa    2220
aatccttcca gatgattttt ctaaccagga gttttaactt cctttaact accctattac     2280 tttctacttc cttaactcat ctatcatatt atatttagtt attatatac taggtcgcct     2340 tgaagaaggg attgtgtttt cataaatctt aataatccct gaggcatcaa gtacagtgat    2400
ttgcatttac taaatgctca acaaatatgt gagggattca cttgaaacta atattagata    2460
attcccagtc aaagtgatct aatagcaaat caattcttca gttttatagg caaagtatga    2520
ctctggtttt ccataatcat aattaatttg tcaactttat aatttaatt aagtaaattt     2580 aattggtaga taaataagta gataaaaaat aatttacctg cttaactacg tttcatatag    2640
cattgcattt ttctttgtaa aatttaagaa ttttgtatta ataaactttt ttacaaaagt    2700
attaattatt cagttattca tcatatactt ttattgactt aaaagtaatt ttattcaaaa    2760
gagttagtat aggactacat gaaaaattca aggccaaggc ttaatttcaa atttcactgc    2820
ctttggctct atcttttaaa acaaaacaaa aaactcccgc acaatatcaa tgggtattta    2880
agtataatat cattctcatt gtgaggagaa aaaataatta tttctgccta gatgctggga    2940
aataaaacaa ctagaagcat gccagtataa tattgactgt tgaaagaaac atttatgaac    3000
```

-continued

```
ctgagaagat agtaagctag atgaatagaa tataattttc attaccttta cttaataatg    3060
aatgcataat aactgaatta gtcatattat aattttactt ataatatatt tgtattttgt    3120
ttgttgaaat tatctaactt t                                              3141

<210> SEQ ID NO 26
<211> LENGTH: 86
<212> TYPE: RNA
<213> ORGANISM: Homo sapiens

<400> SEQUENCE: 26
cuuuaaagcu gucaagccgu guucuagaua aaauaaguau uggacaacuu guuagucucc     60
uuuccaacaa ccugaacaaa uuugau                                         86

<210> SEQ ID NO 27
<211> LENGTH: 862
<212> TYPE: DNA
<213> ORGANISM: Homo sapiens

<400> SEQUENCE: 27
tacctattga tttaatcttt taggcactat tgttataaat tatacaactg gaaaggcgga     60
gttttcctgg gtcagataat agtaattagt ggttaagtct tgctcagctc tagcttccct    120
attctggaaa ctaagaaagg tcaattgtat agcagagcac cattctgggg tctggtagaa    180
ccacccaact caaaggcacc ttagcctgtt gttaataaga ttttcaaaa cttaattctt     240 atcagacctt gcttcttttt aaaactttaa atctgttatg tactttggcc agatatgata    300
cctgagcaat tcttgttctg ggttgtctta tgtgaaaaat aaattcaagg tccttgggac    360
agataatgtg ttttatttat ctttgcatat ccattactta aaacagcatt ggacccacag    420
ctggtacaaa attaattact gttgaattga gcaaatattt attctaaatg tctctgtcaa    480
atgacagagt gtggttgtgt ggattaagtc cctggagaga gttctttgtt ctctcatgtt    540
ctatgctgtg gttcttgctt tatgcaaaaa gaagtaagtt acttaaaacc tggacatgat    600
acttaagatg tccaatcttg attccactga ataaaaatat gcttaaaaat gcactgactt    660
gaaatttgtt ttttgggaaa accgattcta tgtgtagaat gtttaagcac attgctatgt    720
gctccatgta atgattacct agattttagt gtgctcagaa ccacgaagtg tttgatcata    780
taagctcctt ttacttgctt tctttcatat atgattgtta gtttctaggg gtggaagata    840
caatgacacc tgtttttgct gt                                             862

<210> SEQ ID NO 28
<211> LENGTH: 160
<212> TYPE: RNA
<213> ORGANISM: Homo sapiens

<400> SEQUENCE: 28
gacuugcauu ggcacauuuc guguggaucg cuccuuugca aguggcacuc cucauggggc     60
uaaucuggga guuguuacag gcgucugccu ucuguggacu ugguuuccug auaguccuug    120
cccuuuuuca ggcugggcua gggagaauga ugaugaagua                          160

<210> SEQ ID NO 29
<211> LENGTH: 1116
<212> TYPE: DNA
<213> ORGANISM: Homo sapiens

<400> SEQUENCE: 29
```

```
aacctattttt cataacttga aagttttaaa aattatgttt tcaaaaagcc cactttagta      60
aaaccaggac tgctctatgc atagaacagt gatcttcagt gtcattaaat tttttttttt     120 ttttttttt  tgagacagag tctagatctg tcacccaggc tggagtgcag tggcacgatc     180
ttggctcact gcactgcaac ttctgcctcc caggctcaag caattctcct gcctcagcct     240
ccggagtagc tgggattaga ggcgcatgcc accacaccca gctaattttt gtatttagt      300 agagacaggg tttcaccagg ttgcccaggc tggtctcgaa tgcctgacct caggtgatcc     360
gcccacctcg gcctcccaaa gtactgatat tacaggcatg agctaccgcg cccggcctaa     420
aaaatacttt ttaagatggt gtaaatatta ctttctgtat caatggtaca ttttttactt     480
gtcagtctct agaatttctt tataaatatg ttgattcagt tcattttgt  agattataaa     540 acaggtaaaa aaggataaaa catttatgtg aattaaaggg aatacctaat ttttgtgtag     600
agtttattag cttttactac tctggtttat ggatcatcac accagagcct tagttacttt     660
gtgttacaga ataactaata tgagtgaatg aatgacttac acaagtcact gcttaggata     720
aagggcttga gtttgtcagc tagagtatga cagaaagtat ctaagttttg gagtcaaata     780
gcactttgtt tgaatcccag attgcatgct tactagttat gtgaccttag tcaagccact     840
tcacctcact gagtctttgc tttttcatc  tctaaaatag agatacccac cgctcatagg     900
ctgtcataag ggatagagat agcatatgga atgagtctgt acagcgtctg cacatagga     960 ggcatttacc aaacagtagt tattattttt gttaccatct atttgataat aaaataatgc    1020
ccatctgttg aataaaagaa atatgactta aaaccttgag cagttcttaa tagataattt    1080 gacttgttt  tactattaga ttgattgatt gattga                              1116

<210> SEQ ID NO 30
<211> LENGTH: 122
<212> TYPE: RNA
<213> ORGANISM: Homo sapiens

<400> SEQUENCE: 30
gaucagagag cugggaagau cagugaaaga cuugugauua ccucagaaau gauugaaaau      60
auccaaucug uuaaggcaua cugcugggaa gaagcaaugg aaaaaaugau ugaaaacuua     120
ag                                                                    122

<210> SEQ ID NO 31
<211> LENGTH: 3406
<212> TYPE: DNA
<213> ORGANISM: Homo sapiens

<400> SEQUENCE: 31
ttgttccaat aatttcaata ttgttagtaa ttctgtcctt aattttttaa aaatatgttt      60
atcatggtag acttccacct catatttgat gtttgtgaca atcaaatgat tgcatttaag     120
ttctgtcaat attcatgcat tagttgcaca aattcacttt catgggctgt agttttatgt     180
agttggtcca gggtgttatt ttatgctgca agtatattat actgatacgt tattaaagaa     240
tttcctacat atgttcactg ctgctcaata catttatttc gttaaaacaa ttatcaagat     300
actgaaggct gattggtaac tcacatgaaa ctgggagagt atacaattct gaaccaaata     360
gatgattctc tattattata tcttaattta tgtgttatgg tatattaaac atgaaaaaaa     420
ttgtatttgg ttagaatatg tttgctcttc cttaactcgg gaatgacata gggtaatatt     480
cacagattgg gttcctataa atcctccact tgaagtgaag tcagttcaag taatgaaagc     540
tacctcctga gatagaatca gtacttggca cctatctcta gtgttctttc acctcatata     600
```

```
accctttcact gattagtaaa gattatatcc aacaaagaaa gtacagcaca gactgagata    660
tgattactga gataaatttg ggcaaaatat aaactacagc atttctgtag caatgagacc    720
atttttcttc agttgagctc catgttctac aaacttcaat caaaaaaggt tctaggagac    780
tcagtgaaag ttgatacact gttcaaggaa caaataattt cagcacatgg gaatttcaca    840
gggaaaaata tactaaaaag agaggtacca ttttggatgg tgtcaatatg ggttatgagg    900
aattcaggct gctgagtcca gtgtacaatg gaaactgagc tgcaggtgtg tgattgtaac    960
aacaaaagaa atgctgaaat attaagtcct ttgccatgta aatagaaaaa gagtatttat   1020
ttcccaaaca ttattgctca cctgtttttg ttatgccttt caagataaat ccaggaaagg   1080
aattgcattt tctttccaga aaacaagttc ttggggaat tgttcaattg gtagatgttg    1140
tttttctcat taacaagtga gtgctccatc acacttgctg agtgctccat cacacttgct   1200
ctctgcatta ctcctctgcc tgcaaacaca tatatagcaa gggtgatgac aaggatatca   1260
gagggtctgg ttttctcaaa ctcatgataa actcatggct gggtcattct tggtgctgat   1320
tttactttgt tttttgttgt tattgttccc tcttcctcaa aagatgaaat ctatccctct   1380
tacttggaat ttctctttga tatatagcga atgtttggtt gtaacctgta taatctggca   1440
tgaaattgtc actcgaaaag ctagaagtg ttgacataaa tatgggacag caagagttgc    1500
tcctactcaa gagagcaaat ataatgttct ggaagagatt ggcagaattc acatcaaagg   1560
agtgattact tcagcctggg ccactgttgt actggtcaaa aggctgtgca agctctctg    1620 aaaatccact cttttattgc tctttagtaa taaagtcact ttcaatttta aaaataacaa   1680
actgatatat ttttatgact cataaaatgt tagcaattat attatggaga atctactttc   1740
tgggtgattc ttacaaatgt tcttggatct atttttttt cttatagtac ctattcttcc    1800 cattttctc agctctagtt aatatatttc aacaacagtt caacaaattt aacatttta    1860 taaaagtgt ttcctatcat tttataaata ccagcctagt ccatgttatt ccttttcttg   1920
ttgaggagaa aggacacaca ttgtaaattc aaatatagac ctctactgtg ctatttaatc   1980
ttggtaacaa ctccacaaag gagatgcat gttttccttc tatagaggta gattctgtaa    2040
agttagaggg aagagtgact tgcttaagat ggcataagct gtaactggca gaaccaggat   2100
tcaaagccag gtgggatgcc aaaatcataa tctgtcttca gtgtcaagtt actgaaattg   2160
gtaaacatta gacctaaata gacggaattg caatccgggt tgggcacatt aaactccatt   2220
ttcttcatca atgtgctcag attacatttt acttttcagg ctaaaaatgg aaaaaagag    2280 tccctcttag ttctgcactt gagaatgaga atagcttttc tgaattatac aaggaagaag   2340
aactaatgcc caaatgccag gtacccacat gcactatgcc atggcacagc tgttgccccc   2400
tttcaccaga gccctctctc tgtatcctgg ttgacctttc cttgggcaag agctgggtgg   2460
ggaggatcac aagtgactcc aatttggatg gcttcgggaa gactgggacc gagctgaagg   2520
cagtgttgtc ctctgcactc cctgttttct gtctgctgga gcactgaagc ctcacatatg   2580
tattaaaaaa ataatttcca tttgcatttc agactagaag attgaacgta tagtgtaatg   2640
tgattgcaaa taattatatt gaaatgagac agagaggatg tagtatctac tgtcataatt   2700
tttcaaaacc cacctgcaac ttgaattaaa agaaccactg gggttttttt ttttgtttca   2760
aacgcaaatc ctggaaacct actgagactc attcagtcag tatctctaag aggcaagctt   2820
gagactgtat atttaaaaag catctcaggt gattttaca catgctaagg cttaagaacc    2880
acttctctgt agcttatatg ttattttcaa tgttcctcaa agccaagtta gaatttccaa   2940
```

| | |
|---|---|
| agtgttaaga atccattaga caatcacaga attgtctttt tcctttataa atcttgcaat | 3000 |
| gttgttctca tttccatact taattactta aaacaccaac caaccaacaa gcaaaaaatg | 3060 |
| attagtctaa ctaatattac aagttaataa tgaagtaaag gtttaaaaat aatgtcataa | 3120 |
| taatgttaat aacaaattat taattataat ttaaaaataa tatttataat ttaaaaataa | 3180 |
| tatttacaag tactacaagc aaaacactgg tactttcatt gttatctttt catataaggt | 3240 |
| aactgaggcc cagagagatt aaataacatg cccaaggtca cacaggtcat atgatgtgga | 3300 |
| gccaggttaa aaatataggc agaaagactc tagagaccat gctcagatct tccattccaa | 3360 |
| gatccctgat atttgaaaaa taaaataaca tcctgaattt tattgt | 3406 |

<210> SEQ ID NO 32
<211> LENGTH: 243
<212> TYPE: RNA
<213> ORGANISM: Homo sapiens

<400> SEQUENCE: 32

| | |
|---|---|
| acagaacuga aacugacucg gaaggcagcc uaugugagau acuucaauag cucagccuuc | 60 |
| uucuucucag gguucuuugu gguguuuuua ucugugcuuc ccuaugcacu aaucaaagga | 120 |
| aucauccucc ggaaauauu caccaccauc ucauucugca uuguucugcg cauggcgguc | 180 |
| acucggcaau uucccugggc uguacaaaca ugguaugacu cucuuggagc aauaaacaaa | 240 |
| aua | 243 |

<210> SEQ ID NO 33
<211> LENGTH: 1649
<212> TYPE: DNA
<213> ORGANISM: Homo sapiens

<400> SEQUENCE: 33

| | |
|---|---|
| gtaccataat gctgcattat atactatgat ttaaataatc agtcaataga tcagttctaa | 60 |
| tgaactttgc aaaaatgtgc gaaaagatag aaaaagaaat ttccttcact aggaagttat | 120 |
| aaaagttgcc agctaatact aggaatgttc accttaaact tttcctagca tttctctgga | 180 |
| cagtatgatg gatgagagtg gcattttatg ccaaattacc ttaaaatccc aataatactg | 240 |
| atgtagctag cagctttgag aaattctaaa gttttcaagt gataagactc aatttataca | 300 |
| aagctaattg gataaacttg tatatgatta agaagcaaat aaatacttat tatgcttttt | 360 |
| tgctgtttat ttaaatattt aacccagaaa ataagtcact gtgacagaaa taaaaatgag | 420 |
| agagaagggt gagccactct taggtagttc tggcattatt taatctaggc cagaggttgc | 480 |
| aaatggtgtc ccatagaact aattttggct cctagacctg tcttatttaa cctttcattt | 540 |
| aaaaaatttg tattggttgc cagcaattaa aaattgggag atgtctcaca cacacacaca | 600 |
| cataaacaca cacactcatg tgtgcagcct cttttgaaga attggaataa ctagtcaact | 660 |
| gcgtcctcct tttccacaag ctgtgacagc tccctgctca cagagcacct gccctctcct | 720 |
| gttcatcatg ctctcttctc agtcccattc cttcattata tcacctattt ggtcctgaga | 780 |
| ctaagtgagt ttgagatctg tgatttagac aaagtggtga atctagctct gaatcatagt | 840 |
| aagtagctct gggaatcatc ttgtcttctg ttagcccatt gagagagaaa tagagagaga | 900 |
| gagagagaga agaaagaag aagaaacaga tctggggaga gtcactgaat gggagcatag | 960 |
| agacagagaa acagatctag aaaaccaaac tgggagaaaa tgagagaaac caaagagag | 1020 |
| gtagagagga gcagagaaga aaatgaagaa gcaaggcaag gaccaggctt ttcattatt | 1080 |
| tcttatggcc aagacttcag tatgcgtgga cttaattctt ccttatgctc ctaccttccc | 1140 |

```
tagggaaact gatttggagt ctctaataga gcccttcttt tagaatcaca gtttgatgcc      1200
ttaaaactag ttatataacct tcacatgctt ccttaaccca cagaagtgat gctaatgagg     1260
cccttaataa ggagcgtgct attaagatga agacattcat ttttttctc cgtccaatgt       1320 tggattaagg cacattagtg ggtaattcag ggttgctttg taaattcatc actaaggtta      1380
gcatgtaata gtacaaggaa gaatcagttg tatgttaaat ctaatgtata aaaagttttta    1440 taaaatatca tatgtttaga gagtatattt caaatatgat gaatcctagt gcttggcaaa      1500
ttaactttag aacactaata aaattatttt attaagaaat aattactatt tcattattaa      1560
aattcatata taagatgtag cacaatgaga gtataaagta gatgtaataa tgcattaatg      1620
ctattctgat tctataatat gttttgct                                          1649

<210> SEQ ID NO 34
<211> LENGTH: 89
<212> TYPE: RNA
<213> ORGANISM: Homo sapiens

<400> SEQUENCE: 34
auuucuuaca aaagcaagaa uauaagacau uggaauauaa cuuaacgacu acagaaguag        60
ugauggagaa uguaacagcc uucugggag                                          89

<210> SEQ ID NO 35
<211> LENGTH: 6512
<212> TYPE: DNA
<213> ORGANISM: Homo sapiens

<400> SEQUENCE: 35
aatttttaaa aaattgtttg ctctaaacac ctaactgttt tcttctttgt gaatatggat         60
ttcatcctaa tggcgaataa aattagaatg atgatataac tggtagaact ggaaggagga       120
tcactcactt attttctaga ttaagaagta gaggaatggc caggtgctca tggttgtaat       180
cccagcactt tgggagacca aggcgggtgg atcacctgag gtcaggagtt caagaccagc      240
ctggccaaca tggtaaaacc cggtctctac taaaaataca aaaaattaac tgggcatggt       300
ggcagatgct gtagtcccag ctgctcggga ggctgaggca ggagaatcac ttgaacctgg      360
gaggcggagg ttgcagtgag ctaagatcac gccactgcac tccagcctgg caacaaggc       420 gagactctgt ctgaaaaaga aaaaaaaata aaaataaaaa taaaagaag tggaggaata      480 ttaaatgcaa tataaaagct tttttttattt ttaagtcata caatttgttt cacataacag      540
atcaggaaat aatacagaga tcataagttt tggagctggg tttgaatcct ggctctgcca       600
tttactttct gtgtaatcta agtcaagtta ctgaactttg tgggccctct ggctctccat       660
gtgtaaaatg gagaatatta atatttaact tgcaagtttg ttgtgaagac tgaaggagag       720
aatttaggta aaacattcat cagagtacca tgcacacagt tgttcctcaa taaacattag       780
cttctctgat tgcaagttcc agtctaaagt gctttatata taccagccaa taaaggatg       840 cgagagagat ataccagtgt attgttttct accatttaa acctattttc atccactgtt        900
acaaattcta tcatactgct ccacataaaa aatattatca atgatttta gtctctgaag       960 tgcaatattt gattattgag cacacctgtt gaagtttag tttcttctca cttacatggg      1020
ttgtgtaaag gtaggaggta taaaaccagt gtcctaggtc taaatctttc ttaatgtcat       1080
actttggatt cattgatata agtaacttga gcaccagcgc ttcattttac ttcattttt       1140 aaagatatag taagagtaat tcccatctgc ctagcaaaat tgttttgtag aaaagtttgt      1200
```

```
ggatcagatt tatttacctt tgattttagg aatttcaagt gtcttcgtcg gcatgaagga    1260
aaaatatgca gtttgacatt ttctactact ttcaggtcat tattttccta ctctggtgca    1320
aaaaccctca attcctgtct cactccatct aatcaaatag gtagcatgct tgagccctta    1380
ctatgtgcca ggcactagga taagcacttt atatgttttg tcccaattaa ttctcacagc    1440
atttctatga cctaaataaa attaatattt tcatttcacc aataataaaa tggaggcttc    1500
aaaaagttta gggacttggc tcagctcaca caactggcaa ggactgaaaa tggattttag    1560
tcccaaatgt cataggctag agcccttca  ctaaactgtt gtcttccatc tggtggcatc    1620
ctcttcctcc agtctttgtc acctaaactc tgggcacccc ttgatggcat ttacttatga    1680
tggtgatgct tgttaaactt cctgtttgcg acttcaacgt ccatataaat gagtcttcca    1740
atactgtact tagaacttat attttgtagt gacttcttta aaagcttcct ctcttagtca    1800
tatcctgagt tttgttagca cctggactta ccttactttg gaaatgttgc actctgaaat    1860
ctctttctca gcttggaatt tcctaatctt ccaactgttt gagtctttta attctacatt    1920
tactgccttt ccattcatc  aggatttcta gtctctttaa ttcttccttt tgaactcctc    1980
ctgatttaac ctctgcttat tcgaagaaca ataatttat  tctctcagct gcactctcaa    2040 ttccctttc  cttttggtga tttttctttt cctacagaa  cacttacttt atcagttttg    2100
gagaaggaag tgctatctgg gtaacagtag tgctatctgt tgactctagt caactgtaag    2160
ttttatacat ttattgttta aaccttatat gggtctataa tccttcttgg gaaatccttt    2220
catttgtctt taatttcctt taccatttcc ctaaaggcta ttccagattt ttatcacatt    2280
cacaaaattc ccgtcttttc tcaggatctg ttcaccccca gtagatagcc ttgtctccca    2340
caatacatgg agaaaataga ggccaccgtc atatttgaat gtttccaact tctctcttca    2400
cctttggaat tatctttttc ttcttttgtg tctaagagaa agatgtatac ttcttcttac    2460
ccttgtctga actactctat tttgcttcat cttctcagaa caggggacca gcaattattc    2520
ttcctccaga agcttcaaca tcttttgtca actgactcct tctcatgttt aaatattttc    2580
aagttaaaca atttctttcc tgactttcgc tcacgcaacc tcatgcccaa aaccttatca    2640
ctcttcttcc ctttgctgtc aaggctgttc tcacttcttc acttttgtg  gacttctccc    2700 cactacaaca tagattctgc tatcaccaat ctattaaaac tgttatactc ttgtggaatt    2760
tatcatttaa tttagcttca gtgaaccgtt cttttccagat tattttggcc tcagaccatg    2820
acttctaagt ctgccgtgct tgccacttaa gtgatgatgg gccagtgggt ccccacctag    2880
gcctctgtgt tagtctgttt tcatgttgct gataaagaca tacccaagaa tgggcaattt    2940
acagaagaaa ggggtttgag ggactcacag ttccatgtga ctggggaggc ctcacaatca    3000
tggtggatga tgaaaggcat gtctcacatg gaggcagata agagcataga acttgtgcag    3060
ggaaacttcc ctttattaaa ccaccaggtc ttgtgagact tcttcactat cacgagaata    3120
ggatgggcaa gaccctcccc catgattcaa ttatctccca ctgggtccct cccacaacac    3180
atgggaatta tgggagctat aattcaagat gagatttggg tgaggacata gccaaaccat    3240
atcagcctcc ttctggcttt ttatgttctc cgtgggtgac ctctctcagg ctcaagtgat    3300
aaccaatgtg ctgatgactc tcaaatgcgc atctctggct tcagtttctt ccttgaactt    3360
catacatatg tttccaaatt tcctgcgtgt acctcaaggt tcttgttcat cacttcccaa    3420
gcttcataaa cgcactcatt ttagtgtatt ctctgtctcc tttgatagca tccctgagag    3480
gcaagtccct ggtgagttat atacaactcc tcccttgctc caaacctgag agtaagtaac    3540
attcctatta acatattagg aagctgaggc ttagacagtt taagtaactc aagcatggtt    3600
```

```
acacaactag ctagggcaga gctaaaatgt caggctaggc ttctgtgact ccaaagccct    3660
ttctcactta gcatatcatc acttattttt tttttttaatc acatatatga tttttttttc    3720
tttaagagat agaatcttgc tctatcacgt gggctggagt gcagtggcac aatcatagct    3780
cactgtaacc ttgaacttgg gctcaagtga tcctcctgcc ttagcctact gagtagctag    3840
ggctacagac acacaccacc atgcctagct aattttattt tattttattt tattttttga    3900
gacagagtct cactctgtca cccaggctgg agtgcagtgg tgcgatcttg gctcactgga    3960
acctctgctg cccgggttca agcgattctc ctgcctcagc ctcctgagta gctgggatta    4020
caggtgcctg ccactgtgcc cagctaattt ttgtatttttt agtagagacg gggtttcacc    4080
atcttggcca ggcttgtctt gaactcctga cctcgtgatc cactcgcctc ggcctcccaa    4140
agtgctggga ttacaggtgt gagccaccac gcctggccac ctacctaatt tttaattttt    4200
ttgtagagac agggtctcac tacgttgccc aggctggtct tgaactcctg ttctcaaaca    4260
atcctcctgc ctcggacacc ccaagtgcag ggattacagg catgagtcat tgcagctgac    4320
ctgtatatat gatttttagt atatgtaaat atacatattt attaaatgta aatataaata    4380
taaatgtgtg gagtgatatc cattgaaatg ttaaacatag ttctcagtgg tacaactaca    4440
ggtgatttct cttttcttat ttctggtttt ctgtgttttc caaatttctt gaaatgtgtc    4500
ttctgtaatc agaaataaaa gttattagta acaacagtct tccactggta caagtgctta    4560
ttggataaaa gtcccacttc taagcatgat actcacaact tttaggttaa tagcctttgt    4620
caccttgcca tatacatctg atccagccac tcacaccatt cctgagatat attttgttcc    4680
tttgtgccta aatcattgtg catgcagatc catcttcctg gaacacctat aaccatttct    4740
tagtcctgtg aaatcctact tacatccttc atagcctagc atgtatgtca tttatttggt    4800
caagggtgag ttggttgttc tcttgaatgt actgccatat gacgtggtgt gatttcaatt    4860
gtagcaccaa gctcattgca atattaattc gtttgtcatt ctcccatgta ggatgtttga    4920
agtagtttct aacacagaga ttatactcaa taaatattta ttagataaat aaatgaataa    4980
gggaataaca aatgcctttg tctcatttta aaatactttc attgttagct acccatataa    5040
taaaaaacta aaagcagtag ttttcaagca tgattgttta tgtatgcctt aaaagaattt    5100
tgaaaaccta tgtaccccctg acacactttt aagttaactt ataaattttt caacatagtt    5160
ttaagtggtg gcaaatgatg tagtttcttg tgtattttaa actgcttaag tatgctatac    5220
atggatttct tcaaaaccct gaagctgcag tttcagtgca ttcaatttat ggaaaagaaa    5280
ttaatttata aaattggttc ttattgtcaa gtcaatcagc taaatataac ttgctttctg    5340
tcaggaaaag tctgactttta aaatacagat aagtaataac tattattaat taattaaatt    5400
attaaaatta aaataattaa ataatttgtt aattaaaatg ccttattccc ctacttattt    5460
ctgcaatttg actctaagaa tagataggac atgtagattg ccttaggttt gaaatctggg    5520
tgaaataaga tactgcctcc ttcagtattt ctgcctttgc ttttatggga gcctcttttca    5580 agaaaaagtc attctctcat ggtccctttg tttgagtccc agaggttttc ctactccaga    5640
aagtgcaacg tagtgagact agtactatac tcccttgcat ggtaagtgag aaggctgtct    5700
gtataaaatg agggaaggac tcatgagagg gaagtaggtc aggagaaatg ataggttctc    5760
aggcaggtta attttaggaa agagtgaata gagtccctta aaacaaggtg catctgcttc    5820
ctcctgatca atctttagga ctgtttactt tgatttgaag accactatgc taaagcttcc    5880
cacgggggca atagtgaggc aaggaatttt taaaagggaa ttacttcttc gtagctactt    5940
```

-continued

| | |
|---|---|
| ttgtgaaatg aattcatttg aattatctgg caatctcttc atatttatat tcaacaataa | 6000 |
| ttacttaaag aaatgctttg agcttctcag aggagggtgc taccagtgtg atggagtaga | 6060 |
| attcagattt gggtagtgac tttaaagctg tgtgacttta gtcatttaac tgctgagtca | 6120 |
| cagtctacag cttttgaaaga ggaggattat aaaatctatc tcatgttaat gctgaagatt | 6180 |
| aaataatagt gtttatgtac cccgcttata ggagaagagg gtgtgtgtgt gtgtgtgtgt | 6240 |
| gtgtgtgtgt gtatgtgtat gtatacatgt atgtattcag tctttactga aattaaaaaa | 6300 |
| tctttaactt gataatgggc aaatatctta gttttagatc atgtcctcta gaaaccgtat | 6360 |
| gctatataat tatgtactat aaagtaataa tgtatacagt gtaatggatc atgggccatg | 6420 |
| tgcttttcaa actaattgta cataaaacaa gcatctattg aaaatatctg acaaactcat | 6480 |
| cttttatttt tgatgtgtgt gtgtgtgtgt gt | 6512 |

<210> SEQ ID NO 36
<211> LENGTH: 179
<212> TYPE: RNA
<213> ORGANISM: Homo sapiens

<400> SEQUENCE: 36

| | |
|---|---|
| gauuugggga auuauuugag aaagcaaaac aaaacaauaa caaugaaaaa acuucuaaug | 60 |
| gugaugacag cccucuucuuc aguaauuucu cacuucuugg uacccuguc cugaaagaua | 120 |
| uuaauuucaa gauagaaaga ggacaguugu uggcgguugc uggauccacu ggagcaggc | 179 |

<210> SEQ ID NO 37
<211> LENGTH: 1000
<212> TYPE: DNA
<213> ORGANISM: Homo sapiens

<400> SEQUENCE: 37

| | |
|---|---|
| tcttttgttc ttcactatta agaacttaat ttggtgtcca tgtctctttt tttttctagt | 60 |
| ttgtagtgct ggaaggtatt tttggagaaa ttcttacatg agcattagga gaatgtatgg | 120 |
| gtgtagtgtc ttgtataata gaaattgttc cactgataat ttactctagt ttttttatttc | 180 |
| ctcatattat tttcagtggc ttttttcttcc acatctttat attttgcacc acattcaaca | 240 |
| ctgtatcttg cacatggcga gcattcaata actttattga ataaacaaat catccatttt | 300 |
| atccattctt aaccagaaca gacattttt cagagctggt ccaggaaaat catgacttac | 360 |
| attttgcctt agtaaccaca taaacaaaag gtctccattt ttgttaacat tacaattttc | 420 |
| agaatagatt tagatttgct tatgatatat tataaggaaa aattatttag tgggatagtt | 480 |
| ttttgaggaa atacatagga atgttaattt attcagtggt catcctcttc tccatatccc | 540 |
| accctaagaa caacttaacc tggcatattt ggagatacat ctgaaaaaat agtagattag | 600 |
| aaagaaaaaa cagcaaaagg accaaaactt tattgtcagg agaagacttt gtagtgatct | 660 |
| tcaagaatat aacccattgt gtagataatg gtaaaaactt gctctctttt aactattgag | 720 |
| gaaataaatt taaagacatg aaagaatcaa attagagatg agaaagagct ttctagtatt | 780 |
| agaatgggct aaagggcaat aggtatttgc ttcagaagtc tataaaatgg ttccttgttc | 840 |
| ccatttgatt gtcattttag ctgtggtact ttgtagaaat gtgagaaaaa gtttagtggt | 900 |
| ctcttgaagc ttttcaaaat actttctaga attataccga ataatctaag acaaacagaa | 960 |
| aaagaaagag aggaaggaag aaagaaggaa atgaggaaga | 1000 |

<210> SEQ ID NO 38
<211> LENGTH: 188

<212> TYPE: RNA
<213> ORGANISM: Homo sapiens

<400> SEQUENCE: 38

```
cuucacuucu aauggugauu augggagaac uggagccuuc agagggyaaa auuaagcaca    60
guggaagaau ucauucugu ucucaguuuu ccuggauuau gccuggcacc auuaaagaaa   120
auaucaucuu uggugyuucc uaugaugaau auagauacag aagcgucauc aaagcaugcc   180
aacuagaa                                                            188
```

<210> SEQ ID NO 39
<211> LENGTH: 1000
<212> TYPE: DNA
<213> ORGANISM: Homo sapiens

<400> SEQUENCE: 39

```
aaactatgtg aaaactttt gattatgcat atgaacccett cacactaccc aaattatata    60
tttggctcca tattcaatcg gttagtctac atatatttat gtttcctcta tgggtaagct   120
actgtgaatg gatcaattaa taaaacacat gacctatgct ttaagaagct tgcaaacaca   180
tgaaataaat gcaatttatt ttttaaataa tgggttcatt tgatcacaat aaatgcattt   240
tatgaaatgg tgagaatttt gttcactcat tagtgagaca aacgtcctca atggttattt   300
atatggcatg catataagtg atatgtggta tcttttaaa agataccaca aaatatgcat   360
ctttaaaaat atactccaaa aattattaag attatttaa taattttat aatactatag    420
cctaatggaa tgagcattga tctgccagca gagaattaga ggggtaaaat tgtgaagata   480
ttgtatccct ggctttgaac aaataccata taacttctag tgactgcaat tctttgatgc   540
agaggcaaaa tgaagatgat gtcattactc atttcacaac aatattggag aatgagctaa   600
ttatctgaaa attacatgaa gtattccaag agaaaccagt atatggatct tgtgctgttc   660
actatgtaaa ttgtgtgatg gtgggttcag tagttattgc tgtaaatgtt agggcaggga   720
atatgttact atgaagttta ttgacagtat actccaaata gtgtttgtga ttcaaaagca   780
atatcttttga tagttggcat ttgcaattcc ttatataat cttttatgaa aaaaattgca    840
gagaaagtaa aatgtagctt aaaatacagt atccaaaaaa atggaaaagg gcaaaccgtg   900
gattagatag aaatggcaat tcttataaaa agggttgcat gcttacatga atggctttcc   960
atgtatatac tcagtcattc aacagttttt tttttagagc                        1000
```

<210> SEQ ID NO 40
<211> LENGTH: 91
<212> TYPE: RNA
<213> ORGANISM: Homo sapiens

<400> SEQUENCE: 40

```
acaucuccaa guuugcagag aaagacaaua uaguucuugg agaaggugga aucacacuga    60
guggagguca acgagcaaga auuucuuuag c                                   91
```

<210> SEQ ID NO 41
<211> LENGTH: 2499
<212> TYPE: DNA
<213> ORGANISM: Homo sapiens

<400> SEQUENCE: 41

```
taactaatta ttggtctagc aagcatttgc tgtaaatgtc attcatgtaa aaaaattaca    60
gacatttctc tattgcttta tattctgttt ctggaattga aaaaatcctg gggttttatg   120
```

```
gctagtgggt taagaatcac atttaagaac tataaataat ggtatagtat ccagatttgg    180
tagagattat ggttactcag aatctgtgcc cgtatcttgg tgtcagtgta tttgtttgcc    240
tcatagtata gtttactaca aatggaaaac tctaggattc tgcataatac tggacagaga    300
agatgtaaat atctgttagt tccatcatag accctgccac tccaatgtac acaccagctt    360
taggcttctt ggtatagata acatacatt ttcaaaattt ttcatcataa ttttcataac     420
aaaataggaa ggcaaatgat gtcacttggc ttaaaatcta taatatttaa aataaacagg    480
acaaatgcat taacattgtt gggggaggag gtcccttagt agaaacactc ttggtccaag    540
cattttaaag ctgtcaaaga gatgtaaata tagataatgt atgtcaagga gagagctttg    600
tggttaaact gtaactttca gtttaaacaa ttattggtga ctctgatgtc aaatgtttct    660
caagctttat ctgaacaaaa ttcttctcac tttgttgcca aagtcgttaa caagaaatca    720
cattgactca ttgatgtttt ggctcctttc ccttactttc tgttgctttc caaaagctga    780
gacaggaaac taaccctaac tgagcacctg caattgcctg gtagtattct agtcatgtgt    840
gtacttttgt gtgtatgtaa tccccttaca gctctgcaaa gtaagaattg ttctccctgc    900
tttacagaag agatcataag ataattgagg ctgttagatg ttaacttgcc aaaagccata    960
caggaaaatg gtagagtcac agtttgaacc aggtcctttt gattctttac attaaaccat   1020
gctttgatct tggaaataca ctgtaaggca ataaatcaat agatacggat aattcacagg   1080
cttctaaata aatggaagtt gattgttttt atctgtgagc caaagtaaga cttattctaa   1140
gaattccaca aatttagata agatagagta tatggcttct agacatccaa catagaactg   1200
agtttgtgtt atcagtttaa gatttggttt tgctgtaagg tgcacacact ttgaggaact   1260
aaaaataatt gtctgttctt attctgatca gaatgtgtaa tgtgttgtcc agttttggat   1320
gatgaatttc ttatttctaa tctcataaga aacttgtcat agatgtgagg gagagaatta   1380
agaacagagt gtggggaaga aactgtgtac attttgatgg gatccattat gtagctcttg   1440
catactgtct tcaaaaataa gttacactat aaaggttgtt ttagacttt aaagttttgc    1500 cattggtttt taaaaaaatt tttaaattgg ctttaaaaat ttcttaattg tgtgctgaat   1560
acaattttct ttattacaga agtaccaaca attacatgta taaacagaga atcctatgta   1620
cttgagatat aagtaaggtt actatcaatc acacctgaaa aatttaaatg ttatgaagaa   1680
attatctcat ttctattaat atgggaactg tgtcttcatc tttattactg ttctaaggtc   1740
aactcaatgt agattttact tgcttatggt ttcatatttt agctaaatag taaaataata   1800
tggatataca ttttgttgtg acttactcat actttcctta tttggaactt ttatgaatat   1860
gatatagaga ctgaaactac aaggaacaaa atgcaatatc aattatacag ttgtggcagc   1920
actgctatca atttgttgat agtggttaac acttagaaaa acattttaaa ataatttca    1980 cataagtaat gtaatttatt agctgtctct gacattttac agtttggaat agtttatttt   2040 cttttttggtg tcctcaccaa aacccaacat cttcaagggc aggaactgta taattttgc   2100 cattgtattt tgagcacata gcatggtact tgcctctaaa tagatactat tgttaaaata   2160 tttttttaagg taatatttta aagtgtatgc tatggtacag ttcagtttgt gacttttgct   2220
agtttatgcc acttacagtt agcaaaatca cttcagcagt tcttggaatg ttgtgaaaag   2280
tgataaaaat cttctgcaac ttattccttt attcctcatt taaaataatc taccatagta   2340
aaaacatgta taaagtgct acttctgcac cactttgag aatagtgtta tttcagtgaa     2400
tcgatgtggt gaccatattg taatgcatgt agtgaactgt ttaaggcaaa tcatctacac   2460
tagatgacca ggaaatagag aggaaatgta atttaattt                          2499
```

<210> SEQ ID NO 42
<211> LENGTH: 83
<212> TYPE: RNA
<213> ORGANISM: Homo sapiens

<400> SEQUENCE: 42
gcaguauaca aagaugcuga uuuguauuua uuagacucuc cuuuuggaua ccuagauguu    60
uuaacagaaa aagaaauauu uga                                            83

<210> SEQ ID NO 43
<211> LENGTH: 1474
<212> TYPE: DNA
<213> ORGANISM: Homo sapiens

<400> SEQUENCE: 43
ttctttgaat accttactta taatgctcat gctaaaataa agaaagaca gactgtccca     60 tcatagattg cattttacct cttgagaaat atgttcacca ttgttggtat ggcagaatgt   120
agcatggtat taactcaaat ctgatctgcc ctactgggcc aggattcaag attacttcca   180
ttaaaacctt ttctcaccgc ctcatgctaa accagtttct ctcattgcta tactgttata   240
gcaattgcta tctatgtagt ttttgcagta tcattgcctt gtgatatata ttactttaat   300
tattattata cttaacattt ttatttactt tttgtgttag tattttattc tgtcttctcc   360
ttagatagta accttcttaa gaaaatatat atgctaagtg ttttactggt ttaatatgct   420
tagactactc atctacctca atacttcctt ggagatctcc tcctcagtca cacagagctc   480
aggacttata tttccttgga actcctgtta gggtccaatg tacatgaaat tccctagaca   540
gacagacagt cagttatatg gcttgatttc aaagtttcaa aatgatttaa tggactatca   600
agtagtttat taggagaaca gttattatac tcttctaaaa ataaagactt taagcaataa   660
agatgtatat gtatataaaa tggctgggtt attcctagaa gtacctttct tagaatttag   720
ttaaatttaa tatccaagat actatctttt caaccctgag attgtgaaaa gtaacttcta   780
tcaatataaa ctttactaca tttgtattgt gttagtgtgt tacagtataa tctagaacaa   840
tgtgtctttc tatatgatat atgacatttt aatgcctaaa aaaactgata tgtcttagat   900
gattctagtc aggatttact tctagaatag attaaaattc tatttgagga gagtcaaatt   960
aattatcgaa ttctcagttg ttattattgc tgttttattt ttagtgaaac agattagtct  1020
taatgtaaac acttgagaaa taaattgatg gtcaacctaa aatgtaaaaa agaaattaat  1080
agaaaattta aagagcaaca aagctctgac atttaaaaga aatgaagtac aaatctctag  1140
ggaccttaaa gatcatctaa taatttcctc attttctaga taaataaact gagagacccc  1200
gaggataaat gatttgctca aagtcaaata tctacttaat ataggaaatt taatttcatt  1260
ctcagtctgt taacatgcaa cttttcaata tagcatgtta tttcatgcta tcagaattca  1320
caaggtacca atttaattac tacagagtac ttatagaatc atttaaaata taataaaatt  1380
gtatgataga gattatatgc aataaaacat taacaaaatg ctaaaatacg agacatattg  1440
caataaagta tttataaaat tgatatttat atgt                              1474

<210> SEQ ID NO 44
<211> LENGTH: 720
<212> TYPE: RNA
<213> ORGANISM: Homo sapiens

<400> SEQUENCE: 44

| | |
|---|---:|
| ugugucugua aacugauggc uaacaaaacu aggauuuugg ucacuucuaa aauggaacau | 60 |
| uuaaagaaag cugacaaaau auuaauuuug caugaaggua gcagcuauuu uuaugggaca | 120 |
| uuuucagaac uccaaaaucu acagccagac uuuagcucaa aacucauggg augugauucu | 180 |
| uucgaccaau uuagugcaga aagaagaaau ucaauccuaa cugagaccuu acaccguuuc | 240 |
| ucauuagaag gagaugcucc ugucuccugg acagaaacaa aaaacaauc uuuuaaacag | 300 |
| acuggagagu uuggggaaaa aaggaagaau ucuauucuca auccaaucaa cucuauacga | 360 |
| aaauuuucca uugugcaaaa gacucccuua caaaugaaug gcaucgaaga ggauucugau | 420 |
| gagccuuuag agagaaggcu guccuuagua ccagauucug agcagggaga ggcgauacug | 480 |
| ccucgcauca gcgugaucag cacuggcccc acgcuucagg cacgaaggag gcagucuguc | 540 |
| cugaaccuga ugcacacuc aguuaaccaa ggucagaaca uucaccgaaa gacaacagca | 600 |
| uccacacgaa aagugucacu ggccccucag gcaaacuuga cugaacugga uauauauuca | 660 |
| agaagguuau ucaagaaac uggcuuggaa auaagugaag aaauuaacga agaagacuua | 720 |

<210> SEQ ID NO 45
<211> LENGTH: 2252
<212> TYPE: DNA
<213> ORGANISM: Homo sapiens

<400> SEQUENCE: 45

| | |
|---|---:|
| tatacatcgc ttgggggtat ttcaccccac agaatgcaat tgagtagaat gcaatatgta | 60 |
| gcatgtaaca aaatttacta aaatcatagg attaggataa ggtgtatctt aaaactcaga | 120 |
| aagtatgaag ttcattaatt atacaagcaa cgttaaaatg taaataaca aatgattct | 180 |
| ttttgcaatg gacatatctc ttcccataaa atgggaaagg atttagtttt tggtcctcta | 240 |
| ctaagccagt gataactgtg actataagtt agaaagcatt tgctttatta ccatcttgaa | 300 |
| ccctctgtgg gaagaggtgc agtataaata actgtataaa taaatagtag ctttcattat | 360 |
| ttatagctcg caaataatc tgtatggaag tagcatatat aaggtatata aacatttagc | 420 |
| ctcttgatag gactaactca cattctggtt tgtatatcag tcttgcctga atttagctag | 480 |
| tgtgggcttt tttttatctt gtgagttgc tttatacatt gggtttctga aaagatttct | 540 |
| tttagagaat gtatataagc ttaacatgta ctagtgccaa tcttcagaca gaaattttgt | 600 |
| tctattaggt tttaagaata aaagcatttt attttaaaa caggaaataa tataaaaagg | 660 |
| agagttttg ttgtttagt agaaaactta atgccttgga tgaaatgagc catgggcagg | 720 |
| gttgtaatga attgatatgt ttaatagtat agatcatttg tgaataatat gaccttgac | 780 |
| aagacacaag ccattaacat ctgtaggcag aagtttcctt ctttgtaaaa tgagggaata | 840 |
| aaatagatcc ctaaagtgtg taattttagt attttctaaac tttatgaagg tttcctaaat | 900 |
| gataattcat ctatatagtg ttttttttgtg tgtttgtttg tttgtttgtt tgagatggag | 960 |
| tctcgctctg tcacctaggc tggagtgcaa tggtgcaacc tcggctcact gcaacctctg | 1020 |
| cctcctgggt tcaagctaat ctcctgcctc agcctcctga gtagctgaga ttacaggcat | 1080 |
| gcaccaccat gccgagctaa ttttttgtatt tttagtagag aaggggtttc atcatgttga | 1140 |
| ccaggctggt cttgaactcc tgaccttgtg atccacccac ctcagcctcc caaagtgctg | 1200 |
| gtattacagg cgtgtgccac cacgtccagc ctgagccact gcgcccagcc catctatata | 1260 |
| gtttaatatc aatctaaatg aatttctcag tcctgagcct aaaaatttag ttgtaaagaa | 1320 |
| tgatatcctt gactaataat agtttctatt aatggattgc atctagtgct aggtggcata | 1380 |
| tatttagtcc ccacaactac cctggaaggt atttaaaatt tttcacattt gcagataagg | 1440 |

```
aaactaaagt tcagagttcg gcaacatgct tgaattcaag cagctcctag gatgttaatg    1500
gtggaggttg ggttcaaatc cagatctgtc tgactcaaaa aatgcatact cctaaccagt    1560
gcactatatc ccaattccat aggagcccct ctttgtgatt catagcactt tcccatgagt    1620
tttgttgatt ttgtgagaaa caaaactctt tttcctttgg actgtctgga atctctcttt    1680
ttcaaatttt tgaaatgtat ttctatgcca aaagacaaag atttctagag gaatatgcct    1740
aggatgagaa ttatgtaatt taaatcacag ctggaaagag agaaagtcct aagttactaa    1800
gaaatgttca acacaaatg agctttcagt ctattggaag acctttatag ctagaagtat     1860
actgaactgt acttgtccat ggacccctga agaaacaggt taaatcaaag agagttctgg    1920
gaaacttcat ttagatggta tcattcattt gataaaaggt atgccactgt taagcccttta   1980 atggtaaaat tgtccaataa aatacagtt atataatcag tgatacattt ttagaatttt    2040
gaaaaattac gatgtttctc attttaata aagctgtgtt gctccagtag acattattct    2100
ggctatagaa tgcatcata catggcattt ataatgattt atatttgtta aaatacactt     2160
agattcaagt aatactattc ttttattttc atatattaaa aataaaacca caatggtggc   2220
atgaaactgt actgtcttat tgtaatagcc at                                 2252

<210> SEQ ID NO 46
<211> LENGTH: 125
<212> TYPE: RNA
<213> ORGANISM: Homo sapiens

<400> SEQUENCE: 46
agugcuuuuu ugaugauaug gagagcauac cagcagugac uacauggaac acauaccuuc    60
gauauauuac uguccacaag agcuuaauuu uugugcuaau uggugcuua guaauuuuuc    120 uggca                                                                125

<210> SEQ ID NO 47
<211> LENGTH: 1000
<212> TYPE: DNA
<213> ORGANISM: Homo sapiens

<400> SEQUENCE: 47
aatgttctat tgtaaagtat tactggattt aaagttaaat taagatagtt tggggatgta    60
tacatatata tgcacacaca taaatatgta tatatacaca tgtatacatg tataagtatg    120
catatataca cacatatatc actatatgta tatatgtata tattacatat atttgtgatt   180
ttacagtata taatggtata gattcatata gttcttagct tctgaaaaat caacaagtag    240
aaccactact gatattttat tatttcatat tacatataaa atatatttaa atacaaatat    300
aagaagagtt tttaatagat ttttaataat aaaggttaag agattcgaaa gctcaaagta    360
gaaggctttt atttggattg aaattaaaca attagaatca ctgttgatat tttattattt    420
catattacat ataaaatata tttaaatata agataagta ttttaatag attttataat      480 aaatgttaag agattaaaaa actgaaaata gaaggctttt atttggattg aaattaaagg   540
ccaggcatgg tggttcatgc ctgtaatccc agaattttag gagactgagt ggggaggatt    600
gcttgagccc aggggtcaag accagcctgg gcaacacagt gagacaccgt atctacaaaa   660
taattaaaaa attagctggg catggtggtg tgtgcctgta tgctaccatt aactaaggag    720
gctgaggtgg gagaatcgct tgagcctggg aggtcaaggc tgccctgaac tgtgattgtg   780
ccattgcatt ccagcctggg tgccagagag agaccctatc tctaaataaa taataagta    840
```

```
aataaataaa cagcaacaac aaaaacactc aaagcaaatc tgtactaaat tttgaattca      900
ttctgagagg tgacagcatg ctggcagtcc tggcagccct cgctcactct cagggcctcc      960
ttgaccttga cgcccactct ggctgtgcgt gaggagccct                           1000
```

<210> SEQ ID NO 48
<211> LENGTH: 34
<212> TYPE: RNA
<213> ORGANISM: Homo sapiens

<400> SEQUENCE: 48

```
uggcugcuuc uuugguugug cuguggcucc uugg                                   34
```

<210> SEQ ID NO 49
<211> LENGTH: 648
<212> TYPE: DNA
<213> ORGANISM: Homo sapiens

<400> SEQUENCE: 49

```
tattccatgt cctattgtgt agattgtgtt ttatttctgt tgattaaata ttgtaatcca       60
ctatgtttgt atgtattgta atccactttg tttcatttct cccaagcatt atggtagtgg      120
aaagataagg ttttttgttt aaatgatgac cattagttgg gtgaggtgac acattcctgt      180
agtcctagct cctccacagg ctgacgcagg aggatcactt gagcccagga gttcagggct      240
gtagtgttgt atcattgtga gtagccaccg cactccagcc tggacaatat agtgagatcc      300
tatatctaaa ataaaataaa ataaaatgaa taaattgtga gcatgtgcag ctcctgcagt      360
ttctaaagaa tatagttctg ttcagtttct gtgaaacaca ataaaaatat ttgaaataac      420
attacatatt tagggttttc ttcaaatttt ttaatttaat aaagaacaac tcaatctcta      480
tcaatagtga gaaacatat ctatttctt gcaataatag tatgattttg aggttaaggg       540
tgcatgctct tctaatgcaa aatattgtat ttatttagac tcaagtttag ttccatttac      600
atgtattgga aattcagtaa gtaactttgg ctgccaaata acgatttc                   648
```

<210> SEQ ID NO 50
<211> LENGTH: 247
<212> TYPE: RNA
<213> ORGANISM: Homo sapiens

<400> SEQUENCE: 50

```
acuccucuuc aagacaaagg gaauaguacu cauaguagaa auaacagcua ugcagugauu       60
aucaccagca ccaguucgua uuauguguuu uacauuuacg ugggaguagc cgacacuuug      120
cuugcuaugg gauucuucag aggucuacca cuggugcaua ucuaaaucac agugucgaaa      180
auuuuacacc acaaaauguu acauucuguu cuucaagcac cuaugucaac ccucaacacg      240
uugaaag                                                               247
```

<210> SEQ ID NO 51
<211> LENGTH: 2871
<212> TYPE: DNA
<213> ORGANISM: Homo sapiens

<400> SEQUENCE: 51

```
ttactaggtc taagaaatga aactgctgat ccaccatcaa tagggcctgt ggttttgttg       60
gttttctaat ggcagtgctg gcttttgcac agaggcatgt gccctttgtt gaacctccat      120
ttgactggca tgcacatgtc tcagatatta taggttatca tatattgttg ctcctaatat      180
ttctgtgtta gataattaga gtagcttggt ttgtaagaat gtgatgttgg tgggactgta      240
```

```
gcagaacaag aaggcccttta tgggtcagtc atacctctct tttcaaatat ttggtctagc    300
tctcttctgg gcatcttgtt gccaatatat agtattgctc aaaagggcag gagatttgaa    360
gtgatcaagg aaaatatatt ttttctattg attaagtctt ttgatggggt agaataatct    420
aatttcatgt aactgctcaa agttatatgg taggggatc ccaaatgtat tttaaaacta    480
tttttatatc atcatatttg aagtaataga aagtcagagt agcagaataa aggtactaaa    540
aattttaaaa actaataagg tactttgaaa gaaatcaatt atgttgattc ctcattaaac    600
aaatttgcac ttaaagactg aggttaataa ggatttcccc aagttttttc atagcaacct    660
gtgagcactt tctctgttga ggcatttatg gtatgaaaag atgagtaagg cacagttctt    720
gccctggaga aggtcacagg tgagaggagg agttgacaca gaaacatttg atataaagca    780
aggaataaat tccaagacta aaattttcag aaatctaaaa aactcaagat aagaaaaacc    840
cattatattt tctgggtaac aaaatttcag tgttattaac atgtaggaag atcttgatat    900
ttattctgaa gcccatgtgt gttgctgaaa tattgccgca tttgcatata ctcatcacca    960
tcctctgttt tggagctaag aattttagac tcaagatgtc taattaagtt gatccattga   1020
ttttattttt tatggaaatc tgagacccac agaaggcagg ggatttgccc acatttctag   1080
aagagtcaga catgagcgat gaggcacagt ggaaagaaca tgagcattgc ctgagctctg   1140
agttggcgct ataagagcag tgatcatggg caagtgactc ttctgagcct tggcctcctc   1200
acctgttaag tgaagaaaag aatatttcag aagatctttg tgagaatgaa acaaggcaat   1260
ttacttgcct gctacatagc caatgggaaa tcaatataag ttccccgtgg ttcccttctg   1320
tggggttttg ttcccacaga gggtgcactg gccattccac ttcttctttt ccaagctcct   1380
cattcccttt aacgctgttc atagttggtt ccaaaccatt tgaaatataa taagcaccag   1440
gatggttttt tctttccacc aaagcaaatt tcattttcta aacactgttt ataaatatca   1500
atggctattt tttcaatttt tgattatcat gaaaatatac aaatatgttt aattaaatat   1560
gctaaagaat gtattaataa atatgtatta ataattcct acatataagg cctttttgct   1620
tggggtatgg gtgatacaaa ataaatgtgg catgaaccca ctgacctcta gcaatttata   1680
acctagaaaa agagttatga tatgtttata agttcctgtg atataagaca tgcatatagt   1740
cattataaca gaggtgcaaa caagatgtat caagtatgtc cagaggagga agagattaat   1800
cccagctgga ggaaacactg atgctttctt gcagcagggg catttgagtt gagaaaggga   1860
ggaaacatag attttgacaa tgagagctga ggggaaaggg gtttcaggtg gagggaaccg   1920
catgtggaaa gcagggaggt aggaaagtgt agagtgtgtt taaagaatag accagtttgg   1980
ctgaaacagg atatttgagc agaggaagct tgtactaggt aggtgggttg aggccaaatt   2040
atgcaaggca ttaaatatta aactaggaat tttggacttt atcctgcagt ttatgggggg   2100
taaatgataa gattcaatat cactttattt gtacagtatt atgttacatt ttatctaatt   2160
gtttgtttaa ttcctgtcta gacaatgaat tcctcaaggg caaggagcat ggcttattca   2220
cctcagtaat ttcagtgcct agcattgtgc ctggtacaaa gtggacactt gtatataacc   2280 tttttttaatt gaagcaacaa gttgtcaacc ttacaaatgt gaatccgtga ttcagatgac   2340
aggttgaaat gtagattgtc tgcgaagagg gcagaaagag agtatgacaa aggaggacaa   2400
gacagtgggg caggcaggga gagagagcag ccagggtttc ggtagaggta tgtcaaaaag   2460
gtatggaagt cagaggagaa ggagaccct atgttataga atacaaatgg aagggaaatg   2520
atgacaacag taagttgtca ttaaatgcaa ggttgcaaaa gtaagattgt aaagcaggat   2580
```

```
gagtacccac ctattcctga cataatttat agtaaaagct atttcagaga aattggtcgt    2640
tacttgaatc ttacaagaat ctgaaacttt taaaaaggtt taaaagtaaa agacaataac    2700
ttgaacacat aattatttag aatgtttgga agaaacaaa aatttctaag tctatctgat     2760
tctatttgct aattcttatt tgggttctga atgcgtctac tgtgatccaa acttagtatt    2820
gaatatattg atatatcttt aaaaaattag tgttttttga ggaatttgtc a             2871
```

<210> SEQ ID NO 52
<211> LENGTH: 76
<212> TYPE: RNA
<213> ORGANISM: Homo sapiens

<400> SEQUENCE: 52

```
ugggauucuu aauagauucu ccaaagauau agcaauuuug gaugaccuuc ugccucuuac    60
cauauuugac uucauc                                                   76
```

<210> SEQ ID NO 53
<211> LENGTH: 3745
<212> TYPE: DNA
<213> ORGANISM: Homo sapiens

<400> SEQUENCE: 53

```
taaaaataag taccgttaag tatgtctgta ttattaaaaa aacaataaca aaagcaaatg    60
tgattttgtt ttcattttttt atttgattga gggttgaagt cctgtctatt gcattaattt    120
tgtaattatc caaagccttc aaaatagaca taagtttagt aaattcaata ataagtcaga    180
actgcttacc tggcccaaac ctgaggcaat cccacattta gatgtaatag ctgtctactt    240
gggagtgatt tgagaggcac aaaggaccat cttttcccaaa atcactggcc acaaagtgtg    300
acattttggc attggcatca ctatttgatg gaagccaacc tcccccccaaa aggcctgtat    360 tagaatgaag atggattccc tgggtgggtt acacttgaaa ctagcctcac ccatgaacac    420
tttggcacag attagctagc ccattccccc acagtaagga ccataaggaa gggacagaag    480
caaagataag ttttagaaca aaagagaggg gaaagaaaaa atctagggtt ttatgagggc    540
tgtccctgag tgatagatgt gaataggcct ccagggcagg ctggctcaga ggctgactct    600
ttgggttggg gtgactgatt ggtggtgagg atggagaaga aaaggggagt ggaggaggtg    660
aaagtgacct tgggacatta ggtctccata agtgacagga tttaaggagt gttgtaagct    720
gtggttgttg gaccaggttt aagcacagct tcctgagctt cctgactggt ttaggtcaag    780
ctccagagag caaatgccac agtctcagtg atctccttgg agaaacagtt ggaataggat    840
gttgcccatg ttgggatgag tcattgtccg ctcttgctct ttccctaccc ctgcaaaata    900
ataatactgt atttgattga acatataaaa caaagaagg attatcacat aagtatgtat    960
atataaccaa cattggcagg tgcagaaaaa ccagactgtc agtttgcctc atctgaaatg    1020
attgacacaa acaaatatat ttactgtccc aagtgaactt tggcattttg gatatccttc    1080
agttgttctg tttaaagata taacttagaa gcagctgatg gaatatttaa atccatgcgt    1140
tgaattcatg cattcaaaga aacatgtcct gagtcactaa atgctgacat tgttttttca    1200
tgttaagagt gtaaataact ggtcccaaat ataatattat tacatcagat aaaaactgga    1260
atgtgaacct cttaacttga ttgtgaaagt atttgccaat ggtgcctctt gataattatt    1320
tgaggctcac ttcagaactc ctctggaagg gttaattttt aaatagtcat tttataaatt    1380
aacatttttg acatatgtga tggctctcaa atttttctt ttatgccagt ttgaatcatt    1440
tctgctcaat ttttttttttt aattgggatg gagtctcact ctgttgccca ggctggagtg    1500
```

-continued

```
cagtgatgca atcttggctg actgcaacct ccacctcctc ggttcaagcg attctctcgc      1560
atcagcctcc agagtagctg ggattacagg cgcgcaccac catgcctgga taattttgt       1620 attattacta gagatggggt ttcaccacgt tggccaggct ggtcttgaac tcctgaactc      1680
ctgacctcaa gtgatccacc tgcctcagcc tcttaaagag ctggaattat aggtgtgagc     1740
cactgcacca ggccctgttc aactttaat gctaagattc atttgttgtt gtttcacaag     1800
tgattaggca gaggtctttt atattaattt acccatttta tttgtaagag agtctcatat    1860
taaggaagca taatatatga caatccaaat acagtacaaa tttggttaat tttgattttg     1920
ttaaataatt aatcacaggg gtccttcaaa ttgtgagctc ctctggttat acttatgttt    1980
tacctctggt tatacttaat ttcaaacaaa tgaaatttca ttctattcat gatatttcag    2040
aagcagatct gttgcacaaa ataaagcata cctataaatt ttctttttt aaaaaaaagt     2100 ctctgttcac tctatttct attattttc tcttttaaa atttgaattt tattgtggca      2160
agtccactta acatgagatt taccctctta acagattttt atgtgtaaaa tacaatattg    2220
ttcaccatgg gtaaatgttg cacagcagat ctctggaact tattcatttt gcactactga    2280
aattttatac ctgttgatta gtatctcccc atttccctct ctcccctgtc ctgttaccca    2340
tggttctgtt ctttgcttct ttgagtttga gtattttgat acctcatgta atcttcattc    2400
tattttctaa ctttgacaat gttctgacaa atttgctttc cggattggag cactgtatag    2460
tgaaaattga aaatcttggt tattttctac agattcccac tattttacct tgagcagaca    2520
cttatcttga agggtctcag atttgtcact tgtagaatgg ggaatataaa cctgataatg    2580
gtccctttca gttctaaagt tatatcagtt gaaaatacat gtgtcactta tggtaacggg    2640
tagagaactg gctcactgaa cagcatatgg atattataaa gtggttttt ttaatccttt     2700 ctgcagacag ttactttata ctttattcaa atggattatt gtgaagtaca tgttagcgga    2760
ctttgtacct tttaaaaatg tatgtatttg gtgtaatgta gaaatataga aatttattaa    2820
gtatgattta tttcaatgtt aagcatgaga aaatatgctc cgaaaggtta gatagcttgc    2880
ctaaatgaca agcttgtatt tcaagcagaa cttctgaat caaaagactc caagacgaat    2940
gcccagcttt caaaaactgt ctaaccaaaa taaatcctaa gattcacctt catactaaaa    3000
ttatttaaaa atagtttatt ttaaattaat attcacttaa aatgtattta tcatgcaata    3060
ctttaaagtg tctgggaaat gaaaatatcc aaagatcaaa gaacaccatg ttttcaaact    3120
tcaaaaatgt tatcagtgac ctaaacaatt tttaaaattt tcatagagcc tatgaaaaat    3180
gtacttgcaa atggctactt tctgactagg aatagaatgg ggagagtatt tagtccaaca    3240
atgatagact ggattaagaa aatgtggcac atatacacca tggaacacta tgcagccata    3300
aaaaatgatg agttcatgtc ctttgtaggg acatggatga aattggaaaa catcattctc    3360
agtaaactat cgcaagaaca aaaaaccaaa caccgcatat tctcactcat aggtgggaat    3420
tgaacaatga gatcacatgg acacaggaag gggaatatca cactctgggg actgttgtgg    3480 ggtggggga gggggaggg atagcactgg gagatatacc taatgctaga tgacgagtta    3540
gtgggtgcag tgcaccagca tggcacatgt atacatatgt aactaacctg cacaatgtgc    3600
acatgtaccc taaaacttaa agtataataa aaaaaataaa aaaagtttg aggtgtttaa     3660 agtatgcaaa aaaaaaaaaa gaaataaatc actgacacac tttgtccact ttgcaatgtg    3720
aaaatgttta ctcaccaaca tgttt                                          3745
```

<210> SEQ ID NO 54

<211> LENGTH: 147
<212> TYPE: RNA
<213> ORGANISM: Homo sapiens

<400> SEQUENCE: 54

```
uguuauuaau gugauuggaa gcuauagcag uugucgcagu uuuacaaccc uacaucuuug      60
uugcaacagu gccagugaua guggcuuuua uuauguugag agcauauuuc cuccaaaccu     120
cacagcaacu caaacaacug gaaucug                                        147
```

<210> SEQ ID NO 55
<211> LENGTH: 891
<212> TYPE: DNA
<213> ORGANISM: Homo sapiens

<400> SEQUENCE: 55

```
acagtgaatg tgcgatactc atcttgtaaa aaagctataa gagctatttg agattcttta      60
ttgttaatct acttaaaaaa aattctgctt ttaaactttt acatcatata acaataattt    120
ttttctacat gcatgtgtat ataaaaggaa actatattac aaagtacaca tggattttt     180 ttcttaatta atgaccatgt gacttcattt tggttttaaa ataggtatat agaatcttac    240
cacagttggt gtacaggaca ttcatttata ataaacttat atcagtcaaa ttaaacaagg    300
atagtgctgc tattactaaa ggtttctctg ggttcccaaa tgatacttga ccaaatttgt    360 cccctttggct tgttgtcttc agacacccctt tcttcatgtg ttggagctgc catttcgtgt   420
gcccccaaac tctacttgag ctgttaggga atcacatttt gcagtgacag ccttagtgtg    480
ggtgcatttt caggcaatac tttttcagta tatttctgct ttgtagatta ttagctaaat    540
caagtcacat aaacttcctt aatttagata cttgaaaaaa ttgtcttaaa agaaaatttt    600
tttagtaaga attaatttag aattagccag aaaactccca gtggtagcca agaaagagga    660
ataaatattg gtggtaattt tttaagttcc catctctggt agccaagtaa aaaagaggg     720 taactcatta ataaaataac aaatcatatc tattcaaaga atggcaccag tgtgaaaaaa    780 agcttttaa ccaatgacat tgtgatatg attattctaa tttagtcttt tcaggtaca      840 agatattatg aaattacatt ttgtgtttat gttatttgca atgttttcta t             891
```

<210> SEQ ID NO 56
<211> LENGTH: 224
<212> TYPE: RNA
<213> ORGANISM: Homo sapiens

<400> SEQUENCE: 56

```
caggagucca auuuucacuc aucuuguuac aagcuuaaaa ggacuaugga cacuucgugc      60
cuucggacgg cagccuuacu uugaaacucu guuccacaaa gcucugaauu uacauacugc    120
caacugguuc uuguaccugu caacacugcg cugguuccaa augagaauag aaaugauuuu    180
ugucaucuuc uucauugcug uuaccuucau uuccauuuua acaa                     224
```

<210> SEQ ID NO 57
<211> LENGTH: 2784
<212> TYPE: DNA
<213> ORGANISM: Homo sapiens

<400> SEQUENCE: 57

```
atgaactcat taactttagc taagcattta agtaaaaaat tttcaatgaa taaaatgctg      60
cattctatag gttatcaatt tttgatatct ttagagttta gtaattaaca aatttgttgg    120
tttattattg aacaagtgat ttctttgaat ttccattgtt ttattgttaa acaaataatt    180
```

```
tccttgaaat cggatatata tatatatatg tatatatata tatatatata tatatatata    240
catatatata tatagtatta tccctgtttt cacagtttta aaaaccgatg cacacagatt    300
gtcagatagc aattctgtga ttgaagggga aatatgtcac ctcttcatac tcatattggt    360
gaagggtcct agcttcaaaa ttaatagatt cctaaagagg ggaaatgaaa catccgcatt    420
tacacacaca cacacacaca cacacacaga gttcctcttg tcggtaagtt ttgttttttt    480
taaatctcta ctagataaaa tttgttatct aattgtgagt tttacacaaa gaaaaactgt    540
cacagaaaag aaagacagtg tcacatttt caaagaaaa agaagaaaag aaagtgccat     600 gttttttcaaa tacaaatgtt ctggattgat tttaggatct ttagtgaaaa acaaagtatt  660
tcataataag taaaataaaa atctatgtag gtaaatttgt ttctctaatt taagaatttg   720
aatttctgag tatttatgat aagtgttgaa ataacttctt atatgtgaca gtgaatactg   780
gcagagcaaa tgccaaatca atgccaaatc tgtaggatca tttgattgta ggaacagaat  840
tctactcaaa ccgaaagcag gcatttgctg gagttacaga aaggcctcat ggaacaccga   900
gaaggtggtg ccattcgact cttaaagaag ctgcaacagg cacaagagag tcagctgcag   960
ctcttcttct tgagtctata tctgtcctgg gtccattcct ttttgtggtt gcttcattcc  1020
tttctctctc tgaagactgg ttttttctggt ctaccagggc tatgccacat tgactttatg 1080
tagtgtctcc attctggcct cctgaattta caggagagtt cctctgtaca aactcaaagt  1140
cctggagaga acagaaaaca gcttcctttt ggctcagggg tccaactgca gtctactctg  1200
ctgctatgag gatagtgggt tcaccaccct tgttgttctc tcagctaggg cagtgggaaa  1260
tgactctatg aaaggaatat acatgggcag gcaaatgtac taatcctcat cagtactgta  1320
attttaagca actttaaaaa attcttttaa gttatttgaa aataagatca aagaaggctg  1380
aattacataa atgaagattt gttaacaatt aattcaaacc aatataacac atgctataac  1440
atggttgagt gtgattgagt cttgatttat taggggcaat aatcaaaaca tttaacaatc  1500
attatagtac agaacttacc aatcaaatca gatgctcagc cggagtggat gttggccacc  1560
cagctattat tatccctggc tcaattggtc ttcagctgtg ttaacttgca acattaatt    1620 aactatctaa gccctcatt ttcctcaagt gtaaatagac acaataatat tacctattcc    1680
ataggtgtgg ggtgaatagt aaatgtaata atttgtccaa aacacttagt atagtgcctg  1740
gtccatggta aatactaaat aaatgttatc tgacttatta ttaaaatttt atcttctcag  1800
cttaaccttc agaacagtaa tatattgggg tctagataaa tcttgcctat atgaaaataa  1860
tttaatacta catgcagata tatgctgtgt atattatgcc ttctgttaga ggaattgcag  1920
aaacaaaaat ttcaattaat aataagatga attatttctc ccaattgtag aatcttttga  1980
caattttatc atgcattaca gatgtaagaa ctcttgattg ggacttgata gtctaacttt  2040
ataataattt aagaacattc ctcttagaga atttctatgg ccataatact gaacacatga  2100
attttaatta gctgtcctct ttagccctaa aaaaaaaatt actgtaattt aacacttaag  2160
tgttgttctt cccaggtaca gtaatctttt ttttttttt tttttttttt tgcatagagg    2220
gtaatctttt ctctttccaa atggcagaac tgttagtttt ctgactgtcc ggtgaaattc  2280
taagtccact tacttcccaa tagcatgcaa ttagcaaagg tcctccttgc aaaggcacag  2340
aacacaccta aacatcttgc agatgctgtt tggacactct tccctgcttt tggtctctt    2400 tgtaaagcag ctcatctgga tacaggatct cttttcccca ttgcccattc taatatatgt   2460
taccgttatt acttatagaa taatagtaga agagacaaat atggtaccta cccattacca  2520
```

| | |
|---|---|
| acaacacctc caataccagt aacattttt aaaaagggca acactttcct aatattcaat | 2580 |
| cgctctttga tttaaaatcc tggttgaata cttactatat gcagagcatt attctattag | 2640 |
| tagatgctgt gatgaactga gatttaaaaa ttgttaaaat tagcataaaa ttgaaatgta | 2700 |
| aatttaatgt gatatgtgcc ctaggagaag tgtgaataaa gtcgttcaca gaagagagaa | 2760 |
| ataacatgag gttcatttac gtct | 2784 |

<210> SEQ ID NO 58
<211> LENGTH: 97
<212> TYPE: RNA
<213> ORGANISM: Homo sapiens

<400> SEQUENCE: 58

| | |
|---|---|
| agaaggagaa ggaagaguug guauuauccu gacuuuagcc augaauauca ugaguacauu | 60 |
| gcagugggcu guaaacucca gcauagaugu ggauagc | 97 |

<210> SEQ ID NO 59
<211> LENGTH: 1000
<212> TYPE: DNA
<213> ORGANISM: Homo sapiens

<400> SEQUENCE: 59

| | |
|---|---|
| tcttatcatc tttttaactt ttatgaaaaa aattcagaca agtaacaaag tatgagtaat | 60 |
| agcatgagga agaactatat accgtatatt gagcttaaga aataaaacat tacagataaa | 120 |
| ttgagggtca ctgtgtatct gtcattaaat ccttatctct tctttccttc tcatagatag | 180 |
| ccactatgaa gatctaatac tgcagtgagc attctttcac ctgtttcctt attcaggatt | 240 |
| ttctaggaga ataccotagg ggttgtattg ctgggtcata ggattcaccc atgcttaact | 300 |
| gagtggtgcc aaattgtcct caagtctgtt gtactgatat atatccccat caagagagta | 360 |
| caagaattct catagctatg tatcttcaac aacacttggt gtctggtaga tgtgaagtga | 420 |
| ttactaaaaa tatagggaag ctgcatacat aattattggc ttttgctgtt ctcttacatt | 480 |
| aatttcttat tcatgttgat tactcatttg tcacctagtt ttttcttcct taattaaatt | 540 |
| gtaggaattt atgaattatg gattgatcat cagctctata catttcaaac ataatccctc | 600 |
| agtcagtggc ttggcttata gagtcttttg atgaaaagaa gcttttaagt ttaataaagt | 660 |
| tcaatttatt gtcttttcct ttatgttttg tgcttttggt atcttgatta agaactcctt | 720 |
| ccttatattg ggttctcaaa tttagcagca taacattttc atactattat ttaaatttt | 780 |
| ttcacattat ttagtgatag caccttctt attcctaaag tgtttatcat tgccttctgt | 840 |
| ctttctgctt gataaatatt gccacacatt tgtatacttt attagtgtgt acaaagacca | 900 |
| cattttagtt gtgttatttc tcttgttttg gttttctaga atgcagagcc attaatatta | 960 |
| tagtaatgct tatgtgctaa taccatatca ggggcacaaa | 1000 |

<210> SEQ ID NO 60
<211> LENGTH: 245
<212> TYPE: RNA
<213> ORGANISM: Homo sapiens

<400> SEQUENCE: 60

| | |
|---|---|
| ugcgaucugu gagccgaguc uuuaaguuca uugacaugcc aacagaaggu aaaccuacca | 60 |
| agucaaccaa accauacaag aauggccaac ucucgaaagu uaugauuauu gagaauucac | 120 |
| acgugaagaa agaugacauc uggccccucag ggggccaaau gacugucaaa gaucucacag | 180 |
| caaaauacac agaaggugga aaugccauau uagagaacau uuccuucuca auaaguccug | 240 |

```
gccag                                                                        245

<210> SEQ ID NO 61
<211> LENGTH: 1000
<212> TYPE: DNA
<213> ORGANISM: Homo sapiens

<400> SEQUENCE: 61
atttgaacac tgcttgcttt gttagactgt gttcagtaag tgaatcccag tagcctgaag    60
caatgtgtta gcagaatcta tttgtaacat tattattgta cagtagaatc aatattaaac   120
acacatgttt tattatatgg agtcattatt tttaatatga aatttaattt gcagagtcct   180
gaacctatat aatgggttta ttttaaatgt gattgtactt gcagaatatc taattaattg   240
ctaggttaat aactaaagaa gccattaaat aaatcaaaat tgtaacatgt tttagatttc   300
ccatcttgaa aatgtcttcc aaaaatatct tattgctgac tccatctatt gtcttaaatt   360
ttatctaagt tccattctgc caaacaagtg atactttttt tctagctttt ttcagtttgt   420
ttgttttgtt tttctttgaa gttttaattc agacatagat tatttttttcc cagttattta   480 ctatatttat taagcatgag taattgacat tattttgaaa tccttcttat ggatcccagc   540
actgggctga acacatagaa ggaacttaat atatactgat ttctggaatt gattcttgga   600
gacagggatg gtcattatcc atatacttca ggctccataa acatatttct taattgcctt   660
caaatcccta ttctggactg ctctataaat ctagacaaga gtattatata ttttgattga   720 tatttttttag ataaaataaa agggagctga aaactgaatt gcaaactgaa ttttaaaact   780
ttatctctct gtggttaatt gcaaacacag atacaaaaat atagagagag atacagttag   840
taaagatgtt aggtcaccgt tactaacact gacatagaaa cagttttgct catgagtttc   900
agaatatatg agtttgattt tgcccatgga ttttagaata tttgataaac atttaatgca   960
ttgtacaaat tctgtgaaaa catatatata ggatgtgcga                         1000

<210> SEQ ID NO 62
<211> LENGTH: 152
<212> TYPE: RNA
<213> ORGANISM: Homo sapiens

<400> SEQUENCE: 62
ugggccucuu gggaagaacu ggaucaggga agaguacuuu guuaucagcu uuuugagac     60 uacugaacac ugaaggagaa uccagaucg auggugugc uugggauuca auaacuuugc    120
aacaguggag gaaagccuuu ggagugauac ca                                 152

<210> SEQ ID NO 63
<211> LENGTH: 1000
<212> TYPE: DNA
<213> ORGANISM: Homo sapiens

<400> SEQUENCE: 63
caaaaggact tagccagaaa aaaggcaact aaattatatt ttttactgct atttgatact     60
tgtactcaag aaattcatat tactctgcaa aatatatttg ttatgcattg ctgtcttttt   120
tctccagtgc agttttctca taggcagaaa agatgtctct aaaagtttgg aattctcaaa   180
ttctggttat tgaaatgttc atagctttga tagtgttttt cagaagacca aatttacagt   240
gggagccttg ggcttttgtt ttttaacagc tcttttttgt tcctgcttca gtggcctgac   300
ctccaagtta gcaatcgcca ggttgagaaa tgctttgcga gacataacag atgctcctga   360
```

```
aataacaaac acttggaatc atgaggtagt ggaattgaaa atagaaagtg tagtgattgt    420
tttttgttat ttggatggga tgaacaatgt cagattagtc tgtaactatt ttttttttaat   480 gtcactctga tttggtcaca aaggatctct agtctcattg ccttagtatc attctacgaa    540
ttagaatgtg ttactgtgta agagcacttc ttgtatatga gagaaatagc aacagttcca    600
gtttaaagtg atataaatgg aaaccaagaa atgtctttac tgggaccaaa tctggacagc    660
atttactgta ttttgctgg tattttctct agtctttccg ggtatattca catttaatga    720
tcacttttct cccttttgtgc taatggacac tgaatccatt ccactaccat agttcttgct    780
aatactactc tacttttttac acaaaattaa aatgccagga gcacctccag gtagactgac    840
tataaatcta gactgaaaaa aaagcttgta tttcttaaca gattaccttg tggaacattt    900
gctcctttca actaatgagg cactaaatat tgtaactgct caactggtgc ttttaattta    960
tttgtctaga ctttgtcatg ttgccagaag ctttatcctg                         1000

<210> SEQ ID NO 64
<211> LENGTH: 86
<212> TYPE: RNA
<213> ORGANISM: Homo sapiens

<400> SEQUENCE: 64
aaguauuuau uuuucugga acauuuagaa aaacuugga ucccaugaa caguggagug       60 aucaagaaau auggaaaguu gcagau                                         86

<210> SEQ ID NO 65
<211> LENGTH: 1000
<212> TYPE: DNA
<213> ORGANISM: Homo sapiens

<400> SEQUENCE: 65
gctgctaact gaaatgattt tgaaaggggt aactcatacc aacacaaatg gctgatatag    60
ctgacatcat tctacacact ttgtgtgcat gtatgtgtgt gcacaacttt aaaatggagt   120
accctaacat acctggagca acaggtactt ttgactggac ctaccctaa ctgaaatgat    180 tttgaaagag gtaactcata ccaacacaaa tggttgatat ggctaagatc attctacaca   240 cttttgtgtgc atgtatttct gtgcacaact tcaaaatgga gtaccctaaa atacctggcg   300
cgacaagtac ttttgactga gcctacttct ctcctcactg gtatggctcc aaccatcagg   360
ccctatcttg gtccatttag ctgctaaaa taaaatacca aagactgagc tgcttataag    420
caatctttgg aggctgagaa gtcaaagatc aaggtgccag caggtttgct gtctcgtgag    480
agcatacttc ctggttcatt gatggtgctt tcttgctgtg tcctcacata atggaaaggg    540
caagacctct ctggtgtctc ttttacaatg gcactaatcc catcatgagg gctttgttct    600
catgacctaa tcacctccca catgtcctac attctaatac tatcaccttg ggggttagga    660
ttttaacata tgaatttgag gaggtggcgg gggggacaca aatatttaga ccatagcatt    720
tcactcctga cctccaaagt tcatgtcttc ttcacatgca aaatacattc attccatccc    780
aatagccccc aaagtcttaa cttgttccag catcaactta caaggctaaa gtccaaggtt    840
tcatctaaat atcagctaaa tcagcacaaa cagctaaatc aggtagagtg ggacttaagg    900
tgtgattcct ctttaggcag attgctctcc aactatgaaa ttgtgaaatc aaacctatta    960
tgtactttca aaataaaatg gtgaaacagg cacaggctag                         1000

<210> SEQ ID NO 66
<211> LENGTH: 169
```

<212> TYPE: RNA
<213> ORGANISM: Homo sapiens

<400> SEQUENCE: 66
uugggcucag aucugugaua gaacaguuuc cugggaagcu ugacuuuguc cuuguggaug    60
ggggcugugu ccuaagccau ggccacaagc aguugaugug cuuggcuaga ucuguucuca   120
guaaggcgaa gaucuugcug cuugaugaac ccagugcuca uuuggaucc              169

<210> SEQ ID NO 67
<211> LENGTH: 578
<212> TYPE: DNA
<213> ORGANISM: Homo sapiens

<400> SEQUENCE: 67
tttcagatgt tctgttactt aatagcacag tgggaacaga atcattatgc ctgcttcatg    60
gtgacacata tttctattag gctgtcatgt ctgcgtgtgg gggtctcccc caagatatga   120
aataattgcc cagtggaaat gagcataaat gcatatttcc ttgctaagag tcttgtgttt   180
tcttccgaag atagttttta gtttcataca aactcttccc ccttgtcaac acatgatgaa   240
gcttttaaat acatgggcct aatctgatcc ttatgatttg cctttgtatc ccatttatac   300
cataagcatg tttatagccc caaataaaga agtactggtg attctacata atgaaaaatg   360
tactcattta ttaaagtttc tttgaaatat ttgtcctgtt tatttatgga tacttagagt   420
ctaccccatg gttgaaaagc tgattgtggc taacgctata tcaacattat gtgaaaagaa   480
cttaaagaaa taagtaattt aaagagataa tagaacaata gacatattat caaggtaaat   540
acagatcatt actgttctgt gatattatgt gtggtatt                          578

<210> SEQ ID NO 68
<211> LENGTH: 102
<212> TYPE: RNA
<213> ORGANISM: Homo sapiens

<400> SEQUENCE: 68
acauaccaaa uaauuagaag aacucuaaaa caagcauuug cugauugcac aguaauucuc    60
ugugaacaca ggauagaagc aaugcuggaa ugccaacaau uu                      102

<210> SEQ ID NO 69
<211> LENGTH: 1323
<212> TYPE: DNA
<213> ORGANISM: Homo sapiens

<400> SEQUENCE: 69
tctttataac tttacttaag atctcattgc ccttgtaatt cttgataaca atctcacatg    60
tgatagttcc tgcaaattgc aacaatgtac aagttctttt caaaaatatg tatcatacag   120
ccatccagct ttactcaaaa tagctgcaca agttttttcac tttgatctga gccatgtggt   180
gaggttgaaa tatagtaaat ctaaaatggc agcatattac taagttatgt ttataaatag   240
gatatatata cttttttgagc cctttatttg gggaccaagt catacaaaat actctactgt   300
ttaagatttt aaaaaaggtc cctgtgattc tttcaataac taaatgtccc atggatgtgg   360
tctgggacag gcctagttgt cttacagtct gatttatggt attaatgaca aagttgagag   420
gcacatttca ttttttctagc catgatttgg gttcaggtag tacctttctc aaccaccttc   480
tcactgttct taaaaaaact gtcacatggc caggcacagt ggcttacatc tgtaatccca   540
atactttggg aggctgaggt gggggggatta cttgaggcca ggaattcaag accagcccag   600

```
gcaacatagt gaggccccat ctgtctttat taaaacaaaa caaaactgtc acagcttctt    660
tcaagtgatg tttacaaatt ccctatggtt tagtcacaag gaagttctga ggatgatgta    720
tcacgtcatt tctgttcagg cttttgagcc tcctggaggt aaatggtttc cttactgaag    780
gcttgttatt accatgatta tcactaagct tgaagtaaca aattaggggg gcagactcac    840
aacctcttgc cctgccatgg acaagttcaa gaatctaagt aaagtcctct attgtctgat    900
cttggatttg ctcaacctga acaagccaag gaggtgtatt aaactcaggc acatcctgac    960
caatttggaa ttcttaagct tcagatcact gtggaagagg ctcaactctt tatggtgctg   1020
tagacttacg ctcattttct aggtaattta taagggacct aatatttgt tttcaaagca   1080 acttcagttc tactaaacct ccctgaagaa tcttccagct gctgagtaga aaatcacaac   1140
taatttcaca gatggtagaa cctccttaga gcaaaaggac acagcagtta aatgtgacat   1200
acctgattgt tcaaaatgca aggctctgga cattgcattc tttgactttt attttccttt   1260
gagcctgtgc cagtttctgt ccctgctctg gtctgacctg ccttctgtcc cagatctcac   1320
taa                                                                 1323

<210> SEQ ID NO 70
<211> LENGTH: 197
<212> TYPE: RNA
<213> ORGANISM: Homo sapiens

<400> SEQUENCE: 70
ucauagaaga gaacaaagug cggcaguacg auuccaucca gaaacugcug aacgagagga     60
gccucuuccg gcaagccauc agccccuccg acagggugaa gcucuuuccc caccggaacu    120
caagcaagug caagucuaag ccccagauug cugcucugaa agaggagaca gaagaagagg    180
ugcaagauac aaggcuu                                                   197

<210> SEQ ID NO 71
<211> LENGTH: 315
<212> TYPE: RNA
<213> ORGANISM: Homo sapiens

<400> SEQUENCE: 71
gcucuguuuc cuguggggau ggcauccagc gccggcguga caccugccuc ggaccccagg     60
cccaggcgcc ugugccagcu gauuucugcc agcacuugcc caagccggug acugugcgug    120
gcugcugggc ugggcccugu gugggacagg guacgcccag ccuggugccc cacgaagaag    180
ccgcugcucc aggacggacc acagccaccc cugcuggugc cucccuggag uguccccagg    240
cccggggccu gcucuucucc ccggcucccc agccucggcg gcuccugccc gggcccagg    300 aaaacucagu gcagu                                                     315

<210> SEQ ID NO 72
<211> LENGTH: 445
<212> TYPE: RNA
<213> ORGANISM: Homo sapiens

<400> SEQUENCE: 72
guccuguccu ccuuccuguc aggcagcugc ugcaggaggg gugggcaaag gcaucuuccu     60
cugggaagga cuggcacaag cacuuggucc cugggüugug ugccuggag gccgggauca    120 gggcuggccc ucuuucuccc uggcaaagca aaacccccu uuuacuacua ucaaggggaa    180
guaacuugaa gguaggaacc cagcuuguga gcccccuagc cucugggcug cucugcaugu    240
gcccccucuu gcuggaucau cugguagcag cccugugccc ugagggugau gcucugaccu    300
```

```
augcagcccc ccucccuguc cugagaaggc uuccagcugg gccuuggagg acagggucca    360
ccccuaccuc cuggucuccu uccucagcuu ggaagcccg gagccugccc ugcugggaau     420
cggggaagca cugcuuaccu gucuc                                          445
```

<210> SEQ ID NO 73
<211> LENGTH: 143
<212> TYPE: RNA
<213> ORGANISM: Homo sapiens

<400> SEQUENCE: 73

```
ugccuguggc aggcagcacc uugagccaac aggaaccauu gacaugcgag gcccagggca    60
ggcagacugu gcaguggcca uugggcggcc ccucggggag guggugaccc uccgcguccu   120
ugagaguucu cucaacugca gug                                           143
```

<210> SEQ ID NO 74
<211> LENGTH: 173
<212> TYPE: RNA
<213> ORGANISM: Homo sapiens

<400> SEQUENCE: 74

```
ggacauguug cugcuuuggg gccggcucac cuggaggaag augugcagga agcuguugga    60
caugacuuuc agcuccaaga ccaacacgcu gguggugagg cagcgcugcg ggcggccagg   120 aggugggug cugcugcggu augggagcca gcuugcuccu gaaaccuucu aca           173
```

<210> SEQ ID NO 75
<211> LENGTH: 1170
<212> TYPE: RNA
<213> ORGANISM: Homo sapiens

<400> SEQUENCE: 75

```
gccaggccuu cuccaccucc cuugggugcu ccaguccugg cagggaggcu gggugggugc    60
ugcuggggau gggggccaguc ccaguggggc aguggggaaga uacggaggga acugacugag  120
auggaaggaa cugggguugg ccagugucag ucugcacgug ccaggagggg ucacaggau    180 gaaugcuaua ucccuccuuu uugggaccgu gcagcaagau ggacggaugu gggacauggu   240
ccacauccuc agucaguccc ucaggccucu gccccacacc caccugcccc gcccccaccc   300
cuccagccuu ucaagggcuu uuaggguuuu guggaagcca cugucccuca gcccuguuuc   360
agugcacugg guaagcagaa caugcuugua caugcaugug cacccacaag cacaccucag   420
gcagaggaug ccaccucagg gacuccagcc uugcccgugg cccccucgau auccucugau   480
agcccucucg guugccuggg gggcuugcc cucucccaac agcccgagcu ggccgaaguu    540
ggcuucccua gcugguucca gagguuccuc ggcuccccca ggugucuggg gcuuagugc    600 aacaggggcu uagccucugc agagaccuag ugcgccgccu ccuugcccca gaccugcccg   660
ggcagagagc cguguaugug ucccagugca caggcgcugc uggcccugc caaaggcca    720 caagcccacu gucaccguuc acauugcuuc ucgcuucccg gccagcccc gcccacacag    780 gcaucugccu ugaaagaggu gcaggaggua caggcaggug ggggcuccag ugagcucuga   840
ggaacagcag uggccgccau ggguggagcc uaucuuuguu gccaguuuca guguuaaaca   900
cucuugcacg ugugacauca uugagcccua aagaccacuc ugcucagugc augccauugu   960
uuccuucagu uacagaggag ggaaccgag cccagaacau uuagccuuug ccuaaaguca    1020
cugggccagg aaguggguaga gguggggguuc agcaggauuu gccuggaac cccaauauug  1080
```

```
accacagugc caugcugccc ugcacggcuc ccuggcugug aguguccug gccucuggca    1140 ccaccggucu gucugguuc cuaugcccu                                     1170

<210> SEQ ID NO 76
<211> LENGTH: 181
<212> TYPE: RNA
<213> ORGANISM: Homo sapiens

<400> SEQUENCE: 76
augugacaug cagcucuuug ggcccugggg ugaaaucgug agccccucgc ugaguccagc     60
cacgaguaau gcaggggcu gccggcucuu cauuaugug gcuccgcacg cacggauugc    120
cauccaugcc cuggccacca acaugggcgc ugggaccgag ggagccaaug ccagcuacau    180
c                                                                   181

<210> SEQ ID NO 77
<211> LENGTH: 149
<212> TYPE: RNA
<213> ORGANISM: Homo sapiens

<400> SEQUENCE: 77
accucuugga caggauuaac gaauaugugg gcaaagccgc cacucguuua uccauccucu     60
cguuacuggg ucaugucaua agacugcagc caucuuggaa gcauaagcuc ucucaagcac    120
cucuuuugcc uucuuuacua aaaugucuc                                     149

<210> SEQ ID NO 78
<211> LENGTH: 2074
<212> TYPE: RNA
<213> ORGANISM: Homo sapiens

<400> SEQUENCE: 78
auguuuguaa ggauuugaau gaaaugguuu uaugaguaua guuucugaaa uuuuaggcaa     60
cuuaaagcaa ggaagcuaga uuuuaacuuu uagaguuuaa aaccuucuag gcauuuggcu    120
uuucucaaau agaauguugu ccagaguugg uacuaguaa guucucaaau acaucacuau    180
gacuauugaa uaccugucc augcaaguau ggaaaaauuu cgaucagaug gguucaaugu    240
uacauuauuc caaaccucuu gauuucguca ucguuuagcc uucccucauu uaaaaacauc    300
cuggauuauc uuuugggaau cccuguuucu aaauuaucuu uuagcuauua gaaaaauggc    360
uuaaaguuuc uguuaaccau uuaggaguau ggucugguug cagcuauaau uaagacuuug    420
uugauguaaa uucuacuaag uugcauucua uuuuuugcac uaaauuuagu gcauuuuucu    480
auauagggag ucaaaaucua aauagaacuu uaugguuuua guuuaacag uggcgugcag    540 ccauacucag gguuauugu uuaaucuguu uuaguuccug gacuguuuu cuaucuauaa    600 aauaagaaaa uguggguuaau auuaacugcc uguaccucac agagacauga aaauauccaa    660
uaguauuugu uccaggaugg caguaccauu ggauucaucu gcuacagcac caugcaaauu    720
gauuuuugug ucugccaaga aggguaacuc uuuuauuauc ccuagaggug gucccaagg    780 agucacauug gcagggauu auaaaaacau gcauuaauu cagaaaaaau aggaacaguu    840
uuaacaacuu aauguuuuuu aaacaaaugg auugaugaga auauaaucua auaauggau    900 uggugagaau auaaucuaaa uggauugaug agaauauaau cuaaauggau ggugagaau    960 auaaucuaaa uggauugaug agaauauaau cuauuuuga ggcacaucau uuaguucaga   1020
uugcaaaaca cuuaucuuuu ccaaaagagu acguuuuguu aaucauggau aagcuucag    1080 uuagacuguu aggaaaauga aaucagggcu aguucuuucu gcugagaauc auuauauagu    1140
```

| | |
|---|---|
| cucauauauu cucaauucuc cuaccaauau auuauucuua cuggauaucu uccguaauga | 1200 |
| aaggcuugau gcuugaugua aaaaucaaaa uauauuuaaa acuuuauucc cagacucaua | 1260 |
| gauuccuauu cuaauaggaa uaauggaugu cuuaaccuac auaguagucu uuugauuaau | 1320 |
| aucuuguuuc auaaaucuga auuucaucua ccuggcaaac auucaugauu uaauuauggg | 1380 |
| ucaggugagc ugcuguagcu agcuagucag agcugauuga guaccauug gguguuaagu | 1440 |
| gucuucaguu agccugaagu uauuuauuug acuuaauauu uaaacuguag gcgugcugaa | 1500 |
| agguuuccau auauauauau uuuaauuuac uggucucuaa auacugcuuu gaagugagcc | 1560 |
| uuuaaguuga cuuguuagug cuauaugaau uucccuuca auuauacuuc uguuguaguu | 1620 |
| cuuuaaaaaa uaguaaguua cuugucaaug ugcaguuuuu uuuuuuuuua auuaacaaaa | 1680 |
| aguaaguauc uuaggauuug guugaaugaa ugaaacagag cagugcuccu uguuuuguu | 1740 |
| gaaaagcagc uccuuuuguu uucauccaac ugcuaucaau agggcauccu aaggcugcag | 1800 |
| gacuggggug uccccaaguc aaguuugaac ucgucucccg gaugccuuug cauaggugug | 1860 |
| uuguaaaugg uccucacuga cucauuacag uagaguuggg gcucagguu cuguugaguc | 1920 |
| uguuugaaug uuauccccuc aguaauccuu agggauaggg aaaugaguac gugagucaac | 1980 |
| uugugauuug ugauucucuc aguguuuaga gccucuucau guacuguaca augccgaucc | 2040 |
| uggugccagu gccugacaga cguuccugu uuga | 2074 |

<210> SEQ ID NO 79
<211> LENGTH: 141
<212> TYPE: RNA
<213> ORGANISM: Homo sapiens

<400> SEQUENCE: 79

| | |
|---|---|
| uggacacuga cgucguuguc cucacaacag gcgucuuggu guugauaacc augcuaccaa | 60 |
| ugauuccaca gucugggaaa cagcaucuuc uugauuucuu ugacauuuuu ggccgucugu | 120 |
| caucauggug ccugaagaaa c | 141 |

<210> SEQ ID NO 80
<211> LENGTH: 112
<212> TYPE: RNA
<213> ORGANISM: Homo sapiens

<400> SEQUENCE: 80

| | |
|---|---|
| gugugcuacu ucuaccccuu acuccacguc ucggcugaug uguuaaaua ugccagggca | 60 |
| gcuaccucag acucugaguu ccccaucgac acggcugaua acugaaccac ca | 112 |

<210> SEQ ID NO 81
<211> LENGTH: 319
<212> TYPE: RNA
<213> ORGANISM: Homo sapiens

<400> SEQUENCE: 81

| | |
|---|---|
| gugucaacua gugugccugc ucucuccucu gcuuucuggu gaagcugacc cuuggguca | 60 |
| gauuuaguau gugguuggga aaauuucaca cugcucauuu caggagucac uuuuaaggau | 120 |
| ccaugauauu agcaaagaaa guuacuguug ccucuuagu ucaucuugaa gucugauuu | 180 |
| acaaaaugca acuuguuucu ugauacgcuu uuaauaagau gccuuuucu agaugaaaaa | 240 |
| gcuaaauuua agcugaacac uggccaugga uauaaaccuc guggaugacu uagcauuccu | 300 |
| uugccacugc ugauguacu | 319 |

<210> SEQ ID NO 82
<211> LENGTH: 108
<212> TYPE: RNA
<213> ORGANISM: Homo sapiens

<400> SEQUENCE: 82
cuacucuuug gagcccaucu augguuugug guaugaccac uccuccaacu ucuccuggaa    60
augucccacc ugaucuguca cacccuuaca guaaagucuu ugguacaa                108

<210> SEQ ID NO 83
<211> LENGTH: 289
<212> TYPE: RNA
<213> ORGANISM: Homo sapiens

<400> SEQUENCE: 83
uaugucuuag guuggauuug auuaguuggu uuuggccugc cuuuaauggc aggaggagcu    60
cucuuuuaga ucuaagggac cacuugcugu uguaaacuug uuuuugacac uuauugcaaa   120
ucccuggggc uuucagaaug uguaaaguga accuaaaaac aaaaaagaga gagacugauc   180 uagauccccca gaaaguuaac ucuagcagcu uuauuuauag uaauaguuau aggcugaaaa   240
aaaaucggca guuuuucuaa uaguugggcu cagguguucau auauguucu              289

<210> SEQ ID NO 84
<211> LENGTH: 118
<212> TYPE: RNA
<213> ORGANISM: Homo sapiens

<400> SEQUENCE: 84
agguggaaaa ggaacuccuc ugggaacccc agcaaccucu ccuccuccag ccccacucug    60
ucauucggau gacuacgugc acauuucacu cccccaggcc acagucacac cccccagg     118

<210> SEQ ID NO 85
<211> LENGTH: 141
<212> TYPE: RNA
<213> ORGANISM: Homo sapiens

<400> SEQUENCE: 85
gaugaugggc ucccugcugg ccgccacuac ggaggcsccu ggcgaguacu ucuucucaga    60
cggggugcgg cucaagaagu accggggcau gggcucacug gaugccaugg agaagagcag   120
cagcagccag aaacgauacu u                                             141

<210> SEQ ID NO 86
<211> LENGTH: 269
<212> TYPE: RNA
<213> ORGANISM: Homo sapiens

<400> SEQUENCE: 86
cugacccugg gccccaccug ggcagaucag cccacaaccc uucagggccc gcucaugcca    60
ccgacuuccc cagauggcag ccaguccca uauggugguu cuggaaacug aggcacaggg   120
cuuaaguagc agacccagga ucuguccccug ggccaucuga cucagcccag ugaggggugg   180
ccugggggac cuuccuggc gguaucccgu uuuugcccuu aagagguggg guggguccu    240 cugagcuuca agcugcuggg cucagucuu                                    269

<210> SEQ ID NO 87
<211> LENGTH: 140
<212> TYPE: RNA
<213> ORGANISM: Homo sapiens

```
<400> SEQUENCE: 87
gagggggaua aagugaagau cgcgcagggu gucucgggcu ccauccagga caaaggaucc      60
auucagaagu ucgugcccua ccucauagca ggcauccaac acggcugcca ggauaucggg     120
gcccgcagcc ugucuguccu                                                 140

<210> SEQ ID NO 88
<211> LENGTH: 49
<212> TYPE: RNA
<213> ORGANISM: Homo sapiens

<400> SEQUENCE: 88
aggccuuugu uggacagaug aagagugacu uguuucugga ugauucuaa                  49

<210> SEQ ID NO 89
<211> LENGTH: 204
<212> TYPE: RNA
<213> ORGANISM: Homo sapiens

<400> SEQUENCE: 89
uucccuagag aaaccucgag cccuggugca ggucacugug ucugggggugc cggggguguug    60 cgggcugcgu guccuugcug ggugucugug gcuccaugug gucacaccac ccgggagcag    120
guuugcucgg aagcccaggg uguccgcgcg ugacuggacg ggggugggcu gugugugugu    180
cacauccccu gguaccuugc ugac                                           204

<210> SEQ ID NO 90
<211> LENGTH: 181
<212> TYPE: RNA
<213> ORGANISM: Homo sapiens

<400> SEQUENCE: 90
cuggugugcu ggcccuccgg cgagggaacg cucaguuggc cggaccugcu cagugacccg     60
uccauugugg guagcaaucu gcggcagcug gcacggggcc aggcgggcca ugggcugggc    120
ccagaggagg acggcuucuc ccuggccagc cccuacucgc cugccaaauc cuucucagca    180
u                                                                    181

<210> SEQ ID NO 91
<211> LENGTH: 57
<212> TYPE: RNA
<213> ORGANISM: Homo sapiens

<400> SEQUENCE: 91 cugggguggag aggagggggc ucugaagcuc acccuugcag cugggcccac ccuaugc       57

<210> SEQ ID NO 92
<211> LENGTH: 90
<212> TYPE: RNA
<213> ORGANISM: Homo sapiens

<400> SEQUENCE: 92
ugaagaccug auccagcagg uccuugccga gggggucagc agcccagccc cuacccaaga     60
cacccacaug gaaacggacc ugcucagcag                                      90

<210> SEQ ID NO 93
<211> LENGTH: 191
<212> TYPE: RNA
<213> ORGANISM: Homo sapiens
```

<400> SEQUENCE: 93

```
ucuugcugga agcccuguac uucucacugg uggccaagcg gcugcacccg gaugaagaug    60
acacccuggu agagagcccg gcugugacgc cugugagcgc acgugugccc cgcguacggc   120
caccccacgg cuuugcacuc uuccuggcca aggaagaagc ccgcaagguc aagaggcuac   180
auggcaugcu g                                                        191
```

<210> SEQ ID NO 94
<211> LENGTH: 430
<212> TYPE: RNA
<213> ORGANISM: Homo sapiens

<400> SEQUENCE: 94

```
ccugggugcg gccugugccc cugccaccuc cgucucuugu cucccaccuc ccacccaugc    60
acgcaggaca cuccuguccc ccuuccucca ccucagaagg cccuuagggg uucaaugcuc   120
ugcagccuuu gcccgucucu ccuccuaccc cacgcccccc acuugcugcc ccagucccug   180
ccagggccca gcuccaaugc ccacuccugc cuggcccuga aggcccccuaa gcaccacugc   240 aguggccugu gugucugccc caggugggg uuccgggcag ggugugugcu gccauuaccc    300
uggccaggua gagucuuggg gcgcccccug ccagcucacc uuccgcagc cacaccugcc    360 gcagccaugg cuccagccgu ugccaaagcc cugcugucac ugugggcugg ggccaggcug   420
accacagggc                                                          430
```

<210> SEQ ID NO 95
<211> LENGTH: 136
<212> TYPE: RNA
<213> ORGANISM: Homo sapiens

<400> SEQUENCE: 95

```
gccuccuggu guacaugcuu uuucugcugg ugacccugcu ggccagcuau ggggaugccu    60
caugccaugg gcacgccuac cgucugcaaa gcgccaucaa gcaggagcug cacagccggg   120
ccuuccuggc caucac                                                   136
```

<210> SEQ ID NO 96
<211> LENGTH: 341
<212> TYPE: RNA
<213> ORGANISM: Homo sapiens

<400> SEQUENCE: 96

```
ggcauccggu gcacuggucu gucuucuggg cuuuaguuuu gccuuuaguc cagccagacc    60 cuagggggaca uguggacaug guagauacc uuuguggcug cuagaacugg agguagguc    120 ugcuggcauc aguaggcaga ggggagggac acagguccgu gucuugcagu gcacaggacg   180
ggcccaugac agacaacugu cugccccaga acaucccccag gauaaggcug agaagcccag   240
gucuagccgu ggccagcagg gcagugggag ccauguuccc ugggucucug guggccgcuc   300
acucgaggcg ggcauggggc aguaggggcu ggagcgugug a                       341
```

<210> SEQ ID NO 97
<211> LENGTH: 109
<212> TYPE: RNA
<213> ORGANISM: Homo sapiens

<400> SEQUENCE: 97

```
ucugaggagc ucuggccaug gauggcccac gugcugcugc ccuacgucca cgggaaccag    60
uccagcccag agcuggggcc cccacggcug cggcagggugc ggcugcagg              109
```

<210> SEQ ID NO 98
<211> LENGTH: 93
<212> TYPE: RNA
<213> ORGANISM: Homo sapiens

<400> SEQUENCE: 98
augagucugc uuugcccugg gaugaccaua gaccacaagu uaccuggcgg ggggauggac    60
aguuuuuugc ugugagucuu guuugcccag aaa    93

<210> SEQ ID NO 99
<211> LENGTH: 331
<212> TYPE: RNA
<213> ORGANISM: Homo sapiens

<400> SEQUENCE: 99
gaaauauauu gcaguuaaac aacaauaaaa aauuuuuauc uuauuaaaau uaaggaaaau    60
uuucuuucuu uugcuuugag uagggauuua auuauacaua ugaggcaagg augugcugcu   120
uuaaauguga aaugagguua gaguuaagaa uuagaagagu ccuugaggc cauuuggucc    180 auccuccuac cugguggaca caaauuugua acaaaauuaa ucuaauuggc uauguaaaac   240
cauggcaguu uuuauuugua aggaaggugu ugaauaguu cugaauugac aacuuuuauc    300
auaauguuuu aaguguguau guguguuuga c    331

<210> SEQ ID NO 100
<211> LENGTH: 87
<212> TYPE: RNA
<213> ORGANISM: Homo sapiens

<400> SEQUENCE: 100
ggcucggaag gucagagugu ggaaccgaga guuugcuuug cagucaacca gugagccugu    60
ggcaggacug ggaccagccc uggcuug    87

<210> SEQ ID NO 101
<211> LENGTH: 1120
<212> TYPE: RNA
<213> ORGANISM: Homo sapiens

<400> SEQUENCE: 101
ugggagaaga aaccuuagag aaauucuugg aaccagagua gaggugguGG uacacaugga    60
uacagaugau acagauguuu guguaacaca aaaggauuuu uacguuucuu cauuugguua   120
uaaggcugua ucuaucuuug uuucuucuuu uuuuuuuuc uuauucccug aagcucgaau    180
ucaacucgaa uaguagauuu uacgcuuccu cacagauuuc auuguccaa ggccgcauau     240 auuuugcauu ccuaacucuu aaaaggcugu gguuuuaagg caggguauau augaagccau    300
uguacagagc agaaaaauggu guuuagaagg aaggcccag uuugcaaggc ucuggggggc    360
aaauggugcu uuugugaaaa uuagggaaag agcucccuuc cuuggcacaa aauuccuaca    420
gcagaggauc ugcuugccaa ggagcaugca ggcuggauuc agacccugcu cuuccuucc    480 auucuccucc uuggcccagu acccuugugc agguuacaau ugccuguca uauguggcug    540 ccugauuuua gauagaagau guaucccuc uguucggug auaucuguug uauguagacc     600
ucuuguuucc caccaguauc ugaaugguau uauaugauag agcagaagag aaauguauuu    660
gaauuaaaac ccuagagaca aauaugaaua agaugaggca auuagagugu uucaacauu     720 uggugaaguc uuaaaaaaga ccuacuggag cauagaauau ugcugaagu uguauaaugg    780

```
aaggagaaau agauuugau uuuuaggaca uuauaccugg aaugguuuag auaacuuauu    840
auuuuuaaag ucauccaaau gcaauguaaa uauguaaggu uuugugggca aauggagccu    900
cuguguaaaa caggaaaagg cacucuuucc ucugggcaag uacaguccca cagugggaug    960
aaccgcucgc cgagagacaa gggacacaug ggauuuaaaa cuuccuugga uaaagauauu   1020
cauuaauucg uucauucauu cauucauguu ugcuggaaaa aaaacucuuc uggauuuuau   1080
cuauucuuua guuaggugag cuuucgauau uguaacacuc                         1120

<210> SEQ ID NO 102
<211> LENGTH: 120
<212> TYPE: RNA
<213> ORGANISM: Homo sapiens

<400> SEQUENCE: 102
cccucaggca guuugauugc aucuacacaa gauaaaccca accagcagga uauuguguuu     60
uuugagaaaa auggacuccu ucauggacac uuuacacuuc ccuuccuuaa agaugagguu    120

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccagtggtat tgcttacc                                                   18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ctgtcttgta accttgat                                                   18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cctgtcttgt aaccttga                                                   18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
acctgtcttg taaccttg                                                   18

<210> SEQ ID NO 107
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aacctgtctt gtaacctt                                                 18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaacctgtct tgtaacct                                                 18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
taaacctgtc ttgtaacc                                                 18

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ttaaacctgt cttgtaac                                                 18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cttaaacctg tcttgtaa                                                 18

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ccttaaacct gtcttgta                                                 18

<210> SEQ ID NO 113
<211> LENGTH: 18
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 113
tccttaaacc tgtcttgt                                                18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctccttaaac ctgtcttg                                                18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tctccttaaa cctgtctt                                                18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtctccttaa acctgtct                                                18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ggtctcctta aacctgtc                                                18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tggtctcctt aaacctgt                                                18

<210> SEQ ID NO 119
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 119
ttggtctcct taaacctg                                                   18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
attggtctcc ttaaacct                                                   18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tattggtctc cttaaacc                                                   18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctattggtct ccttaaac                                                   18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tctattggtc tccttaaa                                                   18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ttctattggt ctccttaa                                                   18

<210> SEQ ID NO 125
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 125
tttctattgg tctcctta                                                   18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtttctattg gtctcctt                                                   18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
accggacccc cagggccc                                                   18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgcctaccgg accccag                                                    18

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ccccatgcct accggacc                                                   18

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
atgaccccca tgcctacc                                                   18

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
cctccatgac ccccatgc                                                18

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tctcccctcc atgacccc                                                18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gaggaggacg ccggcttc                                                18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gctgggagga ggacgccg                                                18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
agtcggctgg gaggagga                                                18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cagggagtcg gctgggag                                                18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 137
ggcgccaggg agtcggct                                              18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tgggcggcgc cagggagt                                              18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ccccacctgg gtctggcc                                              18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cccagcccca cctgggtc                                              18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cggtccccag ccccacct                                              18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tccctcggtc cccagccc                                              18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 143
ggaggctgcg atctgggc                                                        18

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ctgcgatctg ggctcccc                                                        18

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
atctgggctc cccccacc                                                        18

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ggctcccccc accttgtg                                                        18

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ttgtgtccct cggtcccc                                                        18

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ccaccttgtg tccctcgg                                                        18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
``` tcccccccacc ttgtgtcc                                           18

<210> SEQ ID NO 150
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
caggaaggag gacaggac                                            18

<210> SEQ ID NO 151
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ccugacagga aggaggac                                            18

<210> SEQ ID NO 152
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
agcugccuga caggaagg                                            18

<210> SEQ ID NO 153
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gcagcagcug ccugacag                                            18

<210> SEQ ID NO 154
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
cuccugcagc agcugccu                                            18

<210> SEQ ID NO 155
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155

-continued caccccuccu gcagcagc					18

<210> SEQ ID NO 156
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uugcccaccc cuccugca					18

<210> SEQ ID NO 157
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ugccuuugcc caccccuc					18

<210> SEQ ID NO 158
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gaagaugccu uugcccac					18

<210> SEQ ID NO 159
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gagacaggua agcagugc					18

<210> SEQ ID NO 160
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
agguaagcag ugcuuccc					18

<210> SEQ ID NO 161
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
agcagugcuu ccccgauu					18

<210> SEQ ID NO 162
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ugcuuccccg auucccag                                                 18

<210> SEQ ID NO 163
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ccccgauucc cagcaggg                                                 18

<210> SEQ ID NO 164
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
auucccagca gggcaggc                                                 18

<210> SEQ ID NO 165
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
cagcagggca ggcuccgg                                                 18

<210> SEQ ID NO 166
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
agcagggcag gcuccggg                                                 18

<210> SEQ ID NO 167
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gggcuuccaa gcugagga                                                 18

<210> SEQ ID NO 168
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
agguggagaa ggccuggc                                                 18

<210> SEQ ID NO 169
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aagggaggug gagaaggc                                                 18

<210> SEQ ID NO 170
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
cacccaaggg agguggag                                                 18

<210> SEQ ID NO 171
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uggagcaccc aagggagg                                                 18

<210> SEQ ID NO 172
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
aggacuggag cacccaag                                                 18

<210> SEQ ID NO 173
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cugccaggac uggagcac                                                 18

```
<210> SEQ ID NO 174
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ccucccugcc aggacugg                                                      18

<210> SEQ ID NO 175
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
cccagccucc cugccagg                                                      18

<210> SEQ ID NO 176
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
agggacauag gaacccag                                                      18

<210> SEQ ID NO 177
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cauaggaacc cagacaga                                                      18

<210> SEQ ID NO 178
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gaacccagac agaccggu                                                      18

<210> SEQ ID NO 179
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cagacagacc gguggugc                                                      18

<210> SEQ ID NO 180
```

<210> SEQ ID NO 180
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 180
agaccggugg ugccagag                                           18

<210> SEQ ID NO 181
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 181 ggugguogcca gaggccag                                          18

<210> SEQ ID NO 182
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 182
ugccagaggc caggacaa                                           18

<210> SEQ ID NO 183
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 183
gaggccagga caacucac                                           18

<210> SEQ ID NO 184
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 184
cagcugccug acaggaag                                           18

<210> SEQ ID NO 185
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 185
gcagcugccu gacaggaa                                           18

<210> SEQ ID NO 186
<211> LENGTH: 18

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
agcagcugcc ugacagga                                                 18

<210> SEQ ID NO 187
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
cagcagcugc cugacagg                                                 18

<210> SEQ ID NO 188
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gcagcagcug ccugacag                                                 18

<210> SEQ ID NO 189
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
ugcagcagcu gccugaca                                                 18

<210> SEQ ID NO 190
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
cugcagcagc ugccugac                                                 18

<210> SEQ ID NO 191
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ccugcagcag cugccuga                                                 18

<210> SEQ ID NO 192
<211> LENGTH: 18
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 192
uccugcagca gcugccug                                              18

<210> SEQ ID NO 193
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
cuccugcagc agcugccu                                              18

<210> SEQ ID NO 194
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ccuccugcag cagcugcc                                              18

<210> SEQ ID NO 195
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
cccuccugca gcagcugc                                              18

<210> SEQ ID NO 196
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ccccuccugc agcagcug                                              18

<210> SEQ ID NO 197
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
accccuccug cagcagcu                                              18

<210> SEQ ID NO 198
<211> LENGTH: 18
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 198
ucaaauccuu acaaacau                                                 18

<210> SEQ ID NO 199
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uucauucaaa uccuuaca                                                 18

<210> SEQ ID NO 200
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
accauuucau ucaaaucc                                                 18

<210> SEQ ID NO 201
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
auaaaaccau uucauuca                                                 18

<210> SEQ ID NO 202
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uacucauaaa accauuuc                                                 18

<210> SEQ ID NO 203
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
aacuauacuc auaaaacc                                                 18

<210> SEQ ID NO 204
<211> LENGTH: 18
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 204
ucagaaacua uacucaua                                                    18

<210> SEQ ID NO 205
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
aaauuucaga aacuauac                                                    18

<210> SEQ ID NO 206
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ucaaacagga aacgucug                                                    18

<210> SEQ ID NO 207
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
caggaaacgu cugucagg                                                    18

<210> SEQ ID NO 208
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
aacgucuguc aggcacug                                                    18

<210> SEQ ID NO 209
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
cugucaggca cuggcacc                                                    18

<210> SEQ ID NO 210
<211> LENGTH: 18
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 210
aggcacuggc accaggau                                                    18

<210> SEQ ID NO 211
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
cuggcaccag gaucggca                                                    18

<210> SEQ ID NO 212
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
accaggaucg gcauugua                                                    18

<210> SEQ ID NO 213
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
gaucggcauu guacagua                                                    18

<210> SEQ ID NO 214
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
aggcacacua guugacac                                                    18

<210> SEQ ID NO 215
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
agagcaggca cacuaguu                                                    18

<210> SEQ ID NO 216
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 216
aggagagagc aggcacac                                                18

<210> SEQ ID NO 217
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
agcagaggag agagcagg                                                18

<210> SEQ ID NO 218
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
cagaaagcag aggagaga                                                18

<210> SEQ ID NO 219
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uucaccagaa agcagagg                                                18

<210> SEQ ID NO 220
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ucagcuucac cagaaagc                                                18

<210> SEQ ID NO 221
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
aagggucagc uucaccag                                                18

<210> SEQ ID NO 222
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 222
aguacaucag caguggca                                                18

<210> SEQ ID NO 223
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
aucagcagug gcaaagga                                                18

<210> SEQ ID NO 224
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
caguggcaaa ggaaugcu                                                18

<210> SEQ ID NO 225
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
gcaaaggaau gcuaaguc                                                18

<210> SEQ ID NO 226
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ggaaugcuaa gucaucca                                                18

<210> SEQ ID NO 227
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gcuaagucau ccacgagg                                                18

<210> SEQ ID NO 228
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228

```
gucauccacg agguuuau                                                   18

<210> SEQ ID NO 229
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
ccacgagguu uauaucca                                                   18

<210> SEQ ID NO 230
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
aauccaaccu aagacaua                                                   18

<210> SEQ ID NO 231
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
aaucaaaucc aaccuaag                                                   18

<210> SEQ ID NO 232
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
caacuaauca aauccaac                                                   18

<210> SEQ ID NO 233
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
aaaaccaacu aaucaaau                                                   18

<210> SEQ ID NO 234
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
```
aggccaaaac caacuaau                                             18

<210> SEQ ID NO 235
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
aaggcaggcc aaaaccaa                                             18

<210> SEQ ID NO 236
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
cauuaaaggc aggccaaa                                             18

<210> SEQ ID NO 237
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ccugccauua aaggcagg                                             18

<210> SEQ ID NO 238
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
agaacauaua ugaacacu                                             18

<210> SEQ ID NO 239
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
auauaugaac acugagcc                                             18

<210> SEQ ID NO 240
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ugaacacuga gcccaacu                                             18

<210> SEQ ID NO 241
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
acugagccca acuauuag                                                 18

<210> SEQ ID NO 242
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gcccaacuau uagaaaaa                                                 18

<210> SEQ ID NO 243
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
acuauuagaa aaacugcc                                                 18

<210> SEQ ID NO 244
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uagaaaaacu gccgauuu                                                 18

<210> SEQ ID NO 245
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
aaacugccga uuuuuuuu                                                 18

<210> SEQ ID NO 246
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gggcccaggg ucag                                                     14

<210> SEQ ID NO 247
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
cugaucugcc cagguggg                                                   18

<210> SEQ ID NO 248
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gugggcugau cugcccag                                                   18

<210> SEQ ID NO 249
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ggguuguggg cugaucug                                                   18

<210> SEQ ID NO 250
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
cugaaggguu gugggcug                                                   18

<210> SEQ ID NO 251
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
gggcccugaa ggguugug                                                   18

<210> SEQ ID NO 252
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ugagcgggcc cugaaggg                                                   18

```
<210> SEQ ID NO 253
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uggcaugagc gggcccug                                                       18

<210> SEQ ID NO 254
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
aagacugagc ccagcagc                                                       18

<210> SEQ ID NO 255
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ugagcccagc agcuugaa                                                       18

<210> SEQ ID NO 256
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
ccagcagcuu gaagcuca                                                       18

<210> SEQ ID NO 257
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
agcuugaagc ucagagga                                                       18

<210> SEQ ID NO 258
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gaagcucaga ggacccca                                                       18

<210> SEQ ID NO 259
```

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
ucagaggacc ccacccca                                                18

<210> SEQ ID NO 260
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260 ggacccacc ccaccucu                                                 18

<210> SEQ ID NO 261
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
ccaccccacc ucuuaagg                                                18

<210> SEQ ID NO 262
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
augagcgggc ccugaagg                                                18

<210> SEQ ID NO 263
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
caugagcggg cccugaag                                                18

<210> SEQ ID NO 264
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
gcaugagcgg gcccugaa                                                18

<210> SEQ ID NO 265
<211> LENGTH: 18
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ggcaugagcg ggcccuga                                                   18

<210> SEQ ID NO 266
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
uggcaugagc gggcccug                                                   18

<210> SEQ ID NO 267
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
guggcaugag cgggcccu                                                   18

<210> SEQ ID NO 268
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
gguggcauga gcgggccc                                                   18

<210> SEQ ID NO 269
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
cgguggcaug agcgggcc                                                   18

<210> SEQ ID NO 270
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ucgguggcau gagcgggc                                                   18

<210> SEQ ID NO 271
<211> LENGTH: 18
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 271
gucgguggca ugagcggg                    18

<210> SEQ ID NO 272
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 272
cgagguuucu cuagggaa                    18

<210> SEQ ID NO 273
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 273
gggcucgagg uuucucua                    18

<210> SEQ ID NO 274
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 274
caccagggcu cgagguuu                    18

<210> SEQ ID NO 275
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 275
accugcacca gggcucga                    18

<210> SEQ ID NO 276
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
cagugaccug caccaggg                    18

<210> SEQ ID NO 277
<211> LENGTH: 18
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 277
agacacagug accugcac                                                 18

<210> SEQ ID NO 278
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
accccagaca cagugacc                                                 18

<210> SEQ ID NO 279
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
ccggcacccc agacacag                                                 18

<210> SEQ ID NO 280
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
gucagcaagg uaccaggg                                                 18

<210> SEQ ID NO 281
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
gggauguguc acacacac                                                 18

<210> SEQ ID NO 282
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
gugucacaca cacagccc                                                 18

<210> SEQ ID NO 283
<211> LENGTH: 18
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 283
acacacacag cccacccc                                                   18

<210> SEQ ID NO 284
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
cacagcccac ccccgucc                                                   18

<210> SEQ ID NO 285
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
cccacccccg uccaguca                                                   18

<210> SEQ ID NO 286
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ccccguccag ucacgcac                                                   18

<210> SEQ ID NO 287
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
uccagucacg cacggaca                                                   18

<210> SEQ ID NO 288
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
ccccuccucu caccccag                                                   18

<210> SEQ ID NO 289
<211> LENGTH: 18
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 289 agagccccu ccucucac                                                  18

<210> SEQ ID NO 290
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gcuucagagc cccucccu                                                 18

<210> SEQ ID NO 291
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ggugagcuuc agagcccc                                                 18

<210> SEQ ID NO 292
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
gcaaggguga gcuucaga                                                 18

<210> SEQ ID NO 293
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
cagcugcaag ggugagcu                                                 18

<210> SEQ ID NO 294
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
gggcccagcu gcaagggu                                                 18

<210> SEQ ID NO 295
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 295
agggugggcc cagcugca                                                        18

<210> SEQ ID NO 296
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296 gcaugggug ggcccagc                                                         18

<210> SEQ ID NO 297
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
gcacaggccg cacccagg                                                        18

<210> SEQ ID NO 298
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
gggcacaggc cgcaccca                                                        18

<210> SEQ ID NO 299
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
gagacggagg uggcaggg                                                        18

<210> SEQ ID NO 300
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
gacaagagac ggaggugg                                                        18

<210> SEQ ID NO 301
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 301
ugggagacaa gagacgga                                              18

<210> SEQ ID NO 302
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ggagguggga gacaagag                                              18

<210> SEQ ID NO 303
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303 ggguggggagg ugggagac                                             18

<210> SEQ ID NO 304
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ugcaugggug ggaggugg                                              18

<210> SEQ ID NO 305
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
gcccuguggu cagccugg                                              18

<210> SEQ ID NO 306
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
guggucagcc uggcccca                                              18

<210> SEQ ID NO 307
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
```
cagccuggcc ccagccca                                            18

<210> SEQ ID NO 308
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uggccccagc ccacagug                                            18

<210> SEQ ID NO 309
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ccagcccaca gugacagc                                            18

<210> SEQ ID NO 310
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
ccacagugac agcagggc                                            18

<210> SEQ ID NO 311
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gugacagcag ggcuuugg                                            18

<210> SEQ ID NO 312
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
agcagggcuu uggcaacg                                            18

<210> SEQ ID NO 313
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
accagugcac cggaugcc                                                    18

<210> SEQ ID NO 314
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
gacagaccag ugcaccgg                                                    18

<210> SEQ ID NO 315
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
cagaagacag accagugc                                                    18

<210> SEQ ID NO 316
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
aagcccagaa gacagacc                                                    18

<210> SEQ ID NO 317
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
aacuaaagcc cagaagac                                                    18

<210> SEQ ID NO 318
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
ggcaaaacua aagcccag                                                    18

<210> SEQ ID NO 319
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
cuaaaggcaa aacuaaag                                                    18

```
<210> SEQ ID NO 320
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cuggacuaaa ggcaaaac                                                 18

<210> SEQ ID NO 321
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
ucacacgcuc cagcccu                                                  18

<210> SEQ ID NO 322
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
cgcuccagcc ccuacugc                                                 18

<210> SEQ ID NO 323
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
cagccccuac ugcccau                                                  18

<210> SEQ ID NO 324
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
ccuacugccc caugcccg                                                 18

<210> SEQ ID NO 325
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
ugccccaugc ccgccucg                                                 18
```

```
<210> SEQ ID NO 326
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
caugcccgcc ucgaguga                                                 18

<210> SEQ ID NO 327
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
ccgccucgag ugagcggc                                                 18

<210> SEQ ID NO 328
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ucgagugagc ggccacca                                                 18

<210> SEQ ID NO 329
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uuaacugcaa uauauuuc                                                 18

<210> SEQ ID NO 330
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
guuguuuaac ugcaauau                                                 18

<210> SEQ ID NO 331
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
uuauuguugu uuaacugc                                                 18
```

```
<210> SEQ ID NO 332
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332 auuuuuauu guuguuua                                                    18

<210> SEQ ID NO 333
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uaaaaauuuu uuauuguu                                                   18

<210> SEQ ID NO 334
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
uaagauaaaa auuuuuua                                                   18

<210> SEQ ID NO 335
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
uuuaauaaga uaaaaauu                                                   18

<210> SEQ ID NO 336
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
uuaauuuuaa uaagauaa                                                   18

<210> SEQ ID NO 337
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
gucaaacaca cauacaca                                                   18

<210> SEQ ID NO 338
```

<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
acacacauac acacuuaa                                              18

<210> SEQ ID NO 339
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
cauacacacu uaaaacau                                              18

<210> SEQ ID NO 340
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
acacuuaaaa cauuauga                                              18

<210> SEQ ID NO 341
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
uaaaacauua ugauaaaa                                              18

<210> SEQ ID NO 342
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
cauuaugaua aaaguugu                                              18

<210> SEQ ID NO 343
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ugauaaaagu ugucaauu                                              18

<210> SEQ ID NO 344
<211> LENGTH: 18

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
aaaguuguca auucagaa                                                18

<210> SEQ ID NO 345
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
cuaagguuuc uucuccca                                                18

<210> SEQ ID NO 346
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
uuucucuaag guuucuuc                                                18

<210> SEQ ID NO 347
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
aagaauuucu cuaagguu                                                18

<210> SEQ ID NO 348
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
guuccaagaa uuucucua                                                18

<210> SEQ ID NO 349
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
cucugguucc aagaauuu                                                18

<210> SEQ ID NO 350
<211> LENGTH: 18
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 350
cucuacucug guuccaag                                                 18

<210> SEQ ID NO 351
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
accaccucua cucugguu                                                 18

<210> SEQ ID NO 352
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
guaccaccac cucuacuc                                                 18

<210> SEQ ID NO 353
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
gaguguuaca auaucgaa                                                 18

<210> SEQ ID NO 354
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uuacaauauc gaaagcuc                                                 18

<210> SEQ ID NO 355
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
auaucgaaag cucaccua                                                 18

<210> SEQ ID NO 356
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
gaaagcucac cuaacuaa                                                 18

<210> SEQ ID NO 357
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
cucaccuaac uaaagaau                                                 18

<210> SEQ ID NO 358
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
cuaacuaaag aauagaua                                                 18

<210> SEQ ID NO 359
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
uaaagaauag auaaaauc                                                 18

<210> SEQ ID NO 360
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
aauagauaaa auccagaa                                                 18

<210> SEQ ID NO 361
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
aauuuuuuau uguuguuu                                                 18

<210> SEQ ID NO 362
<211> LENGTH: 18
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 362 aaauuuuua uuguuguu                                                      18

<210> SEQ ID NO 363
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363 aaaauuuuu auuguugu                                                      18

<210> SEQ ID NO 364
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
aaaaauuuuu uauuguug                                                     18

<210> SEQ ID NO 365
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uaaaaauuuu uuauuguu                                                     18

<210> SEQ ID NO 366
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
auaaaaauuu uuuauugu                                                     18

<210> SEQ ID NO 367
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
gauaaaaauu uuuuauug                                                     18

<210> SEQ ID NO 368
<211> LENGTH: 18
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 368
agauaaaaau uuuuuauu                                                   18

<210> SEQ ID NO 369
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
aagauaaaaa uuuuuuau                                                   18

<210> SEQ ID NO 370
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
gaguguuaca auaucgaa                                                   18

<210> SEQ ID NO 371
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
aguguuacaa uaucgaaa                                                   18

<210> SEQ ID NO 372
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
guguuacaau aucgaaag                                                   18

<210> SEQ ID NO 373
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
uguuacaaua ucgaaagc                                                   18

<210> SEQ ID NO 374
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
guuacaauau cgaaagcu                                                        18

<210> SEQ ID NO 375
<211> LENGTH: 1000
<212> TYPE: DNA
<213> ORGANISM: Homo sapiens

<400> SEQUENCE: 375
ccaaataagg tctgaatgac acaaatttta gaactctcca gagaaaagaa agatgctgag          60
ggaaaaagca taggtttggg actcactaaa tcccagttca attcctttct ttaataaata         120
tattcaattt tacctgagaa agctctcgtg ctctcgaatt ttatttagaa atttctcttt         180
gtacatgatt gatttcacaa tccttcttct gcctcctctt ctactttctt ctttctagat         240
tttcctatct ttatgaagat tattctgcct tatcctcaac agttagaaac aatattttg          300 aaaatcacta cggtatcctg catagtgatt cccatgcca actttactaa tttccattat          360
aaattattat ttattgatgc ctagagggca gatgagtgta gctgctatgg agtgaggaga         420
caaaacataa gaaagttatg atcctaccct caggtaatga ttcagacatg ataattaagt         480
caacaaattg atagaaacta atcactaact ctctggctat agtcattctt tcaatgaata         540
gctcattact gagtatgcat gctacagtaa caaaattata taaggctgtt gattaaatgt         600
tgattaagtg catgtcttat tcagagtttt tttatatttg aaatggaaga ggctggactt         660
cagtaatttg ctataaactg ctagtatatg attatttggg ggcagttatt ttttaaagaa         720
taatttaaat atggaatgtt tagcagtttg ttttttccct gggaaaaacc atactattat         780
tccctcccaa tcccttttgac aaagtgacag tcacattagt tcagagatat tgatgttta         840 tacaggtgta gcctgtaaga gatgaagcct ggtatttata gaaattgact tattttattc         900
tcatatttac atgtgcataa ttttccatat gccagaaaag ttgaatagta tcagattcca         960
aatctgtatg gagaccaaat caagtgaata tctgttcctc                              1000

<210> SEQ ID NO 376
<211> LENGTH: 1000
<212> TYPE: DNA
<213> ORGANISM: Homo sapiens

<400> SEQUENCE: 376
gcccgccttg gcctcccaaa gtgttgggat tagtggcgtg agccactgcc ccggcctatt          60
actcctttag agtgatttag agccatgttt acttatggta acttgacagt aatgggaata         120
accactgatg aaacgtaaag cctttgtcta attgtttacc tagttcttcc ttgtggttca         180 tgaaatttttt catctctgta cagtttgaaa attaagatga taatatttag agatatttta         240
ttcctttgtg aagagaaaaa aggctttcat taacagaaat cagtggcaat aacttaataa         300
atacaatcag ctggtgttcc tatagtattt aaaagaaaac agaaagttta ctagatttca         360
gccagttttc agactattta atgtctattc ttactataat agaaaatata taatttgatc         420
ttgttctcat ttttcaaaga cctttaatac atgatttag tagttgaaaa tgaagtttaa          480
tgatagttta tgcctctact tttaaaaaca aagtctaaca gattttctc atgttaaatc          540 acagaaaaag ccacctgaca ttttaacttg tttttgattt gacagtgaaa tcttataaat         600
ctgccacagt tctaaaccaa taagatcaa ggtataaggg aaaaatgtag aatgtttgtg          660
tgtttatttt ttccacccttg ttctaagcac agcaatgagc attcgtaaaa gccttacttt         720

| | |
|---|---|
| atttgtccac cctttttcatt gttttttaga agcccaacac ttttctttaa cacatacaat | 780 |
| gtggcctttt catgaaatca attccctgca cagtgatata tggcagagca ttgaattctg | 840 |
| ccaaatatct ggctgagtgt ttggtgttgt atggtctcca tgagattttg tctctataat | 900 |
| acttgggtta atctccttgg atatacttgt gtgaatcaaa ctatgttaag ggaaatagga | 960 |
| caactaaaat atttgcacat gcaacttatt ggtcccactt | 1000 |

<210> SEQ ID NO 377
<211> LENGTH: 1000
<212> TYPE: DNA
<213> ORGANISM: Homo sapiens

<400> SEQUENCE: 377

| | |
|---|---|
| atttcctctc agggttaccc tctgatccct attttactaa atcgttataa aacaaaatga | 60 |
| ggaattatgt gtccttccct tttgaagcca atgtaacaag atgggtaaga attagacctc | 120 |
| ctgagttcaa aatccctgga ttcagatcta ttcctgtata ttcaggagaa gtggtaataa | 180 |
| attcgatgga caatttggtt tagtagtcga ttgaggaccc tgatgaggta tatttgggaa | 240 |
| aacataactt ccgctctctc tcattgactc acgggccttt gaggagtcca ggagtcattg | 300 |
| gaatctggcc tgaggttgag gctgctggca aaactccttc cccaaagtcc attcctattg | 360 |
| ctgactgaga agggactagc attggaagtg gctgatttta ataccgcta gtgctggtgt | 420 |
| gctcctccct cccattccca gctctgcttt gtgtagttgc cttgagaagc taagttcatt | 480 |
| ctgaaaataa tgccattgca caaaacactt ttgaaagttc tagtttgaaa ttacatcagg | 540 |
| tcacttggtc tgtgtggcct cagtttcttc atctgccatg tgaaaataat aatgcctact | 600 |
| ctgtagcaaa gaaagtctct atagtaaaca aaaaaaaagc ctactctgat actgaaagtt | 660 |
| gttatgaaaa ataaaaaagg gaaatgcttt agaaactgtt aagtgctatg tagatgttac | 720 |
| taattaacaa accatttcag aaactatact ttttatttta tggccactat tcactgttta | 780 |
| acttaaaata cctcatatgt aaacttgtct cccactgttg ctataacaaa tcccaagtct | 840 |
| tatttcaaag taccaagata ttgaaaatag tgctaagagt ttcacatatg gtatgaccct | 900 |
| ctatataaac tcattttaag tctcctctaa agatgaaaag tcttgtgttg aaattctcag | 960 |
| ggtattttat gagaaataaa tgaaatttaa tttctctgtt | 1000 |

<210> SEQ ID NO 378
<211> LENGTH: 1000
<212> TYPE: DNA
<213> ORGANISM: Homo sapiens

<400> SEQUENCE: 378

| | |
|---|---|
| gaggctgagg caggagaatg gcgtgaaccc aggaggcaga acttgcagtg agccgagatc | 60 |
| gcgccactgc actctagcct gggtgacaga gtgagactct gtctctaaat aaataaataa | 120 |
| ataaataaat aaataaataa aatcagtgct ttttcttcct ctgctacctc ctttccttct | 180 |
| actcagtttt agtcagtagt attatctttt ttcagattta tctttgtatt gttaaatctg | 240 |
| cttatgcttc tattacttta tttattagct ttaaatgata cctttttgact ttcagctttt | 300 |
| cttaataaag caatcagcaa atttccttta cactccacac ttatacccca tttcctttgt | 360 |
| ttgtttattt ggttttttact tctaactttt cttattgtca ggacatataa catatttaaa | 420 |
| ctttgttttt caactcgaat tctgccatta gtttttaattt ttgttcacag ttatataaat | 480 |
| ctttgttcac tgatagtcct tttgtactat catctcttaa atgactttat actccaagaa | 540 |
| aggctcatgg gaacaatatt acctgaatat gtctctatta cttaatctgt acctaataat | 600 |

| | |
|---|---|
| atgaaggtaa tctactttgt aggatttctg tgaagattaa ataaattaat atagttaaag | 660 |
| cacatagaac agcactcgac acagagtgag cacttggcaa ctgttagctg ttactaacct | 720 |
| ttcccattct cctccaaac ctattccaac tatctgaatc atgtgcccct tctctgtgaa | 780 |
| cctctatcat aatacttgtc acactgtatt gtaattgtct cttttacttt cccttgtatc | 840 |
| ttttgtgcat agcagagtac ctgaaacagg aagtatttta aatattttga atcaaatgag | 900 |
| ttaatagaat ctttacaaat aagaatatac acttctgctt aggatgataa ttggaggcaa | 960 |
| gtgaatcctg agcgtgattt gataatgacc taataatgat | 1000 |

<210> SEQ ID NO 379
<211> LENGTH: 1000
<212> TYPE: DNA
<213> ORGANISM: Homo sapiens

<400> SEQUENCE: 379

| | |
|---|---|
| gaggaggtgg aaacgaatgt acaaggatgg gaggagaaaa gggagagaga cttttttttt | 60 |
| tttaaggcga gagtttacta cctatctaac tcttcgcatt cttgaagtct cagaccaaat | 120 |
| cccatcggtt tgaaagcctc tagggtattc tatctattgt atacttctgt tatgtacaaa | 180 |
| attaatttgc caattaattg tgaactgttt tataaactat cttaaaatgg ttagttaaat | 240 |
| ctttgggata gtatttagct ttctccagga ttatgactta ccttctaaat tagacataca | 300 |
| atgcctagga gtcaaggact attttgcata aattccagtc ttcttttaca atgcctagaa | 360 |
| tgattgttac cacagaaata ttcattacct gggagaaagg atgacaggag gggcagaatg | 420 |
| aatggagaga ggtcgtgaga atgaggtgct gaggatggac gaggaagaaa gctgttttag | 480 |
| ttgggaggat aggtgacaga agcatggaaa ggaattgcct tggacccatg gaagcccagt | 540 |
| gaagatactt agatcctgca ggggtgtgaa taatgttctt ttagtttctc ttcttaggag | 600 |
| gtttgttcat tttgggagat ttcttttgaa aagagtgaac ttaaattgga gaaaagtaca | 660 |
| ttttagtatg ttgataacat ttgaatttgt aaaatggacc tatggatgat ctacacatat | 720 |
| ttatatcccc ataaatatac acatatttta atttttggta ttttataatt attatttaat | 780 |
| gatcattcat gacattttaa aaattacaga aaaatttaca tctaaaattt cagcaatgtt | 840 |
| gtttttgacc aactaaataa attgcatttg aaataatgga gatgcaatgt tcaaaatttc | 900 |
| aactgtggtt aaagcaatag tgtgatatat gattacatta gaaggaagat gtgcctttca | 960 |
| aattcagatt gagcatacta aaagtgactc tctaattttc | 1000 |

<210> SEQ ID NO 380
<211> LENGTH: 1000
<212> TYPE: DNA
<213> ORGANISM: Homo sapiens

<400> SEQUENCE: 380

| | |
|---|---|
| tagaacagag cacagatgat ctaaatataa aaagaactac aaaaatcaca gttgtttaaa | 60 |
| aaggtttttt gtttgtttat atatggtgca gaacatttgt tccttagcca aatgtttcca | 120 |
| ccttgagaaa gctatagaga ttctatgtag tcctagtacc aataatatgt tttaacctga | 180 |
| atgtacctta tctttattca taaactgtga cttttttcac tgctgaaact ttttttttta | 240 |
| agacaatctc actctgtcgt ccagtctgga gtgcagcagt ggtgtgatct tggctcactg | 300 |
| caacctctac cttctgtgtt caagcaattc tggtgcctcg gccacctgag tagttgggat | 360 |
| cacaggtgta caccaccagg cctggctaat agttttttgat atttctagta gagatgagtt | 420 |

| | |
|---|---|
| ttgccacatt ggccaggctg gcctgaaact cctggcctca agtgatctgc ctgccttggc | 480 |
| ctcccaaagt gttggtatta caagtgtgag ccactgtgcc tggcctgaaa ctcataattc | 540 |
| atttccatta atattaatct cacctttttcc aataattaat tgatttcaca agtattagtc | 600 |
| ccctataatc attgaatggc taataaaatt atttatagca aacagattaa ttatctgcca | 660 |
| gcagtctgag attagtttct ttaaaaaatg tttattattt aaaacattca gctgtgatct | 720 |
| tggctttctt gtgaggttca atagtttcta ttgagtaaag gagagaaatg gcagagaatt | 780 |
| tacttcagtg aaatttgaat tccattaact taatgtggtc tcatcacaaa taatagtact | 840 |
| tagaacacct agtacagctg ctggacccag gaacacaaag caaaggaaga tgaaattgtg | 900 |
| tgtaccttga tattggtaca cacatcaaat ggtgtgatgt gaatttagat gtgggcatgg | 960 |
| gaggaatagg tgaagatgtt agaaaaaaaa tcaactgtgt | 1000 |

<210> SEQ ID NO 381
<211> LENGTH: 1000
<212> TYPE: DNA
<213> ORGANISM: Homo sapiens

<400> SEQUENCE: 381

| | |
|---|---|
| aaataagagc agtaaaattg tgtctaatca gctactaata tctgggaagg attgagccac | 60 |
| aggatcaaag atggtatctt ttaaaaatag aagttgagtg aattcggtct tcaaattctt | 120 |
| tctttttatt catttatatt tatttactca ttagtatatt cattccttta ttcatgtatt | 180 |
| gttcaaatat atattgggta cttattatat gccaagttgt ttttaaaatc acattccaaa | 240 |
| ttcccgtaag tcataattat tcagagatgt atgttttttt taaaaaaaat tgaacacctt | 300 |
| taaaaattat caagtccttt tatttctgta tgcattaaag ataaacttta ctaaatgtta | 360 |
| catgaataga tttataaagc agataaatat ttaatttcaa atataaccct tatatgcaat | 420 |
| tatatttttcc ttagcactaa aaatgaatat ttaagtaatt tatattaaaa gtgtaattat | 480 |
| ttaactgcag atgtatgcca atgacttaaa ttgtttaaag attatagcaa agttgtttaa | 540 |
| aattgtctaa tcatgaagag ttcacttaac cacctggttg acacataaaa ttatagttag | 600 |
| ttactaaggt agttcgagag aaagagaaga atcttcagta gtggttttga ggtgtggtac | 660 |
| attttattat aatataccgg ttatacagca ttgtgcagtg ctgctcatag tagaaataaa | 720 |
| ttttctcttt gatgtcatct attcccttgt gtggcttaca taactgagaa ttaggtgatc | 780 |
| acaaaaataa acaggcctat acagagccca tttatataag tcctggttat ttctcttcag | 840 |
| ttaaactttt aattatatcc aattatttcc tgttagttca ttgaaaagcc cgacaaataa | 900 |
| ccaagtgaca aatagcaagt gttgcatttt acaagttatt ttttaggaag catcaaacta | 960 |
| attgtgaaat tgtctgccat tcttaaaaac aaaaatgttg | 1000 |

<210> SEQ ID NO 382
<211> LENGTH: 1000
<212> TYPE: DNA
<213> ORGANISM: Homo sapiens

<400> SEQUENCE: 382

| | |
|---|---|
| aacaaaactg tccttcacta cagattgaaa agcattatac taaaagacca tttgctcagt | 60 |
| tatagtatat aaaggccaaa tgacttaaaa acaaattatg taaggagaag gaaacaacca | 120 |
| tttattcagt gccactaact gtcagccagt tttttcagtg gtcagttaat gactgcagta | 180 |
| gtgttctacc ttgctcaaag caccctcctc aagttctggc atctaagctg acatcagaac | 240 |
| acagagttgg ggctctctgt gggtcacctc tagcacttga tctcctcatg cagtgcatgg | 300 |

```
tgctctcacg tctatgctat gttcttatgg tctttaggta acaagaataa ttttctttct      360
tttccttact atacattttg ctttctgaaa ttcccttctc gccaatccag gtgaatgtca      420
gaatgtgatt tgacaactgt ccaaagtact cattcactga ggagtggtaa ggccttcgcc      480
caacctgcct tctctgggaa tatactgctg cctgaacata tcattgttta ttgccaggct      540
tgaacttcac caaattaatt tattagggtc aacatctaaa tattagaact atttcagatt      600
aatttttaag tcgtatccac tttgggtact agatcaaatt gcaggtctct gcttctggct      660
tgagcctatg tttagagatg atgtgcatga agacactctt tgcttttcct ttatgcaaaa      720
tgggcatttt caatcttttt gtcattagta aaggtcagtg ataaaggaag tctgcatcag      780
gggtccaatt ccttatggcc agtttctcta ttctgttcca aggttgtttg tctccatata      840
tcaacattgg tcaggattga agtgtgcaa caaggtttga atgaataagt gaaaatcttc       900
cactggtgac aggataaaat attccaatgg ttttattga agtacaatac tgaattatgt       960
ttatggcatg gtacctatat gtcacagaag tgatcccatc                          1000

<210> SEQ ID NO 383
<211> LENGTH: 1000
<212> TYPE: DNA
<213> ORGANISM: Homo sapiens

<400> SEQUENCE: 383
ttgacttgac ttgtgtggtt ccttgtggac cagatggcca ctaaatattc tcatttcaag       60
gcaattggta aaactacac ttcaagaaat ttcattctta attcccctta gtggatgtta       120
ttaaccaaag gcaaagaaa aaagggtaa aaaaaatatt ctaaatgtta atatcaaaaa         180
tattattttc aattcacccc aggcacagag aactaagtat tattattgct attgcaccgg      240
cattccccaa tgagacagtg attttctttt aagacatttt taaataatat aggcagaatt      300
aagtagacgg tgatctggta agtagatgtt tcagggtaac agctgtgcaa tgctccatgc      360
agggaattag attgtcattt tattccttac caggaacata cattcagtta aacaattatt      420
tgacttctgc tcttccactg atttctaagt tgaggctctc tcttgtgcct gtctgatcag      480
ataagtagag ttgtgccttg gtttatagat gagataaatg tgtatttgaa taagcataag      540
ttaaagaaat tttaaaatcc cttaggaagc taggcttatc agagaaatcc aaggaaatac      600
attaacaaac taggaatttg ttctaacagg ttaattataa ctcataaact tattgggttt      660 ttttacccttt taattttata ttacatttgc ttataataag gaatattgct aggaataaaa     720 tttttttaata ttctacaatt aacaattatc tcaatttctt tattctaaag acattgggat     780
tagaaaaatg ttcacaaggg actccaaata ttgctgtagt attttgtttct taaaagaatg    840 atacaaagca gacatgataa aatattaaaa tttgagagaa cttgatggta agtacatggg     900
tgtttcttat tttaaaataa tttttctact tgaaatattt tacaatacaa taagggaaaa     960
ataaaaagtt atttaagtta ttcatacttt cttcttcttt                          1000

<210> SEQ ID NO 384
<211> LENGTH: 1000
<212> TYPE: DNA
<213> ORGANISM: Homo sapiens

<400> SEQUENCE: 384
ataagattct ttctgagcca ttatctcatt ctatattaca gtcaggtgga gcccatctta       60
cctcctcata ctaaattcta gacttctcaa gggcaggaga caatcatctg tatatctctt      120
```

```
tggccttcat acactcagga gtacttgcca aaaataaaca tttaatgcac atttatttga      180
ataattgata agatccaata cttcaataac tttgtcatat ttttatagaa tgggtttcta      240
tatctcattt gcattttcaa actttacttt tactgtctag ctttaaaaaa aaagcctttg      300
actctaatac agccctcata ttctaccccca atatctaaga ggctttatat ctcctagtgt     360
tgtaccacta ttttaactcc agtattttt acttcatagt tttacctatt tgttacagtt      420
agtttttatg aattcaagag atgaaatagca attttccata tgtaatttaa aaaaccccac    480
agttgactat tttatgctat cttttgtcct cagtcatgac agagtagaag atgggaggta     540
gcaccaagga tgatgtcata cctccatcct ttatgctaca ttctatcttc tgtctacata    600
agatgtcata ctagagggca tatctgcaat gtatacatat tatcttttcc agcatgcatt    660
cagttgtgtt ggaataattt atgtacacct ttataaacgc tgagcctcac aagagccatg    720
tgccacgtat tgttttctta ctactttttg ggatacctgg cacgtaatag acactcattg    780
aaagtttcct aatgaatgaa gtacaaagat aaaacaagtt atagactgat tcttttgagc    840
tgtcaaggtt gtaaatagac ttttgctcaa tcaattcaaa tggtggcagg tagtgggggt    900
agagggattg gtatgaaaaa cataagcttt cagaactcct gtgtttatttt ttagaatgtc   960 aactgcttga gtgtttttaa ctctgtggta tctgaactat                         1000

<210> SEQ ID NO 385
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(32)
<223> OTHER INFORMATION: a, c, t, g, unknown or other

<400> SEQUENCE: 385
caggtaagtn nnnnnnnnn nnnnnnnnnn nn                                   32

<210> SEQ ID NO 386
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(17)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other

<400> SEQUENCE: 386
nnnnnnnnnn nnnnnnnyyy yyyyyyyyn agg                                  33

<210> SEQ ID NO 387
<211> LENGTH: 17
<212> TYPE: RNA
<213> ORGANISM: Homo sapiens

<400> SEQUENCE: 387 auuucccac ccuuagg                                                    17
```

-continued

<210> SEQ ID NO 388
<211> LENGTH: 17
<212> TYPE: RNA
<213> ORGANISM: Homo sapiens

<400> SEQUENCE: 388
uaucuuccuc ccacagc                                                       17

<210> SEQ ID NO 389
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
uuuuucccuc ccuuagg                                                       17

<210> SEQ ID NO 390
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
uuucuuccuc ccccagc                                                       17

<210> SEQ ID NO 391
<211> LENGTH: 63
<212> TYPE: DNA
<213> ORGANISM: Homo sapiens

<400> SEQUENCE: 391
gttatgtcct gtcctccttc ctgtcaggca gctgctgcag gaggggtggg caaaggcatc        60
ttc                                                                      63

<210> SEQ ID NO 392
<211> LENGTH: 80
<212> TYPE: DNA
<213> ORGANISM: Homo sapiens

<400> SEQUENCE: 392
tcctcagctt ggaagccccg gagcctgccc tgctgggaat cggggaagca ctgcttacct        60
gtctcctgct cccttttcag                                                    80

<210> SEQ ID NO 393
<211> LENGTH: 58
<212> TYPE: DNA
<213> ORGANISM: Homo sapiens

<400> SEQUENCE: 393
gtatggtgtc aactagtgtg cctgctctct cctctgcttt ctggtgaagc tgacccctt         58

<210> SEQ ID NO 394
<211> LENGTH: 68
<212> TYPE: DNA
<213> ORGANISM: Homo sapiens

<400> SEQUENCE: 394
tggatataaa cctcgtggat gacttagcat tcctttgcca ctgctgatgt actttattaa        60
cttcccag                                                            68

<210> SEQ ID NO 395
<211> LENGTH: 65
<212> TYPE: DNA
<213> ORGANISM: Homo sapiens

<400> SEQUENCE: 395
gttccctgac cctgggcccc acctgggcag atcagcccac aacccttcag ggcccgctca    60
tgcca                                                               65

<210> SEQ ID NO 396
<211> LENGTH: 68
<212> TYPE: DNA
<213> ORGANISM: Homo sapiens

<400> SEQUENCE: 396
ccttaagagg tggggtgggg tcctctgagc ttcaagctgc tgggctcagt cttccaccct    60
ccacgcag                                                            68

<210> SEQ ID NO 397
<211> LENGTH: 70
<212> TYPE: DNA
<213> ORGANISM: Homo sapiens

<400> SEQUENCE: 397
gttccctgac cctgggcccc acctgggcag atcagcccac aacccttcag ggcccgctca    60
tgccaccgac                                                          70

<210> SEQ ID NO 398
<211> LENGTH: 66
<212> TYPE: DNA
<213> ORGANISM: Homo sapiens

<400> SEQUENCE: 398
gtgagcctgg gtgcggcctg tgccctgcc acctccgtct cttgtctccc acctcccacc     60
catgca                                                              66

<210> SEQ ID NO 399
<211> LENGTH: 68
<212> TYPE: DNA
<213> ORGANISM: Homo sapiens

<400> SEQUENCE: 399
cgttgccaaa gccctgctgt cactgtgggc tggggccagg ctgaccacag ggccccccg     60 tccaccag                                                            68

<210> SEQ ID NO 400
<211> LENGTH: 58
<212> TYPE: DNA
<213> ORGANISM: Homo sapiens

<400> SEQUENCE: 400
gtatggaaat atattgcagt taaacaacaa taaaaatttt ttatcttatt aaaattaa      58

<210> SEQ ID NO 401
<211> LENGTH: 68
<212> TYPE: DNA
<213> ORGANISM: Homo sapiens

<400> SEQUENCE: 401

```
ttctgaattg acaactttta tcataatgtt ttaagtgtgt atgtgtgttt gactccactc    60
ccgcacag                                                             68

<210> SEQ ID NO 402
<211> LENGTH: 58
<212> TYPE: DNA
<213> ORGANISM: Homo sapiens

<400> SEQUENCE: 402
gtgagtggga gaagaaacct tagagaaatt cttggaacca gagtagaggt ggtggtac     58

<210> SEQ ID NO 403
<211> LENGTH: 68
<212> TYPE: DNA
<213> ORGANISM: Homo sapiens

<400> SEQUENCE: 403
ttctggattt tatctattct ttagttaggt gagctttcga tattgtaaca ctctgagttt    60
gctttaag                                                             68
```

TARGETED AUGMENTATION OF NUCLEAR GENE OUTPUT

CROSS-REFERENCE

This application claims the benefit of U.S. Provisional Application No. 62/059,847, filed Oct. 3, 2014, which application is incorporated herein by reference.

STATEMENT AS TO FEDERALLY SPONSORED RESEARCH

This invention was made with government support under grant GM042699 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 17, 2015, is named 47991-701.201_SL.txt and is 179,220 bytes in size.

BACKGROUND

Some genetic diseases are caused by haploinsufficiency, in which there is only one functional copy of a gene and that single copy does not produce enough of the gene product. For example, this can be caused by hemizygous deletions, in which one copy of the gene is lost. Other genetic diseases are caused by mutations which alter the gene product, so that it possesses only partial function.

SUMMARY

As described herein, antisense oligomers (ASOs) can be used to increase production of proteins, or functional RNAs in the case of non-protein coding genes, by promoting constitutive splicing (employing the wild-type sequence) at an intron splice site of an intron-containing gene to increase expression of the gene product. The ASOs described for use in these methods promote constitutive splicing and do not correct aberrant splicing resulting from mutation, or promote constitutive splicing and do not modulate alternative splicing. The methods described herein may therefore be used to treat a condition resulting from reduced expression or insufficient activity of a gene product.

Described here are methods of increasing expression in cells of a target protein encoded by a pre-mRNA that comprises at least one retained intron (an RIC pre-mRNA); a retained intron is one that remains present when one or more of the other introns have been spliced out (removed). Expression of the target protein depends on complete splicing (removal) of all introns in the pre-mRNA in the nucleus to generate mature mRNA that is subsequently exported to the cytoplasm and translated into the target protein. Inefficient splicing (removal) of an intron results in a retained intron-containing (RIC) pre-mRNA that accumulates primarily in the nucleus, and if exported to the cytoplasm is degraded, such that RIC pre-mRNA is not translated into the target protein. Treatment with an antisense oligomer (ASO) described by the method herein can promote the splicing of a retained intron from pre-mRNA transcripts (pre-mRNA species comprising one or more introns) and result in an increase in mRNA, which is translated to provide higher levels of target protein.

In embodiments, the method is a method of increasing expression of a target protein or functional RNA by cells having a retained-intron-containing pre-mRNA (RIC pre-mRNA), the RIC pre-mRNA comprising a retained intron, an exon flanking the 5' splice site of the retained intron, an exon flanking the 3' splice site of the retained intron, and wherein the RIC pre-mRNA encodes the target protein or functional RNA. In embodiments, the method comprises contacting the cells with an ASO complementary to a targeted portion of the RIC pre-mRNA encoding the target protein or functional RNA, whereby the retained intron is constitutively spliced from the RIC pre-mRNA encoding the target protein or functional RNA, thereby increasing the level of mRNA encoding the target protein or functional RNA, and increasing the expression of target protein or functional RNA in the cells. In embodiments, the cells are in or are from a subject, and the method is a method of treating the subject to increase expression of the target protein or functional RNA in the subject's cells. In embodiments, the cells are in or are from a subject having a condition caused by a deficient amount or activity of the target protein or a deficient amount or activity of the functional RNA. In embodiments, the target protein or the functional RNA is a compensating protein or a compensating functional RNA that functionally augments or replaces a target protein or functional RNA that is deficient in amount or activity in the subject.

In embodiments, the condition caused by a deficient amount or activity of the target protein or a deficient amount or activity of the functional RNA is not a condition caused by alternative or aberrant splicing of the retained intron to which the ASO is targeted. In embodiments, the condition caused by a deficient amount or activity of the target protein or a deficient amount or activity of the functional RNA is not a condition caused by alternative or aberrant splicing of any retained intron in a RIC pre-mRNA encoding the target protein or functional RNA.

In embodiments, the deficient amount of the target protein is caused by haploinsufficiency of the target protein, wherein the subject has a first allele encoding a functional target protein, and a second allele from which the target protein is not produced, or a second allele encoding a nonfunctional target protein, and wherein the antisense oligomer binds to a targeted portion of a RIC pre-mRNA transcribed from the first allele.

In other embodiments, the subject has a condition caused by an autosomal recessive disorder resulting from a deficiency in the amount or function of the target protein, wherein the subject has a) a first mutant allele from which i) the target protein is produced at a reduced level compared to production from a wild-type allele, ii) the target protein is produced in a form having reduced function compared to an equivalent wild-type protein, or iii) the target protein is not produced, and b) a second mutant allele from which i) the target protein is produced at a reduced level compared to production from a wild-type allele, ii) the target protein is produced in a form having reduced function compared to an equivalent wild-type protein, or iii) the target protein is not produced, and wherein the RIC pre-mRNA is transcribed from the first allele and/or the second allele. In embodiments, the target protein is produced both at a reduced level and in a form having reduced function compared to an equivalent wild-type protein.

In embodiments, the target protein is produced in a form having reduced function compared to the equivalent wild-type protein. In other embodiments, the target protein is produced in a form that is fully-functional compared to the equivalent wild-type protein.

In embodiments, the deficient amount of the functional RNA is caused by haploinsufficiency of the functional RNA, wherein the subject has a first allele encoding a functional RNA that is functional, and a second allele from which the functional RNA is not produced, or a second allele encoding a functional RNA that is nonfunctional, and wherein the antisense oligomer binds to a targeted portion of a RIC pre-mRNA transcribed from the first allele.

In other embodiments, the subject has a condition caused by an autosomal recessive disorder resulting from a deficiency in the amount or function of the functional RNA, wherein the subject has a) a first mutant allele from which i) the functional RNA is produced at a reduced level compared to production from a wild-type allele, ii) the functional RNA is produced in a form having reduced function compared to an equivalent wild-type protein, or iii) the functional RNA is not produced, and b) a second mutant allele from which i) the functional RNA is produced at a reduced level compared to production from a wild-type allele, ii) the functional RNA is produced in a form having reduced function compared to an equivalent wild-type protein, or iii) the functional RNA is not produced, and wherein the RIC pre-mRNA is transcribed from the first allele and/or the second allele. In embodiments, the functional RNA is produced both at a reduced level and in a form having reduced function compared to an equivalent wild-type functional RNA.

In embodiments, the functional RNA is produced in a form having reduced function compared to the equivalent wild-type protein. In other embodiments, the functional RNA is produced in a form that is fully-functional compared to the equivalent wild-type protein.

In embodiments, the targeted portion of the RIC pre-mRNA is in the retained intron within the region +6 relative to the 5' splice site of the retained intron to the region −16 relative to the 3' splice site of the retained intron. In embodiments, the targeted portion of the RIC pre-mRNA is in the retained intron within the region +6 to +100 relative to the 5' splice site of the retained intron; or the region −16 to −100 relative to the 3' splice site of the retained intron. In embodiments, the targeted portion of the RIC pre-mRNA is within the region +2e to −4e in the exon flanking the 5' splice site of the retained intron; or the region +2e to −4e in the exon flanking the 3' splice site of the retained intron.

In embodiments, the antisense oligomer does not increase the amount of the target protein or the functional RNA by modulating alternative splicing of pre-mRNA transcribed from a gene encoding the functional RNA or target protein. In embodiments, the antisense oligomer does not increase the amount of the target protein or the functional RNA by modulating aberrant splicing resulting from mutation of the gene encoding the target protein or the functional RNA.

In embodiments, the RIC pre-mRNA was produced by partial splicing of a full-length pre-mRNA or partial splicing of a wild-type pre-mRNA. In embodiments, the mRNA encoding the target protein or functional RNA is a full-length mature mRNA, or a wild-type mature mRNA. In embodiments, the target protein produced is full-length protein, or wild-type protein. In embodiments, the functional RNA produced is full-length functional RNA, or wild-type functional RNA.

In embodiments, the total amount of the mRNA, or the total amount of mature mRNA, encoding the target protein or functional RNA produced in the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mRNA, or the total amount of mature mRNA, encoding the target protein or functional RNA produced in a control cell.

In embodiments, the total amount of the mRNA encoding the target protein or functional RNA produced in the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mRNA encoding the target protein or functional RNA produced in a control cell.

In embodiments, the total amount of mature mRNA encoding the target protein or functional RNA produced in the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mature mRNA, encoding the target protein or functional RNA produced in a control cell.

In embodiments, the total amount of the target protein or functional RNA produced by the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of the target protein or functional RNA produced by a control cell.

In embodiments, the methods comprise contacting the cells having the RIC pre-mRNA with an antisense oligomer comprising a backbone modification comprising a phosphorothioate linkage or a phosphorodiamidate linkage. In embodiments, the antisense oligomer comprises a phosphorodiamidate morpholino (PMO), a locked nucleic acid (LNA), a peptide nucleic acid (PNA), a 2'-O-methyl, a 2'-Fluoro, or a 2'-O-methoxyethyl moiety. In embodiments, the antisense oligomer comprises at least one modified sugar moiety. In related embodiments, each sugar moiety is a modified sugar moiety.

In embodiments, the antisense oligomer consists of from 8 to 50 nucleobases. In embodiments, the antisense oligomer consists of from 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases. In embodiments, the antisense oligomer is at least 80%, at least 85%, at least 90%, at least 95%, at least 98%, at least 99%, or 100%, complementary to the targeted portion of the RIC pre-mRNA encoding the protein.

In any of the preceding methods, the cell can comprise a population of RIC pre-mRNAs transcribed from the gene encoding the target protein or functional RNA, wherein the population of RIC pre-mRNAs comprises two or more retained introns, and wherein the antisense oligomer binds to the most abundant retained intron in the population of RIC pre-mRNAs. In these embodiments, the binding of the antisense oligomer to the most abundant retained intron can induce splicing out of the two or more retained introns from the population of RIC pre-mRNAs to produce mRNA encoding the target protein or functional RNA.

In other embodiments, the cell comprises a population of RIC pre-mRNAs transcribed from the gene encoding the target protein or functional RNA, wherein the population of RIC pre-mRNAs comprises two or more retained introns, and wherein the antisense oligomer binds to the second most abundant retained intron in the population of RIC pre-mRNAs. In these embodiments, the binding of the antisense oligomer to the second most abundant retained intron can induce splicing out of the two or more retained introns from the population of RIC pre-mRNAs to produce mRNA encoding the target protein or functional RNA.

In the preceding methods, the condition can be a disease or disorder. In these embodiments, the disease or disorder can be selected from: thrombotic thrombocytopenic purpura, tuberous sclerosis complex, polycystic kidney disease, familial dysautonomia, retinitis pigmentosa type 10, retinitis pigmentosa type 11, cystic fibrosis, retinoblastoma, familial adenomatous polyposis, protein S deficiency, beta thalassemia, and sickle cell disease. In related embodiments, the target protein and the RIC pre-mRNA are encoded by a gene selected from: ADAMTS13, TSC1, PKD1, IKBKAP, IMPDH1, PRPF31, CFTR, RB1, APC, PROS1, NEDD4L, HBG1, HBG2, and HBB. In embodiments, the antisense oligomer can bind to a portion of an RIC pre-mRNA selected from SEQ ID NOS: 1-102 and 375-384.

In embodiments, any of the preceding methods further comprises assessing protein expression.

In some embodiments, the subject is a human. In other embodiments, the subject is a non-human animal. In embodiments, the antisense oligomer is administered by intravitreal injection, intrathecal injection, intraperitoneal injection, subcutaneous injection, or intravenous injection of the subject. In embodiments, the cells are ex vivo.

In embodiments, the 9 nucleotides at −3e to −1e of the exon flanking the 5' splice site and +1 to +6 of the retained intron, are identical to the corresponding wild-type sequence. In embodiments, the 16 nucleotides at −15 to −1 of the retained intron and +1e of the exon flanking the 3' splice site are identical to the corresponding wild-type sequence.

Described herein are compositions comprising an antisense oligomer for use in a method as described herein. Also described is a pharmaceutical composition comprising the antisense oligomer, and an excipient. In embodiments, the composition comprising the antisense oligomer is intended for use in a method of increasing expression of a target protein or a functional RNA by cells to treat a condition in a subject associated with a deficient protein or deficient functional RNA, wherein the deficient protein or deficient functional RNA is deficient in amount or activity in the subject, wherein the antisense oligomer enhances constitutive splicing of a retained intron-containing pre-mRNA (RIC pre-mRNA) encoding the target protein or the functional RNA, wherein the target protein is: (a) the deficient protein; or (b) a compensating protein which functionally augments or replaces the deficient protein or in the subject; and wherein the functional RNA is: (a) the deficient RNA; or (b) a compensating functional RNA which functionally augments or replaces the deficient functional RNA in the subject; wherein the RIC pre-mRNA comprises a retained intron, an exon flanking the 5' splice site and an exon flanking the 3' splice site, and wherein the retained intron is spliced from the RIC pre-mRNA encoding the target protein or the functional RNA, thereby increasing production or activity of the target protein or the functional RNA in the subject.

In embodiments, the composition comprising the antisense oligomer is intended for use in a method of treating a disease or disorder associated with a target protein or functional RNA in a subject, the method comprising the step of increasing expression of the target protein or functional RNA by cells of the subject, wherein the cells have a retained-intron-containing pre-mRNA (RIC pre-mRNA) comprising a retained intron, an exon flanking the 5' splice site of the retained intron, an exon flanking the 3' splice site of the retained intron, and wherein the RIC pre-mRNA encodes the target protein or functional RNA, the method comprising contacting the cells with the antisense oligomer, whereby the retained intron is constitutively spliced from the RIC pre-mRNA transcripts encoding the target protein or functional RNA, thereby increasing the level of mRNA encoding the target protein or functional RNA, and increasing the expression of the target protein or functional RNA, in the cells of the subject.

In embodiments, the composition comprising the antisense oligomer is intended for use in a method of treating a condition in the subject resulting from a deficiency in the amount or activity of the target protein or the functional RNA. In embodiments, the condition is a disease or disorder. In embodiments, the disease or disorder is selected from:

thrombotic thrombocytopenic purpura, tuberous sclerosis complex, polycystic kidney disease, familial dysautonomia, retinitis pigmentosa type 10, retinitis pigmentosa type 11, cystic fibrosis, retinoblastoma, familial adenomatous polyposis, protein S deficiency, beta thalassemia, and sickle cell disease. In embodiments, the composition is intended for use in a method wherein the target protein and RIC pre-mRNA are encoded by a gene selected from: ADAMTS13, TSC1, PKD1, IKBKAP, IMPDH1, PRPF31, CFTR, RB1, APC, PROS1, NEDD4L, HBG1, HBG2, and HBB.

In embodiments, the antisense oligomer of the composition targets a portion of the RIC pre-mRNA that is in the retained intron within the region +6 relative to the 5' splice site of the retained intron to the region −16 relative to the 3' splice site of the retained intron. In embodiments, the antisense oligomer of the composition targets a portion of the RIC pre-mRNA that is in the retained intron within the region +6 to +100 relative to the 5' splice site of the retained intron; or the region −16 to −100 relative to the 3' splice site of the retained intron. In embodiments, the antisense oligomer targets a portion of the RIC pre-mRNA that is within the region about 100 nucleotides downstream of the 5' splice site of the at least one retained intron, to about 100 nucleotides upstream of the 3' splice site of the at least one retained intron. In embodiments, the targeted portion of the RIC pre-mRNA is within: the region +2e to −4e in the exon flanking the 5' splice site of the retained intron; or the region +2e to −4e in the exon flanking the 3' splice site of the retained intron.

In embodiments, the antisense oligomer of the composition or as used in the methods described herein does not increase the amount of target protein or functional RNA by modulating alternative splicing of the pre-mRNA transcribed from a gene encoding the target protein or functional RNA. In embodiments, the antisense oligomer of the composition or as used in the methods described herein does not increase the amount of target protein or functional RNA by modulating aberrant splicing resulting from mutation of the gene encoding the target protein or functional RNA.

In embodiments, the RIC pre-mRNA was produced by partial splicing from a full-length pre-mRNA or a wild-type pre-mRNA. In embodiments, the mRNA encoding the target protein or functional RNA is a full-length mature mRNA, or a wild-type mature mRNA. In embodiments, the target protein produced is full-length protein, or wild-type protein. In embodiments, the functional RNA produced is full-length functional RNA, or wild-type functional RNA.

In embodiments, the retained intron is a rate-limiting intron. In embodiments, the retained intron is the most abundant intron in said RIC pre-mRNA. In embodiments, the retained intron is the second most abundant intron in said RIC pre-mRNA.

In embodiments, the antisense oligomer of the composition or as used in the methods described herein, comprises a backbone modification comprising a phosphorothioate linkage or a phosphorodiamidate linkage. In embodiments, the antisense oligomer is an antisense oligonucleotide.

In embodiments, the antisense oligomer comprises a phosphorodiamidate morpholino, a locked nucleic acid, a peptide nucleic acid, a 2'-O-methyl, a 2'-Fluoro, or a 2'-O-methoxyethyl moiety. In embodiments, the antisense oligomer comprises at least one modified sugar moiety. In related embodiments, each sugar moiety is a modified sugar moiety.

The antisense oligomer can consist of from 8 to 50 nucleobases. In embodiments, antisense oligomer consists of 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

In embodiments, the antisense oligomer is at least 80%, at least 85%, at least 90%, at least 95%, at least 98%, at least 99%, or is 100% complementary to the targeted portion of the RIC pre-mRNA encoding the protein. In embodiments, the antisense oligomer binds to a portion of an RIC pre-mRNA selected from SEQ ID NOS: 1-102 and 375-384.

In embodiments, the antisense oligomer is comprised in a pharmaceutical composition comprising an excipient.

Described herein are methods for identifying an antisense oligomer that increases the amount of mRNA encoding a target protein or functional RNA by inducing constitutive splicing of a retained intron from a RIC pre-mRNA encoding the target protein or functional RNA, from among a set of antisense oligomers that each hybridize to a target region of the RIC pre-mRNA, wherein the RIC pre-mRNA comprises at least one retained intron, wherein the antisense oligomers in the set are tiled every 1 to 5 nucleotides, and wherein the antisense oligomers in the set hybridize to the RIC pre-mRNA within the sequence that is: about 100 nucleotides upstream of the 5' splice site of the at least one retained intron, to about 100 nucleotides downstream of the 5' splice site of the at least one retained intron; or about 100 nucleotides upstream of the 3' splice site of the at least one retained intron, to about 100 nucleotides downstream of the 3' splice site of the at least one retained intron; the method comprising: a) delivering a first antisense oligomer in the set to a cell comprising the RIC pre-mRNA; b) measuring the amount of the RIC pre-mRNA and measuring the amount of mRNA encoding the target protein or functional RNA in the cell to which the first antisense oligomer was delivered; c) measuring the amount of the RIC pre-mRNA and measuring the amount of mRNA encoding a target protein or functional RNA in a control cell; and d) comparing the amounts of RIC pre-mRNA and mRNA encoding a target protein or functional RNA measured in b and c; wherein the first antisense oligomer is identified as an antisense oligomer that increases the amount of mRNA encoding the target protein or functional RNA by inducing constitutive splicing of the at least one retained intron from the RIC pre-mRNA based on an observed decrease in the amount of the RIC pre-mRNA and an observed increase in the amount of mRNA encoding the target protein or functional RNA in the cell to which the first antisense oligomer was delivered compared to a control cell; and repeating steps a through d with additional antisense oligomers in the set of antisense oligomers as needed to identify an antisense oligomer that increases the amount of mRNA from a gene in a cell by inducing constitutive splicing of a retained intron from the RIC pre-mRNA.

Also described herein are methods for identifying an antisense oligomer (ASO) for treating a condition, wherein the condition results from insufficient production of a gene product, the method comprising: identifying the presence of at least one RIC pre-mRNA in the nucleus of a cell from a subject having the condition, wherein the RIC pre-mRNA comprises at least one retained intron and is transcribed from a gene encoding the gene product, and wherein the identified RIC pre-mRNA when fully spliced to mature mRNA encodes the gene product in a form that is fully-functional or partially-functional; a) preparing a set of ASOs that each hybridize to a target region of the at least one RIC pre-mRNA, wherein the antisense oligomers in the set are tiled every 1 to 5 nucleotides, and wherein the antisense oligomers in the set hybridize to the at least one RIC pre-mRNA within the sequence that is: about 100 nucleotides upstream of the 5' splice site of the at least one retained intron, to about 100 nucleotides downstream of the 5' splice site of the at least one retained intron; or about 100 nucleotides upstream of the 3' splice site of the at least one retained intron, to about 100 nucleotides downstream of the 3' splice site of the at least one retained intron; b) delivering a first ASO in the set of ASOs to a cell comprising the at least one RIC pre-mRNA; c) measuring the amount of RIC pre-mRNA and measuring the amount of mRNA encoding the gene product in the cell to which the first antisense oligomer was delivered; d) measuring the amount of RIC pre-mRNA and measuring the amount of mRNA encoding the gene product in a control cell; and e) comparing the values obtained in steps c and d; wherein the first antisense oligomer is identified as an antisense oligomer that increases the amount of mRNA encoding the gene product by inducing constitutive splicing of the at least one retained intron from the RIC pre-mRNA based on an observed decrease in the amount of RIC pre-mRNA and an observed increase in the amount of mRNA encoding the gene product in the cell to which the first antisense oligomer was delivered compared to a control cell; and repeating steps a through e with additional antisense oligomers in the set of antisense oligomers as needed to identify an antisense oligomer that increases the amount of a mRNA encoding the gene product from a gene in a cell by inducing constitutive splicing of a retained intron from a RIC pre-mRNA; and further testing such antisense oligomers that increase the amount of a mRNA encoding the gene product in a cell by inducing constitutive splicing of a retained intron from a RIC pre-mRNA for the ability to increase the amount of the gene product produced by a cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 2A shows a cell divided into nuclear and cytoplasmic compartments. In the nucleus, a pre-mRNA transcript of a target gene consisting of exons (rectangles) and introns (connecting lines) undergoes splicing to generate an mRNA, and this mRNA is exported to the cytoplasm and translated into target protein. For this target gene, the splicing of intron 1 is inefficient and a retained intron-containing (RIC) pre-mRNA accumulates primarily in the nucleus, and if exported to the cytoplasm, is degraded, leading to no target protein production. FIG. 2B shows an example of the same cell divided into nuclear and cytoplasmic compartments. Treatment with an antisense oligomer (ASO) promotes the splicing of intron 1 and results in an increase in mRNA, which is in turn translated into higher levels of target protein.

FIG. 6A shows a schematic representation of the PRPF31 gene with numbered rectangles denoting exons and intervening lines denoting introns. Forward ("F") and reverse ("R") primers are indicated by short lines. Below are representative gels showing RT-PCR products corresponding to intron-retention events in PRPF31. The products were separated in a 1.5% ethidium-bromide-stained agarose gel. The top gel corresponds to products from nuclear fraction of HeLa cells, and the bottom gel corresponds to products from nuclear fractions from 293T cells. Asterisks indicate correct products (by size) for intron-retention events. FIG. 6B shows a schematic representation of the RB1 gene with numbered rectangles denoting exons and intervening lines denoting introns. Below are representative gels showing RT-PCR products from HeLa nuclear extracts corresponding to intron-retention events in RB1. The RT-PCR products were separated in a 1.5% ethidium-bromide-stained agarose gel. FIG. 6C shows representative gels of RT-PCR products from 293T cell nuclear extracts corresponding to intron-retention events in RB1. FIG. 6D shows representative gels of RT-PCR products from ARPE-19 cell nuclear extracts corresponding to intron-retention events in PRPF31 and RB1. RT-PCR products were separated in a 1.5% ethidium-bromide-stained agarose gel. FIG. 6E shows representative gels of RT-PCR products from ARPE-19 cell cytoplasmic extracts corresponding to intron-retention events in PRPF31 and RB1. IVS: intervening sequence (intron).

FIG. 7A shows representative gels of RT-PCR products corresponding to intron-retention events in PRPF31. The RT-PCR products from Arpe-19 cell nuclear extracts were separated in a 1.5% ethidium-bromide-stained agarose gel. FIG. 7B shows representative gels of RT-PCR products corresponding to intron-retention events in RB1. The RT-PCR products from Arpe-19 cell nuclear extracts were separated in a 1.5% ethidium-bromide-stained agarose gel. Asterisks indicate correct products (by size) for intron-retention events using the indicated primer pairs. IVS: intervening sequence (intron).

FIG. 8A shows a schematic representation of the HBB reporter gene including numbered rectangles denoting exons. Actual HBB splice site sequences are drawn marking the intron-exon boundaries. The nucleotides within the splice site sequences that are indicated with asterisks show the locations of nucleotide substitutions introduced by site directed mutagenesis to bring the splice site sequences to the consensus sequence (sequences directly below the HBB splice sites). The sequences are set forth in the sequence listing as SEQ ID NOS 387-390, respectively, in order of appearance. A: IVS1 5' splice site mutant, B: IVS1 3' splice site mutant, C: IVS2 5' splice site mutant, D: IVS2 3' splice site mutant. AB, CD, AC and BD: combination mutants. FIG. 8B shows a representative gel of radioactive RT-PCR products of wild-type (WT) and mutant HBB reporters. The RT-PCR products were separated in a 5% polyacrylamide gel. FIG. 8C shows a bar graph of the intensities of bands corresponding to HBB transcripts normalized to GFP. Fold change was plotted relative to the WT HBB product. The black line indicates a ratio of 1, no change.

FIG. 9A shows a schematic representation of the HBB reporter gene. The numbered rectangles denote exons, and intervening lines denote introns. Orange line indicates the IVS1+6 ASO ("+6"), grey line indicates IVS1+7 ASO ("+7"). Black lines indicate forward ("F") and reverse ("R") primers used in PCR amplification of the HBB transcript. FIG. 9B presents a representative gel of radioactive RT-PCR products of wild-type HBB reporters untreated (−), mock-treated (RiM, RNAiMAX or EP, EndoPorter) or treated with non-targeting (NT), or IVS1+7 2'-O-Me (left portion of the gel) or PMO (right portion of the gel) ASOs at the indicated concentrations. The RT-PCR products were separated in a 5% polyacrylamide gel. FIG. 9C shows a bar graph of the intensities of bands corresponding to HBB transcripts normalized to GFP. Fold change was plotted relative to the product from mock-treated cells. Green bars correspond to treatment with the IVS+7 2'-O-Me ASO and orange bars correspond to treatment with the IVS+7 PMO ASO. The black line indicates a ratio of 1, no change.

FIG. 10A shows a schematic representation of the GFP-HBB-T7 reporter gene that has been integrated in the genome of U2OS cells. The rectangle labeled "GFP" denotes the open reading frame of GFP, numbered rectangles denote HBB exons, intervening lines denote introns and the rectangle labeled "T7" denotes the sequence coding for the T7 tag. The line labeled "+7" indicates the IVS1+7 ASO. FIG. 10B presents a representative gel of protein products of wild-type GFP-HBB-T7 reporters mock-treated (RiM, RNAiMAX) or treated with IVS1+7 2'-O-Me ASO at a concentration of 50 nM. The protein products were separated on a 4-20% SDS-polyacrylamide gel. Antibodies against GFP and Beta tubulin were used to detect the protein products. FIG. 10C shows a bar graph of the intensity of bands corresponding to GFP-HBB-T7 protein normalized to Beta tubulin from two biological replicates. Fold change was plotted relative to the product from mock-treated cells. The black line indicates a ratio of 1, no change.

SEQUENCES

Figure 1:
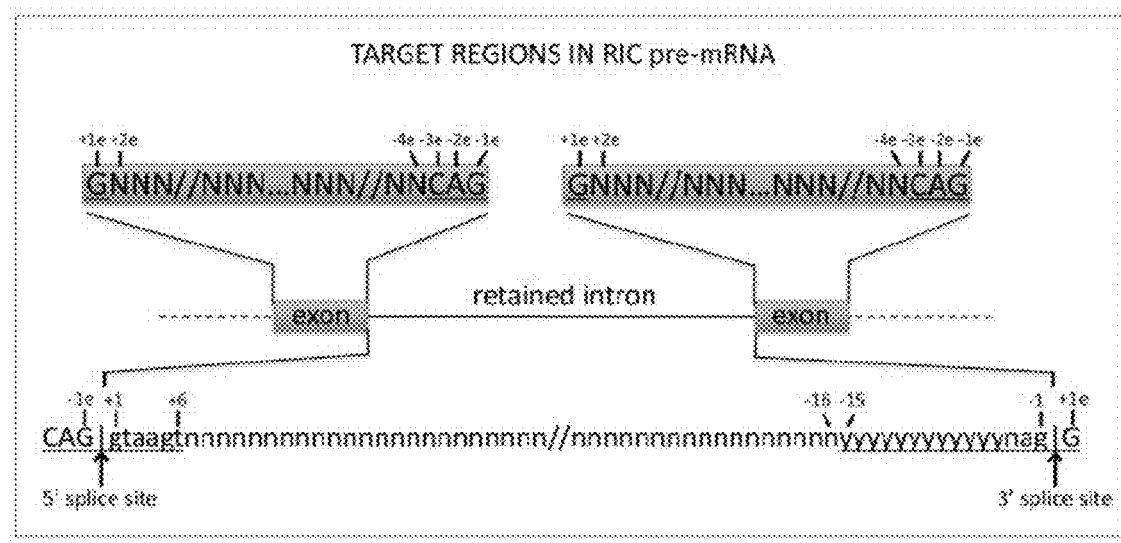
FIG. 1 shows a schematic representation of an exemplary retained-intron-containing (RIC) pre-mRNA transcript. The 5' splice site consensus sequence is indicated with underlined letters (letters are nucleotides; upper case: exonic portion and lower case: intronic portion) from −3e to −1e and +1 to +6 (numbers labeled "e" are exonic and unlabeled numbers are intronic). The 3' splice site consensus sequence is indicated with underlined letters (letters are nucleotides; upper case: exonic portion and lower case: intronic portion) from −15 to −1 and +1e (numbers labeled "e" are exonic and unlabeled numbers are intronic). Intronic target regions for ASO screening comprise nucleotides +6 relative to the 5' splice site of the retained intron (arrow at left) to −16 relative to the 3' splice site of the retained intron (arrow at right). In embodiments, intronic target regions for ASO screening comprise nucleotides +6 to +100 relative to the 5' splice site of the retained intron and −16 to −100 relative to the 3' splice site of the retained intron. Exonic target regions comprise nucleotides +2e to −4e in the exon flanking the 5' splice site of the retained intron and +2e to −4e in the exon flanking the 3' splice site of the retained intron. "n" or "N" denote any nucleotide, "y" denotes pyrimidine. The sequences shown represent consensus sequences for mammalian splice sites and individual introns and exons need not match the consensus sequences at every position (SEQ ID NOS 385 and 386, respectively, in order of appearance).

This application includes nucleotide sequences identified as SEQ ID NOS: 1-403. SEQ ID NOS: 1-384 are listed in Tables 2 to 8 and Tables 11 to 20 before the claims. The nucleotide sequences set forth as SEQ ID NOS: 1-102 and 375-384 in Tables 11 to 20 are examples of sequences that can be targeted by antisense oligomers by the methods described herein. The nucleotide sequences set forth as SEQ ID NOS 103-374 in Tables 2-8 are examples of antisense oligomers useful in the methods described herein. In all tables, upper case letters represent exon sequence and lower case represents intron sequence.

DETAILED DESCRIPTION OF THE INVENTION

Eighty-five percent (85%) of human protein-coding genes have at least one intron; eight is the average number of introns per gene and the number of introns can range from 1 to 316. Individual introns are spliced from the primary transcript with different efficiencies and in most cases only the fully spliced mRNA is exported through nuclear pores for subsequent translation in the cytoplasm. Unspliced and partially spliced transcripts are detectable in the nucleus. It is generally thought that nuclear retention of transcripts that are not fully spliced is a mechanism to prevent the accumulation of potentially deleterious mRNAs in the cytoplasm that may be translated to protein. For some genes, splicing of the least efficient intron is a rate-limiting post-transcriptional step in gene expression, prior to translation in the cytoplasm. If splicing of an intron that is rate-limiting for the nuclear stages of gene expression can be made more efficient, steady-state production of fully-spliced, mature mRNA and translation of the corresponding protein can be augmented. Such methods would also aid in upregulating expression of target genes, which has innumerable clinical and research applications. Increasing the output of a gene (the normal and/or mutant allele) can be useful to compensate for any mutation that reduces the amount of activity of its gene product, e.g., a protein or functional RNA. Many genetic diseases and disorders are the result of reduced protein production or the production a protein that is only partially functional.

As used herein, the term "comprise" or variations thereof such as "comprises" or "comprising" are to be read to indicate the inclusion of any recited feature (e.g. in the case of an antisense oligomer, a defined nucleobase sequence) but not the exclusion of any other features. Thus, as used herein, the term "comprising" is inclusive and does not exclude additional, unrecited features (e.g. in the case of an antisense oligomer, the presence of additional, unrecited nucleobases).

In embodiments of any of the compositions and methods provided herein, "comprising" may be replaced with "consisting essentially of" or "consisting of" The phrase "consisting essentially of" is used herein to require the specified feature(s) (e.g. nucleobase sequence) as well as those which do not materially affect the character or function of the claimed invention. As used herein, the term "consisting" is used to indicate the presence of the recited feature (e.g. nucleobase sequence) alone (so that in the case of an antisense oligomer consisting of a specified nucleobase sequence, the presence of additional, unrecited nucleobases is excluded).

Targeted Augmentation of Nuclear Gene Output

Described herein are methods of increasing expression of a target protein referred to as Targeted Augmentation of Nuclear Gene Output (TANGO). The method involves contacting cells having (comprising) a retained-intron-containing pre-mRNA (RIC pre-mRNA) that comprises a retained intron, an exon flanking the 5' splice site, an exon flanking the 3' splice site, and encodes the target protein with antisense oligomers (ASO) complementary to a targeted portion of a RIC pre-mRNA. Hybridization of the ASOs to the portion of the RIC pre-mRNA results in enhanced splicing at the splice site (5' splice site or 3' splice site) of the retained intron and subsequently increases target protein production.

The terms "pre-mRNA," and "pre-mRNA transcript" may be used interchangeably and refer to any pre-mRNA species that contains at least one intron. Pre-mRNA or pre-mRNA transcripts may comprise a 5'-7-methylguanosine cap and/or a poly-A tail. In some embodiments, the pre-mRNA transcript does not comprise a 5'-7-methylguanosine cap and/or a poly-A tail. A pre-mRNA transcript is a non-productive messenger RNA (mRNA) molecule if it is not translated into a protein (or transported into the cytoplasm from the nucleus).

As used herein, a "retained-intron-containing pre-mRNA" ("RIC pre-mRNA") is a pre-mRNA transcript that contains at least one retained intron. The RIC pre-mRNA contains a retained intron, an exon flanking the 5' splice site of the retained intron, an exon flanking the 3' splice site of the retained intron, and encodes the target protein. An "RIC pre-mRNA encoding a target protein" is understood to encode the target protein when fully spliced. A "retained intron" is any intron that is present in a pre-mRNA transcript when one or more other introns, such as an adjacent intron, encoded by the same gene have been spliced out of the same pre-mRNA transcript. In some embodiments, the retained intron is the most abundant intron in RIC pre-mRNA encoding the target protein. In embodiments, the retained intron is the most abundant intron in a population of RIC pre-mRNAs transcribed from the gene encoding the target protein in a cell, wherein the population of RIC pre-mRNAs comprises two or more retained introns. In embodiments, an antisense oligomer targeted to the most abundant intron in the population of RIC pre-mRNAs encoding the target protein induces splicing out of two or more retained introns in the population, including the retained intron to which the antisense oligomer is targeted or binds. In embodiments, a mature mRNA encoding the target protein is thereby produced. The terms "mature mRNA," and "fully-spliced mRNA," are used interchangeably herein to describe a fully processed mRNA encoding a target protein (e.g., mRNA that is exported from the nucleus into the cytoplasm and translated into target protein) or a fully processed functional RNA. The term "productive mRNA," also can be used to describe a fully processed mRNA encoding a target protein.

In some embodiments, the targeted region is in a retained intron that is the second most abundant intron in RIC pre-mRNA encoding the target protein. For example, the second most abundant retained intron may be targeted rather than the most abundant retained intron due to the uniqueness of the nucleotide sequence of the second most abundant retained intron, ease of ASO design to target a particular nucleotide sequence, and/or amount of increase in protein production resulting from targeting the intron with an ASO. In embodiments, the retained intron is the second most abundant intron in a population of RIC pre-mRNAs transcribed from the gene encoding the target protein in a cell, wherein the population of RIC pre-mRNAs comprises two or more retained introns. In embodiments, an antisense oligomer targeted to the second most abundant intron in the population of RIC pre-mRNAs encoding the target protein induces splicing out of two or more retained introns in the population, including the retained intron to which the antisense oligomer is targeted or binds. In embodiments, fully-spliced (mature) RNA encoding the target protein is thereby produced.

In embodiments, an antisense oligomer is complementary to a targeted region that is within a non-retained intron in a RIC pre-mRNA. In embodiments, the targeted portion of the RIC pre-mRNA is within: the region +6 to +100 relative to the 5' splice site of the non-retained intron; or the region −16 to −100 relative to the 3' splice site of the non-retained intron. In embodiments, the targeted portion of the RIC pre-mRNA is within the region +100 relative to the 5' splice site of the non-retained intron to −100 relative to the 3' splice site of the non-retained intron. As used to identify the location of a region or sequence, "within" is understood to include the residues at the positions recited. For example, a region +6 to +100 includes the residues at positions +6 and +100. In embodiments, fully-spliced (mature) RNA encoding the target protein is thereby produced.

In some embodiments, the retained intron of the RIC pre-mRNA is an inefficiently spliced intron. As used herein, "inefficiently spliced" may refer to a relatively low frequency of splicing at a splice site adjacent to the retained intron (5' splice site or 3' splice site) as compared to the frequency of splicing at another splice site in the RIC pre-mRNA. The term "inefficiently spliced" may also refer to the relative rate or kinetics of splicing at a splice site, in which an "inefficiently spliced" intron may be spliced or removed at a slower rate as compared to another intron in a RIC pre-mRNA.

In some embodiments, the 9-nucleotide sequence at −3e to −1e of the exon flanking the 5' splice site and +1 to +6 of the retained intron is identical to the corresponding wild-type sequence. In some embodiments, the 16 nucleotide sequence at −15 to −1 of the retained intron and +1e of the exon flanking the 3' splice site is identical to the corresponding wild-type sequence. As used herein, the "wild-type sequence" refers to the nucleotide sequence for a target gene in the published reference genome deposited in the NCBI repository of biological and scientific information (operated by National Center for Biotechnology Information, National Library of Medicine, 8600 Rockville Pike, Bethesda, Md. USA 20894). Also used herein, a nucleotide position denoted with an "e" indicates the nucleotide is present in the sequence of an exon (e.g., the exon flanking the 5' splice site or the exon flanking the 3' splice site).

The methods involve contacting cells with an ASO that is complementary to a portion of a pre-mRNA encoding a target protein or functional RNA, resulting in increased expression of a target protein or a functional RNA. As used herein, "contacting" or administering to cells refers to any method of providing an ASO in immediate proximity with the cells such that the ASO and the cells interact. A cell that is contacted with an ASO will take up or transport the ASO into the cell. The method involves contacting a condition or disease-associated or condition or disease-relevant cell with any of the ASOs described herein. In some embodiments, the ASO may be further modified or attached (e.g., covalently attached) to another molecule to target the ASO to a cell type, enhance contact between the ASO and the condition or disease-associated or condition or disease-relevant cell, or enhance uptake of the ASO.

Figure 2A:
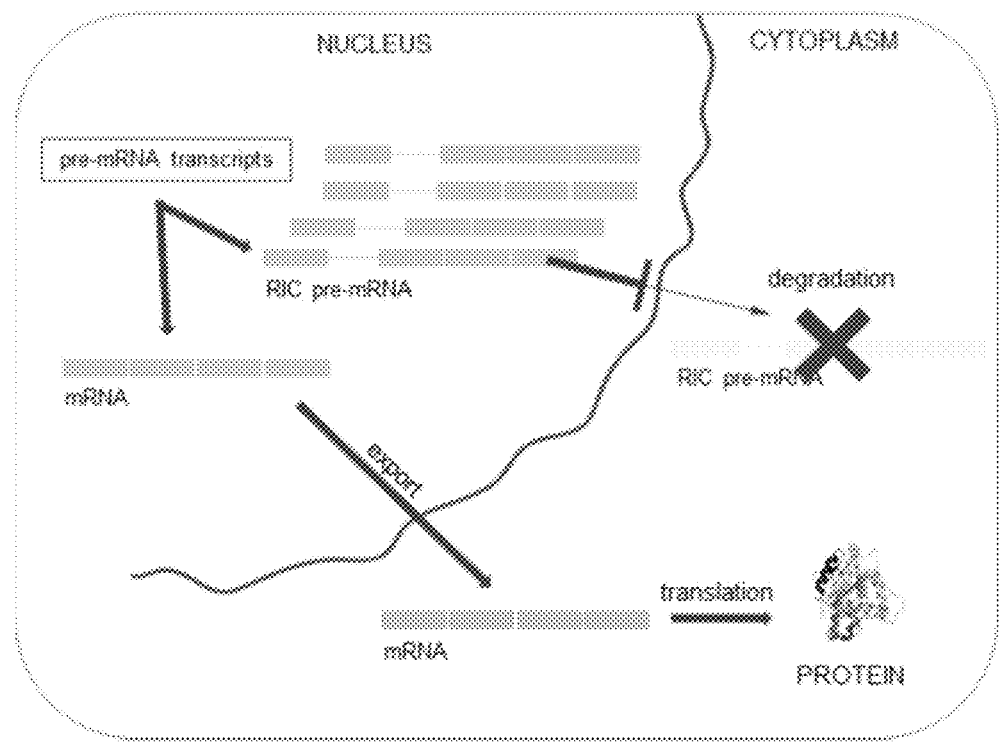
FIG. 2A-2B show schematic representations of the Targeted Augmentation of Nuclear Gene Output (TANGO) approach.
Figure 2B:
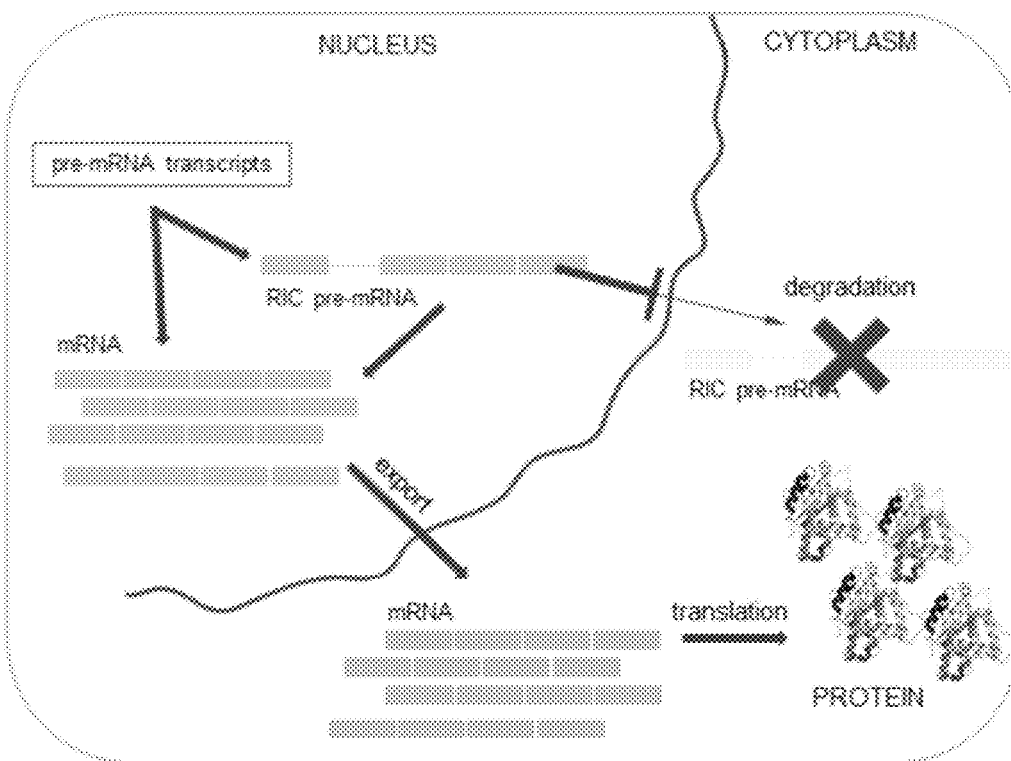

As demonstrated in FIG. 2A, in the nucleus of a cell, a pre-mRNA transcript consisting of exons and introns undergoes splicing to generate an mRNA that can be exported from the nucleus into the cytoplasm of the cell where it is translated into protein. In the instance of a pre-mRNA transcript that contains at least one inefficiently spliced intron (a retained intron), a RIC pre-mRNA occurs, which is maintained in the nucleus, and if it is exported to the cytoplasm it is not translated into protein but is degraded. Without wishing to be bound by any particular theory, in the presence of an ASO that is complementary to a targeted portion of the pre-mRNA transcript, splicing of the retained intron is enhanced thereby increasing the amount of mRNA that can be exported and translated into protein is also increased (FIG. 2B).

As used herein, the term "increasing protein production" or "increasing expression of a target protein" means enhancing the amount of protein (e.g., a target protein) that is translated from an mRNA in a cell. A "target protein" may be any protein for which increased expression/production is desired. In some embodiments, the target protein is a disease-associated protein, such as any of the proteins presented in Table 1. For example, contacting a cell that expresses a RIC pre-mRNA with an ASO that is complementary to a targeted portion of the RIC pre-mRNA transcript results in a measurable increase in the amount of the protein (e.g., a target protein) encoded by the pre-mRNA. Methods of measuring or detecting production of a protein will be evident to one of skill in the art and include, for example, Western blotting, flow cytometry, immunofluorescence microscopy, and ELISA.

In some embodiments, contacting cells with an ASO that is complementary to a targeted portion of a RIC pre-mRNA transcript results in an increase in the amount of protein (e.g., target protein) produced by at least 10, 20, 30, 40, 50, 60, 80, 100, 200, 300, 400, 500, or 1000%, compared to the amount of the protein produced by a cell in the absence of the ASO/absence of treatment. In embodiments, the total amount of target protein produced by the cell to which the antisense oligomer was contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by an control compound. A control compound can be, for example, an oligonucleotide that is not complementary to the targeted portion of the RIC pre-mRNA.

In some embodiments, contacting cells with an ASO that is complementary to a targeted portion of a RIC pre-mRNA transcript results in an increase in the amount of mRNA encoding the target protein or functional RNA, including the mature mRNA encoding the target protein or functional RNA. In some embodiments, the amount of mRNA encoding the target protein or functional RNA, or the mature mRNA encoding the target protein or functional RNA, is increased by at least 10, 20, 30, 40, 50, 60, 80, 100, 200, 300, 400, 500, or 1000%, compared to the amount of the protein produced by a cell in the absence of the ASO/absence of treatment. In embodiments, the total amount of the mRNA encoding the target protein or functional RNA, or the mature mRNA encoding the target protein or functional RNA produced in the cell to which the antisense oligomer was contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to the targeted portion of the RIC pre-mRNA.

In embodiments, contacting cells with an ASO that is complementary to a targeted portion of a RIC pre-mRNA transcript results in an increase in the amount of a functional RNA. In some embodiments, the amount of the functional RNA is increased by at least 10, 20, 30, 40, 50, 60, 80, 100, 200, 300, 400, 500, or 1000%, compared to the amount of the functional RNA produced by the cell in the absence of the ASO/absence of treatment. In embodiments, the total amount of the functional RNA produced in the cell to which the antisense oligomer was contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of the functional RNA produced in an untreated cell, e.g., an untreated cell or a cell treated with a control compound. A control compound can be, for example, an oligonucleotide that is not complementary to the targeted portion of the RIC pre-mRNA. Any of the methods provided herein may be used to increase production of a functional RNA, e.g., an mRNA that does not encode a protein, such as a non-protein-coding RNA. In some embodiments, the functional RNA or non-protein-coding RNA is associated with a condition, e.g., a disease or disorder.

Constitutive Splicing of a Retained Intron from a RIC pre-mRNA

The methods and antisense oligonucleotide compositions provided herein are useful for increasing the expression of a target protein or functional RNA in cells, for example, in a subject having a condition caused by a deficiency in the amount or activity of the target protein or functional RNA, by increasing the level of mRNA encoding the target protein or functional RNA, or the mature mRNA encoding the target protein or functional RNA. In particular, the methods and compositions as described herein induce the constitutive splicing of a retained intron from a RIC pre-mRNA transcript encoding the target protein or functional RNA, thereby increasing the level of mRNA encoding the target protein or functional RNA, or the mature mRNA encoding the target protein or functional RNA and increasing the expression of the target protein or functional RNA.

Constitutive splicing of a retained intron from a RIC pre-mRNA correctly removes the retained intron from the RIC pre-mRNA, wherein the retained intron has wild-type splice sequences. Constitutive splicing, as used herein, does not encompass splicing of a retained intron from a RIC pre-mRNA transcribed from a gene or allele having a mutation that causes alternative splicing or aberrant splicing of a pre-mRNA transcribed from the gene or allele. For example, constitutive splicing of a retained intron, as induced using the methods and antisense oligonucleotides provided herein, does not correct aberrant splicing in or influence alternative splicing of a pre-mRNA to result in an increased expression of a target protein or functional RNA.

In embodiments, constitutive splicing correctly removes a retained intron from a RIC pre-mRNA, wherein the RIC pre-mRNA is transcribed from a wild-type gene or allele, or a polymorphic gene or allele, that encodes a fully-functional target protein or functional RNA, and wherein the gene or allele does not have a mutation that causes alternative splicing or aberrant splicing of the retained intron.

In some embodiments, constitutive splicing of a retained intron from a RIC pre-mRNA encoding the target protein or functional RNA correctly removes a retained intron from a RIC pre-mRNA encoding the target protein or functional RNA, wherein the RIC pre-mRNA is transcribed from a gene or allele from which the target gene or functional RNA is produced at a reduced level compared to production from a wild-type allele, and wherein the gene or allele does not have a mutation that causes alternative splicing or aberrant splicing of the retained intron. In these embodiments, the correct removal of the constitutively spliced retained intron results in production of target protein or functional RNA that is functional when compared to an equivalent wild-type protein or functional RNA.

In other embodiments, constitutive splicing correctly removes a retained intron from a RIC pre-mRNA, wherein the RIC pre-mRNA is transcribed from a gene or allele that encodes a target protein or functional RNA produced in a form having reduced function compared to an equivalent wild-type protein or functional RNA, and wherein the gene or allele does not have a mutation that causes alternative splicing or aberrant splicing of the retained intron. In these embodiments, the correct removal of the constitutively spliced retained intron results in production of partially functional target protein, or functional RNA that is partially functional when compared to an equivalent wild-type protein or functional RNA.

"Correct removal" of the retained intron by constitutive splicing refers to removal of the entire intron, without removal of any part of an exon.

In embodiments, an antisense oligomer as described herein or used in any method described herein does not increase the amount of mRNA encoding the target protein or functional RNA, the amount of the target protein, or the amount of the functional RNA, by modulating alternative splicing or aberrant splicing of a pre-mRNA transcribed from a gene encoding the functional RNA or target protein. Modulation of alternative splicing or aberrant splicing can be measured using any known method for analyzing the sequence and length of RNA species, e.g., by RT-PCR and using methods described elsewhere herein and in the literature. In embodiments, modulation of alternative or aberrant splicing is determined based on an increase or decrease in the amount of the spliced species of interest of at least 10% or 1.1-fold. In embodiments, modulation is determined based on an increase or decrease at a level that is at least 10% to 100% or 1.1 to 10-fold, as described herein regarding determining an increase in mRNA encoding the target protein or functional RNA in the methods of the invention.

In embodiments, the method is a method wherein the RIC pre-mRNA was produced by partial splicing of a wild-type pre-mRNA. In embodiments, the method is a method wherein the RIC pre-mRNA was produced by partial splicing of a wild-type pre-mRNA. In embodiments, the RIC pre-mRNA that was produced by partial splicing of a full-length pre-mRNA. In these embodiments, a full-length pre-mRNA may have a polymorphism in a splice site of the retained intron that does not impair correct splicing of the retained intron as compared to splicing of the retained intron having the wild-type splice site sequence.

In embodiments, the mRNA encoding the target protein or functional RNA is a full-length mature mRNA, or a wild-type mature mRNA. In these embodiments, a full-length mature mRNA may have a polymorphism that does not affect the activity of the target protein or the functional RNA encoded by the mature mRNA, as compared to the activity of the target protein or functional RNA encoded by the wild-type mature mRNA.

Antisense Oligomers

One aspect of the present disclosure is a composition comprising antisense oligomers that enhances splicing by binding to a targeted portion of a RIC pre-mRNA. As used herein, the terms "ASO" and "antisense oligomer" are used interchangeably and refer to an oligomer such as a polynucleotide, comprising nucleobases, that hybridizes to a target nucleic acid (e.g., a RIC pre-mRNA) sequence by Watson-Crick base pairing or wobble base pairing (G-U). The ASO may have exact sequence complementary to the target sequence or near complementarity (e.g., sufficient complementarity to bind the target sequence and enhancing splicing at a splice site). ASOs are designed so that they bind (hybridize) to a target nucleic acid (e.g., a targeted portion of a pre-mRNA transcript) and remain hybridized under physiological conditions. Typically, if they hybridize to a site other than the intended (targeted) nucleic acid sequence, they hybridize to a limited number of sequences that are not a target nucleic acid (to a few sites other than a target nucleic acid). Design of an ASO can take into consideration the occurrence of the nucleic acid sequence of the targeted portion of the pre-mRNA transcript or a sufficiently similar nucleic acid sequence in other locations in the genome or cellular pre-mRNA or transcriptome, such that the likelihood the ASO will bind other sites and cause "off-target" effects is limited. Any antisense oligomers known in the art, for example in PCT Application No. PCT/US2014/054151, published as WO 2015/035091, titled "Reducing Nonsense-Mediated mRNA Decay," can be used to practice the methods described herein.

In some embodiments, ASOs "specifically hybridize" to or are "specific" to a target nucleic acid or a targeted portion of a RIC pre-mRNA. Typically such hybridization occurs with a Tm substantially greater than 37° C., preferably at least 50° C., and typically between 60° C. to approximately 90° C. Such hybridization preferably corresponds to stringent hybridization conditions. At a given ionic strength and pH, the Tm is the temperature at which 50% of a target sequence hybridizes to a complementary oligonucleotide.

Oligomers, such as oligonucleotides, are "complementary" to one another when hybridization occurs in an anti-parallel configuration between two single-stranded polynucleotides. A double-stranded polynucleotide can be "complementary" to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an antisense oligomer (ASO) need not be 100% complementary to that of its target nucleic acid to hybridize. In certain embodiments, ASOs can comprise at least 70%, at least 75%, at least 80%, at least 85%, at least 90%, at least 95%, at least 96%, at least 97%, at least 98%, or at least 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining non-complementary nucleobases may be clustered together or interspersed with complementary nucleobases and need not be contiguous to each other or to complementary nucleobases. Percent complementarity of an ASO with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

An ASO need not hybridize to all nucleobases in a target sequence and the nucleobases to which it does hybridize may be contiguous or noncontiguous. ASOs may hybridize over one or more segments of a pre-mRNA transcript, such that intervening or adjacent segments are not involved in the hybridization event (e.g., a loop structure or hairpin structure may be formed). In certain embodiments, an ASO hybridizes to noncontiguous nucleobases in a target pre-mRNA transcript. For example, an ASO can hybridize to nucleobases in a pre-mRNA transcript that are separated by one or more nucleobase(s) to which the ASO does not hybridize.

The ASOs described herein comprise nucleobases that are complementary to nucleobases present in a target portion of a RIC pre-mRNA. The term ASO embodies oligonucleotides and any other oligomeric molecule that comprises nucleobases capable of hybridizing to a complementary nucleobase on a target mRNA but does not comprise a sugar moiety, such as a peptide nucleic acid (PNA). The ASOs may comprise naturally-occurring nucleotides, nucleotide analogs, modified nucleotides, or any combination of two or three of the preceding. The term "naturally occurring nucleotides" includes deoxyribonucleotides and ribonucleotides. The term "modified nucleotides" includes nucleotides with modified or substituted sugar groups and/or having a modified backbone. In some embodiments, all of the nucleotides of the ASO are modied nucleotides. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728, and Dias and Stein, Mol. Cancer Ther. 2002, 1, 347-355, herein incorporated by reference in their entirety.

The nucleobase of an ASO may be any naturally occurring, unmodified nucleobase such as adenine, guanine, cytosine, thymine and uracil, or any synthetic or modified nucleobase that is sufficiently similar to an unmodified nucleobase such that it is capable of hydrogen bonding with a nucleobase present on a target pre-mRNA. Examples of modified nucleobases include, without limitation, hypoxanthine, xanthine, 7-methylguanine, 5,6-dihydrouracil, 5-methylcytosine, and 5-hydroxymethoylcytosine.

The ASOs described herein also comprise a backbone structure that connects the components of an oligomer. The term "backbone structure" and "oligomer linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligomer linkages of the ASOs described herein may include (but are not limited to) phosphorothioate, phosphorodithioate, phosphoroselenoate, phosphorodiselenoate, phosphoroanilothioate, phosphoraniladate, phosphoramidate, and the like. See e.g., LaPlanche et al. Nucleic Acids Res. 14:9081 (1986); Stec et al. J. Am. Chem. Soc. 106:6077 (1984), Stein et al. Nucleic Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphothioate linkage. In some embodiments, the backbone modification is a phosphoramidate linkage.

Any of the ASOs described herein may contain a sugar moiety that comprises ribose or deoxyribose, as present in naturally occurring nucleotides, or a modified sugar moiety or sugar analog, including a morpholine ring. Non-limiting examples of modified sugar moieties include 2' substitutions such as 2'-O-methyl (2'-O-Me), 2'-O-methoxyethyl (2'MOE), 2'-O-aminoethyl, 2'F; N3'→P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some embodiments, the sugar moiety modification is selected from 2'-O-Me, 2'F, and 2'MOE. In some embodiments, the sugar moiety modification is an extra bridge bond, such as in a locked nucleic acid (LNA). In some embodiments the sugar analog contains a morpholine ring, such as phosphorodiamidate morpholino (PMO). In some embodiments, the sugar moiety comprises a ribofuransyl or 2'deoxyribofuransyl modification. In some embodiments, the sugar moiety comprises 2'4'-constrained 2'O-methyloxyethyl (cMOE) modifications. In some embodiments, the sugar moiety comprises cEt 2',4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. Modifications are known in the art and described in the literature, e.g., by Jarver, et al., 2014, "A Chemical View of Oligonucleotides for Exon Skipping and Related Drug Applications," Nucleic Acid Therapeutics 24(1): 37-47, incorporated by reference for this purpose herein.

In some examples, each monomer of the ASO is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some examples, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modification. In some embodiments, the ASO comprises one or more sugar moiety modification. In some embodiments, the ASO comprises one or more backbone modification and one or more sugar moiety modification. In some embodiments, the ASO comprises 2'MOE modifications and a phosphorothioate backbone. In some embodiments, the ASO comprises a phosphorodiamidate morpholino (PMO). In some embodiments, the ASO comprises a peptide nucleic acid (PNA). Any of the ASOs or any component of an ASO (e.g., a nucleobase, sugar moiety, backbone) described herein may be modified in order to achieve desired properties or activities of the ASO or reduce undesired properties or activities of the ASO. For example, an ASO or one or more component of any ASO may be modified to enhance binding affinity to a target sequence on a pre-mRNA transcript; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligomers having such modifications have been shown to have significantly enhanced resistance to nuclease degradation and increased bioavailability, making them suitable, for example, for oral delivery in some embodiments described herein. See e.g., Geary et al., J Pharmacol Exp Ther. 2001; 296(3):890-7; Geary et al., J Pharmacol Exp Ther. 2001; 296(3):898-904.

Methods of synthesizing ASOs will be known to one of skill in the art. Alternatively or in addition, ASOs may be obtained from a commercial source.

Unless specified otherwise, the left-hand end of single-stranded nucleic acid (e.g., pre-mRNA transcript, oligonucleotide, ASO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, the 5' direction or end of an mRNA is where the initiation or start codon is located, while the 3' end or direction is where the termination codon is located. In some aspects, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "−1," while a nucleotide that is directly adjacent and downstream of the reference point is designated "plus one," e.g., "+1."

In other embodiments, the ASOs are complementary to (and bind to) a targeted portion of a RIC pre-mRNA that is downstream (in the 3' direction) of the 5' splice site of the retained intron in a RIC pre-mRNA (e.g., the direction designated by positive numbers relative to the 5' splice site) (FIG. 1). In some embodiments, the ASOs are complementary to a targeted portion of the RIC pre-mRNA that is within the region +6 to +100 relative to the 5' splice site of the retained intron. In some embodiments, the ASO is not complementary to nucleotides +1 to +5 relative to the 5' splice site (the first five nucleotides located downstream of the 5' splice site). In some embodiments, the ASOs may be complementary to a targeted portion of a RIC pre-mRNA that is within the region between nucleotides +6 and +50 relative to the 5' splice site of the retained intron. In some aspects, the ASOs are complementary to a targeted portion that is within the region +6 to +90, +6 to +80, +6 to +70, +6 to +60, +6 to +50, +6 to +40, +6 to +30, or +6 to +20 relative to 5' splice site of the retained intron.

In some embodiments, the ASOs are complementary to a targeted region of a RIC pre-mRNA that is upstream (5' relative) of the 3' splice site of the retained intron in a RIC pre-mRNA (e.g., in the direction designated by negative numbers) (FIG. 1). In some embodiments, the ASOs are complementary to a targeted portion of the RIC pre-mRNA that is within the region −16 to −100 relative to the 3' splice site of the retained intron. In some embodiments, the ASO is not complementary to nucleotides −1 to −15 relative to the 3' splice site (the first 15 nucleotides located upstream of the 3' splice site). In some embodiments, the ASOs are complementary to a targeted portion of the RIC pre-mRNA that is within the region −16 to −50 relative to the 3' splice site of the retained intron. In some aspects, the ASOs are complementary to a targeted portion that is within the region −16 to −90, −16 to −80, −16 to −70, −16 to −60, −16 to −50, −16 to −40, or −16 to −30 relative to 3' splice site of the retained intron.

In embodiments, the targeted portion of the RIC pre-mRNA is within the region +100 relative to the 5' splice site of the retained intron to −100 relative to the 3' splice site of the retained intron.

In some embodiments, the ASOs are complementary to a targeted portion of a RIC pre-mRNA that is within the exon flanking the 5' splice site (upstream) of the retained intron (FIG. 1). In some embodiments, the ASOs are complementary to a targeted portion of the RIC pre-mRNA that is within the region +2e to −4e in the exon flanking the 5' splice site of the retained intron. In some embodiments, the ASOs are not complementary to nucleotides −1e to −3e relative to the 5' splice site of the retained intron. In some embodiments, the ASOs are complementary to a targeted portion of the RIC pre-mRNA that is within the region −4e to −100e, −4e to −90e, −4e to −80e, −4e to −70e, −4e to −60e, −4e to −50e, −4 to −40e, −4e to −30e, or −4e to −20e relative to the 5' splice site of the retained intron.

In some embodiments, the ASOs are complementary to a targeted portion of a RIC pre-mRNA that is within the exon flanking the 3' splice site (downstream) of the retained intron (FIG. 1). In some embodiments, the ASOs are complementary to a targeted portion to the RIC pre-mRNA that is within the region +2e to −4e in the exon flanking the 3' splice site of the retained intron. In some embodiments, the ASOs are not complementary to nucleotide +1e relative to the 3' splice site of the retained intron. In some embodiments, the ASOs are complementary to a targeted portion of the RIC pre-mRNA that is within the region +2e to +100e, +2e to +90e, +2e to +80e, +2e to +70e, +2e to +60e, +2e to +50e, +2e to +40e, +2e to +30e, or +2 to +20e relative to the 3' splice site of the retained intron. The ASOs may be of any length suitable for specific binding and effective enhancement of splicing. In some embodiments, the ASOs consist of 8 to 50 nucleobases. For example, the ASO may be 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleobases in length. In some embodiments, the ASOs consist of more than 50 nucleobases. In some embodiments, the ASO is from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, 12 to 15 nucleobases, 13 to 50 nucleobases, 13 to 40 nucleobases, 13 to 35 nucleobases, 13 to 30 nucleobases, 13 to 25 nucleobases, 13 to 20 nucleobases, 14 to 50 nucleobases, 14 to 40 nucleobases, 14 to 35 nucleobases, 14 to 30 nucleobases, 14 to 25 nucleobases, 14 to 20 nucleobases, 15 to 50 nucleobases, 15 to 40 nucleobases, 15 to 35 nucleobases, 15 to 30 nucleobases, 15 to 25 nucleobases, 15 to 20 nucleobases, 20 to 50 nucleobases, 20 to 40 nucleobases, 20 to 35 nucleobases, 20 to 30 nucleobases, 20 to 25 nucleobases, 25 to 50 nucleobases, 25 to 40 nucleobases, 25 to 35 nucleobases, or 25 to 30 nucleobases in length. In some embodiments, the ASOs are 18 nucleotides in length. In some embodiments, the ASOs are 15 nucleotides in length. In some embodiments, the ASOs are 25 nucleotides in length.

In some embodiments, two or more ASOs with different chemistries but complementary to the same targeted portion of the RIC pre-mRNA are used. In some embodiments, two or more ASOs that are complementary to different targeted portions of the RIC pre-mRNA are used.

In embodiments, the antisense oligonucleotides of the invention are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties, and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc), N—Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467, "Carbohydrate conjugates as delivery agents for oligonucleotides," incorporated by reference herein.

In some embodiments, the nucleic acid to be targeted by an ASO is a RIC pre-mRNA expressed in a cell, such as a eukaryotic cell. In some embodiments, the term "cell" may refer to a population of cells. In some embodiments, the cell is in a subject. In some embodiments, the cell is isolated from a subject. In some embodiments, the cell is ex vivo. In some embodiments, the cell is a condition or disease-relevant cell or a cell line. In some embodiments, the cell is in vitro (e.g., in cell culture).

Pharmaceutical Compositions

Pharmaceutical compositions or formulations comprising the antisense oligonucleotide of the described compositions and for use in any of the described methods can be prepared according to conventional techniques well known in the pharmaceutical industry and described in the published literature. In embodiments, a pharmaceutical composition or formulation for treating a subject comprises an effective amount of any antisense oligomer as described above, or a pharmaceutically acceptable salt, solvate, hydrate or ester thereof, and a pharmaceutically acceptable diluent. The antisense oligomer of a pharmaceutical formulation may further comprise a pharmaceutically acceptable excipient, diluent or carrier.

Pharmaceutically acceptable salts are suitable for use in contact with the tissues of humans and lower animals without undue toxicity, irritation, allergic response, etc., and are commensurate with a reasonable benefit/risk ratio. (See, e.g., S. M. Berge, et al., J. Pharmaceutical Sciences, 66: 1-19 (1977), incorporated herein by reference for this purpose. The salts can be prepared in situ during the final isolation and purification of the compounds, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In embodiments, the compositions are formulated into any of many possible dosage forms such as, but not limited to, tablets, capsules, gel capsules, liquid syrups, soft gels, suppositories, and enemas. In embodiments, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In embodiments, a pharmaceutical formulation or composition of the present invention includes, but is not limited to, a solution, emulsion, microemulsion, foam or liposome-containing formulation (e.g., cationic or noncationic liposomes).

The pharmaceutical composition or formulation of the present invention may comprise one or more penetration enhancer, carrier, excipients or other active or inactive ingredients as appropriate and well known to those of skill in the art or described in the published literature. In embodiments, liposomes also include sterically stabilized liposomes, e.g., liposomes comprising one or more specialized lipids. These specialized lipids result in liposomes with enhanced circulation lifetimes. In embodiments, a sterically stabilized liposome comprises one or more glycolipids or is derivatized with one or more hydrophilic polymers, such as a polyethylene glycol (PEG) moiety. In embodiments, a surfactant is included in the pharmaceutical formulation or compositions. The use of surfactants in drug products, formulations and emulsions is well known in the art. In embodiments, the present invention employs a penetration enhancer to effect the efficient delivery of the antisense oligonucleotide, e.g., to aid diffusion across cell membranes and/or enhance the permeability of a lipophilic drug. In embodiments, the penetration enhancers is a surfactant, fatty acid, bile salt, chelating agent, or non-chelating nonsurfactant.

In embodiments, the pharmaceutical formulation comprises multiple antisense oligonucleotides. In embodiments, the antisense oligonucleotide is administered in combination with another drug or therapeutic agent. In embodiments, the antisense oligonucleotide is administered with one or more agents capable of promoting penetration of the subject antisense oligonucleotide across the blood-brain barrier by any method known in the art. For example, delivery of agents by administration of an adenovirus vector to motor neurons in muscle tissue is described in U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is described, e.g., in U.S. Pat. No. 6,756,523, "Adenovirus vectors for the transfer of foreign genes into cells of the central nervous system particularly in brain," incorporated herein by reference.

In embodiments, the antisense oligonucleotides are linked or conjugated with agents that provide desirable pharmaceutical or pharmacodynamic properties. In embodiments, the antisense oligonucleotide is coupled to a substance, known in the art to promote penetration or transport across the blood-brain barrier, e.g., an antibody to the transferrin receptor. In embodiments, the antisense oligonucleotide is linked with a viral vector, e.g., to render the antisense compound more effective or increase transport across the blood-brain barrier. In embodiments, osmotic blood brain barrier disruption is assisted by infusion of sugars, e.g., meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids, e.g., glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," each incorporated herein by reference.

In embodiments, the antisense oligonucleotides of the invention are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties, and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc), N—Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467, "Carbohydrate conjugates as delivery agents for oligonucleotides," incorporated by reference herein.

Diseases and Disorders

Any condition, e.g., disease or disorder, that is associated with reduced production or activity of a protein or functional RNA encoded by a pre-mRNA that comprises at least one intron (e.g., 1, 2, 3, 4, 5, 6, 7, 8, 9, 10, or more introns) can be treated by the methods and compositions provided herein. The disease or disorder to be treated may be a result of haploinsufficiency in which one allele of a gene encodes a functional (wild-type) protein and one allele of the gene is mutated and encodes a nonfunctional protein or a protein with reduced/partial function. Other diseases or disorders may be due to hemizygous deletions in which one allele of a gene is lost and the amount of protein produced by the other allele of the gene is not sufficient. Yet other diseases or disorder maybe due to hypomorphic mutations in which the gene encoding a protein is mutated resulting in production of a protein with partial function.

In some embodiments, the methods described herein are used to increase the production of a functional protein. As used herein, the term "functional" refers to the amount of activity or function of a protein that is necessary to eliminate any one or more symptoms of a disease. In some embodiments, the methods are used to increase the production of a partially functional protein or RNA. As used herein, the term "partially functional" refers to any amount of activity or function of a protein or RNA that is less than the amount of activity or function that is necessary to eliminate or prevent any one or more symptoms of a disease. In some embodiments, a partially functional protein or RNA will have at least 10%, at least 20%, at least 30%, at least 40%, at least 50%, at least 60%, at least 70%, at least 75%, at least 80%, 85%, at least 90%, or at least 95% less activity relative to the fully functional protein or RNA.

In embodiments, the method is a method of increasing the expression of a target protein or functional RNA by cells of a subject having a RIC pre-mRNA encoding the target protein or functional RNA, wherein the subject has a condition caused by a deficient amount of activity of the target protein or functional RNA, and wherein the deficient amount of the target protein or functional RNA is caused by haploinsufficiency of the target protein or functional RNA. In such an embodiment, the subject has a first allele encoding a functional target protein or functional functional RNA, and a second allele from which the target protein or functional RNA is not produced. In another such embodiment, the subject has a first allele encoding a functional target protein or functional functional RNA, and a second allele encoding a nonfunctional target protein or nonfunctional functional RNA. In either of these embodiments, the antisense oligomer binds to a targeted portion of the RIC pre-mRNA transcribed from the first allele (encoding functional target protein), thereby inducing constitutive splicing of the retained intron from the RIC pre-mRNA, and causing an increase in the level of mRNA encoding the target protein or functional RNA, and an increase in the expression of the target protein or functional RNA in the cells of the subject.

In related embodiments, the method is a method of increasing the expression of a target protein or functional RNA by cells of a subject having a RIC pre-mRNA encoding the target protein or functional RNA, wherein the subject has a condition caused by an autosomal recessive disorder resulting from a deficiency in the amount or function of the target protein or functional RNA. In these embodiments, the subject has:

a. a first mutant allele from which
 i) the target protein or functional RNA is produced at a reduced level compared to production from a wild-type allele,
 ii) the target protein or functional RNA is produced in a form having reduced function compared to an equivalent wild-type protein, or
 iii) the target protein or functional RNA is not produced; and b. a second mutant allele from which
   i) the target protein or functional RNA is produced at a reduced level compared to production from a wild-type allele,
   ii) the target protein or functional RNA is produced in a form having reduced function compared to an equivalent wild-type protein, or
   iii) the target protein or functional RNA is not produced, and
wherein the RIC pre-mRNA is transcribed from the first allele and/or the second allele. In these embodiments, the antisense oligomer binds to a targeted portion of the RIC pre-mRNA transcribed from the first allele or the second allele, thereby inducing constitutive splicing of the retained intron from the RIC pre-mRNA, and causing an increase in the level of mRNA encoding the target protein or functional RNA and an increase in the expression of the target protein or functional RNA in the cells of the subject. In these embodiments, the target protein or functional RNA having an increase in expression level resulting from the constitutive splicing of the retained intron from the RIC pre-mRNA is either in a form having reduced function compared to the equivalent wild-type protein (partially-functional), or having full function compared to the equivalent wild-type protein (fully-functional).

In embodiments, the level of mRNA encoding the target protein, the target protein or the functional RNA is increased 1.1 to 10-fold, as set forth elsewhere herein, when compared to the amount of mRNA encoding the target protein, the target protein or the functional RNA produced in a control cell, e.g., one that is not treated with the antisense oligomer or one that is treated with an antisense oligomer that does not bind to the targeted portion of the RIC pre-mRNA.

In embodiments, the condition caused by a deficient amount or activity of the target protein or a deficient amount or activity of the functional RNA is not a condition caused by alternative or aberrant splicing of the retained intron to which the ASO is targeted. In embodiments, the condition caused by a deficient amount or activity of the target protein or a deficient amount or activity of the functional RNA is not a condition caused by alternative or aberrant splicing of any retained intron in a RIC pre-mRNA encoding the target protein or functional RNA.

Table 1 provides examples of diseases and target genes associated with each disease that may be treatable using the methods and compositions provided herein.

TABLE 1

| DISEASE | TARGET GENE | NUMBER OF POTENTIAL INTRON TARGETS |
|---|---|---|
| Retinitis pigmentosa type 11 | PRPF31 | 2 |
| Retinoblastoma | RB1 | 1 |
| Beta thalassemia (BTI) | HBB | 1 |
| Beta thalassemia | HBG1/2 | 2 |
| Sickle cell disease | HBG1/2 | 2 |
| Cystic fibrosis | CFTR | 26 |
| Thrombotic thrombocytopenic purpura | ADAMTS13 | 2 |
| Tuberous sclerosis complex | TSC1 | 3 |
| Retinitis pigmentosa 10 | IMPDH1 | 1 |
| Polycystic kidney disease | PKD1 | 4 |
| Familial dysautonomia | IKBKAP | 2 |

In some embodiments, the pre-mRNA transcript that encodes the protein that is causative of the disease is targeted by the ASOs described herein. In some embodiments, a pre-mRNA transcript that encodes a protein is not causative of the disease is targeted by the ASOs. For example, a disease that is the result of a mutation or deficiency of a first protein in a particular pathway may be ameliorated by targeting a pre-mRNA that encodes a second protein, thereby increasing production of the second protein. In some embodiments, the function of the second protein is able to compensate for the mutation or deficiency of the first protein.

Any of the compositions provided herein may be administered to an individual. "Individual" maybe used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In some embodiments, the individual is a human. In other embodiments, the individual may be another eukaryotic organism, such as a plant. In some embodiments, the compositions provided herein are administered to a cell ex vivo.

In some embodiments, the compositions provided herein are administered to an individual as a method of treating a disease or disorder. In some embodiments, the individual has a genetic disease, such as any of the diseases described herein. In some embodiments, the individual is at risk of having the disease, such as any of the diseases described herein. In some embodiments, the individual is at increased risk of having a disease or disorder caused by insufficient amount of a protein or insufficient activity of a protein. If an individual is "at an increased risk" of having a disease or disorder caused insufficient amount of a protein or insufficient activity of a protein, the method involves preventative or prophylactic treatment. For example, an individual may be at an increased risk of having such a disease or disorder because of family history of the disease. Typically, individuals at an increased risk of having such a disease or disorder benefit from prophylactic treatment (e.g., by preventing or delaying the onset or progression of the disease or disorder).

Table 2 provides a non-limiting list of sequences of ASOs for increasing production of a protein encoded by the HBB gene by targeting a region of a RIC pre-mRNA transcribed from the HBB gene.

TABLE 2

List of ASOs targeting the HBB gene

| ASO | Sequence | SEQ ID NO |
|---|---|---|
| Non-targeting | CCAGTGGTATTGCTTACC | 103 |
| HBBIVS1 + 6 | ctgtcttgtaaccttgat | 104 |
| HBBIVS1 + 7 | cctgtcttgtaaccttga | 105 |
| HBBIVS1 + 8 | acctgtcttgtaaccttg | 106 |
| HBBIVS1 + 9 | aacctgtcttgtaacctt | 107 |
| HBBIVS1 + 10 | aaacctgtcttgtaacct | 108 |
| HBBIVS1 + 11 | taaacctgtcttgtaacc | 109 |
| HBBIVS1 + 12 | ttaaacctgtcttgtaac | 110 |
| HBBIVS1 + 13 | cttaaacctgtcttgtaa | 111 |
| HBBIVS1 + 14 | ccttaaacctgtcttgta | 112 |
| HBBIVS1 + 15 | tccttaaacctgtcttgt | 113 |
| HBBIVS1 + 16 | ctccttaaacctgtcttg | 114 |
| HBBIVS1 + 17 | tctccttaaacctgtctt | 115 |

TABLE 2-continued

List of ASOs targeting the HBB gene

| ASO | Sequence | SEQ ID NO |
|---|---|---|
| HBBIVS1 + 18 | gtctccttaaacctgtct | 116 |
| HBBIVS1 + 19 | ggtctccttaaacctgtc | 117 |
| HBBIVS1 + 20 | tggtctccttaaacctgt | 118 |
| HBBIVS1 + 21 | ttggtctccttaaacctg | 119 |
| HBBIVS1 + 22 | attggtctccttaaacct | 120 |
| HBBIVS1 + 23 | tattggtctccttaaacc | 121 |
| HBBIVS1 + 24 | ctattggtctccttaaac | 122 |
| HBBIVS1 + 25 | tctattggtctccttaaa | 123 |
| HBBIVS1 + 26 | ttctattggtctccttaa | 124 |
| HBBIVS1 + 27 | tttctattggtctcctta | 125 |
| HBBIVS1 + 28 | gtttctattggtctcctt | 126 |

Table 3 provides a non-limiting list of sequences of ASOs for increasing production of a protein encoded by the PRPF31 gene by targeting a region of a RIC pre-mRNA transcribed from the PRPF31 gene.

TABLE 3

List of ASOs targeting the PRPF31 gene

| ASO | Sequence | SEQ ID NO |
|---|---|---|
| P31-IVS10 + 6 | accggaccccagggccc | 127 |
| P31-IVS10 + 11 | tgcctaccggaccccag | 128 |
| P31-IVS10 + 16 | ccccatgcctaccggacc | 129 |
| P31-IVS10 + 21 | atgaccccatgcctacc | 130 |
| P31-IVS10 + 26 | cctccatgaccccatgc | 131 |
| P31-IVS10 + 31 | tctcccctccatgacccc | 132 |
| P31-IVS10 − 41 | gaggaggacgccggcttc | 133 |
| P31-IVS10 − 36 | gctgggaggaggacgccg | 134 |
| P31-IVS10 − 31 | agtcggctgggaggagga | 135 |
| P31-IVS10 − 26 | cagggagtcggctgggag | 136 |
| P31-IVS10 − 21 | ggcgccagggagtcggct | 137 |
| P31-IVS10 − 16 | tgggcggcgccagggagt | 138 |
| P31-IVS12 + 6 | ccccacctgggtctggcc | 139 |
| P31-IVS12 + 11 | cccagccccacctgggtc | 140 |
| P31-IVS12 + 16 | cggtccccagccccacct | 141 |
| P31-IVS12 + 21 | tccctcggtccccagccc | 142 |
| P31-IVS12 − 16 | ggaggctgcgatctgggc | 143 |
| P31-IVS12 − 21 | ctgcgatctgggctcccc | 144 |
| P31-IVS12 − 26 | atctgggctcccccacc | 145 |
| P31-IVS12 − 31 | ggctcccccaccttgtg | 146 |

TABLE 3-continued

List of ASOs targeting the PRPF31 gene

| ASO | Sequence | SEQ ID NO |
|---|---|---|
| P31-IVS12 + 26 | ttgtgtccctcggtcccc | 147 |
| P31-IVS12 + 31 | ccaccttgtgtccctcgg | 148 |
| P31-IVS12 + 36 | tcccccaccttgtgtcc | 149 |

Table 4 provides a non-limiting list of sequences of ASOs for increasing production of a protein encoded by the ADAMTS13 gene by targeting a region of a RIC pre-mRNA transcribed from the ADAMTS13 gene.

TABLE 4

List of ASOs targeting the ADAMTS13 gene

| ASO | Sequence | SEQ ID NO |
|---|---|---|
| ADAM-IVS25 + 6 | caggaaggaggacaggac | 150 |
| ADAM-IVS25 + 11 | ccugacaggaaggaggac | 151 |
| ADAM-IVS25 + 16 | agcugccugacaggaagg | 152 |
| ADAM-IVS25 + 21 | gcagcagcugccugacag | 153 |
| ADAM-IVS25 + 26 | cuccugcagcagcugccu | 154 |
| ADAM-IVS25 + 31 | caccccuccugcagcagc | 155 |
| ADAM-IVS25 + 36 | uugcccacccccuccugca | 156 |
| ADAM-IVS25 + 41 | ugccuuugcccaccccuc | 157 |
| ADAM-IVS25 + 46 | gaagaugccuuugcccac | 158 |
| ADAM-IVS25 − 16 | gagacagguaagcagugc | 159 |
| ADAM-IVS25 − 21 | agguaagcagugcuuccc | 160 |
| ADAM-IVS25 − 26 | agcagugcuuccccgauu | 161 |
| ADAM-IVS25 − 31 | ugcuuccccgauucccag | 162 |
| ADAM-IVS25 − 36 | ccccgauucccagcaggg | 163 |
| ADAM-IVS25 − 41 | auucccagcagggcaggc | 164 |
| ADAM-IVS25 − 46 | cagcagggcaggcuccgg | 165 |
| ADAM-IVS25 − 47 | agcagggcaggcuccggg | 166 |
| ADAM-IVS25 − 62 | gggcuuccaagcugagga | 167 |
| ADAM-IVS27 + 6 | aggugagaaggccuggc | 168 |
| ADAM-IVS27 + 11 | aagggagguggagaaggc | 169 |
| ADAM-IVS27 + 16 | cacccaagggagguggag | 170 |
| ADAM-IVS27 + 21 | uggagcacccaagggagg | 171 |
| ADAM-IVS27 + 26 | aggacuggagcacccaag | 172 |
| ADAM-IVS27 + 31 | cugccaggacuggagcac | 173 |
| ADAM-IVS27 + 36 | ccucccugccaggacugg | 174 |
| ADAM-IVS27 + 41 | cccagccuccugccagg | 175 |
| ADAM-IVS27 − 16 | agggacauaggaacccag | 176 |
| ADAM-IVS27 − 21 | cauaggaacccagacaga | 177 |
| ADAM-IVS27 − 26 | gaacccagacagaccggu | 178 |

TABLE 4-continued
List of ASOs targeting the ADAMTS13 gene

| ASO | Sequence | SEQ ID NO |
|---|---|---|
| ADAM-IVS27 − 31 | cagacagaccggugugc | 179 |
| ADAM-IVS27 − 36 | agaccggugugccagag | 180 |
| ADAM-IVS27 − 41 | gguggugccagaggccag | 181 |
| ADAM-IVS27 − 46 | ugccagaggccaggacaa | 182 |
| ADAM-IVS27 − 51 | gaggccaggacaacucac | 183 |
| ADAM-IVS25 + 17 | cagcugccugacaggaag | 184 |
| ADAM-IVS25 + 18 | gcagcugccugacaggaa | 185 |
| ADAM-IVS25 + 19 | agcagcugccugacagga | 186 |
| ADAM-IVS25 + 20 | cagcagcugccugacagg | 187 |
| ADAM-IVS25 + 21a | gcagcagcugccugacag | 188 |
| ADAM-IVS25 + 22 | ugcagcagcugccugaca | 189 |
| ADAM-IVS25 + 23 | cugcagcagcugccugac | 190 |
| ADAM-IVS25 + 24 | ccugcagcagcugccuga | 191 |
| ADAM-IVS25 + 25 | uccugcgcagcugccug | 192 |
| ADAM-IVS25 + 26a | cuccugcagcagcugccu | 193 |
| ADAM-IVS25 + 27 | ccuccugcagcagcugcc | 194 |
| ADAM-IVS25 + 28 | cccuccugcagcagcugc | 195 |
| ADAM-IVS25 + 29 | ccccuccugcagcagcug | 196 |
| ADAM-IVS25 + 30 | accccuccugcagcagcu | 197 |

Table 5 provides a non-limiting list of sequences of ASOs for increasing production of a protein encoded by the TSC1 gene by targeting a region of a RIC pre-mRNA transcribed from the TSC1 gene.

TABLE 5
List of ASOs targeting the TSC1 gene

| ASO | Sequence | SEQ ID NO |
|---|---|---|
| TSC1-IVS5 + 6 | ucaaauccuuacaaacau | 198 |
| TSC1-IVS5 + 11 | uucauucaaauccuuaca | 199 |
| TSC1-IVS5 + 16 | accauucauucaaaucc | 200 |
| TSC1-IVS5 + 21 | auaaaaccauuucauuca | 201 |
| rsci-IVS5 + 26 | uacucauaaaaccauuuc | 202 |
| TSC1-IVS5 + 31 | aacuauacucauaaaacc | 203 |
| TSC1-IVS5 + 36 | ucagaaacuauacucaua | 204 |
| TSC1-IVS5 + 41 | aaauuucagaaacuauac | 205 |
| TSC1-IVSS − 16 | ucaaacaggaaacgucug | 206 |
| TSC1-IVS5 − 21 | caggaaacgucugucagg | 207 |
| TSC1-IVS5 − 26 | aacgucugucaggcacug | 208 |
| TSC1-IVS5 − 31 | cugucaggcacuggcacc | 209 |

TABLE 5-continued
List of ASOs targeting the TSC1 gene

| ASO | Sequence | SEQ ID NO |
|---|---|---|
| TSC1-IVS5 − 36 | aggcacuggcaccaggau | 210 |
| TSC1-IVS5 − 41 | cuggcaccaggaucggca | 211 |
| TSC1-IVS5 − 46 | accaggaucggcauugua | 212 |
| TSC1-IVS5 − 51 | gaucggcauuguacagua | 213 |
| TSC1-IVS10 + 6 | aggcacacuaguugacac | 214 |
| TSC1-IVS10 + 11 | agagcaggcacacuaguu | 215 |
| TSC1-IVS10 + 16 | aggagagagcaggcacac | 216 |
| TSC1-IVS10 + 21 | agcagaggagagagcagg | 217 |
| TSC1-IVS10 + 26 | cagaaagcagaggagaga | 218 |
| TSC1-IVS10 + 31 | uucaccagaaagcagagg | 219 |
| TSC1-IVS10 + 36 | ucagcuucaccagaaagc | 220 |
| TSC1-IVS10 + 41 | aagggucagcuucaccag | 221 |
| TSC1-IVS10 − 16 | aguacaucagcaguggca | 222 |
| TSC1-IVS10 − 21 | aucagcaguggcaaagga | 223 |
| TSC1-IVS10 − 26 | caguggcaaaggaaugcu | 224 |
| TSC1-IVS10 − 31 | gcaaaggaaugcuaaguc | 225 |
| TSC1-IVS10 − 36 | ggaaugcuaagucaucca | 226 |
| TSC1-IVS10 − 41 | gcuaagucauccacgagg | 227 |
| TSC1-IVS10 − 46 | gucauccacgagguuuau | 228 |
| TSC1-IVS10 − 51 | ccacgagguuuauaucca | 229 |
| TSC1-IVS11 + 6 | aauccaaccuaagacaua | 230 |
| TSC1-IVS11 + 11 | aaucaaauccaaccuaag | 231 |
| TSC1-IVS11 + 16 | caacuaaucaaauccaac | 232 |
| TSC1-IVS11 + 21 | aaaaccaacuaaucaaau | 233 |
| TSC1-IVS11 + 26 | aggccaaaaccaacuaau | 234 |
| TSC1-IVS11 + 31 | aaggcaggccaaaaccaa | 235 |
| TSC1-IVS11 + 36 | cauuaaaggcaggccaaa | 236 |
| TSC1-IVS11 + 41 | ccugccauuaaaggcagg | 237 |
| TSC1-IVS11 − 16 | agaacauauaugaacacu | 238 |
| TSC1-IVS11 − 21 | auauaugaacacugagcc | 239 |
| TSC1-IVS11 − 26 | ugaacacugagcccaacu | 240 |
| TSC1-IVS11 − 31 | acugagcccaacuauuag | 241 |
| TSC1-IVS11 − 36 | gcccaacuauuagaaaaa | 242 |
| TSC1-IVS11 − 41 | acuauuagaaaaacugcc | 243 |
| TSC1-IVS11 − 46 | uagaaaaacugccgauuu | 244 |
| TSC1-IVS11 − 51 | aaacugccgauuuuuuuu | 245 |

Table 6 provides a non-limiting list of sequences of ASOs for increasing production of a protein encoded by the IMPDH1 gene by targeting a region of a RIC pre-mRNA transcribed from the IMPDH1 gene.

TABLE 6
List of ASOs targeting the IMPDH1 gene

| ASO | Sequence | SEQ ID NO |
|---|---|---|
| IMP-IVS14 + 6 | gggcccagggucag | 246 |
| IMP-IVS14 + 18 | cugaucugcccaggvggg | 247 |
| IMP-IVS14 + 23 | gugggcugaucugcccag | 248 |
| IMP-IVS14 + 28 | ggguugugggcugaucug | 249 |
| IMP-IVS14 + 33 | cugaaggguugugggcug | 250 |
| IMP-IVS14 + 38 | gggcccugaaggguugug | 251 |
| IMP-IVS14 + 43 | ugagcgggcccugaaggg | 252 |
| IMP-IVS14 + 48 | uggcaugagcgggcccug | 253 |
| IMP-IVS14 − 16 | aagacugagcccagcagc | 254 |
| IMP-IVS14 − 21 | ugagccagcagcuugaa | 255 |
| IMP-IVS14 − 26 | ccagcagcuugaagcuca | 256 |
| IMP-IVS14 − 31 | agcuugaagcucagagga | 257 |
| IMP-IVS14 − 36 | gaagcucagaggacccca | 258 |
| IMP-IVS14 − 41 | ucagaggaccccaccccca | 259 |
| IMP-IVS14 − 46 | ggaccccaccccaccucu | 260 |
| IMP-IVS14 − 51 | ccaccccaccucuuaagg | 261 |
| IMP-IVS14 + 44 | augagcgggcccugaagg | 262 |
| IMP-IVS14 + 45 | caugagcgggcccugaag | 263 |
| IMP-IVS14 + 46 | gcaugagcgggcccugaa | 264 |
| IMP-IVS14 + 47 | ggcaugagcgggcccuga | 265 |
| IMP-IVS14 + 48a | uggcaugagcgggcccug | 266 |
| IMP-IVS14 + 49 | guggcaugagcgggcccu | 267 |
| IMP-IVS14 + 50 | gguggcaugagcgggccc | 268 |
| IMP-IVS14 + 51 | cgguggcaugagcgggcc | 269 |
| IMP-IVS14 + 52 | ucgguggcaugagcgggc | 270 |
| IMP-IVS14 + 53 | gucgguggcaugagcggg | 271 |

Table 7 provides a non-limiting list of sequences of ASOs for increasing production of a protein encoded by the PKD1 gene by targeting a region of a RIC pre-mRNA transcribed from the PKD1 gene.

TABLE 7
List of ASOs targeting the PKD1 gene

| ASO | Sequence | SEQ ID NO |
|---|---|---|
| PKD1-IVS32 + 6 | cgagguuucucuagggaa | 272 |
| PKD1-IVS32 + 11 | gggcucgagguuucucua | 273 |
| PKD1-IVS32 + 16 | caccagggcucgagguuu | 274 |
| PKD1-IVS32 + 21 | accugcaccagggcucga | 275 |
| PKD1-IVS32 + 26 | cagugaccugcaccaggg | 276 |
| PKD1-IVS32 + 31 | agacacagugaccugcac | 277 |
| PKD1-IVS32 + 36 | accccagacacagugacc | 278 |
| PKD1-IVS32 + 41 | ccggcaccccagacacag | 279 |
| PKD1-IVS32 − 16 | gucagcaagguaccaggg | 280 |
| PKD1-IVS32 − 32 | gggaugugucacacacac | 281 |
| PKD1-IVS32 − 37 | gugucacacacacagccc | 282 |
| PKD1-IVS32 − 42 | acacacacagcccacccc | 283 |
| PKD1-IVS32 − 47 | cacagcccaccccgucc | 284 |
| PKD1-IVS32 − 52 | cccaccccguccagvca | 285 |
| PKD1-IVS32 − 57 | ccccguccagucacgcac | 286 |
| PKD1-IVS32 − 62 | uccagucacgcacggaca | 287 |
| PKD1-IVS33 + 6 | ccccuccucucaccccag | 288 |
| PKD1-IVS33 + 11 | agagccccuccucucac | 289 |
| PKD1-IVS33 + 16 | gcuucagagcccccuccu | 290 |
| PKD1-IVS33 + 21 | ggugagcuucagagcccc | 291 |
| PKD1-IVS33 + 26 | gcaagggugagcuucaga | 292 |
| PKD1-IVS33 − 31 | cagcugcaagggugagcu | 293 |
| PKD1-IVS33 − 26 | gggcccgcugcaagggu | 294 |
| PKD1-IVS33 − 21 | agggugggcccagcugca | 295 |
| PKD1-IVS33 − 16 | gcauaggugggcccagc | 296 |
| PKD1-IVS37 + 6 | gcacaggccgcacccagg | 297 |
| PKD1-IVS37 + 8 | gggcacaggccgcaccca | 298 |
| PKD1-IVS37 + 24 | gagacggagguggcaggg | 299 |
| PKD1-IVS37 + 29 | gacaagagacggaggugg | 300 |
| PKD1-IVS37 + 34 | ugggagacaagagacgga | 301 |
| PKD1-IVS37 + 39 | ggaggugggagacaagag | 302 |
| PKD1-IVS37 + 44 | ggguggaggugggagac | 303 |
| PKD1-IVS37 + 49 | ugcauggguggaggugg | 304 |
| PKD1-IVS37 − 16 | gcccuguggucagccugg | 305 |
| PKD1-IVS37 − 21 | guggucagccuggcccca | 306 |
| PKD1-IVS37 − 26 | cagccuggccccagccca | 307 |
| PKD1-IVS37 − 31 | uggccccagcccacagug | 308 |
| PKD1-IVS37 − 36 | ccagcccacagugacagc | 309 |
| PKC1-IVS37 − 41 | ccacagugacagcagggc | 310 |
| PKD1-IVS37 − 46 | gugacagcagggcuuugg | 311 |
| PKD1-IVS37 − 51 | agcagggcuuuggcaacg | 312 |
| PKD1-IVS38 + 6 | accagugcaccggaugcc | 313 |

TABLE 7-continued

List of ASOs targeting the PKD1 gene

| ASO | Sequence | SEQ ID NO |
|---|---|---|
| PKD1-IVS38 + 11 | gacagaccagugcaccgg | 314 |
| PKD1-IVS38 + 16 | cagaagacagaccagugc | 315 |
| PKD1-IVS38 + 21 | aagcccagaagacagacc | 316 |
| PKD1-IVS38 + 26 | aacuaaagcccagaagac | 317 |
| PKD1-IVS38 + 31 | ggcaaaacuaaagcccag | 318 |
| PKD1-IVS38 + 36 | cuaaaggcaaaacuaaag | 319 |
| PKD1-IVS38 + 41 | cuggacuaaaggcaaaac | 320 |
| PKD1-IVS38 − 16 | ucacacgcuccagcccu | 321 |
| PKD1-IVS38 − 21 | cgcuccagccccuacugc | 322 |
| PKD1-IVS38 − 26 | cagccccuacugcccau | 323 |
| PKD1-IVS38 − 31 | ccuacugccccaugcccg | 324 |
| PKD1-IVS38 − 36 | ugccccaugccgccucg | 325 |
| PKD1-IVS38 − 41 | caugcccgccucgaguga | 326 |
| PKD1-IVS38 − 46 | ccgccucgagugagcggc | 327 |
| PKD1-IVS38 − 51 | ucgagugagcggccacca | 328 |

Table 8 provides a non-limiting list of sequences of ASOs for increasing production of a protein encoded by the IKBKAP gene by targeting a region of a RIC pre-mRNA transcribed from the IKBKAP gene.

TABLE 8

List of ASOs targeting the IKBKAP gene

| ASO | Sequence | SEQ ID NO |
|---|---|---|
| IKB-IVS7 + 6 | uuaacugcaauauauuuc | 329 |
| IKB-IVS7 + 11 | guuguuuaacugcaauau | 330 |
| IKB-IVS7 + 16 | uuauuguuguuuaacugc | 331 |
| IKB-IVS7 + 21 | auuuuuuauuguuguuua | 332 |
| IKB-IVS7 + 26 | uaaaaauuuuuauuguu | 333 |
| IKB-IVS7 + 31 | uaagauaaaaauuuuua | 334 |
| IKB-IVS7 + 36 | uuuaauaagauaaaaauu | 335 |
| IKB-IVS7 + 41 | uuaauuuaauaagauaa | 336 |
| IKB-IVS7 − 16 | gucaaacacacauacaca | 337 |
| IKB-IVS7 − 21 | acacacauacacacuuaa | 338 |
| IKB-IVS7 − 26 | cauacacacuuaaaacau | 339 |
| IKB-IVS7 − 31 | acacuuaaaacauuauga | 340 |
| IKB-IVS7 − 36 | uaaaacauuaugauaaaa | 341 |
| IKB-IVS7 − 41 | cauuaugauaaaaguugu | 342 |
| IKB-IVS7 − 46 | ugauaaaaguugucaauu | 343 |
| IKB-IVS7 − 51 | aaaguugucaauucagaa | 344 |
| IKB-IVS8 + 6 | cuaagguuucuucuccca | 345 |
| IKB-IVS8 + 11 | uuucucuaagguuucuuc | 346 |
| IKB-IVS8 + 16 | aagaauuucucuaagguu | 347 |
| IKB-IVS8 + 21 | guuccaagaauuucucua | 348 |
| IKB-IVS8 + 26 | cucugguuccaagaauuu | 349 |
| IKB-IVS8 + 31 | cucuacucugguuccaag | 350 |
| IKB-IVS8 + 36 | accaccucuacucugguu | 351 |
| IKB-IVS8 + 41 | guaccaccaccucuacuc | 352 |
| IKB-IVS8 − 16 | gaguguuacaauaucgaa | 353 |
| IKB-IVS8 − 21 | uuacaauaucgaaagcuc | 354 |
| IKB-IVS8 − 26 | auaucgaaagcucaccua | 355 |
| IKB-IVS8 − 31 | gaaagcucaccuaacuaa | 356 |
| IKB-IVS8 − 36 | cucaccuaacuaaagaau | 357 |
| IKB-IVS8 − 41 | cuaacuaaagaauagaua | 358 |
| IKB-IVS8 − 46 | uaaagaauagauaaaauc | 359 |
| IKB-IVS8 − 51 | aauagauaaaauccagaa | 360 |
| IKB-IVS7 + 22M | aauuuuuuauuguuguuu | 361 |
| IKB-IVS7 + 23M | aaauuuuuuauuguuguu | 362 |
| IKB-IVS7 + 24M | aaaauuuuuuauuguugu | 363 |
| IKB-IVS7 + 25M | aaaaauuuuuuauuguug | 364 |
| IKB-IVS7 + 26M | uaaaaauuuuuuauuguu | 365 |
| IKB-IVS7 + 27M | auaaaaauuuuuuauugu | 366 |
| IKB-IVS7 + 28M | gauaaaaauuuuuuauug | 367 |
| IKB-IVS7 + 29M | agauaaaaauuuuuuauu | 368 |
| IKB-IVS7 + 30M | aagauaaaaauuuuuuau | 369 |
| IKB-IVS8 − 16M | gaguguuacaauaucgaa | 370 |
| IKB-IVS8 − 17M | aguguuacaauaucgaaa | 371 |
| IKB-IVS8 − 18M | guguuacaauaucgaaag | 372 |
| IKB-IVS8 − 19M | uguuacaauaucgaaagc | 373 |
| IKB-IVS8 − 20M | guuacaauaucgaaagcu | 374 |

Methods of Identifying a Retained Intron

Also within the scope of the present disclosure are methods of identifying (determining) a retained intron in a pre-mRNA transcript while an adjacent (upstream or downstream) intron is spliced out of the pre-mRNA in a cell. In one example, the extent of splicing and joining of the exons and removal of each intron from a target gene can be measured by the following method. It will be appreciated by one of skill in the art that any method may be used to determine whether an intron is retained in a pre-mRNA transcript relative to an adjacent intron that is spliced out of the pre-mRNA transcript and whether a target intron is retained to greater extent relative to one or more other introns within the pre-mRNA encoded by the same gene.

I. Screening for Retained Introns

Figure 3:
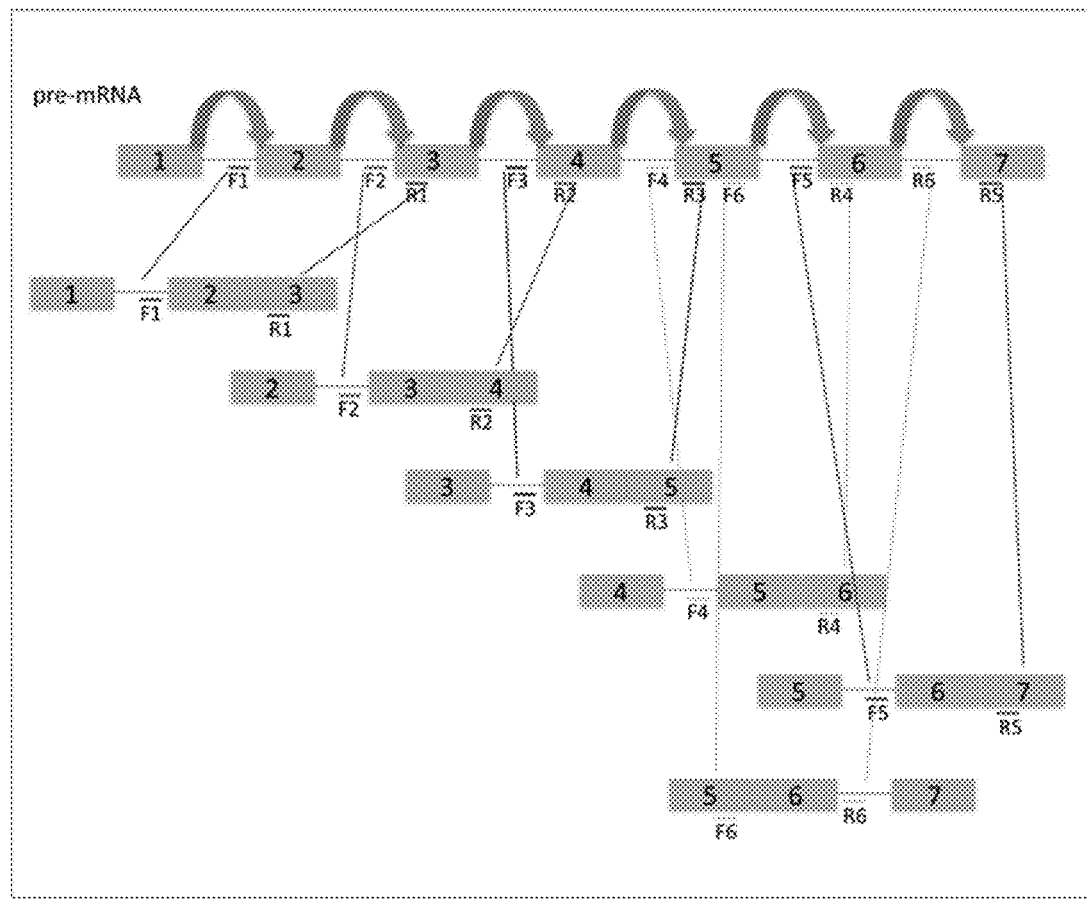
FIG. 3 shows a schematic representation of an example of screening for intron retention using RT-PCR, as described in Example 1, of a 7-exon/6-intron gene. Numbered rectangles denote exons connected by lines denoting introns. Arched arrows indicate splicing events. Short horizontal bars denote primer pairs used to assess intron retention. Forward primer are indicated with "F" and reverse primers are indicated with "R," i.e., pairs F1 and R1, F2 and R2, F3 and R3, F4 and R4, F5 and R5, and F6 and R6. An intron is identified as a retained intron when such an intron is present and an adjacent intron is observed to be spliced out (removed).

A first round of screening for intron retention can be performed using nuclear RNA isolated from cells or tissues (e.g., disease-relevant cells) and analyzed by reverse transcriptase-PCR (RT-PCR), for example, investigating a pre-RNA encoded by a target gene. A target gene may be any gene that contains at least one intron and encodes a protein or a functional RNA that is associated with a disease or disorder or suspected of being associated or causative of a disease or disorder. For RT-PCR analysis, each intron is assessed for retention in the pre-mRNA encoded by a gene by designing a series of primer pairs in which one of the primers of the pair is specific to a region of an intron of the target pre-mRNA and the other primer of the pair is specific to a region of an exon that is two exons upstream or downstream of the intron (FIG. 3). In some embodiments, the upstream or forward primer may be complementary and hybridize to a region within an intron, for example the intron between exons 1 and 2 in FIG. 3; and the downstream or reverse primer may be complementary and hybridize to a region within an exon that is located two exons away from the intron that is being assess, for example within exon 3 as shown in FIG. 3. Alternatively, the upstream or forward primer may be complementary and hybridize to a region within an exon, for example in exon 2 in FIG. 3; and the downstream or reverse primer may be complementary and hybridize to a region within an intron that is two exons away from the forward primer, for example within the intron between exons 3 and 4 as shown in FIG. 3. Design of primer pairs may be repeated for each of the introns encoded by the gene.

Following RT-PCR using each of the primer pairs, the RT-PCR products are analyzed by any method known in the art, for example, separation and visualization in an agarose gel. The approximate size of the RT-PCR product that is expected if the target intron is present may be estimated based on the nucleic acid sequence of the gene and/or pre-mRNA. The absence of a product from the RT-PCR analysis indicates that the target intron was not present and was removed/spliced from the pre-mRNA, and therefore under the conditions tested, is not a retained intron. The presence of a product from the RT-PCR reaction that is of approximately the size of the estimated product indicates that the target intron is present in the pre-mRNA and was not removed/spliced from the pre-mRNA under the conditions tested, such introns are referred to as "retained introns."

In examples in which analysis is desired for many pre-RNAs or on a transcriptome-wide level, the screening for intron retention can be analyzed by RNA-seq or any other high-throughput transcriptional analysis method. RNA-seq analysis is carried out using appropriate mapping of deep sequencing reads and statistical methods to determine intron-retention events across the entire transcriptome.

II. Confirmation of Intron Retention Events

Figure 4:
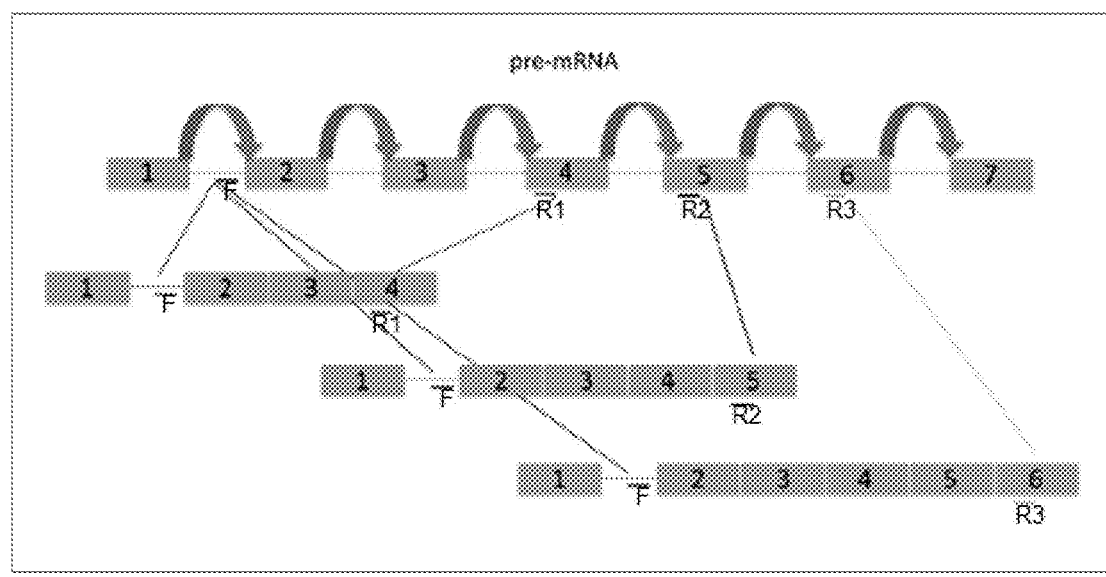
FIG. 4 shows a schematic representation of an example of screening to confirm intron retention using RT-PCR, as described in Example 2, of a 7-exon/6-intron gene. Numbered rectangles denote exons connected by lines denoting introns. Arched arrows indicate splicing events. Short horizontal bars denote primer pairs used to assess intron retention. The forward primer is labeled with an "F" and reverse primers are labeled with "R1," "R2," or "R3." Introns are confirmed as retained introns when such intron is present and one or more adjacent introns is observed to be spliced out (removed).

A second round of screening of introns within a pre-mRNA may be performed to confirm intron-retention events using methods such as RT-PCR. Each of the introns that were identified to be retained introns on the first round of screening described above can be assessed again. For RT-PCR analysis, each retained intron is assessed for retention in the pre-mRNA encoded by gene by designing primer pairs in which one of the primers of the pair is specific to a region of an intron of the target pre-mRNA and the other primer of the pair is specific to a region of an exon that is three, four, or five exons upstream or downstream of the intron (FIG. 4). In the schematic presented in FIG. 4, the retained intron to be assessed is located between exons 1 and 2. The upstream or forward primer is specific to a region and hybridizes within the retained intron and a downstream or reverse primer is designed to hybridize to a region in exon 4, exon 5, and exon 6, exons which are 3, 4, and 5 exons away from the retained intron, respectively. RT-PCR reactions are performed using the forward primer and each of the reverse primers.

Following RT-PCR, the RT-PCR products are analyzed by any method known in the art, for example, separation and visualization in an agarose gel. Based on the molecular size of RT-PCR products from each reaction, it can be determined whether each of the introns (e.g., the intron between exons 2 and 3, 3 and 4, and 4 and 5) is retained in addition to the intron being tested (the retained intron identified above). Retained introns that are found to be retained when one or more adjacent introns have been removed/spliced may be referred to as a an "inefficiently spliced intron."

III. Determining Intron Splicing Efficiency

Any introns in pre-mRNA encoded by a target gene that are identified as persistent introns or inefficiently spliced introns relative to other introns in the same pre-mRNA that are removed/spliced, may be further assessed to determine the proportion or efficiency of intron retention.

Figure 5:
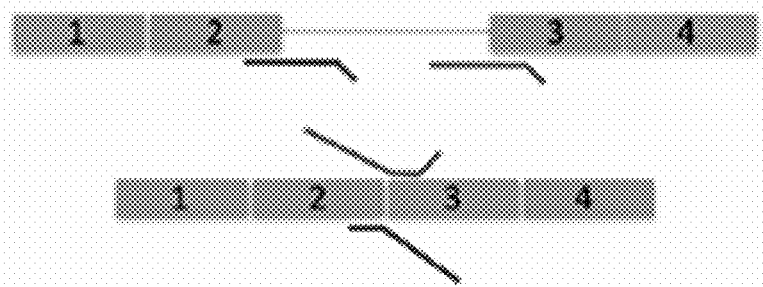
FIG. 5 shows a schematic representation of an exemplary RNase protection assay (RPA) to determine intron-removal efficiency.
Figure 5:
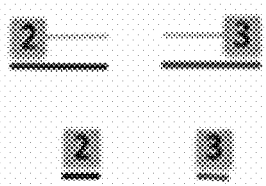
Figure 5:
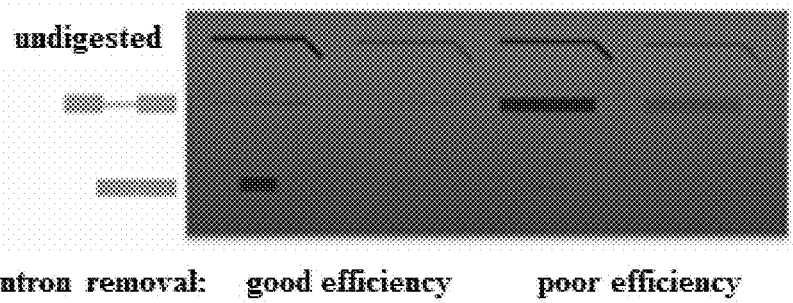

An intron may be assessed to determine the efficiency of intron retention by performing an assay such as an RNase protection assay (FIG. 5). A pair of RNA probes (e.g., radioactively-labeled RNA probes) are designed in which each of the probes is specific to a region spanning the end of the retained intron and the adjacent exon. For example, an RNA probe is designed that hybridizes to the region spanning the 5' end of the retained intron and 3' end of the exon that is upstream of the retained intron; and a second RNA probe is designed that hybridizes to the region spanning the 3' end of the retained intron and the 5' end of the exon that is downstream of the retained intron. In some embodiments, the portion of the probe that hybridizes to the intron is at least 100 nucleotides in length and the portion of the probe that hybridizes to the exon is at least 50 nucleotides in length (FIG. 5). Nuclear RNA extracted from disease-relevant cells, tissues or cell lines is incubated with the pair of RNA probes under conditions in which the probes hybridize to the regions of the pre-mRNA forming regions of double-stranded RNA. The mixture of pre-mRNA and RNA probes digested with RNases that degrade single-stranded RNA, such as RNaseA and/or RNase T1. Double-stranded RNA is protected from degradation.

The RNase digestion reactions are analyzed by any method known in the art, for example, separation and visualization in an agarose gel. The quantity of an RNA molecule that corresponds to the full-length of the RNA probe (e.g., 150 nucleotides) indicates that amount of the retained intron present in the pre-mRNA. The quantity of RNA molecules that corresponds to digested RNA probes (e.g., RNA molecules of approximately 50 nucleotides in length) represented the amount of spliced RNA as the intron to which the RNA probe hybridizes is not present in the pre-mRNA (e.g., was spliced out). The ratio of intron retention (amount of full-length RNA probe, e.g., 100 nucleotide RNA molecules) over spliced RNA (amount of degraded RNA probe, e.g., 50 nucleotide RNA molecules) indicates the efficiency of splicing of the intron. The intron of a pre-mRNA having the highest ratio relative to other introns of the same pre-mRNA indicates the intron is the least efficiently spliced intron or the most highly retained intron of the pre-mRNA encoded by the target gene.

Methods of Identifying an ASO that Enhances Splicing

Also within the scope of the present invention are methods for identifying (determining) ASOs that enhance splicing of a target pre-mRNA, specifically at the target intron. ASOs that specifically hybridize to different nucleotides within the target region of the pre-mRNA may be screened to identify (determine) ASOs that improve the rate and/or extent of splicing of the target intron. In some embodiments, the ASO may block or interfere with the binding site(s) of a splicing repressor(s)/silencer. Any method known in the art may be used to identify (determine) an ASO that when hybridized to the target region of the intron results in the desired effect (e.g., enhanced splicing, protein or functional RNA production). These methods also can be used for identifying ASOs that enhance splicing of the retained intron by binding to a targeted region in an exon flanking the retained intron, or in a non-retained intron. An example of a method that may be used is provided below.

A round of screening, referred to as an ASO "walk" may be performed using ASOs that have been designed to hybridize to a target region of a pre-mRNA. For example, the ASOs used in the ASO walk can be tiled every 5 nucleotides from approximately 100 nucleotides upstream of the 5' splice site of the retained intron (e.g., a portion of sequence of the exon located upstream of the target/retained intron) to approximately 100 nucleotides downstream of the 5' splice site of the target/retained intron and/or from approximately 100 nucleotides upstream of the 3' splice site of the retained intron to approximately 100 nucleotides downstream of the 3' splice site of the target/retained intron (e.g., a portion of sequence of the exon located downstream of the target/retained intron). For example, a first ASO of 15 nucleotides in length may be designed to specifically hybridize to nucleotides +6 to +20 relative to the 5' splice site of the target/retained intron. A second ASO is designed to specifically hybridize to nucleotides +11 to +25 relative to the 5' splice site of the target/retained intron. ASOs are designed as such spanning the target region of the pre-mRNA. In embodiments, the ASOs can be tiled more closely, e.g., every 1, 2, 3, or 4 nucleotides. Further, the ASOs can be tiled from 100 nucleotides downstream of the 5' splice site, to 100 nucleotides upstream of the 3' splice site.

One or more ASOs, or a control ASO (an ASO with a scrambled sequence, sequence that is not expected to hybridize to the target region) are delivered, for example by transfection, into a disease-relevant cell line that expresses the target pre-mRNA (e.g., the RIC pre-mRNA described elsewhere herein). The splicing-inducing effects of each of the ASOs may be assessed by any method known in the art, for example by reverse transcriptase (RT)-PCR using primers that span the splice junction, as described herein (see "Identification of intron-retention events"). A reduction or absence of the RT-PCR product produced using the primers spanning the splice junction in ASO-treated cells as compared to in control ASO-treated cells indicates that splicing of the target intron has been enhanced. In some embodiments, the splicing efficiency, the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced protein production). Any method known in the art for assessing and/or quantifying protein production, such as Western blotting, flow cytometry, immunofluorescence microscopy, and ELISA, can be used.

A second round of screening, referred to as an ASO "micro-walk" may be performed using ASOs that have been designed to hybridize to a target region of a pre-mRNA. The ASOs used in the ASO micro-walk are tiled every 1 nucleotide to further refine the nucleotide acid sequence of the pre-mRNA that when hybridized with an ASO results in enhanced splicing.

Regions defined by ASOs that promote splicing of the target intron are explored in greater detail by means of an ASO "micro-walk", involving ASOs spaced in 1-nt steps, as well as longer ASOs, typically 18-25 nt.

As described for the ASO walk above, the ASO micro-walk is performed by delivering one or more ASOs, or a control ASO (an ASO with a scrambled sequence, sequence that is not expected to hybridize to the target region), for example by transfection, into a disease-relevant cell line that expresses the target pre-mRNA. The splicing-inducing effects of each of the ASOs may be assessed by any method known in the art, for example by reverse transcriptase (RT)-PCR using primers that span the splice junction, as described herein (see "Identification of intron-retention events"). A reduction or absence of the RT-PCR product produced using the primers spanning the splice junction in ASO-treated cells as compared to in control ASO-treated cells indicates that splicing of the target intron has been enhanced. In some embodiments, the splicing efficiency, the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced protein production). Any method known in the art for assessing and/or quantifying protein production, such as Western blotting, flow cytometry, immunofluorescence microscopy, and ELISA, can be used.

ASOs that when hybridized to a region of a pre-mRNA result in enhanced splicing and increased protein production may be tested in vivo using animal models, for example transgenic mouse models in which the full-length human gene has been knocked-in or in humanized mouse models of disease. Suitable routes for administration of ASOs may vary depending on the disease and/or the cell types to which delivery of the ASOs is desired. ASOs may be administered, for example, by intravitreal injection, intrathecal injection, intraperitoneal injection, subcutaneous injection, or intravenous injection. Following administration, the cells, tissues, and/or organs of the model animals may be assessed to determine the effect of the ASO treatment by for example evaluating splicing (efficiency, rate, extent) and protein production by methods known in the art and described herein. The animal models may also be any phenotypic or behavioral indication of the disease or disease severity.

EXAMPLES

The present invention will be more specifically illustrated by the following Examples. However, it should be understood that the present invention is not limited by these examples in any manner.

Example 1: Intron-Retention Events are Intrinsic to Genes and are Non-Productive A first round of screening was performed for intron-retention events in the PRPF31 (retinitis pigmentosa type 11) and RBI (retinoblastoma) genes using the methods described herein (FIG. 3). Briefly, RNA extracts were isolated from nuclear fractions of HeLa (human epithelial cervical adenocarcinoma) and 293T (human embryonic kidney epithelial) cells, and nuclear and cytoplasmic fractions of ARPE-19 (human retina) cells. Reverse transcriptase PCR (RT-PCR) was performed using the RNA extracts from each of the cell types. In brief, cDNA synthesis was carried out with oligo dT to generate a DNA copy of Poly-A RNA (fully transcribed RNA) only, and PCR was performed to assess for intron retention in PRPF31 and RB1 transcripts. The PCR products were separated on a 1.5% ethidium-bromide-stained agarose gel (FIGS. 6A-6D). Results show several intron-retention events (marked by black asterisk) for both genes (PRPF31 and RB1) in the nucleus of each of the three cell lines tested (FIGS. 6A-6D).

Tables 9 and 10 list all intron-retention events that occur in the three cell-lines tested for PRPF31 and RB1, respectively. The events (presence or absence of intron retention) that occur across all three cell-lines are indicated with an asterisk. The tables show that there is a very high concordance across the three cell lines indicating that the intron-retention events are intrinsic to the genes and are not affected by different cellular environments.

Figure 6A:
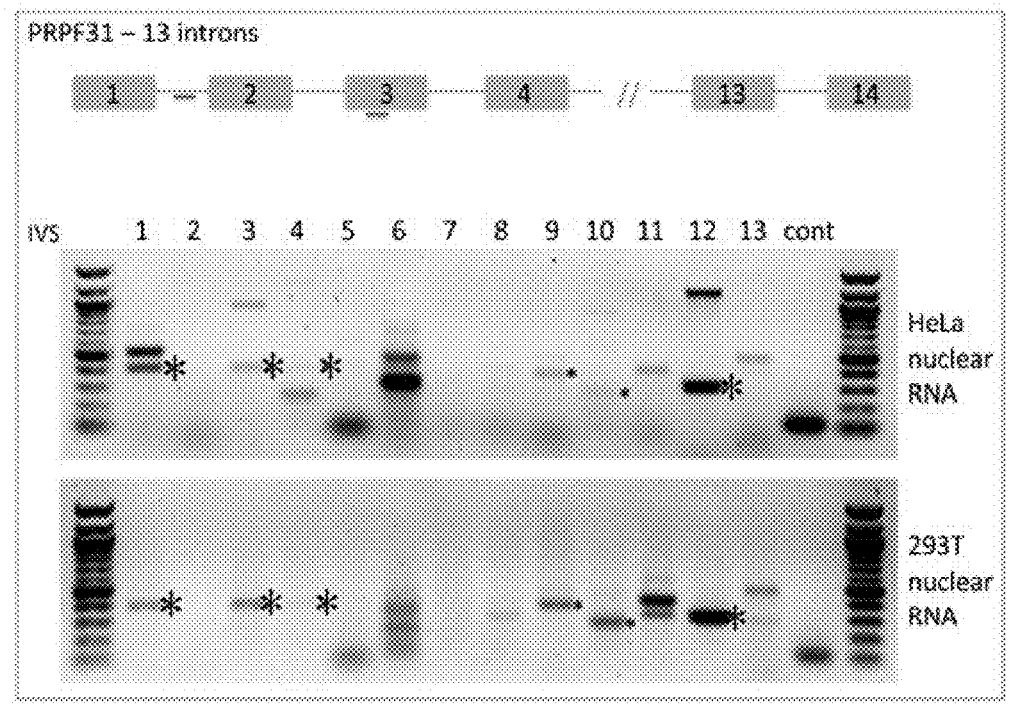
FIGS. 6A-6E show the identification of intron-retention events in the PRPF31 and RB1 genes, as described in Example 1.
Figure 6B:
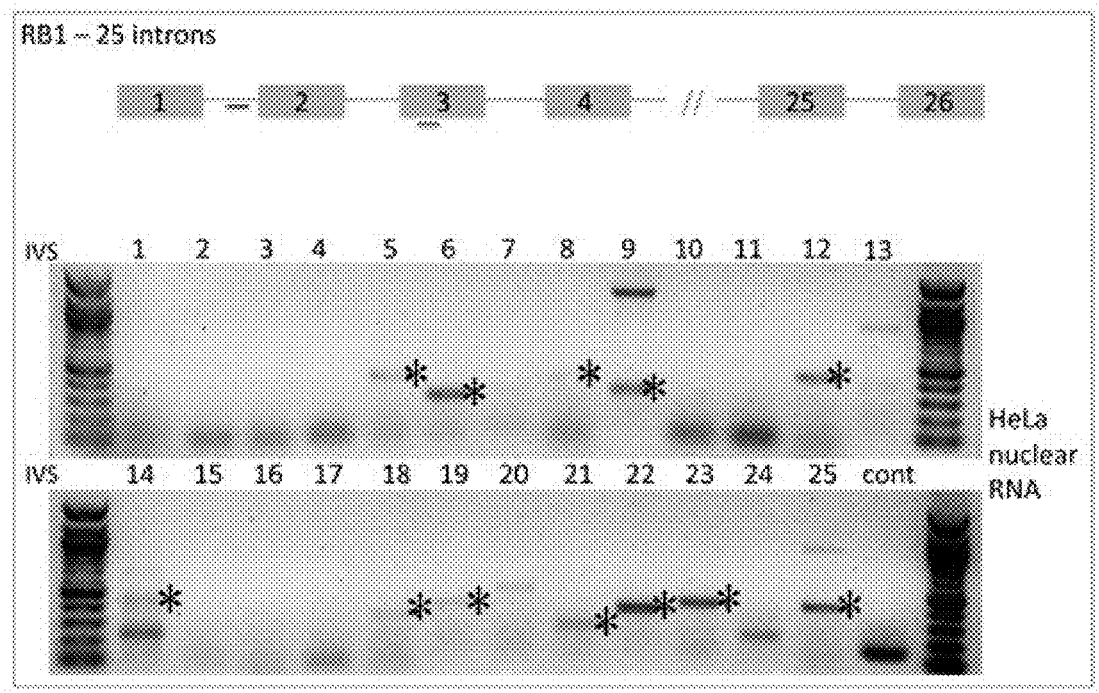
Figure 6C:
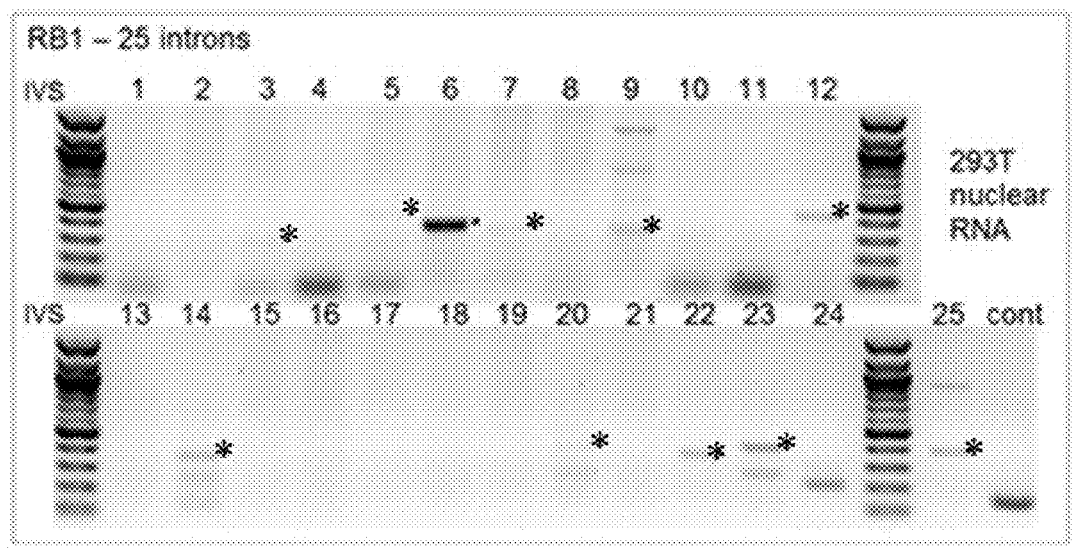
Figure 6D:
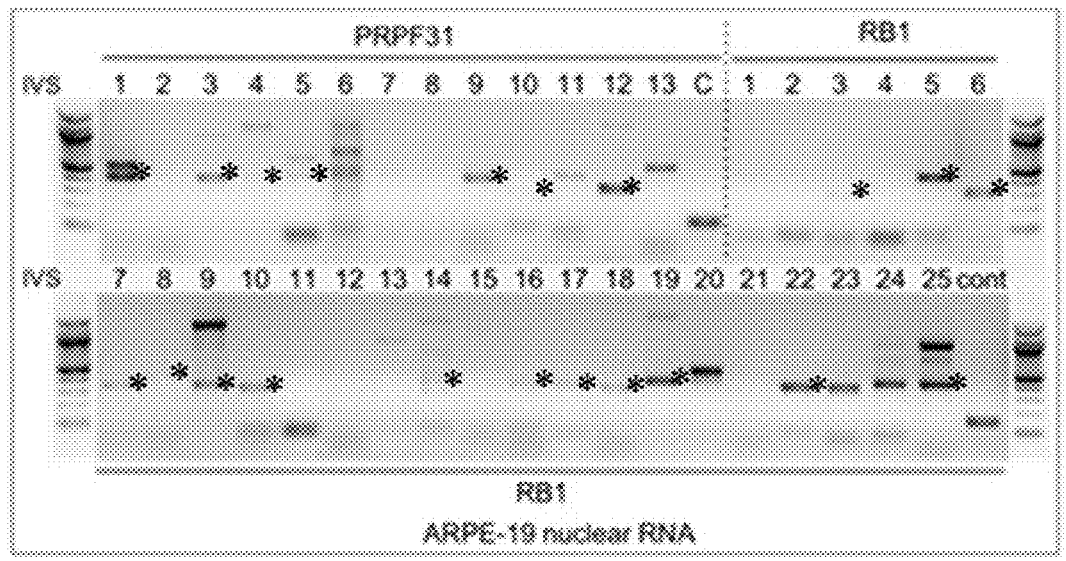
Figure 6E:
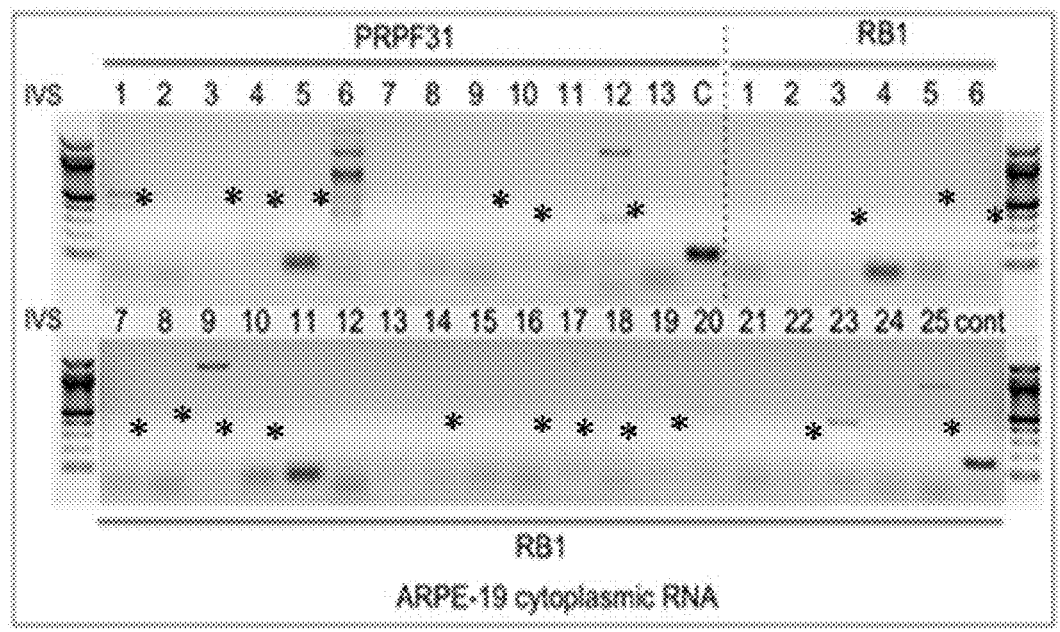

To address whether these events are non-productive (i.e. able to result in protein production), RT-PCR was performed using the cytoplasmic fraction of ARPE-19 cells (FIG. 6E). Results show that the majority of the observed intron-retention events are not present in the cytoplasm of ARPE-19 cells (FIG. 6E, asterisks mark where the bands should be) indicating, as expected, that the intron-retention events are result in the transcript being either retained in the nucleus or degraded by nonsense-mediated mRNA decay in the cytoplasm, and are therefore non-productive transcripts.

TABLE 9

Summary of results for intron-retention events in the PRPF31 gene.
PRPF31

| 293T | Retina | HeLa | Intron |
|---|---|---|---|
| Yes | Yes | Yes | 1* |
| No | No | No | 2* |
| Yes | Yes | Yes | 3* |
| Yes | Yes | Yes | 4* |
| No | Yes | No | 5 |
| No | No | No | 6* |
| No | No | No | 7* |
| No | No | No | 8* |
| ? | Yes | ? | 9 |
| ? | Yes | ? | 10 |
| No | No | No | 11* |
| Yes | Yes | Yes | 12* |
| No | No | No | 14* |

"Yes" indicates the presence of intron retention; "no" indicates the absence of intron retention; and "?" indicates non-conclusive results. Cases in which there is concordance between the three cell lines are labeled with an asterisk.

TABLE 10

Summary of results for intron-retention events in the RB1 gene.
RB1

| 293T | Retina | HeLa | Intron |
|---|---|---|---|
| No | No | No | 1* |
| No | No | No | 2* |
| Yes | Yes | No | 3 |
| No | No | No | 4* |
| Yes | Yes | Yes | 5* |
| Yes | Yes | Yes | 6* |
| Yes | Yes | No | 7 |
| No | Yes | Yes | 8 |

TABLE 10-continued

Summary of results for intron-retention events in the RB1 gene.
RB1

| 293T | Retina | HeLa | Intron |
|---|---|---|---|
| Yes | Yes | Yes | 9* |
| No | Yes | No | 10 |
| No | No | No | 11* |
| Yes | No | Yes | 12 |
| No | No | No | 13* |
| Yes | Yes | Yes | 14* |
| No | No | No | 15* |
| No | Yes | No | 16 |
| No | Yes | No | 17 |
| No | Yes | Yes | 18 |
| No | Yes | Yes | 19 |
| Yes | No | No | 20 |
| No | No | Yes | 21 |
| Yes | Yes | Yes | 22* |
| Yes | Yes | Yes | 23* |
| No | No | No | 24* |
| Yes | Yes | Yes | 25* |

"Yes" indicates the presence of intron retention; "no" indicates the absence of intron retention. Cases in which there is concordance between the three cell lines are labeled with an asterisk.

Example 2: Confirmation of Intron Retention Events

Figure 7A:
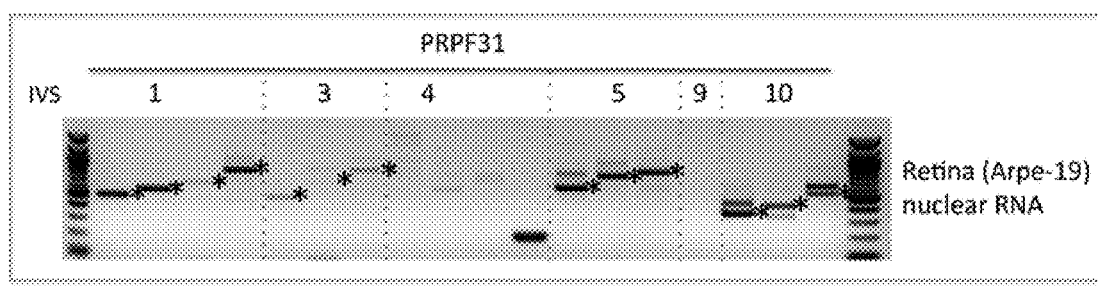
FIGS. 7A-7B show the identification of intron-retention events in the PRPF31 and RB1 genes, as described in Example 2.
Figure 7B:
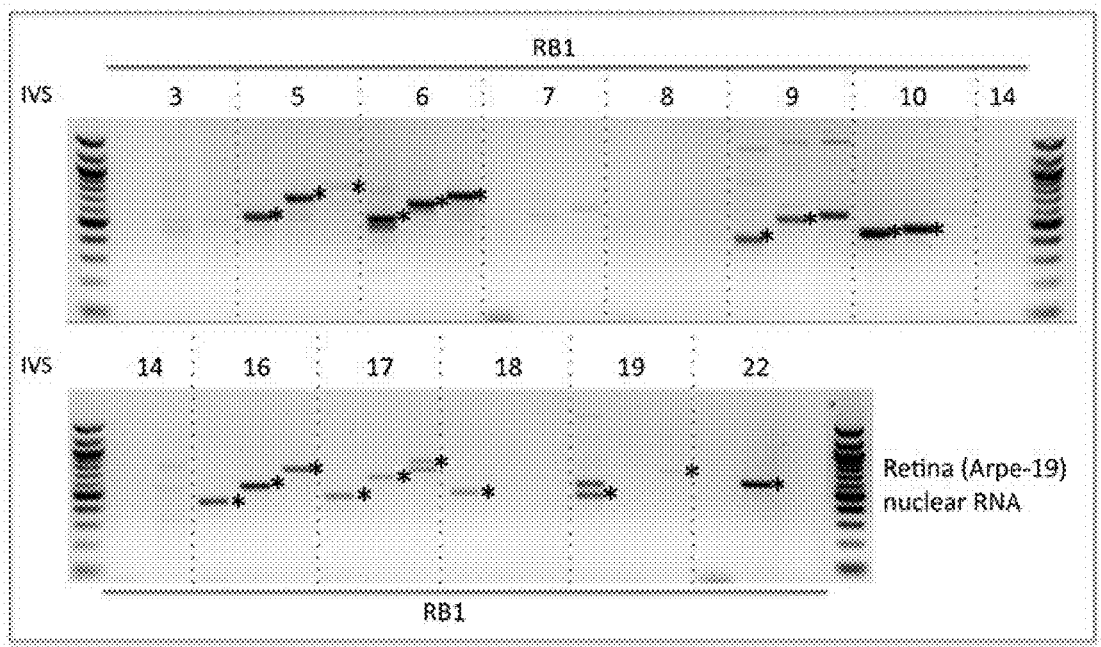

A second round of screening was performed for intron-retention events in the PRPF31 (retinitis pigmentosa type 11) and RB1 (retinoblastoma) genes using the methods described herein (FIG. 4). Briefly, nuclear RNA extracts from ARPE-19 (human retina) cells were used to perform reverse transcriptase PCR (RT-PCR) as described in Example 1. In this example, intron retention was assessed in the scenario in which more than one intron has been spliced out (removed) from the pre-mRNA. Results show fewer intron-retention events (marked by black asterisk) for both genes (PRPF31 and RBI) (FIGS. 7A-7B) compared to results in FIGS. 6A-D) narrowing down the number of candidate intron retention events.

Figure 8A:
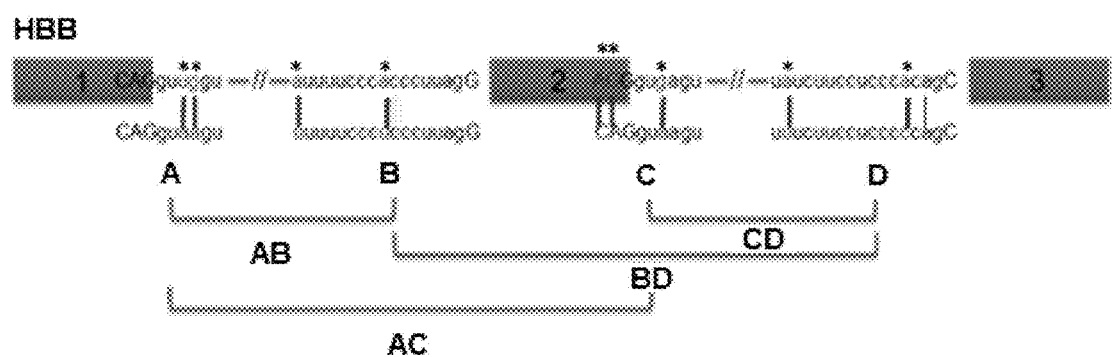
FIGS. 8A-8C show increased gene expression by promoting splicing efficiency via mutagenesis of splice sites, as described in Example 3.
Figure 8B:
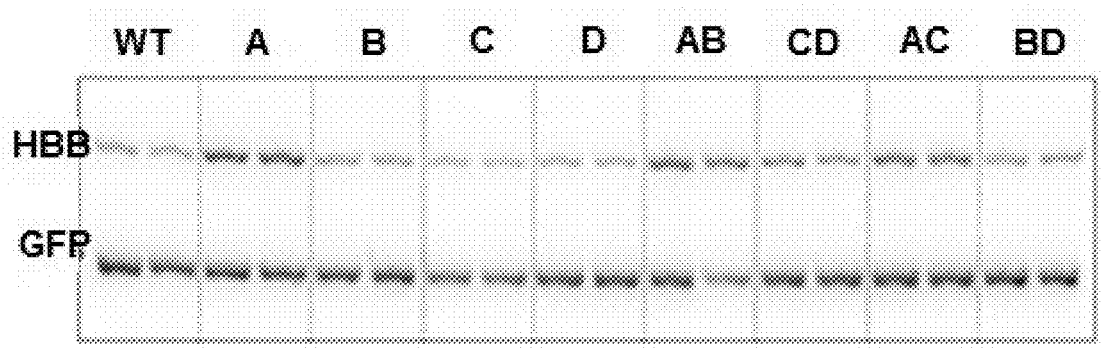
Figure 8C:
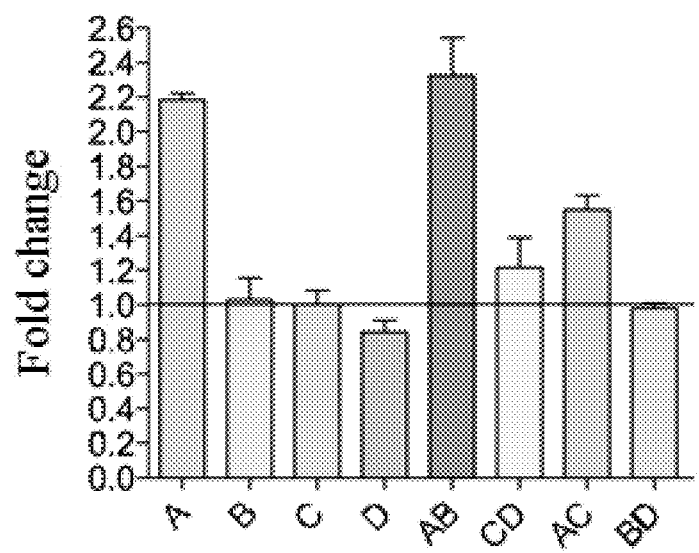

Example 3: Improved Splicing Efficiency Via Mutagenesis or ASO Targeting of Intronic Regions Increases Gene Expression We aimed to improve the splicing efficiency of each of the two introns of the HBB (human beta globin) gene, which is involved in beta thalassemia, and assess whether this would result in increased transcript level. The entire HBB open reading frame was cloned in a minigene reporter. Mutations were introduced into the 5' and 3' splice sites of both introns in order to bring them to perfect consensus sequences. FIG. 8A shows a schematic representation of the HBB gene and the mutations introduced at the splice sites. Minigene reporters carrying mutations in each splice site as well as combinations of these mutations were transfected into HEK293 (human embryonic kidney epithelial) cells, independently, for 24 hrs using Fugene transfection reagent. Radioactive RT-PCR results show that mutations improving only the 5' splice site of intron 1 (IVS1) increase HBB transcript level (FIG. 8B). Quantification of the intensity of the bands corresponding to HBB PCR products of mutant minigenes were normalized to that of GFP and plotted in relation to wild type HBB. The bars indicate an increase of more than 2-fold in the expression level of HBB when the splicing efficiency of intron 1 is improved (FIG. 8C). We have previously observed that that HBB intron 1 is inefficiently spliced and is the rate limiting intron in the gene (data not shown). Here we show that by improving splicing efficiency of an inefficiently spliced intron, a significant increase in gene expression can be achieved.

Figure 9A:
FIGS. 9A-9C show that ASOs targeting sequences immediately downstream of HBB IVS1 5' splice site increase HBB mRNA, as described in Example 3.
Figure 9B:
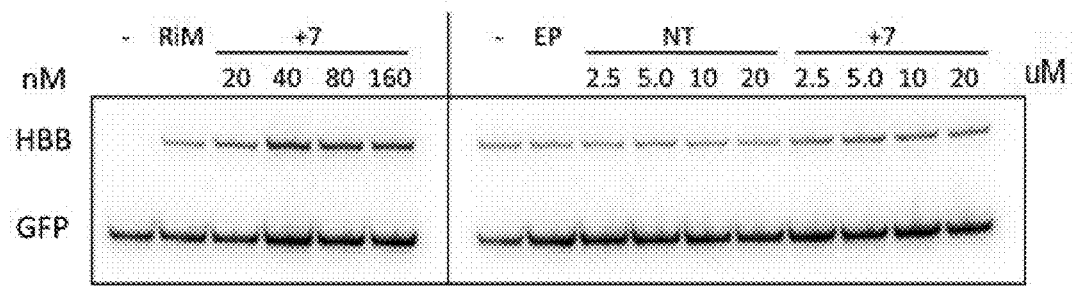
Figure 9C:
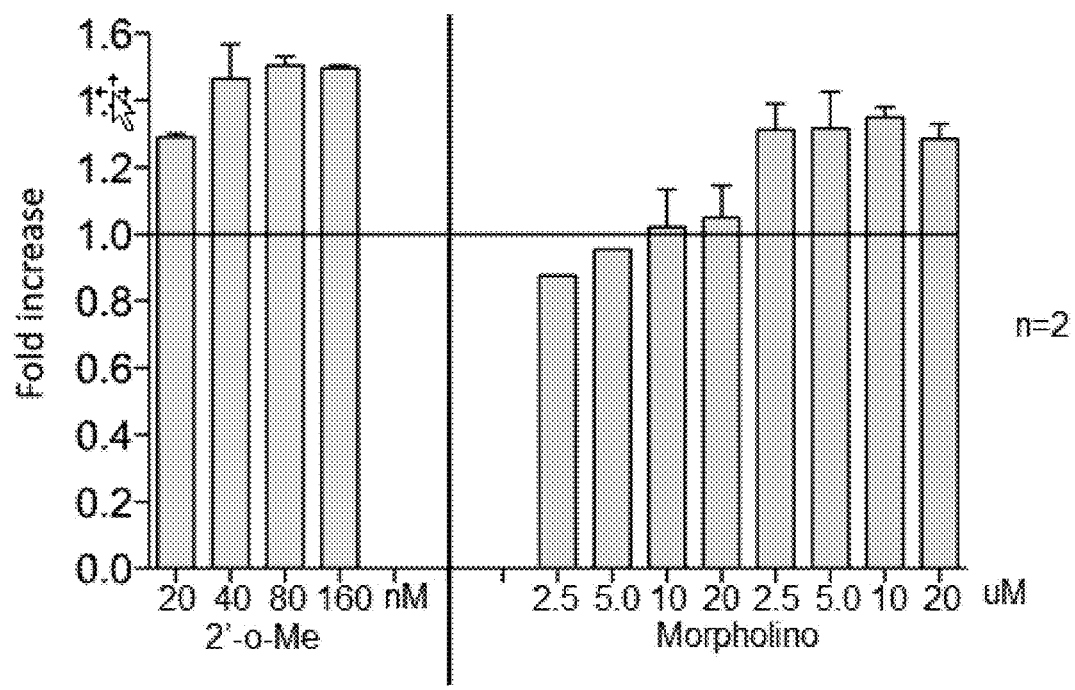

To determine whether we can also achieve an increase in HBB-reporter gene (minigene) expression by improving splicing efficiency of HBB intron 1 using ASOs. To this end an 18-mer 2'-O-Me ASO was generated to target intron 1 starting at positions +7 and two 18-mer PMO-ASOs were generated to target intron 1 starting at positions +6 and +7, respectively, relative to the 5' splice junction (FIG. 9A; Table 2, SEQ ID NO: 104 and 105, respectively). HEK293 cells were first co-transfected with wild-type HBB minigene reporter and GFP (as a transfection control) using Fugene transfection reagent. Four hours later, cells were either untransfected, mock-transfected, or transfected with each of the targeting ASOs or a non-targeting ASO control, independently, using RNAiMAX (RiM) (Invitrogen) or Endo-Porter (EP) (GeneTools) delivery reagents. Experiments were performed using increasing concentrations of the ASOs as indicated in FIG. 9B) for 48 hrs. Radioactive RT-PCR results show that the +7 targeting ASO with both chemistries increase HBB transcript level compared to the mock-transfected or non-targeting ASO (FIG. 9B). Similar results were obtained for the +6 PMO-ASO (data not shown). Intensities of the bands corresponding to the HBB PCR products from targeting-ASO-transfected cells were normalized to GFP and plotted relative to the normalized HBB PCR product from mock-treated cells. Results of this analysis indicate that both targeting ASOs (+6 and +7) increase HBB transcript level by nearly 50% (FIG. 9C). These results indicate that improving the splicing efficiency of the rate limiting intron in the HBB gene using ASOs leads to an increase in gene expression.

Figure 10A:
FIGS. 10A-10C show that IVS1+7 2'-O-Me ASO targeting sequences immediately downstream of the HBB IVS1 5' splice site increase GFP-HBB-T7 protein levels, as described in Example 4.
Figure 10B:
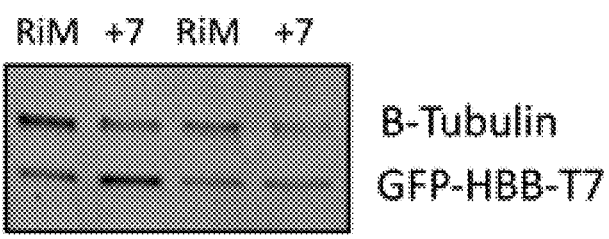

Example 4: Improved Splicing Efficiency Via ASO Targeting an Intronic Region Increases Protein Production In order to detect an increase in protein production upon targeting HBB intron 1 with the +7 2'-O-Me ASO, we generated a reporter construct consisting of the HBB minigene flanked upstream by the GFP open reading frame and downstream by a sequence coding the T7 tag (FIG. 10A). This reporter was integrated in the genome of U2OS cells mimicking an endogenous gene. U2OS cells expressing the GFP-HBB-T7 reporter were mock-transfected or transfected with the +7 2'-O-Me ASO and protein extracts were analyzed by western blot. Briefly, protein extracts from two independent biological replicates were run on a 4-20% SDS-polyacrylamide gel, transferred to a nitrocellulose membrane. To evidence an increase in protein production, an anti-GFP antibody was used to detect a protein product from the GFP-HBB-T7 reporter and an anti-Beta tubulin antibody was used to detect Beta tubulin as a loading control. FIG. 10B shows western blots results indicating that GFP-HBB-T7 protein (bottom band) is increased upon treatment with the +7 2'-O-Me ASO. Intensities of the bands corresponding to the GFP-HBB-T7 protein from targeting-ASO-transfected cells were normalized to endogenous Beta tubulin and plotted relative to the normalized GFP-HBB-T7 protein band from mock-treated cells.

Figure 10C:
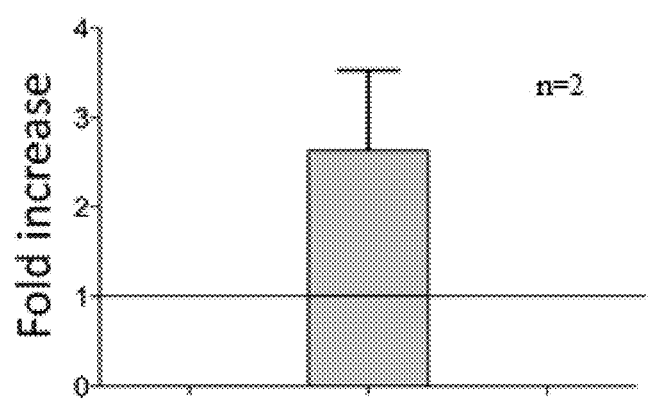

Results of this analysis indicate that the targeting ASO (+7) increase GFP-HBB-T7 protein level by more than 2.5 fold (FIG. 10C). These results demonstrate that promoting splicing efficiency by using an ASO targeted to a region downstream of the 5' splice site of the rate-limiting intron leads to an increase in target protein production as depicted in FIG. 2.

Figure 11:
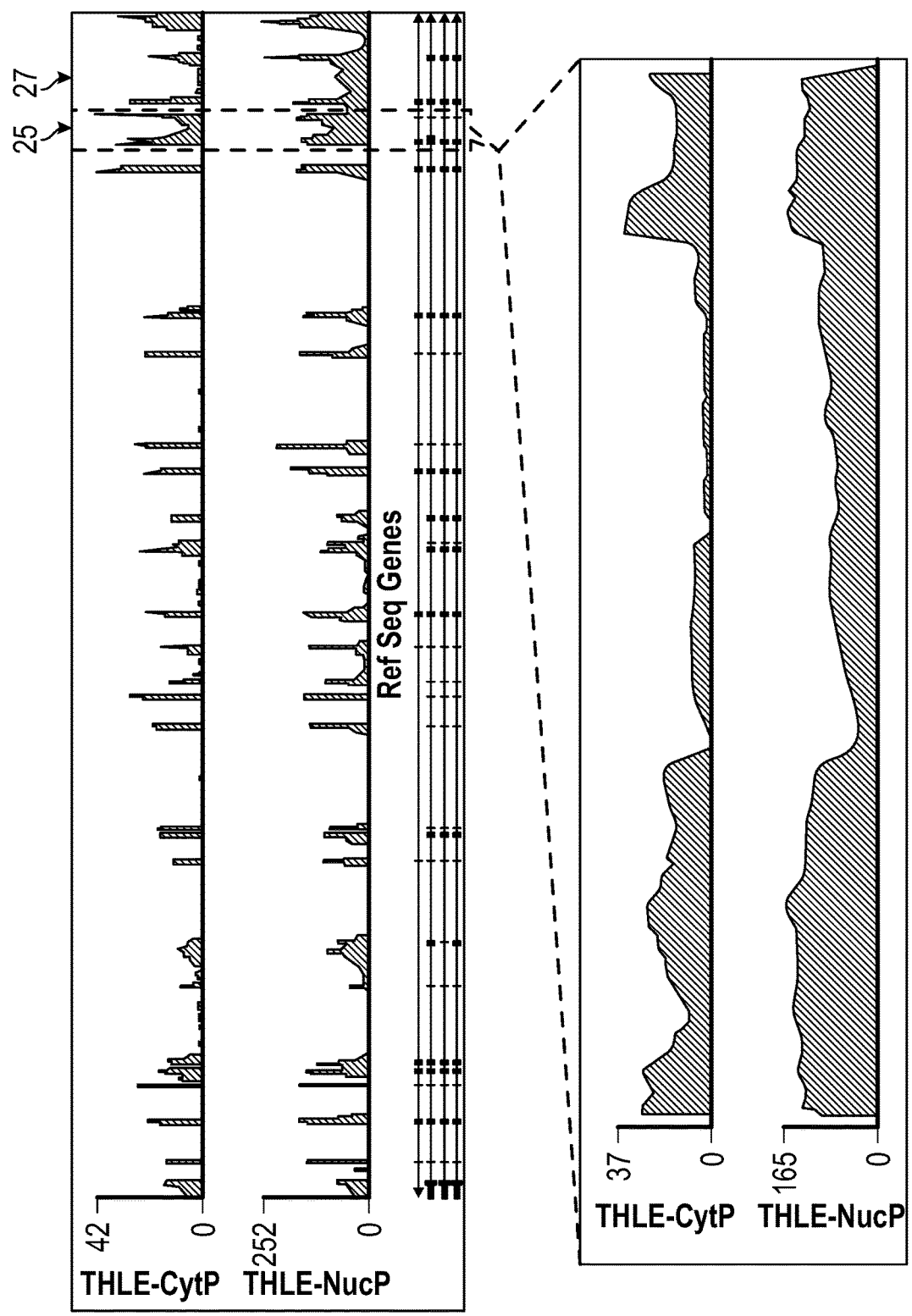
FIG. 11 shows the identification of intron-retention events in the ADAMTS13 gene using RNA sequencing (RNAseq), visualized in the UCSC Genome Browser, as described in Example 5. The top panel shows the read density corresponding to the ADAMTS13 transcript expressed in THLE-3 (human liver epithelial) cells and localized in either the cytoplasmic (top) or nuclear fraction (bottom). At the bottom of this panel, a graphic representation of all the refseq. isoforms of the ADAMTS13 gene is shown to scale. The read density is shown as peaks. The highest read density corresponds to exons (black boxes), while no reads are observed for the majority of the introns (lines with arrow heads) in neither cellular fraction. Higher read density is detected for introns 25 and 27 (pointed by the arrows) in the nuclear fraction compared to the cytoplasmic fraction indicating that splicing efficiency of introns 25 and 27 is low, resulting in intron retention. The retained-intron containing pre-mRNA transcripts are retained in the nucleus and are not exported out to the cytoplasm. The read density for intron 25 in THLE-3 cells is shown in detail in the bottom picture.

Example 5: Identification of Intron Retention Events in ADAMTS13 Transcripts by RNAseq Using Next Generation Sequencing We performed whole transcriptome shotgun sequencing using next generation sequencing to reveal a snapshot of transcripts produced by the ADAMTS13 gene to identify intron-retention events. For this purpose, we isolated polyA+RNA from nuclear and cytoplasmic fractions of THLE-3 (human liver epithelial) cells and constructed cDNA libraries using Illumina's TruSeq Stranded mRNA library Prep Kit. The libraries were pair-end sequenced resulting in 100-nucleotide reads that were mapped to the human genome (Feb. 2009, GRCh37/hg19 assembly). The sequencing results for ADAMTS13 are shown in FIG. 11. Briefly, FIG. 11 shows the mapped reads visualized using the UCSC genome browser, operated by the UCSC Genome Informatics Group (Center for Biomolecular Science & Engineering, University of California, Santa Cruz, 1156 High Street, Santa Cruz, Calif. 95064) and described by, e.g., Rosenbloom, et al., 2015, "The UCSC Genome Browser database: 2015 update," Nucleic Acids Research 43, Database Issue (doi: 10.1093/nar/gku1177) and the coverage and number of reads can be inferred by the peak signals. The height of the peaks indicates the level of expression given by the density of the reads in a particular region. A schematic representation of all ADAMTS13 isoforms (drawn to scale) is provided by the UCSC genome browser (below the read signals) so that peaks can be matched to ADAMTS13 exonic and intronic regions. Based on this display, we identified two introns (25 and 27, indicated by arrows) that have high read density in the nuclear fraction of THLE-3 cells, but have very low to no reads in the cytoplasmic fraction of these cells (as shown for intron 25 in the bottom diagram of FIG. 11). This indicates that both introns are retained and that the intron-25 and intron-27 containing transcripts remain in the nucleus. This suggests that these retained intron-containing (RIC) ADAMTS13 pre-mRNAs are non-productive, as they are not exported out to the cytoplasm.

Example 6: Validation of Intron Retention Events Identified by RNAseq Analysis of ADAMTS13

Figure 12:
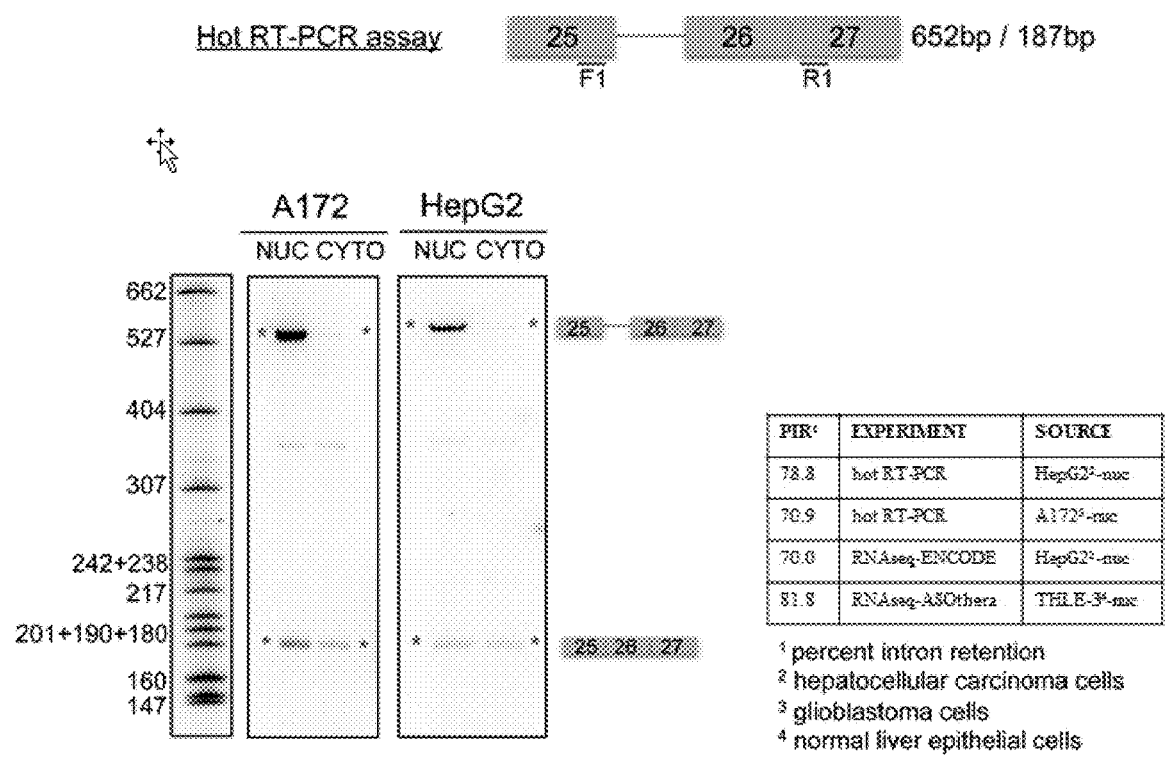
FIG. 12 shows the validation of the bioinformatic analysis via radioactive-RT-PCR as described in Example 6. A schematic representation of the radioactive RT-PCR assay to validate the bioinformatic prediction shown in FIG. 11 is depicted in FIG. 12. The numbered rectangles denote exons, and intervening lines denote introns. Black lines indicate forward ("F1") and reverse ("R1") primers used in the PCR amplification of the ADAMTS-13 transcript resulting in two products, the intron-25-retained (652 bp) and the correctly spliced (187 bp) products. Below are representative gels showing radioactive RT-PCR products from nuclear and cytoplasmic fractions of A172 (glioblastoma, left) and HepG2 (hepatocellular carcinoma, right) cells separated in a 5% polyacrylamide gel. Asterisks indicate correct products (by size). Results show a band corresponding to the intron- 25 retained product in the nuclear fractions of both cell lines that is absent from both cytoplasmic fractions. A summary of the quantification on ADAMTS13 intron-25 retention calculated as percent intron retention (PIR) from radioactive RT-PCR and RNAseq experiments is shown on the table on the right.

Validation of the intron 25-retention event in the ADAMTS13 (thrombotic thrombocytopenic purpura) gene was performed using the methods described herein (FIG. 12). Briefly, nuclear and cytoplasmic RNA extracts from A172 (human glioblastoma) and HepG2 (human hepatocellular carcinoma) cells were used to perform radioactive reverse transcriptase PCR (RT-PCR) as described in Example 1. In this example, intron retention was assessed using primers positioned in exon 25 and exon 27 leading to the amplification of both intron-25 containing transcript and correctly spliced transcript. The products were run in a 5% polyacrylamide gel and visualized by phosphorimaging. Intron 25 retention levels were calculated as percent intron retention (PIR) of the intensity of the band corresponding to the intron-25 containing product over total transcript (intron-containing plus correctly spliced). Quantification of the bands indicated that approximately 80% of ADAMTS13 transcripts contain intron 25 and that this product is retained in the nucleus. Moreover, the radioactive RT-PCR results validated the bioinformatic predictions demonstrating that the bioinformatic analysis of the RNAseq results is a powerful tool to identify intron-retention events.

Example 7: Design of ASO-Walk Targeting Intron 25 of ADAMTS13

Figure 13:
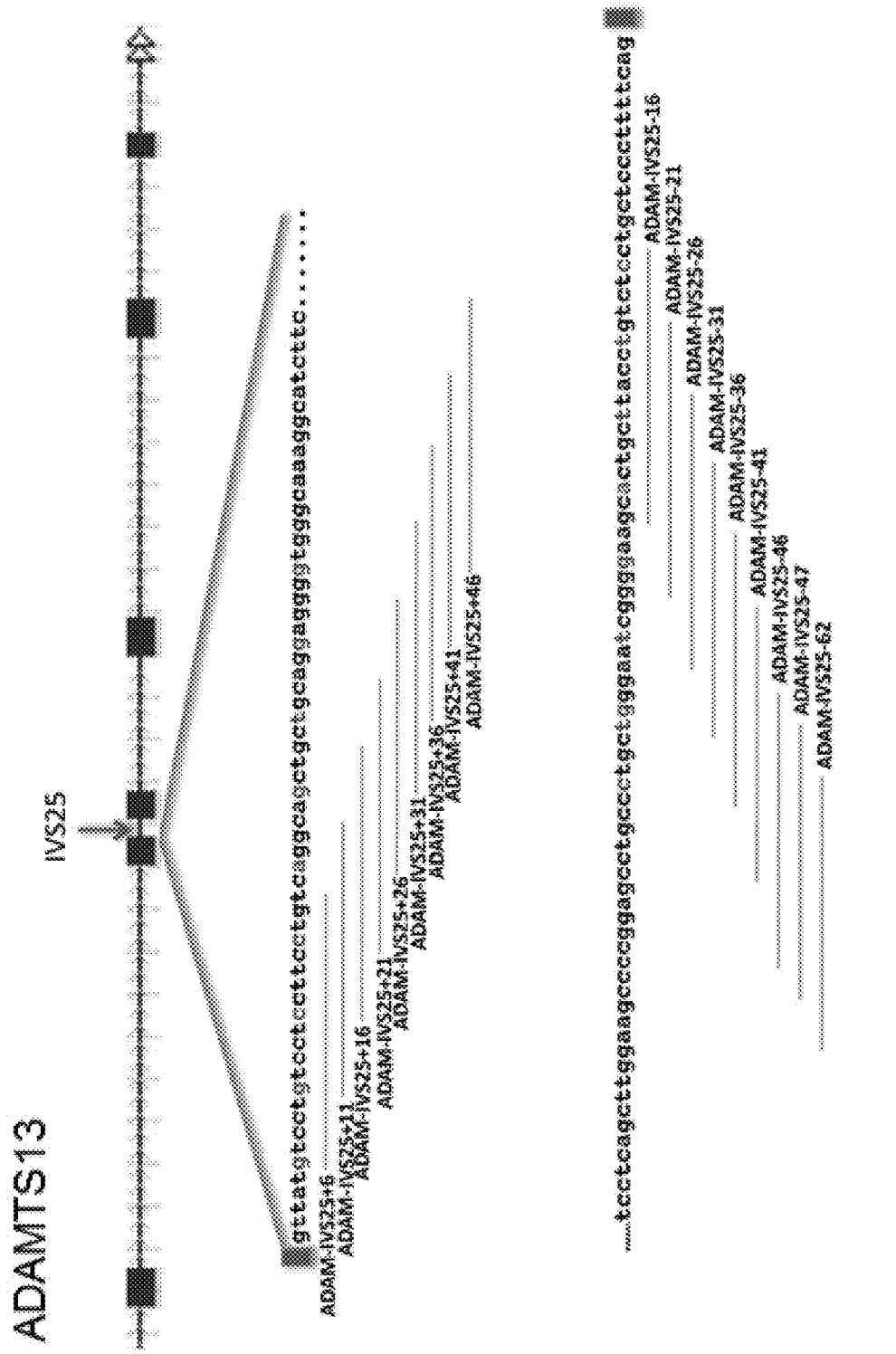
FIG. 13 shows a graphic representation of the ASO walk performed for ADAMTS13 IVS 25 targeting sequences immediately downstream of the 5' splice site or upstream of the 3' splice site using 2'-O-Me ASOs, PS backbone, as described in Example 7. ASOs were designed to cover these regions by shifting 5 nucleotides at a time. Exons 24 to 29 and the intronic sequences to are drawn to scale. The figure discloses SEQ ID NOS 391 and 392, respectively, in order of appearance.

An ASO walk was designed to target intron 25 using the method described herein (FIG. 13). A region immediately downstream of intron 25 5' splice site spanning nucleotides +6 to +58 and a region immediately upstream of intron 25 3' splice site spanning nucleotides −16 to −79 of the intron were targeted with 2'-O-Me RNA, PS backbone, 18-mer ASOs shifted by 5-nucleotide intervals (with the exception of 1 ASO, ADAM-IVS25-47, to avoid a stretch of four guanines) (FIG. 13; Table 4, SEQ ID NO:150 to 167). These target regions were selected based on the knowledge that intronic regulatory elements concentrate in sequences adjacent to splice sites.

Figure 14:
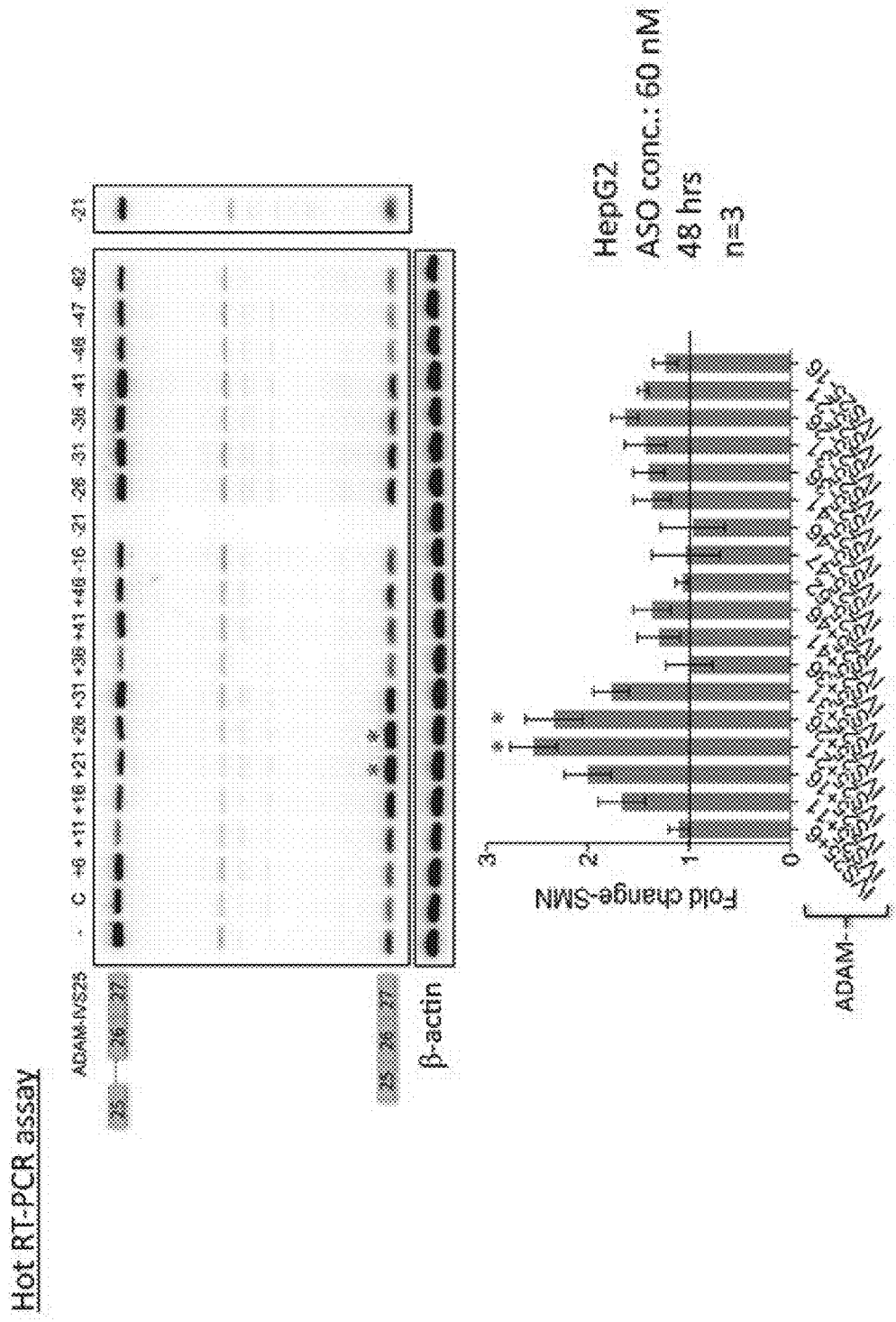
FIG. 14 depicts the results of the ASO-walk targeting intron 25 as described in Example 8. At the top, a representative gel shows radioactive RT-PCR products of ADAMTS13 mock-treated (−, RNAiMAX only), SMN-control ASO treated, or treated with a 2'-O-Me ASO targeting intron 25 as described in FIG. 13, at 60 nM concentration in HepG2 cells. Quantification of the bands corresponding to ADAMTS13 products normalized to Beta actin from 3 independent experiments is plotted in the bar graph below as fold change with respect to the SMN-control-ASO treated products. The black line indicates a ratio of 1, no change. Asterisks indicate ASOs that lead to the highest increase in mRNA levels.

Example 8: Improved Splicing Efficiency Via ASO-Targeting of ADAMTS13 Intron 25 Increases Transcript Levels To determine whether we can achieve an increase in ADAMTS13 expression by improving splicing efficiency of ADAMTS13 intron 25 using ASOs we used the method described herein (FIG. 14). To this end, HepG2 cells were mock-transfected, or transfected with each of the targeting ASOs described in FIG. 13 and Table 4, SEQ ID NO:150 to 167, or a non-targeting SMN-ASO control, independently, using RNAiMAX (RiM) (Invitrogen) delivery reagents. Experiments were performed using 60 nM ASOs (as indicated in FIG. 14) for 48 hrs. Radioactive RT-PCR results show that the +21 and +26 targeting ASOs increase ADAMTS13 transcript level compared to the mock-transfected or non-targeting ASO (FIG. 14). Intensities of the bands corresponding to the ADAMTS13 PCR products from targeting-ASO-transfected cells were normalized to Beta actin and plotted relative to the normalized ADAMTS13 PCR product from control ASO-treated cells. Results of this analysis indicate that both targeting ASOs (+21 and +26) increase ADAMTS13 transcript level nearly 2.5 fold (FIG. 14). These results indicate that improving the splicing efficiency of a rate limiting intron in the ADAMTS13 gene using ASOs leads to an increase in gene expression.

Example 9: Dose Response Effect of ASOs Targeting ADAMTS13 Intron 25

Figure 15:
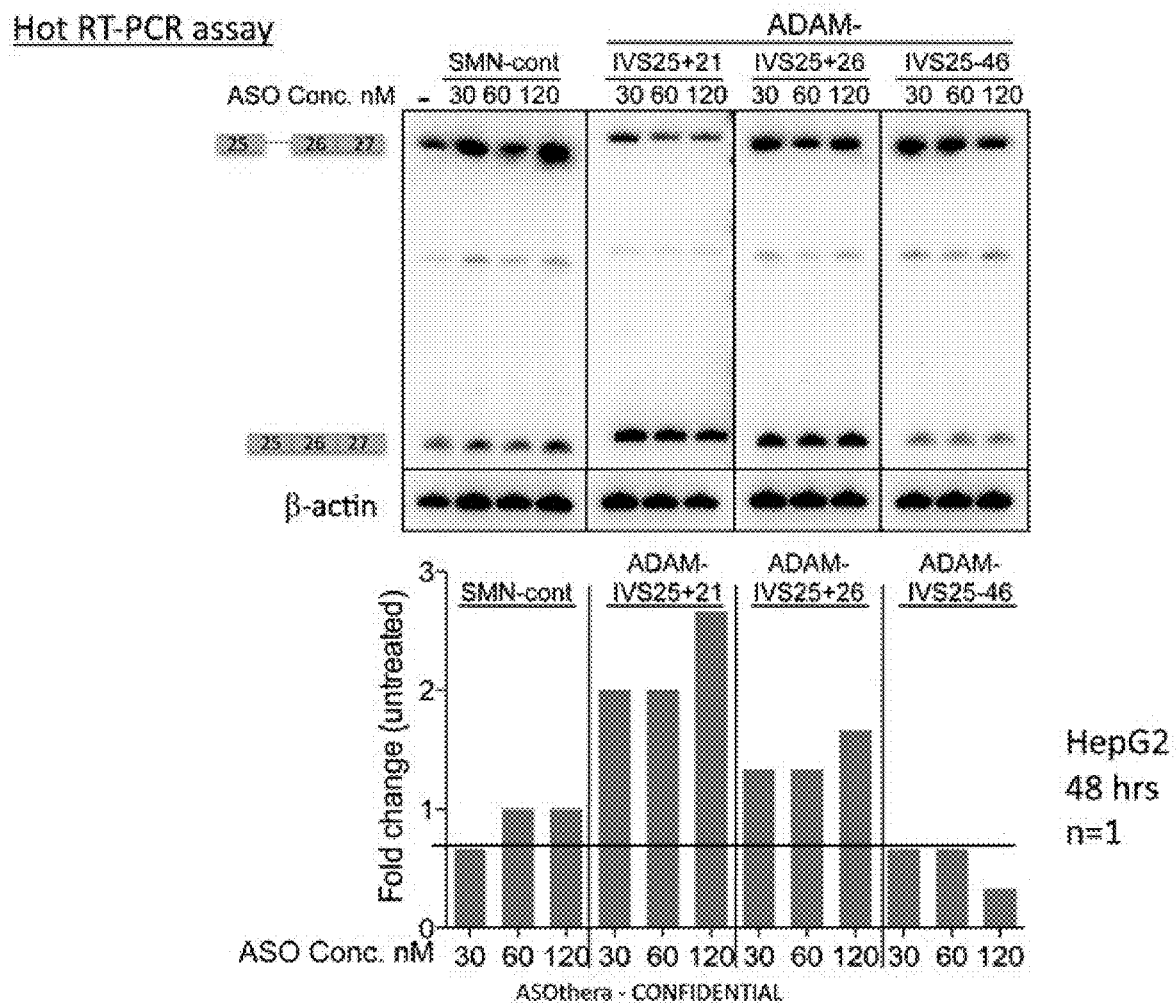
FIG. 15 shows dose-response curves for ADAM-IVS25+21, ADAM-IVS25+26, the two best targeting ASOs, and ADAM-IVS-46, an ASO that resulted in a reduction of ADAMTS13 transcript, as described in Example 9. In the top panel a representative gel shows radioactive RT-PCR ADAMTS13 products from HepG2 cells mock-, SMN-control-, ADAM-IVS25+21-, ADAM-IVS25+26-, or ADAM-IVS-46-treated at the indicated concentrations. The RT-PCR products were separated in a 5% polyacrylamide gel. Quantification of the bands corresponding to ADAMTS13 products normalized to Beta actin is plotted in the bar graph below as fold change relative to the mock-treated products. The black line indicates a ratio of 1, no change.

To determine a dose-response effect of the +21 and +26 ASOs, as well as the −46 ASOs that showed the opposite effect (FIG. 14), we used the method described herein (FIG. 15). HepG2 cells were mock-transfected, or transfected with each of the three ASOs, or a non-targeting SMN-ASO control, independently, using RNAiMAX (RiM) (Invitrogen) delivery reagents at increasing concentrations as indicated in FIG. 15 for 48 hrs. Radioactive RT-PCR results show that the +21 and +26 targeting ASOs increase ADAMTS13 transcript level compared to the mock-transfected or non-targeting ASO whereas the −46 ASO decreases ADAMTS13 transcript level compared to the mock-transfected or non-targeting ASO (FIG. 15). Intensities of the bands corresponding to the ADAMTS13 PCR products from targeting-ASO-transfected cells were normalized to Beta actin and plotted relative to the normalized ADAMTS13 PCR product from control ASO-treated cells.

Results of this analysis indicate that both targeting ASOs (+21 and +26) increase ADAMTS13 transcript level nearly 2.5 fold (FIG. 15). These results confirm that improving the splicing efficiency of a rate limiting intron in the ADAMTS13 gene using ASOs leads to an increase in gene expression.

Figure 16:
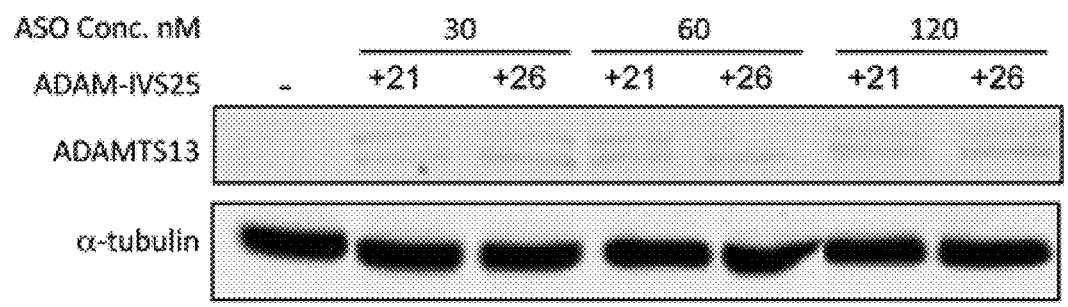
FIG. 16 illustrates an increase in ADAMTS13 protein resulting from the treatment of HepG2 cells with ADAM-IVS25+21 and ADAM-IVS25+26 ASOs, as described in Example 10. In the top panel a representative gel shows ADAMTS13 protein products from HepG2 cells mock-, ADAM-IVS25+21-, or ADAM-IVS25+26-treated at the indicated concentrations. The protein products were separated on an 8% SDS-polyacrylamide gel. Antibodies against ADAMTS-13 and alpha tubulin were used to detect the protein products. The bar graph below shows the quantifications of the intensity of bands corresponding to ADAMTS-13 protein levels from ADAM-IVS25+21-treated cells, normalized to alpha tubulin. Fold change was plotted relative to the product from mock-treated cells. The black line indicates a ratio of 1, no change. ADAM-IVS25+21 increases ADAMTS13 protein product in a dose-dependent manner.
Figure 16:
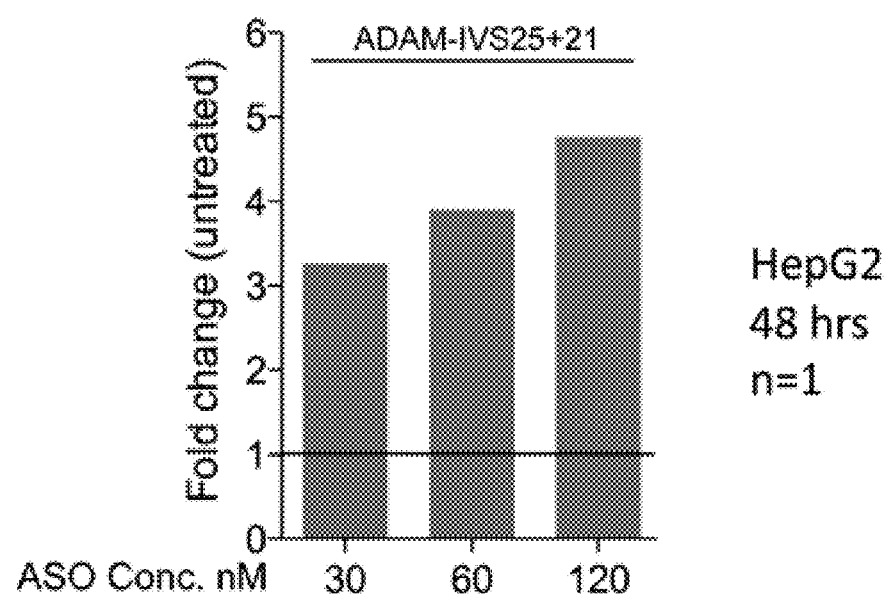

Example 10: Improved Splicing Efficiency Via ASO-Targeting of ADAMTS13 Intron 25 Increases Protein Levels In order to detect an increase in protein production upon targeting ADAMTS13 intron 25 with the +21 or +26 ASOs, we used the method described herein (FIG. 16). HepG2 cells were mock-transfected, or transfected with each of the three ASOs, or a non-targeting SMN-ASO control, independently, using RNAiMAX (RiM) (Invitrogen) delivery reagents at increasing concentrations as indicated in FIG. 16 for 48 hrs. Briefly, protein extracts from HepG2 treated cells were run on an 8% SDS-polyacrylamide gel, and transferred to a nitrocellulose membrane. To evidence an increase in protein production, an anti-ADAMTS13 antibody or anti-Alpha tubulin antibody was used to detect ADAMTS13 and Alpha tubulin as a loading control, respectively. FIG. 16 shows western blot results indicating that ADAMTS13 (top panel) is increased in a dose dependent manner upon treatment with the +21 or +26 ASO. Intensities of the bands corresponding to the ADAMTS13 protein from targeting-ASO-transfected cells were normalized to endogenous Alpha tubulin and plotted relative to the normalized ADAMTS13 protein band from mock-treated cells. Results of this analysis indicate that the targeting ASOs (+21 and +26) increase ADAMTS13 protein level more than 3 fold (FIG. 16). These results demonstrate that promoting splicing efficiency by using an ASO targeted to a region downstream of the 5' splice site of ADAMTS13 intron 25, a rate-limiting intron, leads to an increase in target protein production as depicted in FIG. 2.

Example 11: Design of ASO-Microwalk Targeting the +21 to +26 Region of ADAMTS13 Intron 25

Figure 17:
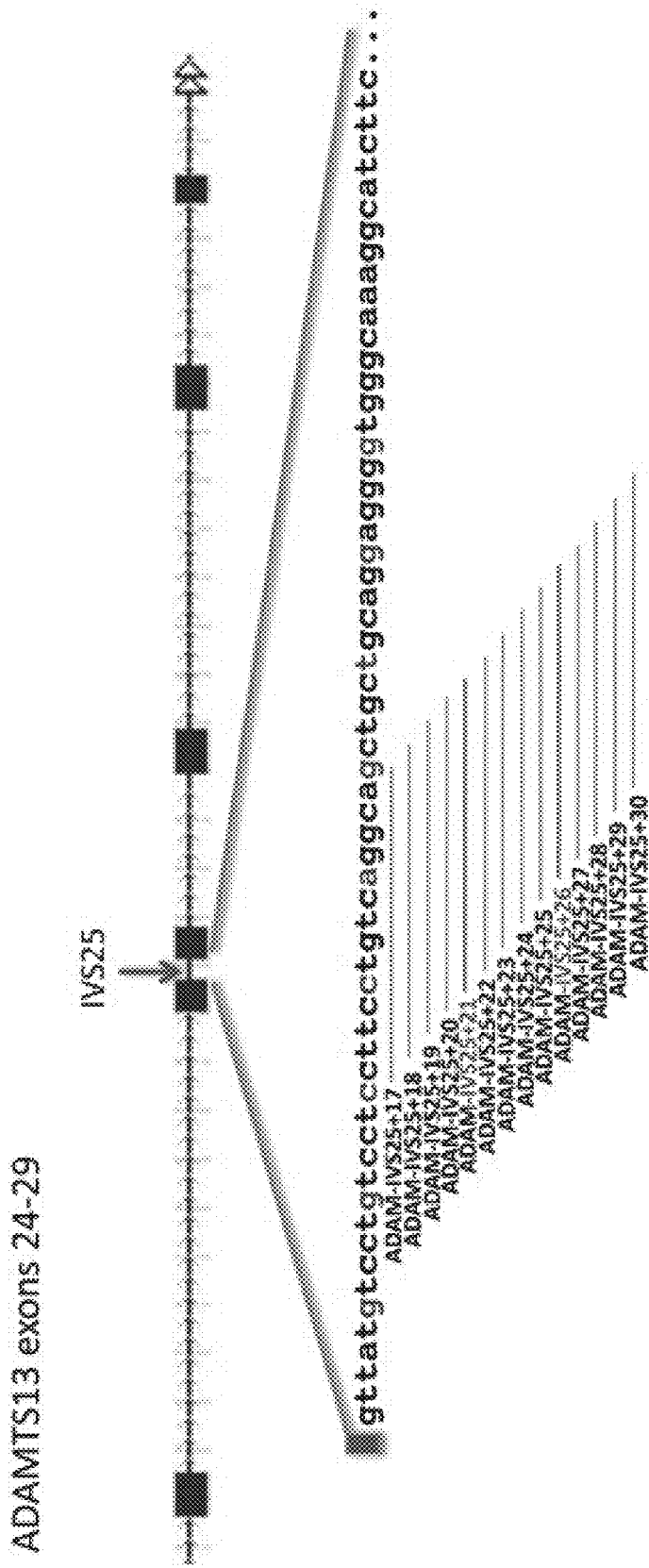
FIG. 17 shows a graphic representation of the ASO microwalk performed for ADAMTS13 IVS 25 targeting sequences in the region of ADAM-IVS25+21 and ADAM-IVS25+26 ASOs using 2'-O-Me, 5'-Me-Cytosine ASOs, as described in Example 11. ASOs were designed to cover the region by shifting 1 nucleotide at a time. Exons 24 to 29 and the intronic sequences are drawn to scale. The figure discloses SEQ ID NO: 391.

An ASO microwalk was designed to target intron 25 +21 to +26 region using the method described herein (FIG. 17). A region downstream of intron 25 5' splice site spanning +17 to +46 were targeted with 2'-O-Me, 5'-Me-Cytosine RNA, PS backbone, 18-mer ASOs shifted by 1-nucleotide interval (FIG. 17; Table 4, SEQ ID NO:184 to 197). This target region was selected based on the observed effect of ASOs +21 and +26 (FIG. 16).

Figure 18:
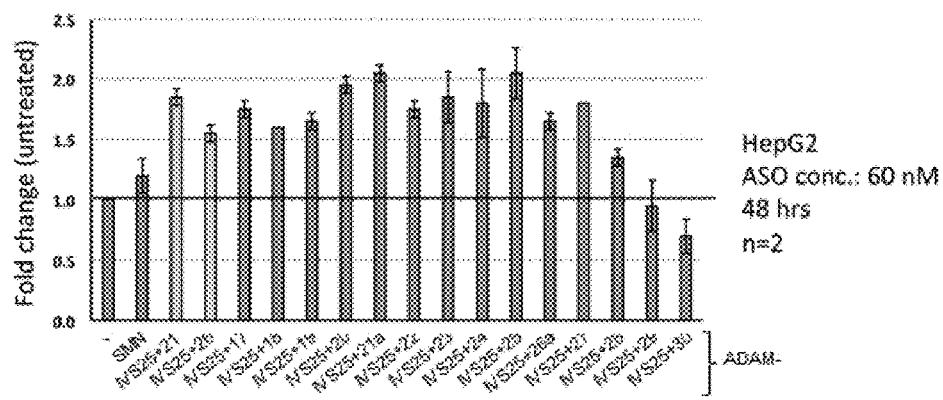
FIG. 18 depicts the results of the ASO-microwalk targeting the ADAM-IVS25+21 and ADAM-IVS25+26 region in intron 25, as described in Example 12. At the top, a representative gel shows radioactive RT-PCR products of ADAMTS13 mock-treated (−), SMN-control ASO treated, or treated with a 2'-O-Me, 5'-Me-Cytosine ASOs (described in FIG. 17) at 60 nM concentration in HepG2. Quantification of the bands corresponding to ADAMTS13 products normalized to Beta actin from 2 independent experiments is plotted in the bar graph below as fold change relative to the mock-treated products. The black line indicates a ratio of 1, no change. The two light-grey bars indicate IVS25 2'-O-Me ASOs ADAM-IVS25+21 and ADAM-IVS25+26 described in FIGS. 14 and 15.

Example 12: Improved Splicing Efficiency Via ASO Microwalk Targeting of ADAMTS13 Intron 25 +21 to +26 Region Increases Transcript Levels To determine whether we can achieve an increase in ADAMTS13 expression by improving splicing efficiency of ADAMTS13 intron 25 using microwalk ASOs, we employed the method described herein (FIG. 18). To this end, HepG2 cells were mock-transfected, or transfected with each of the targeting ASOs described in FIG. 17 and Table 4 SEQ ID NO:184 to 197, or a non-targeting SMN-ASO control, independently, using RNAiMAX (RiM) (Invitrogen) delivery reagents. Experiments were performed using 60 nM ASOs (as indicated in FIG. 18) for 48 hrs. Radioactive RT-PCR results show that the +21 with 5'-Me-Cytosines and +25 targeting ASOs further increase ADAMTS13 transcript level compared to the mock-transfected or non-targeting ASO, as well as the two original +21 and +26 ASOs (light grey bars, FIG. 18). Intensities of the bands corresponding to the ADAMTS13 PCR products from targeting-ASO-transfected cells were normalized to Beta actin and plotted relative to the normalized ADAMTS13 PCR product from control ASO-treated cells. Results of this analysis indicate that both targeting ASOs (+21 and +25) increase ADAMTS13 transcript level by nearly 2.0 fold (FIG. 18). These results indicate that improving the splicing efficiency of a rate limiting intron in the ADAMTS13 gene using ASOs leads to an increase in gene expression, and the refinement of the target region by a microwalk can lead to the identification of more efficient ASOs.

Figure 19:
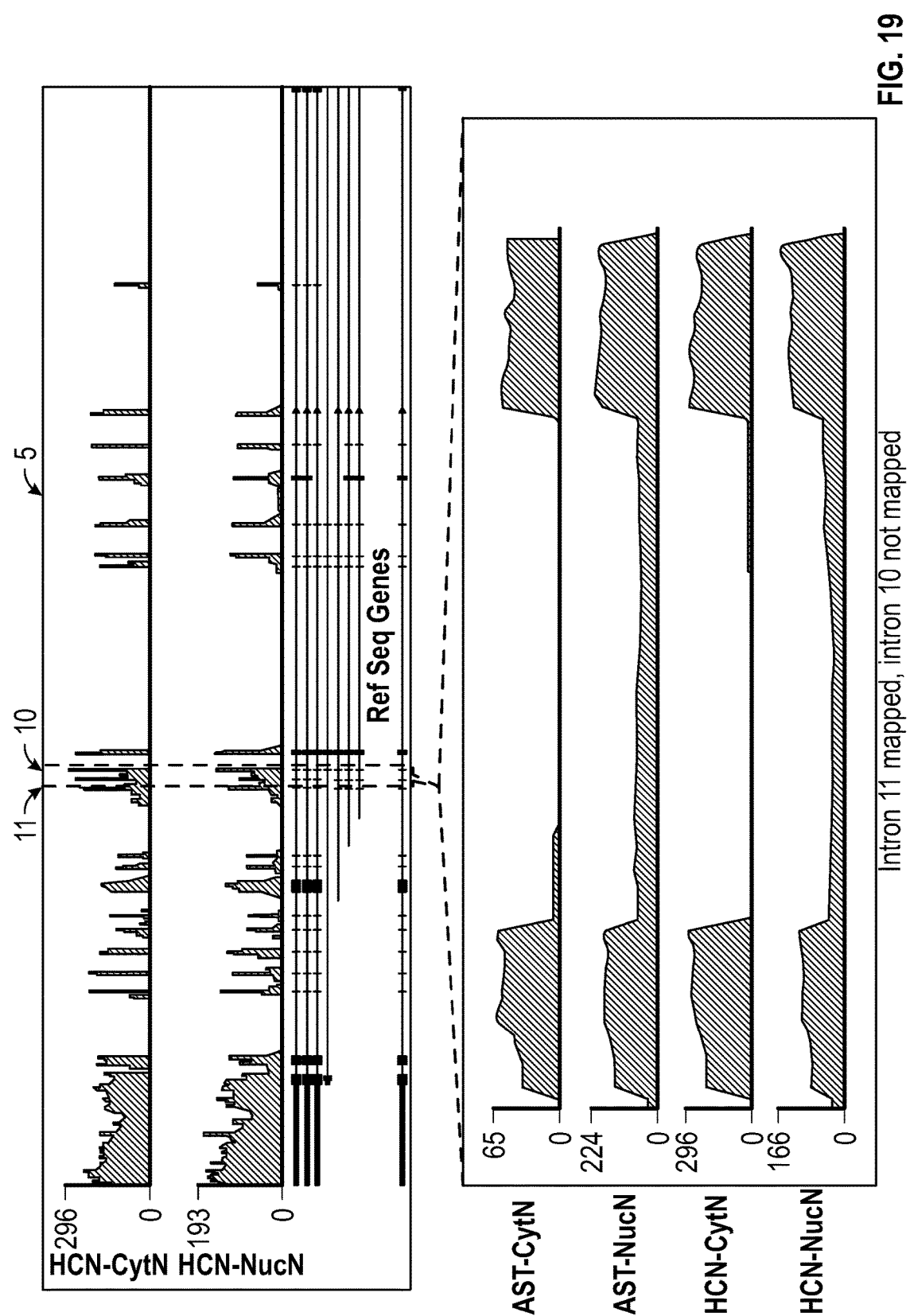
FIG. 19 shows the identification of intron-retention events in the TSC1 gene using RNA sequencing (RNAseq), visualized in the UCSC genome browser as described in Example 13. The top panel shows the read density corresponding to the TSC1 transcript expressed in HCN (primary human cortical neuron) cells and localized in either the cytoplasmic (top) or nuclear fraction (bottom). At the bottom of this panel, a graphic representation of all the refseq. isoforms of the TSC1 gene is shown to scale. The read density is shown as peaks. The highest read density corresponds to exons (black boxes), while no reads are observed for the majority of the introns (lines with arrow heads) in neither cellular fraction. Higher read density is detected for introns 5, 10, and 11 (pointed by the arrows) in the nuclear fraction compared to the cytoplasmic fraction indicating that splicing efficiency of introns 5, 10 and 11 is low, resulting in intron retention. The retained-intron containing pre-mRNA transcripts are retained in the nucleus and are not exported out to the cytoplasm. The read density for intron 10 is shown in detail in the bottom picture for HCN cells and AST (primary human astrocyte) cells.

Example 13: Identification of Intron Retention Events in TSC1 Transcripts by RNAseq Using Next Generation Sequencing We performed whole transcriptome shotgun sequencing using next generation sequencing to reveal a snapshot of transcripts produced by the TSC1 gene to identify intron-retention events. For this purpose, we isolated polyA+RNA from nuclear and cytoplasmic fractions of primary human astrocytes (AST) and primary human cortical neuron (HCN) cells and constructed cDNA libraries using Illumina's TruSeq Stranded mRNA library Prep Kit. The libraries were pair-end sequenced resulting in 100-nucleotide reads that were mapped to the human genome (February 2009, GRCh37/hg19 assembly). The sequencing results for TSC1 are shown in FIG. 19. Briefly, FIG. 19 shows the mapped reads visualized using the UCSC genome browser and the coverage and number of reads can be inferred by the peak signals. The height of the peaks indicates the level of expression given by the density of the reads in a particular region. A schematic representation of all TSC1 isoforms (drawn to scale) is provided by the UCSC genome browser (below the read signals) so that peaks can be matched to TSC1 exonic and intronic regions. Based on this display, we identified three introns (5, 10 and 11, indicated by arrows) that have high read density in the nuclear fraction of AST and HCN cells, but have very low to no reads in the cytoplasmic fraction of these cells (as shown for intron 10 in the bottom diagram of FIG. 19). This indicates that both introns are retained and that the intron-5, intron-10, and intron-11 containing transcripts remain in the nucleus. This suggests that these retained intron-containing (RIC) TSC1 pre-mRNAs are non-productive, as they are not exported out to the cytoplasm.

Example 14: Validation of Intron Retention Events Identified by RNAseq Analysis of TSC1

Figure 20:
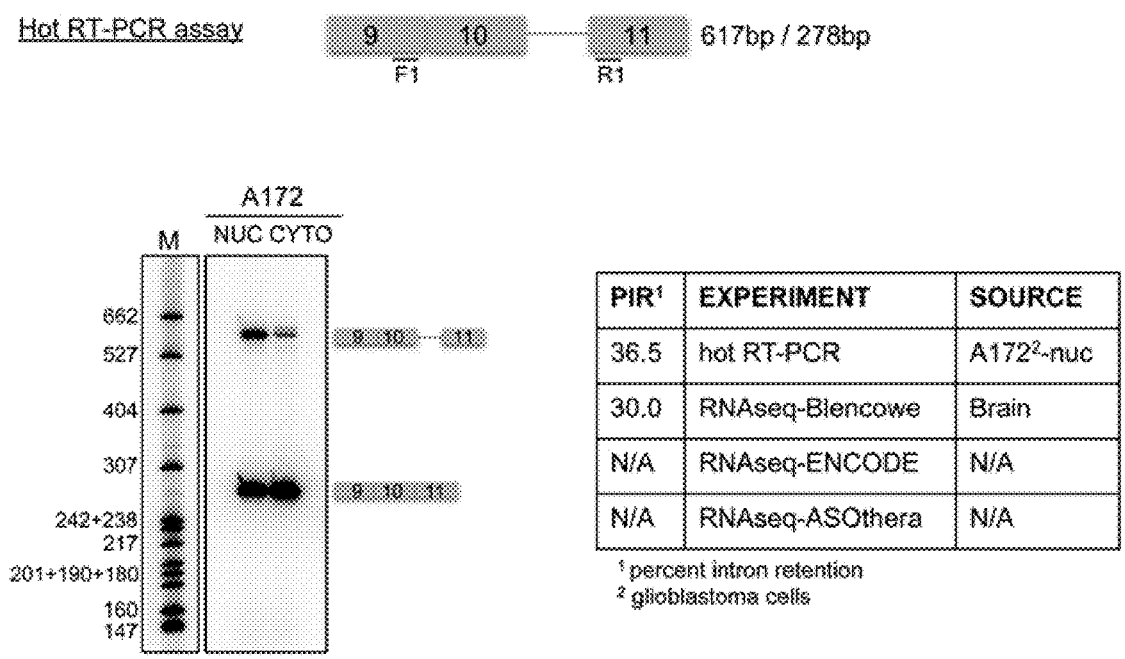
FIG. 20 shows a schematic representation of the radioactive RT-PCR assay to validate the bioinformatic prediction shown in FIG. 19, as described in Example 14. The numbered rectangles denote exons, and intervening lines denote introns. Black lines indicate forward ("F1") and reverse ("R1") primers used in the PCR amplification of the TSC1 transcript resulting in two products, the intron-10-retained (617 bp) and the correctly spliced (278 bp) products. Below are representative gels showing radioactive RT-PCR products from nuclear and cytoplasmic fractions of A172 (glioblastoma) cells separated in a 5% polyacrylamide gel. Results show a band corresponding to the intron-10 retained product in the nuclear fractions of A172 cells that is significantly reduced in the cytoplasmic fraction. Quantification of the bands indicated that approximately 36% of TSC1 transcripts contain intron 10 and that this product is retained in the nucleus. Moreover, as shown for ADAMTS13, the radioactive RT-PCR results validated the bioinformatic predictions. A summary of the quantification on TSC1 intron-10 retention calculated as percent intron retention (PIR) from radioactive RT-PCR and RNAseq experiments is shown on the table on the right.

Validation of the intron 10-retention event in the TSC1 (tuberous sclerosis complex 1) gene was performed using the methods described herein (FIG. 20). Briefly, nuclear and cytoplasmic RNA extracts from A172 (human glioblastoma) cells were used to perform radioactive reverse transcriptase PCR (RT-PCR) as described in Example 1. In this example, intron retention was assessed using primers positioned in exon 9 and exon 11 leading to the amplification of both intron-10 containing transcript and correctly spliced transcript. The products were run in a 5% polyacrylamide gel and visualized by phosphorimaging. Intron 10 retention levels were calculated as percent intron retention (PIR) of the intensity of the band corresponding to the intron-10 containing product over total transcript (intron-containing plus correctly spliced). Quantification of the bands indicated that approximately 36% of TSC1 transcripts contain intron 10 and that this product is retained in the nucleus. Moreover, the radioactive RT-PCR results validated the bioinformatic predictions demonstrating that the bioinformatic analysis of the RNAseq results is a powerful tool to identify intron-retention events.

Example 15: Design of ASO-Walk Targeting Intron 10 of TSC1

Figure 21:
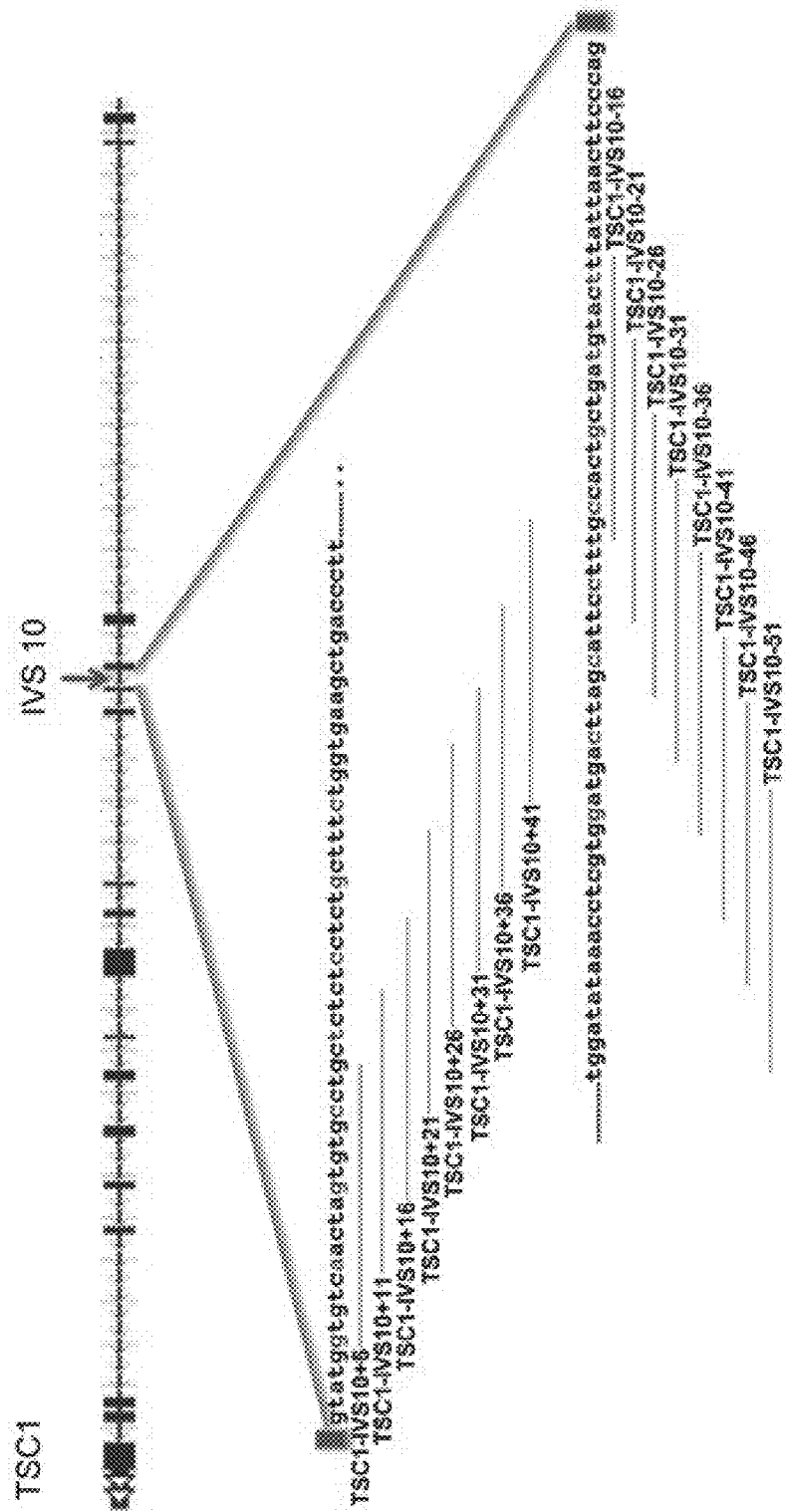
FIG. 21 shows a graphic representation of the ASO walk performed for TSC1 IVS 10 targeting sequences immediately downstream of the 5' splice site or upstream of the 3' splice site using 2'-O-Me ASOs, PS backbone, as described in Example 15. ASOs were designed to cover these regions by shifting 5 nucleotides at a time. TSC1 exon-intron structure is drawn to scale. The figure discloses SEQ ID NOS 393 and 394, respectively, in order of appearance.

An ASO walk was designed to target intron 10 using the method described herein (FIG. 21). A region immediately downstream of intron 10 5' splice site spanning nucleotides +6 to +58 and a region immediately upstream of intron 10 3' splice site spanning nucleotides −16 to −68 of the intron were targeted with 2'-O-Me RNA, PS backbone, 18-mer ASOs shifted by 5-nucleotide intervals (FIG. 21; Table 5, SEQ ID NOS: 214 to 229). These target regions were selected based on the knowledge that intronic regulatory elements concentrate in sequences adjacent to splice sites.

Figure 22:
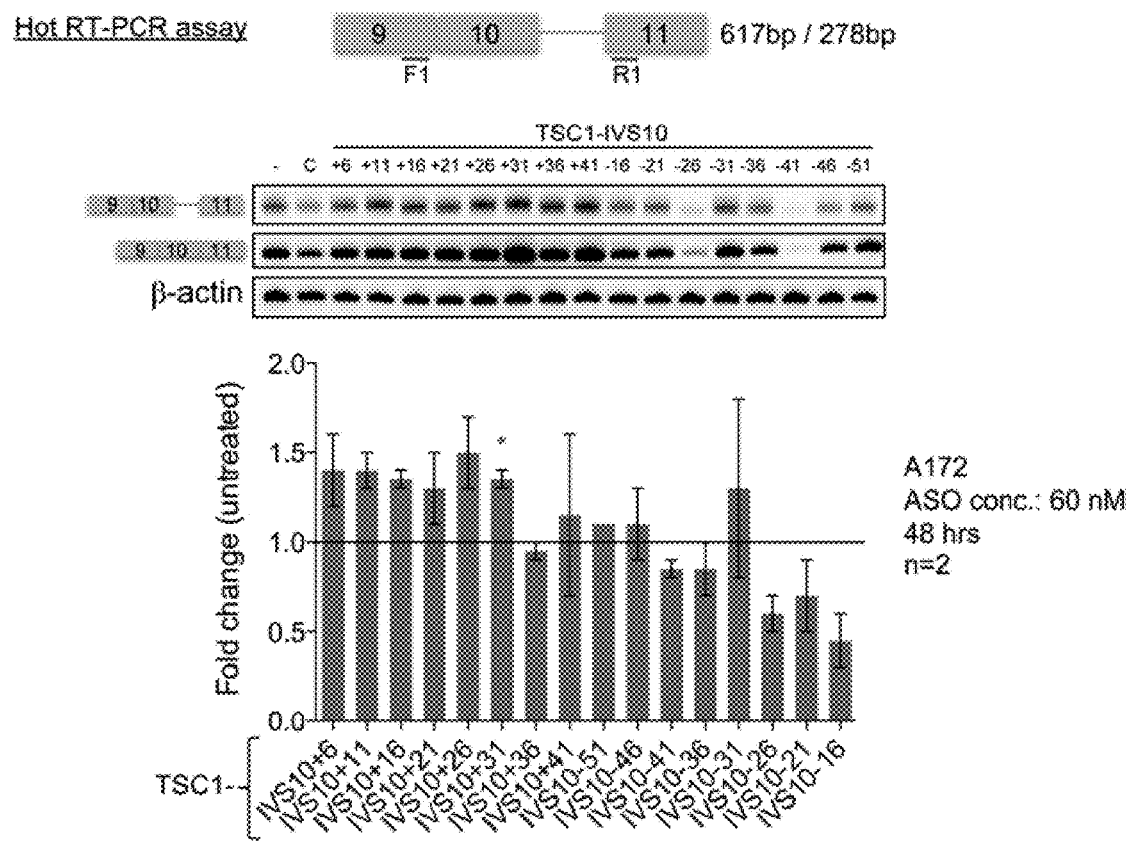
FIG. 22 depicts the results of the ASO-walk targeting intron 10, as described in Example 16. At the top, a representative gel shows radioactive RT-PCR products of TSC1 mock-treated (−), SMN-control ASO treated, or treated with a 2′-O-Me ASO targeting intron 10 as described in FIG. 21, at 60 nM concentration in A172 cells. Quantification of the bands corresponding to TSC1 products normalized to Beta actin from 2 independent experiments is plotted in the bar graph below as fold change with respect to the mock-treated products. The black line indicates a ratio of 1, no change. Asterisks indicate ASOs that lead to an increase in TSC1 mRNA levels.

Example 16: Improved Splicing Efficiency Via ASO-Targeting of TSC1 Intron 10 Increases Transcript Levels To determine whether we can achieve an increase in TSC1 expression by improving splicing efficiency of TSC1 intron 10 using ASOs, we used the method described herein (FIG. 22). To this end, A172 cells were mock-transfected, or transfected with each of the targeting ASOs described in FIG. 21 and Table 5, SEQ ID NOS: 214 to 229, or a non-targeting SMN-ASO control, independently, using RNAiMAX (RiM) (Invitrogen) delivery reagents. Experiments were performed using 60 nM ASOs (as indicated in FIG. 22) for 48 hrs. Radioactive RT-PCR results show that the +31 targeting ASO increases TSC1 transcript level compared to the mock-transfected or non-targeting ASO (FIG. 22). Intensities of the bands corresponding to the TSC1 PCR products from targeting-ASO-transfected cells were normalized to Beta actin and plotted relative to the normalized TSC1 PCR product from mock-treated cells. Results of this analysis indicate that several ASOs (including +31) increase TSC1 transcript level nearly 1.5 fold (FIG. 22). These results indicate that improving the splicing efficiency of a rate limiting intron in the TSC1 gene using ASOs leads to an increase in gene expression.

Example 17: Dose Response Effect of ASOs Targeting TSC1 Intron 10

Figure 23:
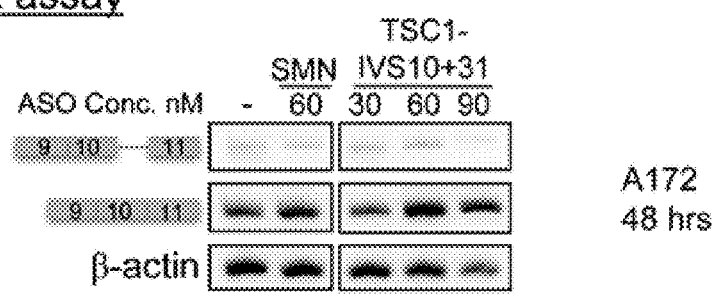
FIG. 23 shows a dose-response curve for TSC1-IVS10+31 ASO, as described in Example 17. In the top panel a representative gel shows radioactive RT-PCR TSC1 products from A172 cells mock-, SMN-control-, or TSC1-IVS10+31-treated at the indicated concentrations. The RT-PCR products were separated in a 5% polyacrylamide gel. Quantification of the bands corresponding to TSC1 products normalized to Beta actin is plotted in the bar graph on the left below as fold change relative to the mock-treated products. RT-qPCR results of the same experiment are plotted relative to mock-treated products on the right bar graph confirming the radioactive RT-PCR results. The black line indicates a ratio of 1, no change.
Figure 23:
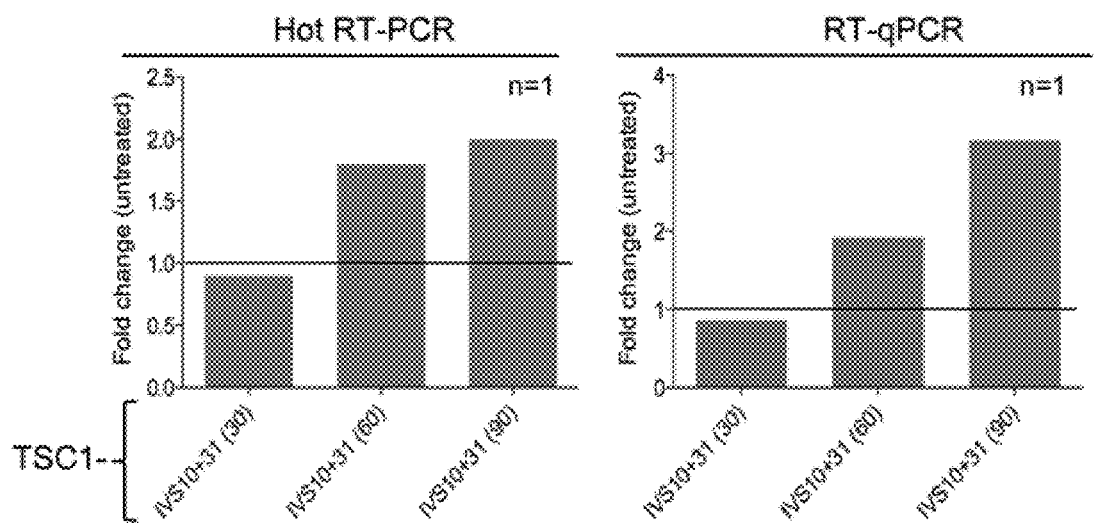

To determine a dose-response effect of the +31 ASO, we used the method described herein (FIG. 23). A172 cells were mock-transfected, or transfected with the +31 ASO, or a non-targeting SMN-ASO control, independently, using RNAiMAX (RiM) (Invitrogen) delivery reagents at increasing concentrations as indicated in FIG. 23 for 72 hrs. Radioactive RT-PCR results show that the +31 targeting ASO increases TSC1 transcript level compared to the mock-transfected or non-targeting ASO (FIG. 23). Intensities of the bands corresponding to the TSC1 PCR products from targeting-ASO-transfected cells were normalized to Beta actin and plotted relative to the normalized TSC1 PCR product from mock-treated cells. Results of this analysis indicate the +31 targeting ASO increases TSC1 transcript level in a dose-dependent manner nearly 2.0 fold (FIG. 23). These results were confirmed by RTqPCR using primers elsewhere in the TSC1 transcript, showing a 3-fold increase, and a dose-dependant response to the ASO treatment. These results confirm that improving the splicing efficiency of a rate limiting intron in the TSC1 gene using ASOs leads to an increase in gene expression.

Figure 24:
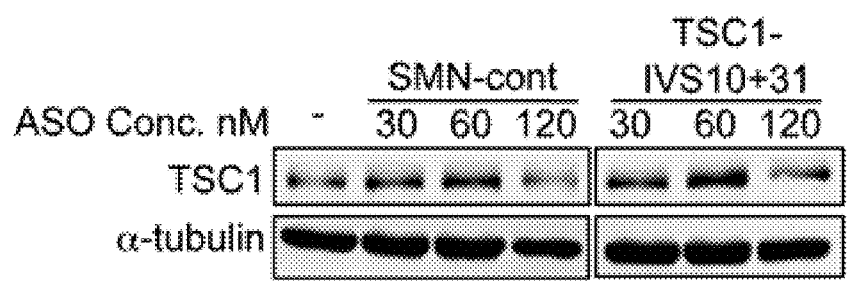
FIG. 24 illustrates an increase in TSC1 protein resulting from the treatment of A172 cells with TSC1-IVS10+31 ASO, as described in Example 18. In the top panel a representative gel shows TSC1 protein products from A172 cells mock-, SMN-control-, or TSC1-IVS10+31 ASO-treated at the indicated concentrations. The protein products were separated on a 10% SDS-polyacrylamide gel. Antibodies against TSC1 and alpha tubulin were used to detect the protein products. The bar graph below shows the quantifications of the intensity of bands corresponding to TSC1 protein levels from TSC1-IVS10+31-treated cells, normalized to alpha tubulin. Fold change was plotted relative to the product from mock-treated cells. The black line indicates a ratio of 1, no change. TSC1-IVS10+31 increases TSC1 protein product.
Figure 24:
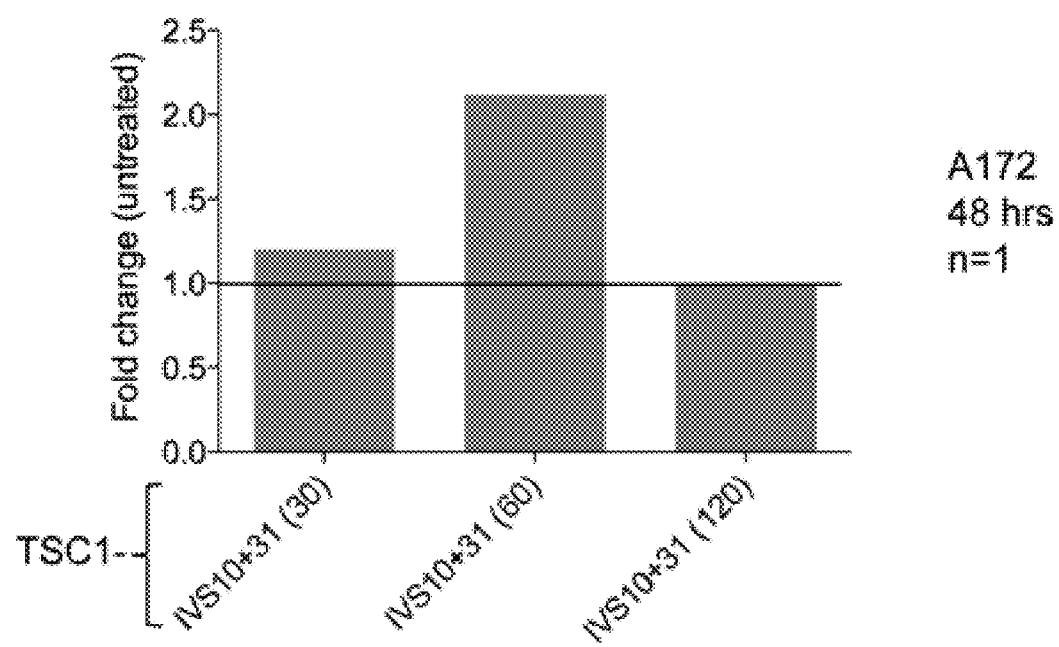

Example 18: Improved Splicing Efficiency Via ASO-Targeting of TSC1 Intron 10 Increases Protein Levels In order to detect an increase in protein production upon targeting TSC1 intron 10 with the +31 ASO, we used the method described herein (FIG. 24). A172 cells were mock-transfected, or transfected with the +31 ASO, or a non-targeting SMN-ASO control, independently, using RNAiMAX (RiM) (Invitrogen) delivery reagents at increasing concentrations as indicated in FIG. 24 for 72 hrs. Briefly, protein extracts from A172 treated cells were run on a 10% SDS-polyacrylamide gel, and transferred to a nitrocellulose membrane. To evidence an increase in protein production, an anti-TSC1 antibody or anti-Alpha tubulin antibody was used to detect TSC1 and Alpha tubulin as a loading control, respectively. FIG. 24 shows western blot results indicating that TSC1 (top panel) is increased in a dose dependent manner upon treatment with the +31 ASO at 30 and 60 nM. Intensities of the bands corresponding to the TSC1 protein from targeting-ASO-transfected cells were normalized to endogenous Alpha tubulin and plotted relative to the normalized TSC1 protein band from mock-treated cells. Results of this analysis indicate that the targeting ASO (+31) increases TSC1 protein level more than 2 fold (FIG. 24). These results demonstrate that promoting splicing efficiency by using an ASO targeted to a region downstream of the 5' splice site of TSC1 intron 10, a rate-limiting intron, leads to an increase in target protein production as depicted in FIG. 2.

Figure 25:
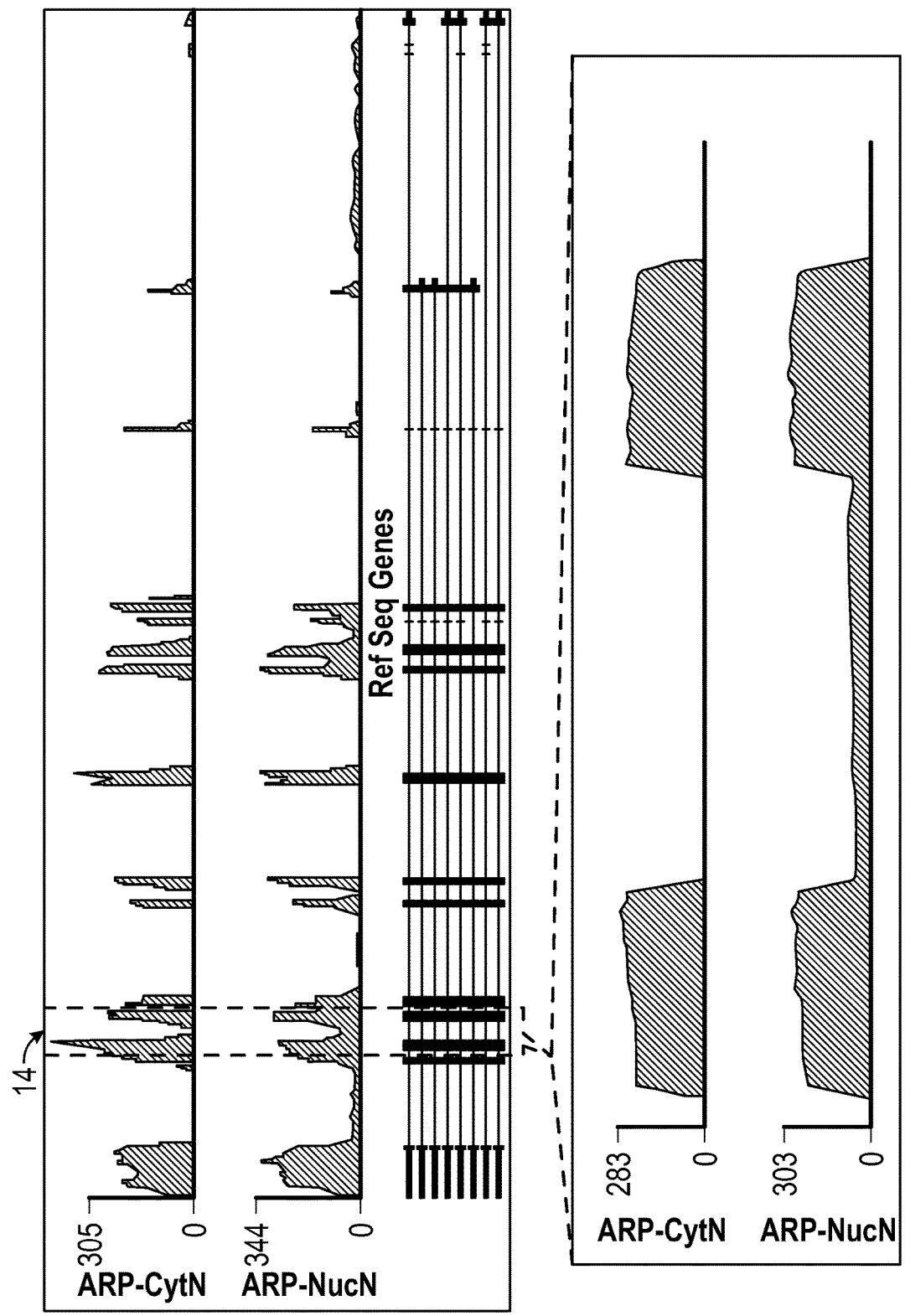
FIG. 25 shows the identification of intron-retention events in the IMPDH1 gene using RNA sequencing (RNAseq), visualized in the UCSC genome browser as described in Example 19. The top panel shows the read density corresponding to the IMPDH1 transcript expressed in ARPE19 (human retinal epithelial) cells and localized in either the cytoplasmic (top) or nuclear fraction (bottom). At the bottom of this panel, a graphic representation of all the refseq. isoforms of the IMPDH1 gene is shown to scale. The read density is shown as peaks. The highest read density corresponds to exons (black boxes), while no reads are observed for the majority of the introns (lines with arrow heads) in either cellular fraction. Higher read density is detected for intron 14 (pointed by the arrow) in the nuclear fraction compared to the cytoplasmic fraction indicating that splicing efficiency of intron 14 is low, resulting in intron retention. The retained-intron containing pre-mRNA transcripts are retained in the nucleus and are not exported out to the cytoplasm. The read density for intron 14 is shown in detail in the bottom picture for ARPE19 cells.

Example 19: Identification of Intron Retention Events in IMPDH1 Transcripts by RNAseq Using Next Generation Sequencing We performed whole transcriptome shotgun sequencing using next generation sequencing to reveal a snapshot of transcripts produced by the IMPDH1 gene (retinitis pigmentosa 10) to identify intron-retention events. For this purpose, we isolated polyA+RNA from nuclear and cytoplasmic fractions of ARPE-19 (human retina epithelial) cells and constructed cDNA libraries using Illumina's TruSeq Stranded mRNA library Prep Kit. The libraries were pair-end sequenced resulting in 100-nucleotide reads that were mapped to the human genome (February 2009, GRCh37/hg19 assembly). The sequencing results for IMPDH1 are shown in FIG. 25. Briefly, FIG. 25 shows the mapped reads visualized using the UCSC genome browser and the coverage and number of reads can be inferred by the peak signals. The height of the peaks indicates the level of expression given by the density of the reads in a particular region. A schematic representation of all IMPDH1 isoforms (drawn to scale) is provided by the UCSC genome browser (below the read signals), so that peaks can be matched to IMPDH1 exonic and intronic regions. Based on this display, we identified one intron (14, indicated by arrow) that has high read density in the nuclear fraction of ARPE-19 cells, but has no reads in the cytoplasmic fraction of these cells (as shown for intron 14 in the bottom diagram of FIG. 25). This indicates that intron 14 is retained and that the intron-14 containing transcript remains in the nucleus. This suggests that the retained intron-containing (RIC) IMPDH1 pre-mRNAs is non-productive, as it is not exported out to the cytoplasm.

Example 20: Design of ASO-Walk Targeting Intron 14 of IMPDH1

Figure 26:
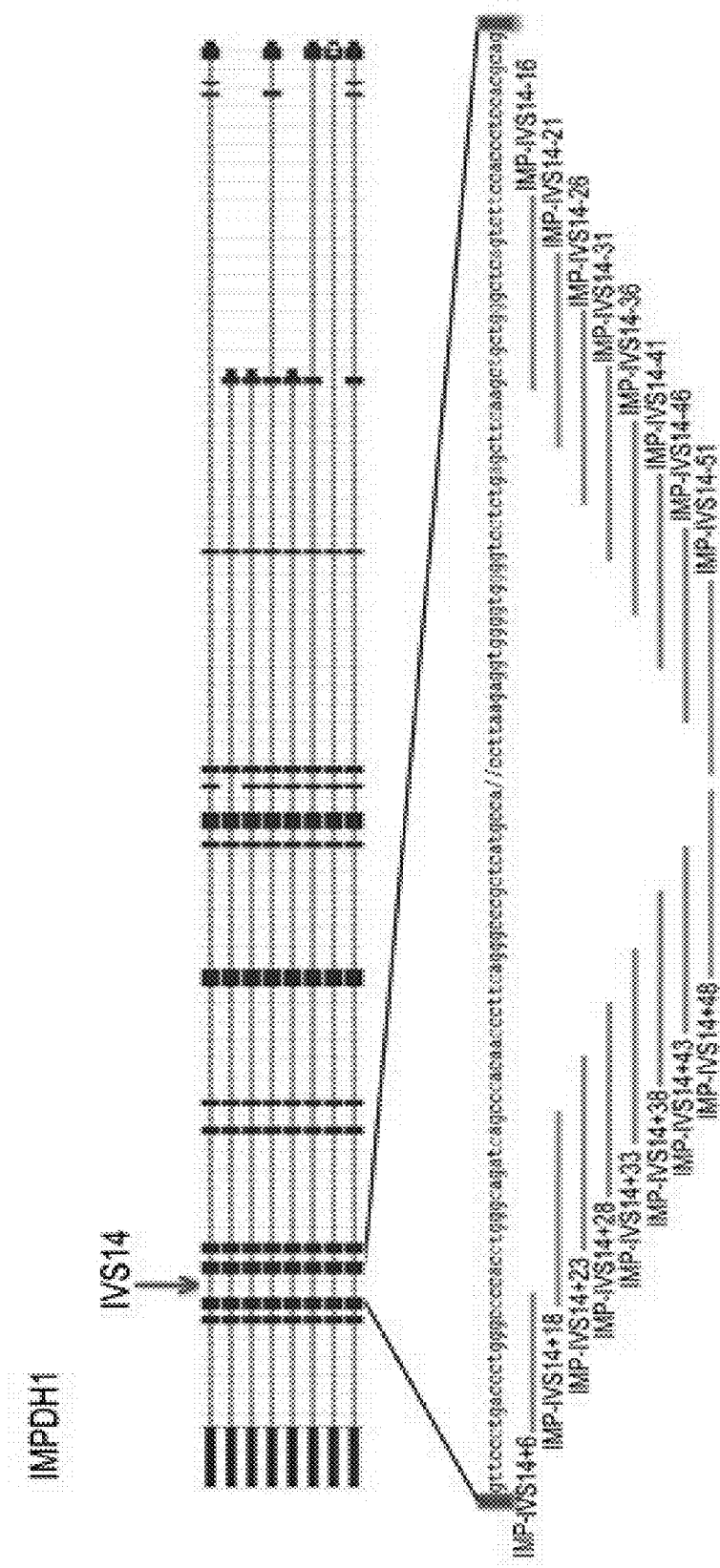
FIG. 26 shows a graphic representation of the ASO walk performed for IMPDH1 IVS 14 targeting sequences immediately downstream of the 5′ splice site or upstream of the 3′ splice site using 2′-O-Me ASOs, as described in Example 20, PS backbone. ASOs were designed to cover these regions by shifting 5 nucleotides at a time, unless a stretch of four guanines is present in the ASOs. IMPDH1 exon-intron structure is drawn to scale. The figure discloses SEQ ID NOS 395 and 396, respectively, in order of appearance.

An ASO walk was designed to target intron 14 using the method described herein (FIG. 26). A region immediately downstream of intron 14 5' splice site spanning nucleotides +6 to +65 and a region immediately upstream of intron 14 3' splice site spanning nucleotides −16 to −68 of the intron were targeted with 2'-O-Me RNA, PS backbone, 18-mer ASOs shifted by 5-nucleotide intervals (with the exception of 1 ASO, IMP-IVS14+18, to avoid a stretch of four guanines) (FIG. 26; Table 6, SEQ ID NOS: 246 to 261). These target regions were selected based on the knowledge that intronic regulatory elements concentrate in sequences adjacent to splice sites.

Figure 27:
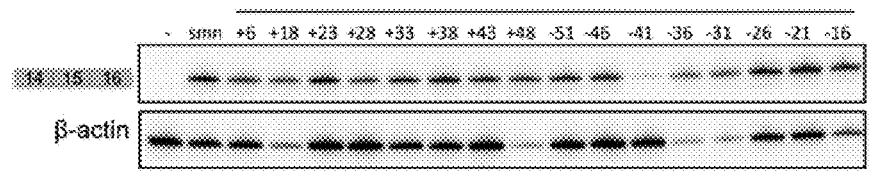
FIG. 27 depicts the results of the ASO-walk targeting intron 14, as described in Example 21. At the top, a representative gel shows radioactive RT-PCR products of IMPDH1 mock-treated (−), SMN-control ASO-treated, or treated with a 2′-O-Me ASO targeting intron 14 as described in FIG. 21, at 60 nM concentration in ARPE19 cells. Quantification of the bands corresponding to IMPDH1 products normalized to Beta actin from 2 independent experiments is plotted in the bar graph below as fold change relative to the mock-treated products. The black line indicates a ratio of 1, no change. Asterisks indicate the ASO that lead to the highest increase in IMPDH1 mRNA levels.
Figure 27:
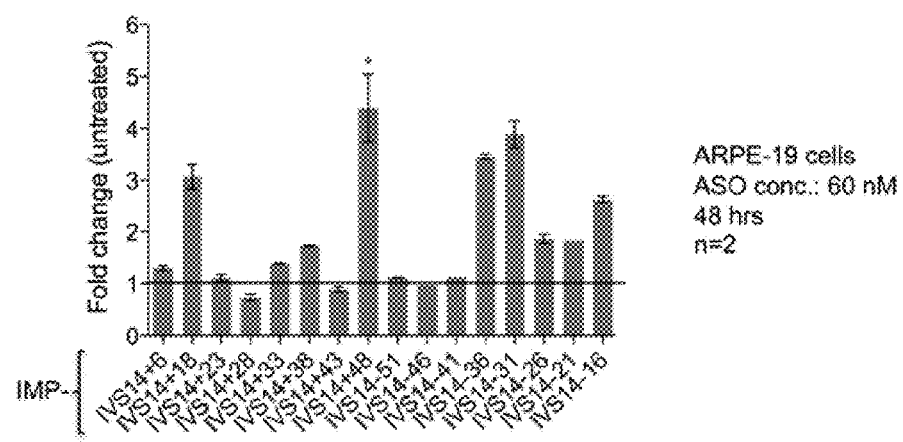

Example 21: Improved Splicing Efficiency Via ASO-Targeting of IMPDH1 Intron 14 Increases Transcript Levels To determine whether we can achieve an increase in IMPDH1 expression by improving splicing efficiency of IMPDH1 intron 14 using ASOs, we used the method described herein (FIG. 27). To this end, ARPE-19 cells were mock-transfected, or transfected with each of the targeting ASOs described in FIG. 26 and Table 6, SEQ ID NOS: 246 to 261, or a non-targeting SMN-ASO control, independently, using RNAiMAX (RiM) (Invitrogen) delivery reagents. Experiments were performed using 60 nM ASOs (as indicated in FIG. 27) for 48 hrs. Radioactive RT-PCR results show that the +48 targeting ASO increases IMPDH1 transcript level compared to the mock-transfected or non-targeting ASO (FIG. 27). Intensities of the bands corresponding to the IMPDH1 PCR products from targeting-ASO-transfected cells were normalized to Beta actin and plotted relative to the normalized IMPDH1 PCR product from control ASO-treated cells. Results of this analysis indicate that the targeting ASO (+48) increases IMPDH1 transcript level 4.0 fold (FIG. 27). These results indicate that improving the splicing efficiency of a rate limiting intron in the IMPDH1 gene using ASOs leads to an increase in gene expression.

Example 22: Dose Response Effect of ASO +48 Targeting IMPDH1 Intron 14

Figure 28:
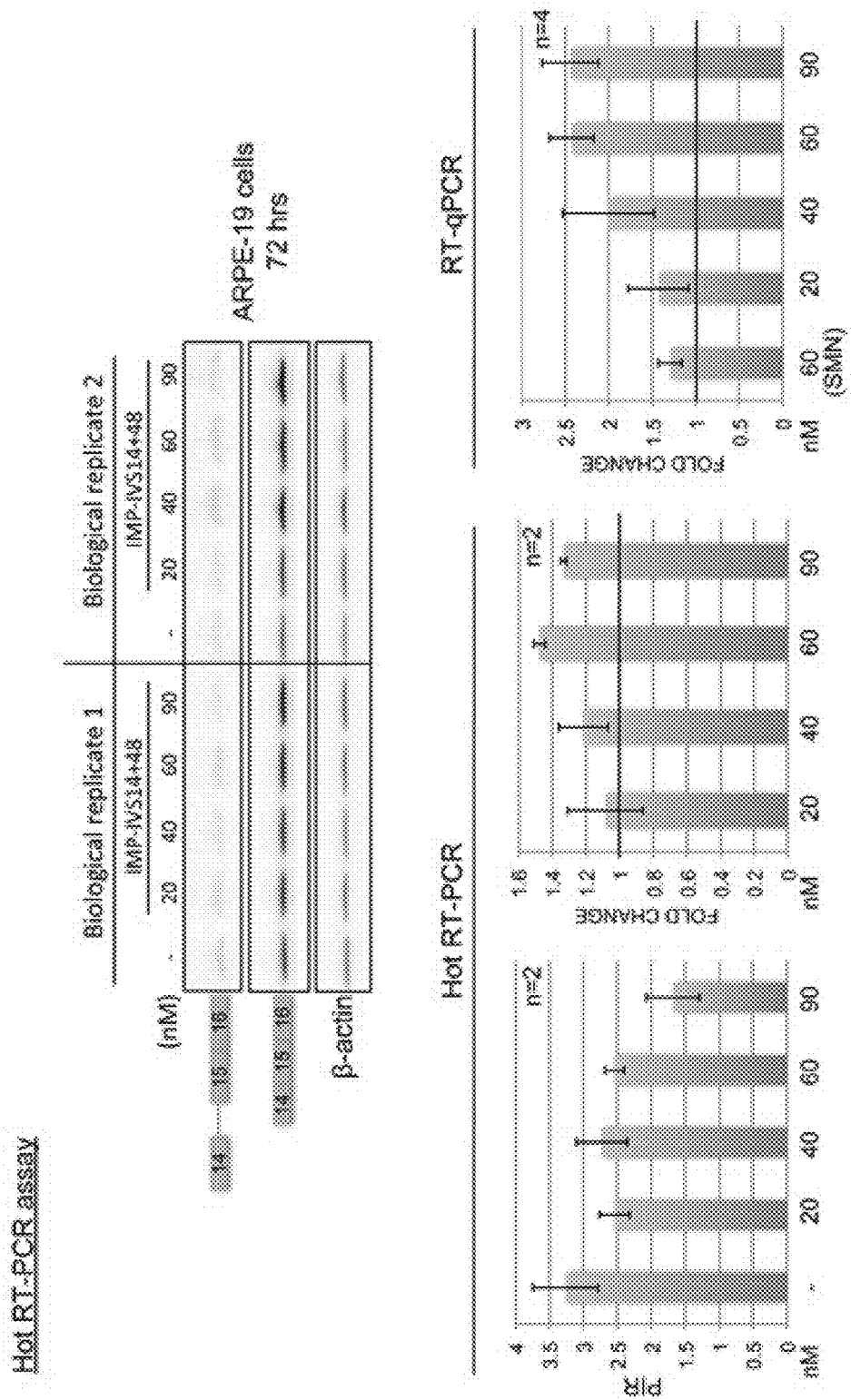
FIG. 28 shows an increase in IMPDH1 gene expression levels in a dose-dependent manner resulting from the treatment of ARPE19 cells with IMP-IVS14+48 ASO at the indicated concentrations, as described in Example 22. Radioactive RT-PCR products of IMPDH1 (intron-14 retained and correctly spliced) and Beta actin from ARPE-19 cells were separated on a 5% polyacrylamide gel. The bar graph on the left demonstrates a dose-dependent reduction in percent intron retention (PIR) calculated relative to the total transcript (intron-14 retained and correctly spliced) from IMP-IVS14+48 ASO-treated cells compared to mock-treated cells (two independent experiments). Fold change of correctly spliced transcript level from two independent experiments was plotted relative to the mock-treated cells in the middle graph showing a dose-dependent increase in IMPDH1 transcript level. RT-qPCR (right bar graph) was performed and the resulting values were normalized to Beta actin. Fold change of four biological replicates was plotted relative mock-treated IMPDH1 products, confirming the radioactive RT-PCR results.

To determine a dose-response effect of the +48 ASO, we used the method described herein (FIG. 28). ARPE-19 cells were mock-transfected, or transfected with the +48 ASO, or a non-targeting SMN-ASO control, independently, using RNAiMAX (RiM) (Invitrogen) delivery reagents at increasing concentrations as indicated in FIG. 28 for 72 hrs. Radioactive RT-PCR results show that the +48 targeting ASO increases IMPDH1 transcript level compared to the mock-transfected or non-targeting ASO in a dose-dependant manner (FIG. 28). Intensities of the bands corresponding to the IMPDH1 PCR products from targeting-ASO-transfected cells were normalized to Beta actin and plotted relative to the normalized IMPDH1 PCR product from mock-treated cells. Results of this analysis indicate that the targeting ASO (+48) increases IMPDH1 transcript level nearly 1.5 fold (FIG. 28, middle graph). These results were confirmed by RTqPCR using primers elsewhere in the IMPDH1 transcript, showing a 2.5-fold increase, and a dose-dependant response to the ASO treatment (FIG. 28, right graph). In addition PIR was calculated (as described in Example 6) for intron 14 retention and the values were plotted indicating that as the ASO concentration and the correctly spliced transcript increases, a reduction in intron 14 retention is observed (FIG. 28, left graph). These results confirm that improving the splicing efficiency of a rate limiting intron in the IMPDH1 gene using ASOs leads to an increase in gene expression.

Figure 29:
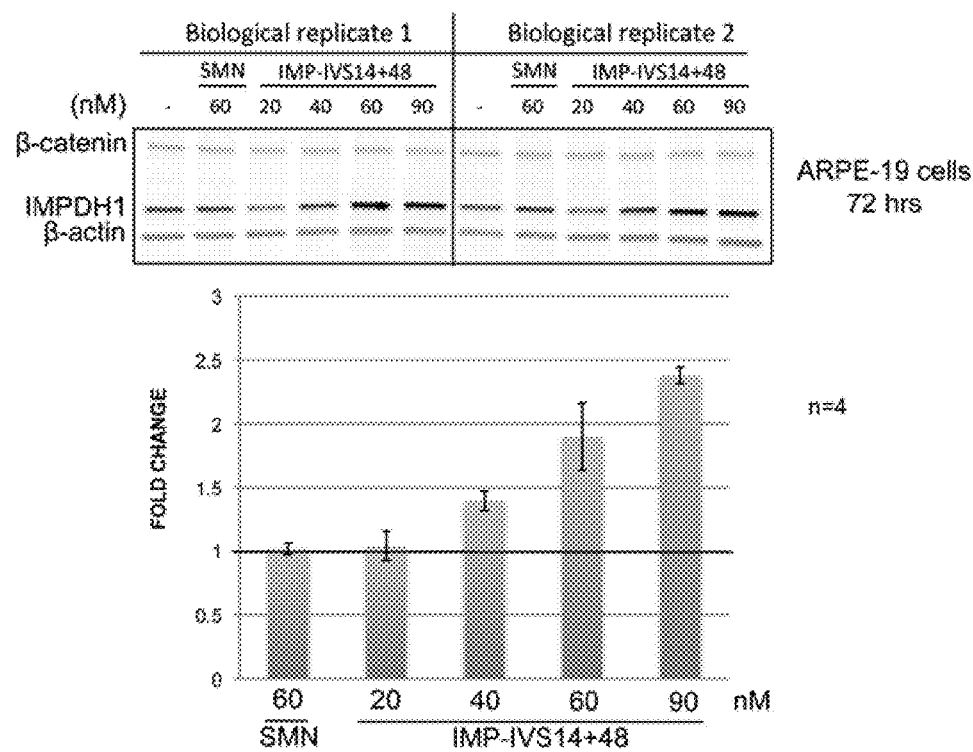
FIG. 29 shows an increase in IMPDH1 protein levels achieved via IMP-IVS14+48 ASO targeting at the indicated concentrations in ARPE19 cells, as described in Example 23. Protein lysates from ARPE-19 cells were separated on a 4-20% SDS-polyacrylamide gel. Antibodies against IMPDH1, Beta actin and Beta catenin were used to detect protein products. The intensity of the IMPDH1 protein bands was normalized to the intensity of the Beta actin bands and the fold change was computed relative to the mock-treated products from four biological replicates, and plotted in the bar graph below.

Example 23: Improved Splicing Efficiency Via ASO-Targeting of IMPDH1 Intron 14 Increases Protein Levels In order to detect an increase in protein production upon targeting IMPDH1 intron 14 with the +48 ASO, we used the method described herein (FIG. 29). ARPE-19 cells were mock-transfected, or transfected with the +48 ASO, or a non-targeting SMN-ASO control, independently, using RNAiMAX (RiM) (Invitrogen) delivery reagents at increasing concentrations as indicated in FIG. 29 for 72 hrs. Briefly, protein extracts from ARPE-19 treated cells were run on an 4-20% SDS-polyacrylamide gel, and transferred to a nitrocellulose membrane. To evidence an increase in protein production, an anti-IMPDH1 antibody, anti-Beta catenin antibody, or Beta actin was used to detect IMPDH1, and Beta catenin or Beta actin as loading controls, respectively. FIG. 29 shows western blot results indicating that IMPDH1 is increased in a dose dependent manner upon treatment with the +48 ASO. Intensities of the bands corresponding to the IMPDH1 protein from targeting-ASO-transfected cells were normalized to endogenous Beta actin and plotted relative to the normalized IMPDH1 protein band from mock-treated cells. Results of this analysis indicate that the targeting ASO (+48) increase IMPDH1 protein level nearly 2.5 fold (FIG. 29). These results demonstrate that promoting splicing efficiency using an ASO targeted to a region downstream of the 5' splice site of IMPDH1 intron 14, a rate-limiting intron, leads to an increase in target protein production as depicted in FIG. 2.

Example 24: Design of ASO-Microwalk Targeting the +48 Region of IMPDH1 Intron 14

Figure 30:
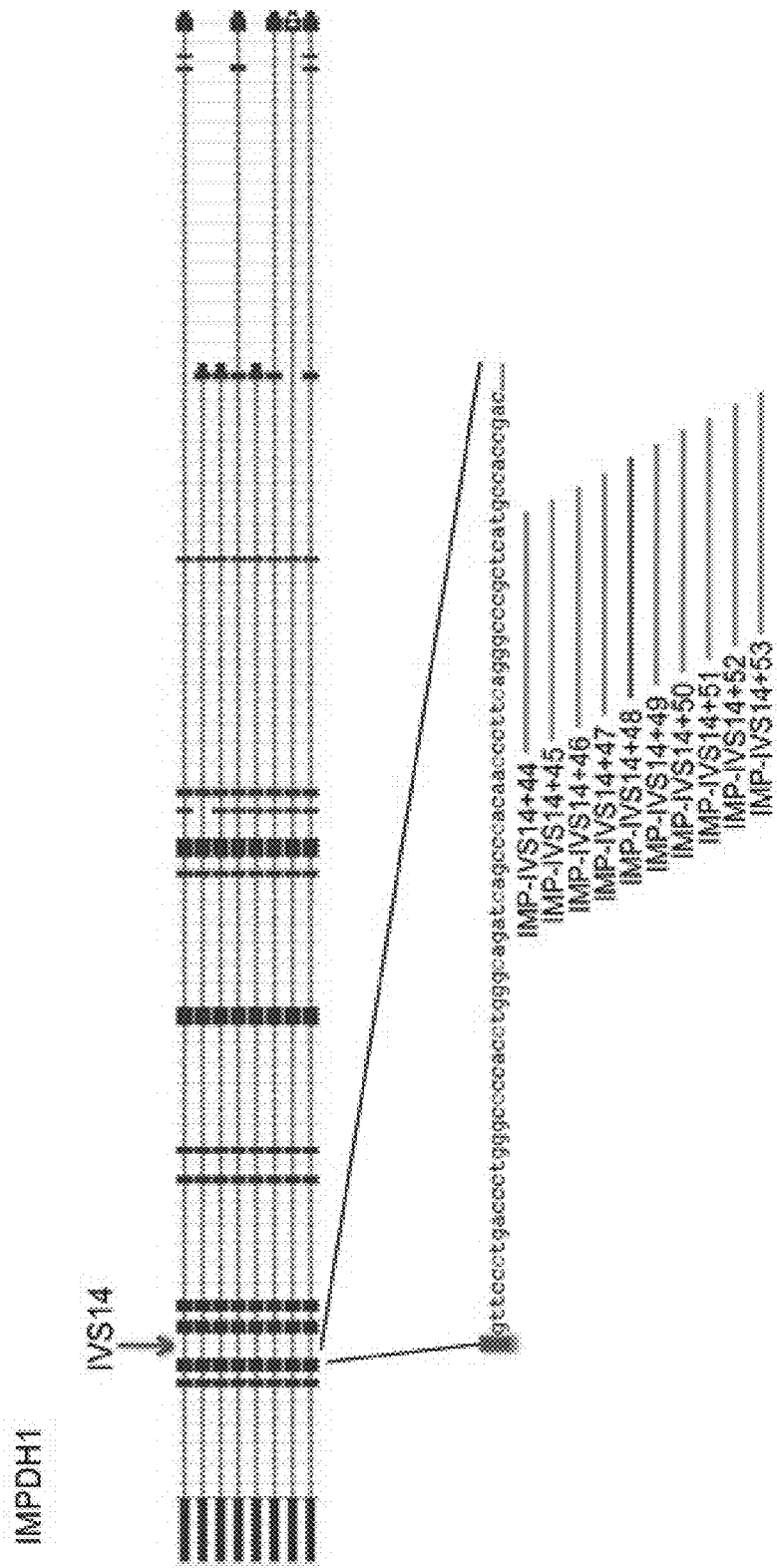
FIG. 30 shows a graphic representation of the ASO microwalk performed for IMPDH1 IVS14 targeting sequences in the region of IMP-IVS14+48 ASO using 2′-O-Me, 5′-Me-Cytosine ASOs, as described in Example 24. ASOs were designed to cover the region by shifting 1 nucleotide at a time. IMPDH1 exon-intron structure is drawn to scale. The figure discloses SEQ ID NO: 397.

An ASO microwalk was designed to target intron 14 +44 to +70 region using the method described herein (FIG. 30). A region downstream of intron 14 5' splice site spanning +44 to +70 were targeted with 2'-O-Me, 5'-Me-Cytosine RNA, PS backbone, 18-mer ASOs shifted by 1-nucleotide interval (FIG. 30; Table 6, SEQ ID NOS: 262 to 271). This target region was selected based on the observed effect of ASO +48 (FIG. 29).

Figure 31:
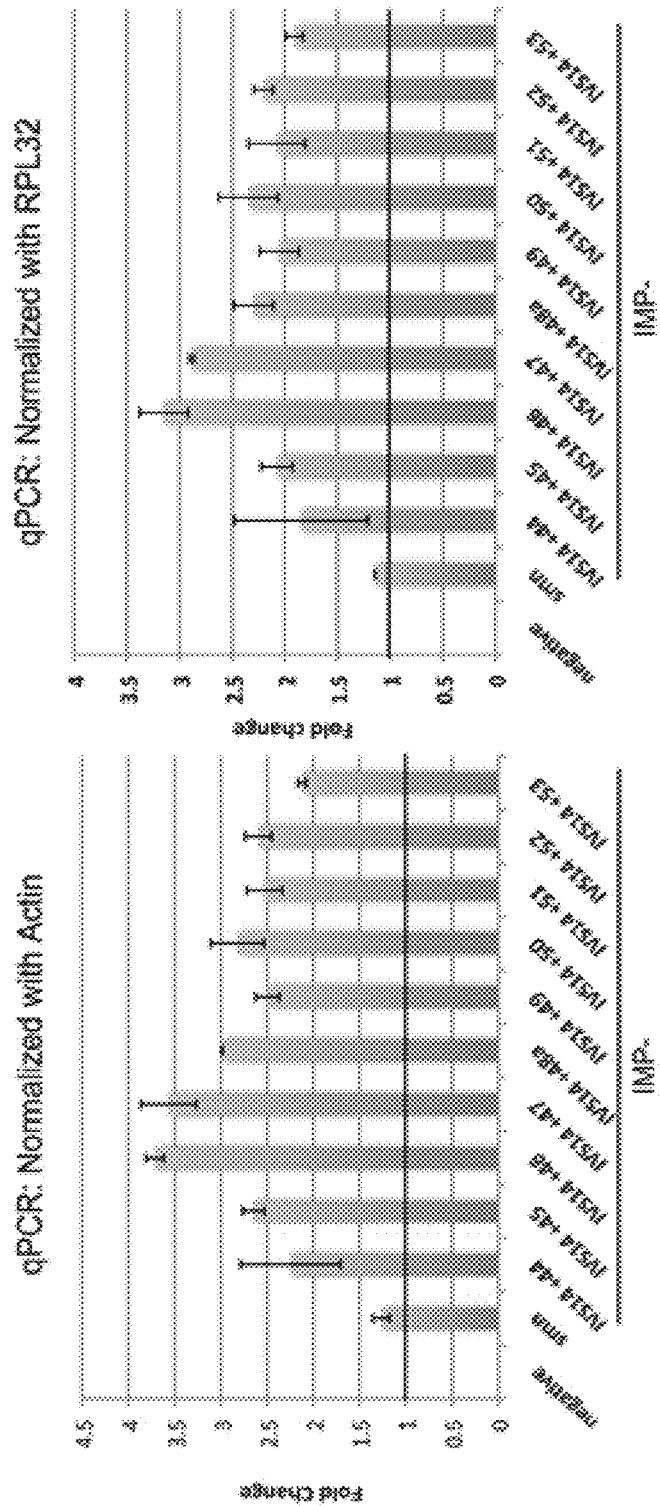
FIG. 31 shows an increase in MPDH1 expression levels resulting from a microwalk as shown in FIG. 30, as described in Example 25. RT-qPCR was performed on total RNA extracted from ARPE-19 cells, which were treated at an ASO concentration of 60 nM. Ct values of the IMPDH1 gene were normalized to the ct values Beta Actin (left) and RPL32 (right) house keeping genes, and the fold change was plotted relative to the products from mock-treated cells in the bar graphs. The microwalk identified two additional ASOs that further increase IMPDH1 transcript levels.

Example 25: Improved Splicing Efficiency Via ASO Microwalk Targeting of IMPDH1 Intron 14 +48 Region Increases Transcript Levels To determine whether we can achieve an increase in IMPDH1 expression by improving splicing efficiency of IMPDH1 intron 14 using microwalk ASOs, we employed the method described herein (FIG. 31). To this end, ARPE-19 cells were mock-transfected, or transfected with each of the targeting ASOs described in FIG. 30 and Table 6, SEQ ID NOS: 262 to 271, or a non-targeting SMN-ASO control, independently, using RNAiMAX (RiM) (Invitrogen) delivery reagents. Experiments were performed using 60 nM ASOs (as indicated in FIG. 31) for 48 hrs. RT-qPCR results show that the +46 and +47 targeting ASOs further increase IMPDH1 transcript level compared to the mock-transfected or non-targeting ASO, as well as the original +48 ASO (FIG. 31). Results of this analysis indicate that both targeting ASOs (+46 and +47) increase IMPDH1 transcript level more than 3.0 fold (FIG. 31). These results indicate that improving the splicing efficiency of a rate limiting intron in the IMPDH1 gene using ASOs leads to an increase in gene expression, and the refinement of the target region by a microwalk can lead to the identification of more efficient ASOs.

Figure 32:
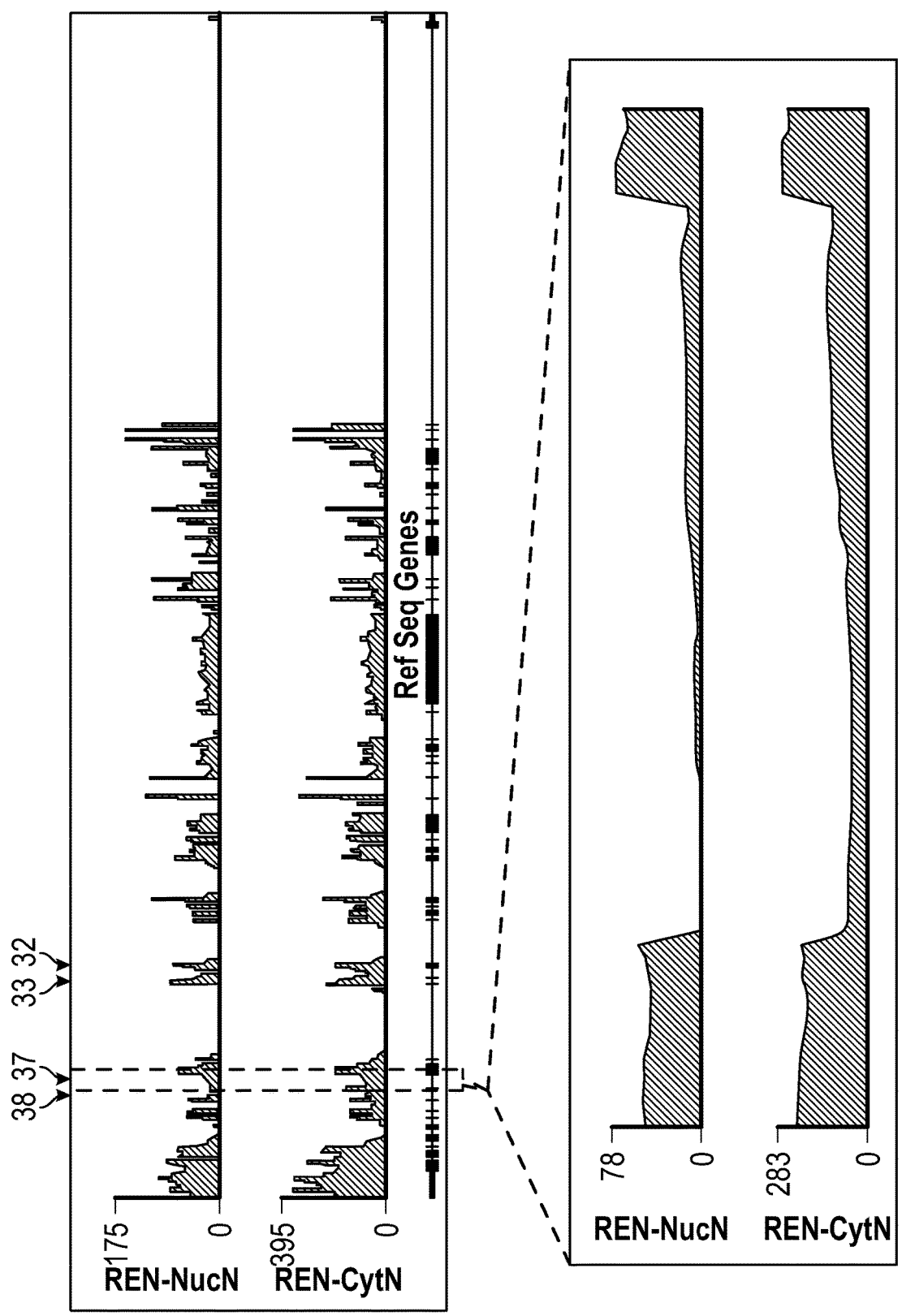
FIG. 32 shows the identification of intron-retention events in the PKD1 gene using RNA sequencing (RNAseq), visualized in the UCSC genome browser as described in Example 26. The top panel shows the read density corresponding to the PKD1 transcript expressed in primary human renal epithelial cells (REN) and localized in either the cytoplasmic (top) or nuclear fraction (bottom). At the bottom of this panel, a graphic representation of the refseq. isoform of the PKD1 gene is shown to scale. The read density is shown as peaks. The highest read density corresponds to exons (black boxes), while no reads are observed for the majority of the introns (lines with arrow heads) in neither cellular fraction. Higher read density is detected for introns 32, 33, 37, and 38 (pointed by the arrows) in the nuclear fraction compared to the cytoplasmic fraction indicating that splicing efficiency of these introns is low, resulting in intron retention. The retained-intron containing pre-mRNA transcripts are retained in the nucleus and are not exported out to the cytoplasm. The read density for intron 37 is shown in detail in the bottom picture for REN cells.

Example 26: Identification of Intron Retention Events in PKD1 Transcripts by RNAseq Using Next Generation Sequencing We performed whole transcriptome shotgun sequencing using next generation sequencing to reveal a snapshot of transcripts produced by the PKD1 gene (polycystic kidney disease) to identify intron-retention events. For this purpose, we isolated polyA+RNA from nuclear and cytoplasmic fractions of primary human renal epithelial (REN) cells and constructed cDNA libraries using Illumina's TruSeq Stranded mRNA library Prep Kit. The libraries were pair-end sequenced resulting in 100-nucleotide reads that were mapped to the human genome (February 2009, GRCh37/hg19 assembly). The sequencing results for PKD1 are shown in FIG. 32. Briefly, FIG. 32 shows the mapped reads visualized using the UCSC genome browser and the coverage and number of reads can be inferred by the peak signals. The height of the peaks indicates the level of expression given by the density of the reads in a particular region. A schematic representation of all PKD1 isoforms (drawn to scale) is provided by the UCSC genome browser (below the read signals) so that peaks can be matched to PKD1 exonic and intronic regions. Based on this display, we identified four introns (32, 33, 37 and 38, indicated by arrows) that have high read density in the nuclear fraction of REN cells, but have very low to no reads in the cytoplasmic fraction of these cells (as shown for intron 37 in the bottom diagram of FIG. 32). This indicates that the four introns are retained and that the intron-32, intron-33, intron-37, and intron-38 containing transcripts remain in the nucleus. This suggests that these retained intron-containing (RIC) PKD1 pre-mRNAs are non-productive, as they are not exported out to the cytoplasm.

Example 27: Design of ASO-Walk Targeting Intron 37 of PKD1

Figure 33:
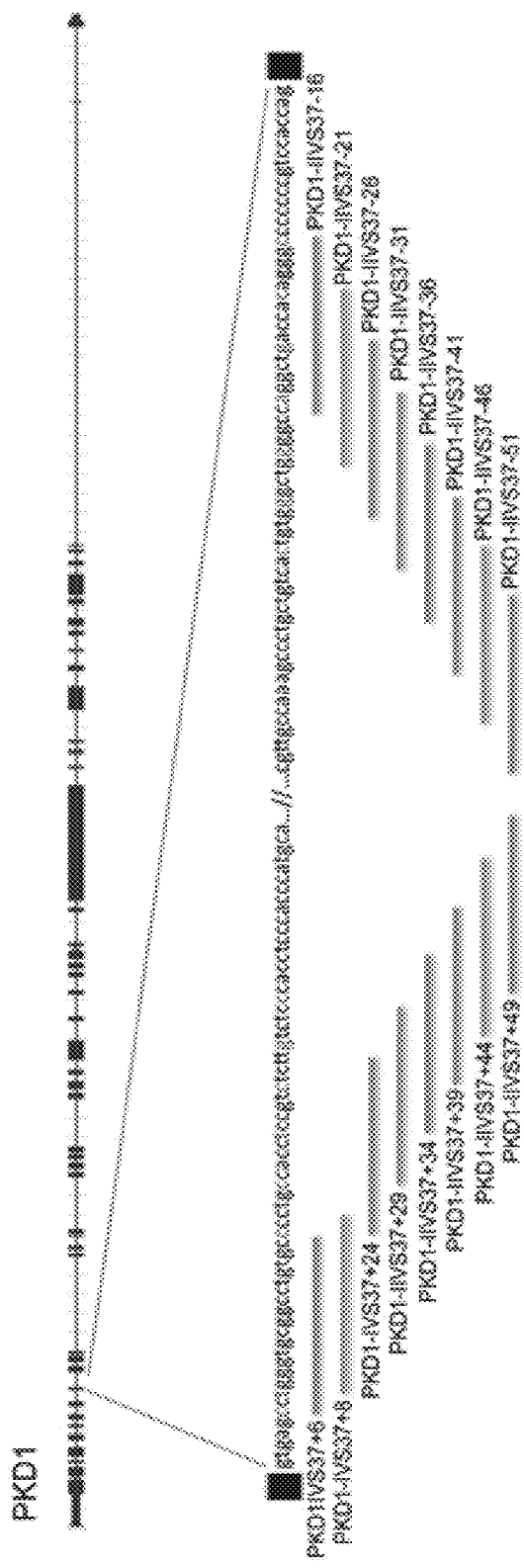
FIG. 33 shows a graphic representation of the ASO walk performed for PKD1 IVS 37 targeting sequences immediately downstream of the 5' splice site or upstream of the 3' splice site using 2'-O-Me ASOs, PS backbone, as described in Example 27. ASOs were designed to cover these regions by shifting 5 nucleotides at a time, unless a stretch of four guanines is present in the ASOs. PKD1 exon-intron structure is drawn to scale. The figure discloses SEQ ID NOS 398 and 399, respectively, in order of appearance.

An ASO walk was designed to target intron 37 using the method described herein (FIG. 33). A region immediately downstream of intron 37 5' splice site spanning nucleotides +6 to +66 and a region immediately upstream of intron 37 3' splice site spanning nucleotides −16 to −51 of the intron were targeted with 2'-O-Me RNA, PS backbone, 18-mer ASOs shifted by 5-nucleotide intervals (with the exception of 2 ASOs, PKD1-IVS37+8 and +24, to avoid a stretch of four guanines) (FIG. 33; Table 7, SEQ ID NOS: 297 to 312). These target regions were selected based on the knowledge that intronic regulatory elements concentrate in sequences adjacent to splice sites.

Figure 34:
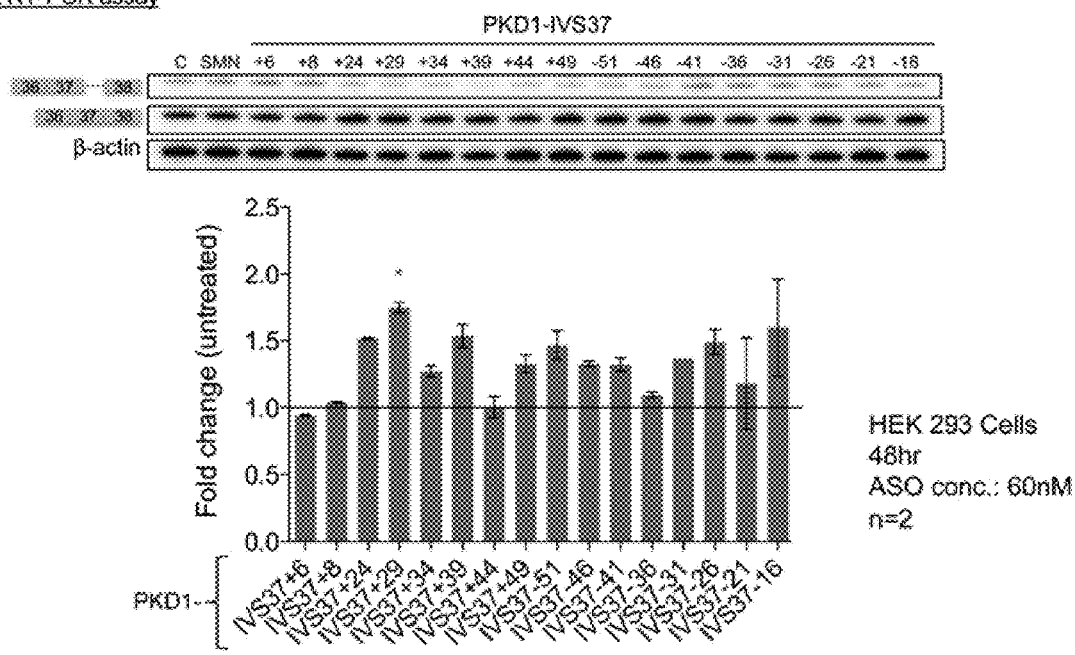
FIG. 34 depicts the results of the ASO-walk targeting intron 37, as described in Example 28. At the top, a representative gel shows radioactive RT-PCR products of PKD1 mock-treated (C), SMN-control ASO-treated, or treated with a 2'-O-Me ASO targeting intron 37 as described in FIG. 33, at 60 nM concentration in HEK293 (human embryonic kidney epithelial) cells. Quantification of the bands corresponding to PKD1 products normalized to Beta actin from 2 independent experiments is plotted in the bar graph below as fold change relative to the mock-treated products. The black line indicates a ratio of 1, no change. Asterisks indicate the ASO that lead to the highest increase in PKD1 mRNA levels.

Example 28: Improved Splicing Efficiency Via ASO-Targeting of PKD1 Intron 37 Increases Transcript Levels To determine whether we can achieve an increase in PKD1 expression by improving splicing efficiency of PKD1 intron 37 using ASOs, we used the method described herein (FIG. 34). To this end, HEK293 cells were mock-transfected, or transfected with each of the targeting ASOs described in FIG. 33 and Table 7, SEQ ID NOS: 297 to 312, or a non-targeting SMN-ASO control, independently, using RNAiMAX (RiM) (Invitrogen) delivery reagents. Experiments were performed using 60 nM ASOs (as indicated in FIG. 34) for 48 hrs. Radioactive RT-PCR results show that the +29 targeting ASO increases PKD1 transcript level compared to the mock-transfected or non-targeting ASO (FIG. 34). Intensities of the bands corresponding to the PKD1 PCR products from targeting-ASO-transfected cells were normalized to Beta actin and plotted relative to the normalized PKD1 PCR product from mock-treated cells. Results from this analysis indicate that the +29 ASO increases PKD1 transcript level 1.8 fold (FIG. 34). These results indicate that improving the splicing efficiency of a rate limiting intron in the PKD1 gene using ASOs leads to an increase in gene expression.

Example 29: Dose Response Effect of ASOs Targeting PKD1 Intron 37

Figure 35:
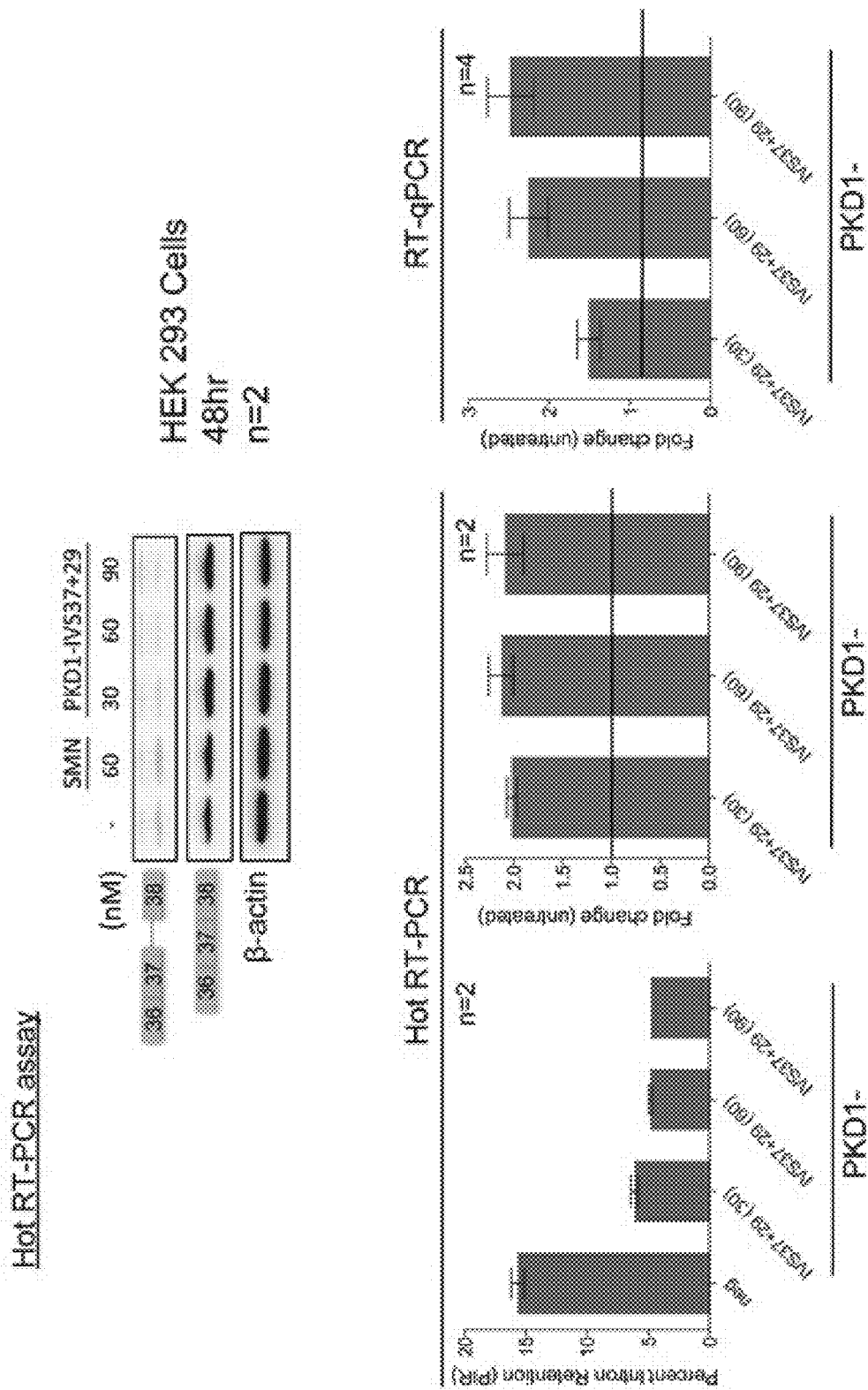
FIG. 35 shows an increase in PKD1 gene expression levels in a dose-dependent manner resulting from the treatment of HEK293 cells with PKD1-IVS37+29 ASO at the indicated concentrations, as described in Example 29. Radioactive RT-PCR products of PKD1 (intron-37 retained and correctly spliced) and Beta actin from HEK293 cells were separated on a 5% polyacrylamide gel. The bar graph on the left demonstrates a dose-dependent reduction in percent intron retention (PIR) calculated relative to the total transcript (intron-37 retained and correctly spliced) from PKD1-IVS37+29 ASO-treated cells compared to mock-treated cells (two independent experiments). Fold change of correctly spliced transcript level from two independent experiments was plotted relative to the mock-treated cells in the middle graph showing an increase in PKD1 transcript level. RT-qPCR (right bar graph) was performed and the resulting values were normalized to Beta actin. Fold change of four biological replicates was plotted relative mock-treated PKD1 products, confirming the radioactive RT-PCR results and showing a dose-dependent increase in PKD1 transcript level.

To determine a dose-response effect of the +29 ASO, we used the method described herein (FIG. 35). HEK293 cells were mock-transfected, or transfected with the +29 ASO, or a non-targeting SMN-ASO control, independently, using RNAiMAX (RiM) (Invitrogen) delivery reagents at increasing concentrations as indicated in FIG. 35 for 48 hrs. Radioactive RT-PCR results show that the +29 targeting ASO increases PKD1 transcript level compared to the mock-transfected or non-targeting ASO (FIG. 35). Intensities of the bands corresponding to the PKD1 PCR products from targeting-ASO-transfected cells were normalized to Beta actin and plotted relative to the normalized PKD1 PCR product from mock-treated cells. Results of this analysis indicate the +29 targeting ASO increases PKD1 transcript level in a dose-dependent manner more than 2.0 fold (FIG. 35, middle graph). These results were confirmed by RTqPCR using primers elsewhere in the PKD1 transcript, showing more than 2-fold increase, and a dose-dependant response to the ASO treatment (FIG. 35, right graph). In addition, PIR was calculated (as described in Example 6) for intron 37 retention and the values were plotted indicating that as the ASO concentration and the correctly spliced transcript increases, a reduction in intron 37 retention is observed (FIG. 35, left graph). These results confirm that improving the splicing efficiency of a rate limiting intron in the PKD1 gene using ASOs leads to an increase in gene expression.

Figure 36:
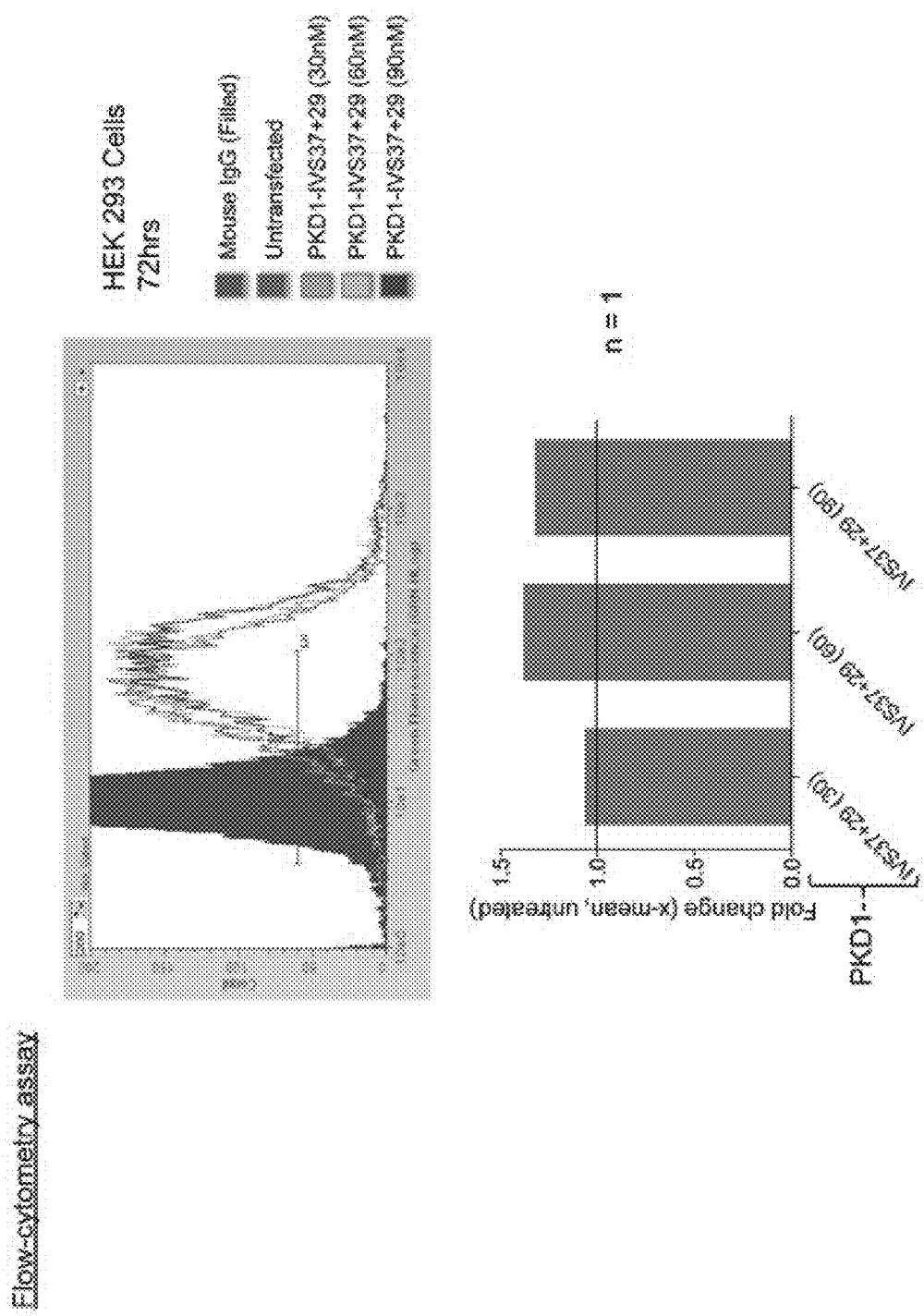
FIG. 36 shows an increase in PKD1 protein levels achieved via PKD1-IVS37+29 ASO targeting at the indicated concentrations in HEK293 cells, as described in Example 30. HEK293 were fixed and permeabilized and treated with an antibodies against PKD1, or an IgG isotype control. Flow-cytometry analysis was performed for 10,000 treated cells in each condition and the fluorescence intensity was plotted. The fold change was computed relative to the mock-treated (untransfected) products and plotted in the bar graph below indicating an increase in PKD1 level upon treatment with PKD1-IVS37+29 ASO.

Example 30: Improved Splicing Efficiency Via ASO-Targeting of PKD1 Intron 37 Increases Protein Levels In order to detect an increase in protein production upon targeting PKD1 intron 37 with the +29 ASO, we used the method described herein (FIG. 36). HEK293 cells were mock-transfected, or transfected with the +29 ASO, or a non-targeting SMN-ASO control, independently, using RNAiMAX (RiM) (Invitrogen) delivery reagents at increasing concentrations as indicated in FIG. 36 for 72 hrs. Briefly, cells were fixed and permeabilized and treated with an anti-PKD1 antibody or IgG isotype control antibody. Cells were analyzed by flow cytometry by counting 10,000 cells. FIG. 36 shows a plot of the fluorescence intensity/per cell count indicating that a higher ASO concentrations cell have a stronger PKD1 signal compared to mock-treated (untreated) cells. Fold change of the fluorescence intensity corresponding to the +29 ASO-treated cells relative to the fluorescence intensity corresponding to the mock-treated cells was plotted. Results of this analysis indicate that the targeting ASO (+29) increases PKD1 protein level nearly 1.5 fold (FIG. 36). These results demonstrate that promoting splicing efficiency by using an ASO targeted to a region downstream of the 5' splice site of PKD1 intron 37, a rate-limiting intron, leads to an increase in target protein production as depicted in FIG. 2.

Figure 37:
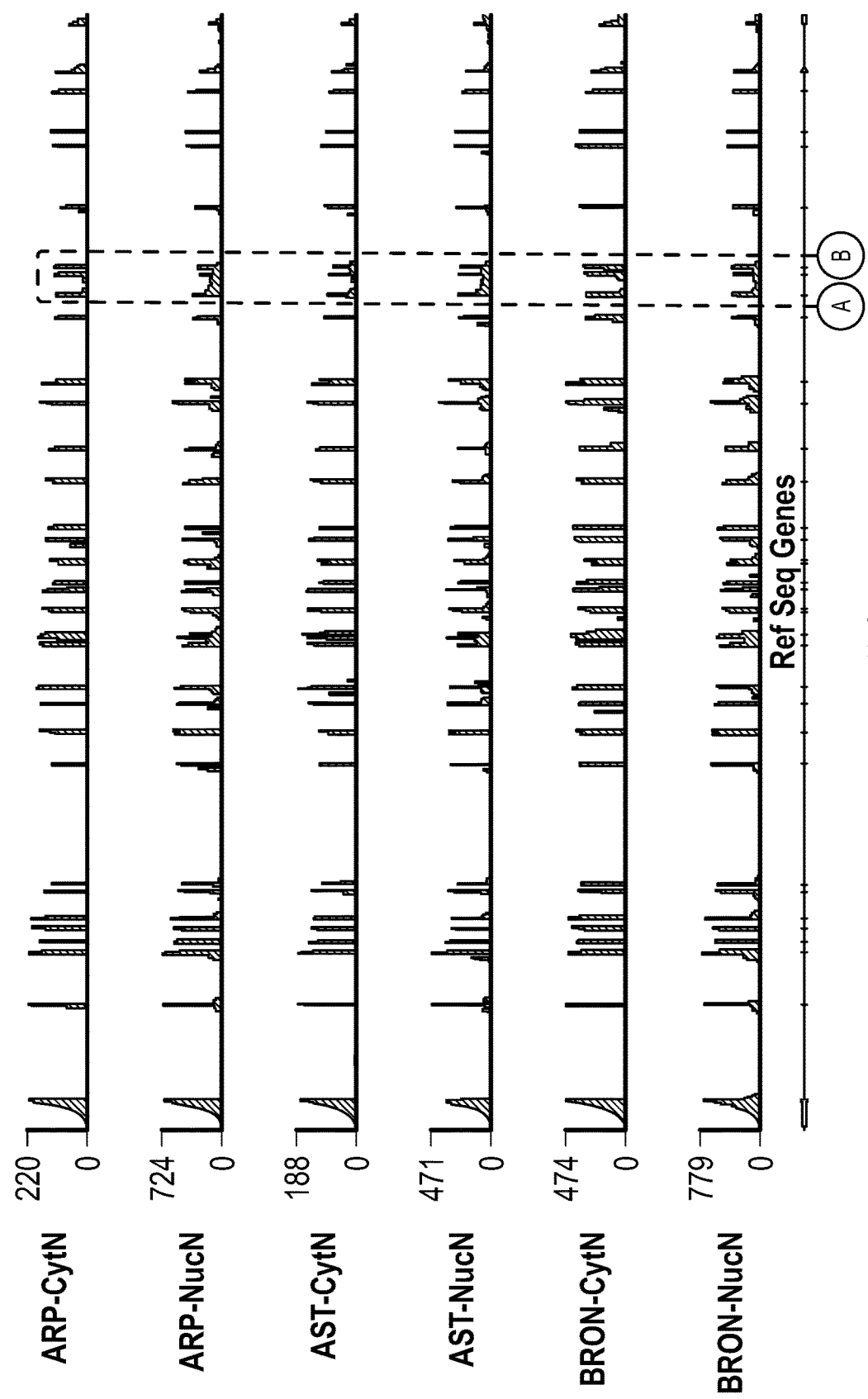
FIG. 37 shows the identification of intron-retention events in the IKBKAP gene using RNA sequencing (RNAseq), visualized in the UCSC genome browser as described in Example 31. The top panel shows the read density corresponding to the PKD1 transcript expressed in ARPE19, AST, primary human bronchial epithelial cells (BRON), HCN, REN, and THLE3 cells and localized in either the cytoplasmic (top for each cell line) or nuclear fractions (bottom for each cell line). At the bottom of this panel, a graphic representation of the refseq. isoform of the IKBKAP gene is shown to scale. The read density is shown as peaks. The highest read density corresponds to exons (black boxes), while no reads are observed for the majority of the introns (lines with arrow heads) in neither cellular fraction. Higher read density is detected for introns 7 and 8 (pointed by the arrows) in the nuclear fraction compared to the cytoplasmic fraction indicating that splicing efficiency of these introns is low, resulting in intron retention. The retained-intron containing pre-mRNA transcripts are retained in the nucleus and are not exported out to the cytoplasm. The read densities for introns 7 and 8 are shown in detail in the bottom picture for all the analyzed cells.
Figure 37:
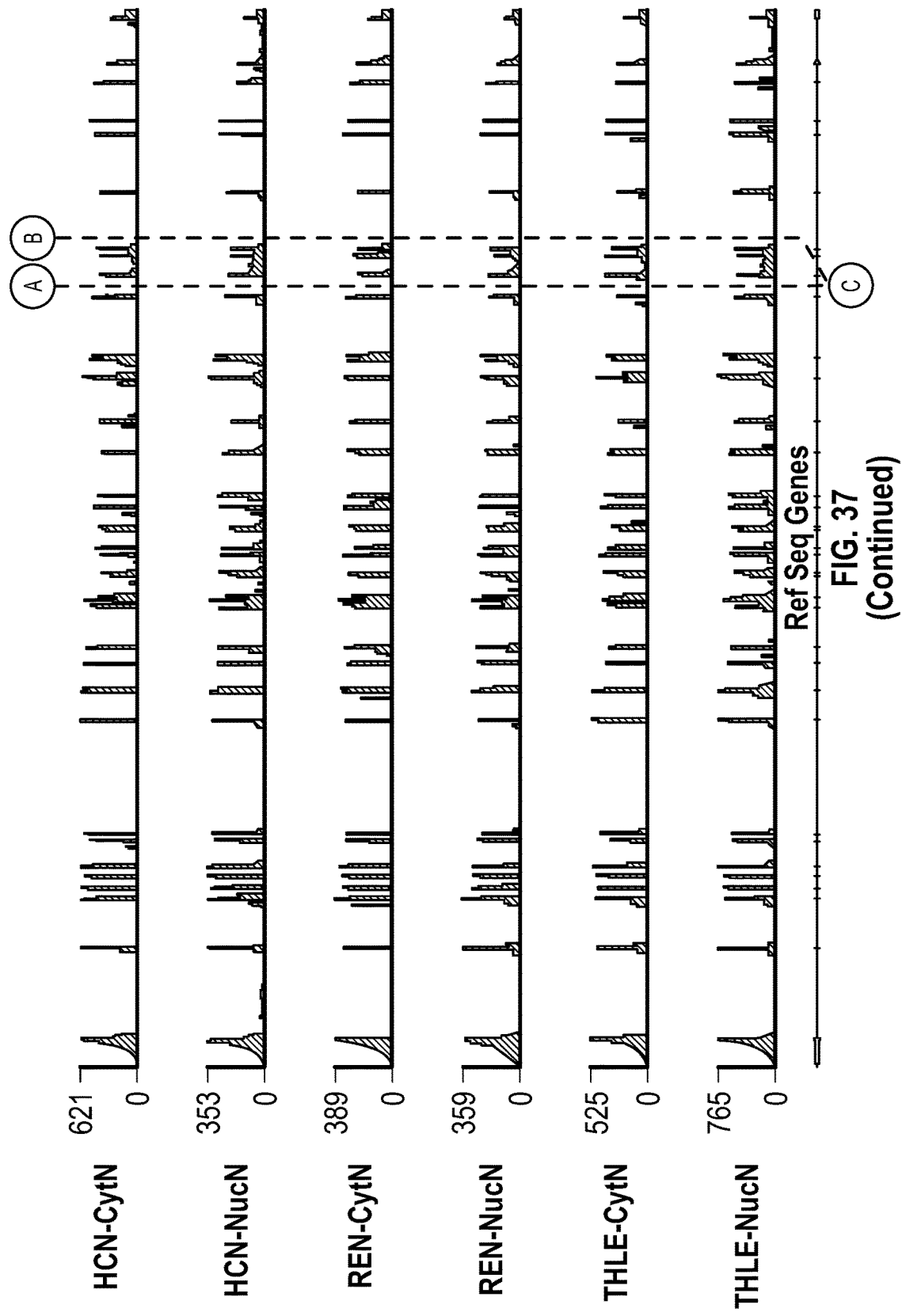
Figure 37:
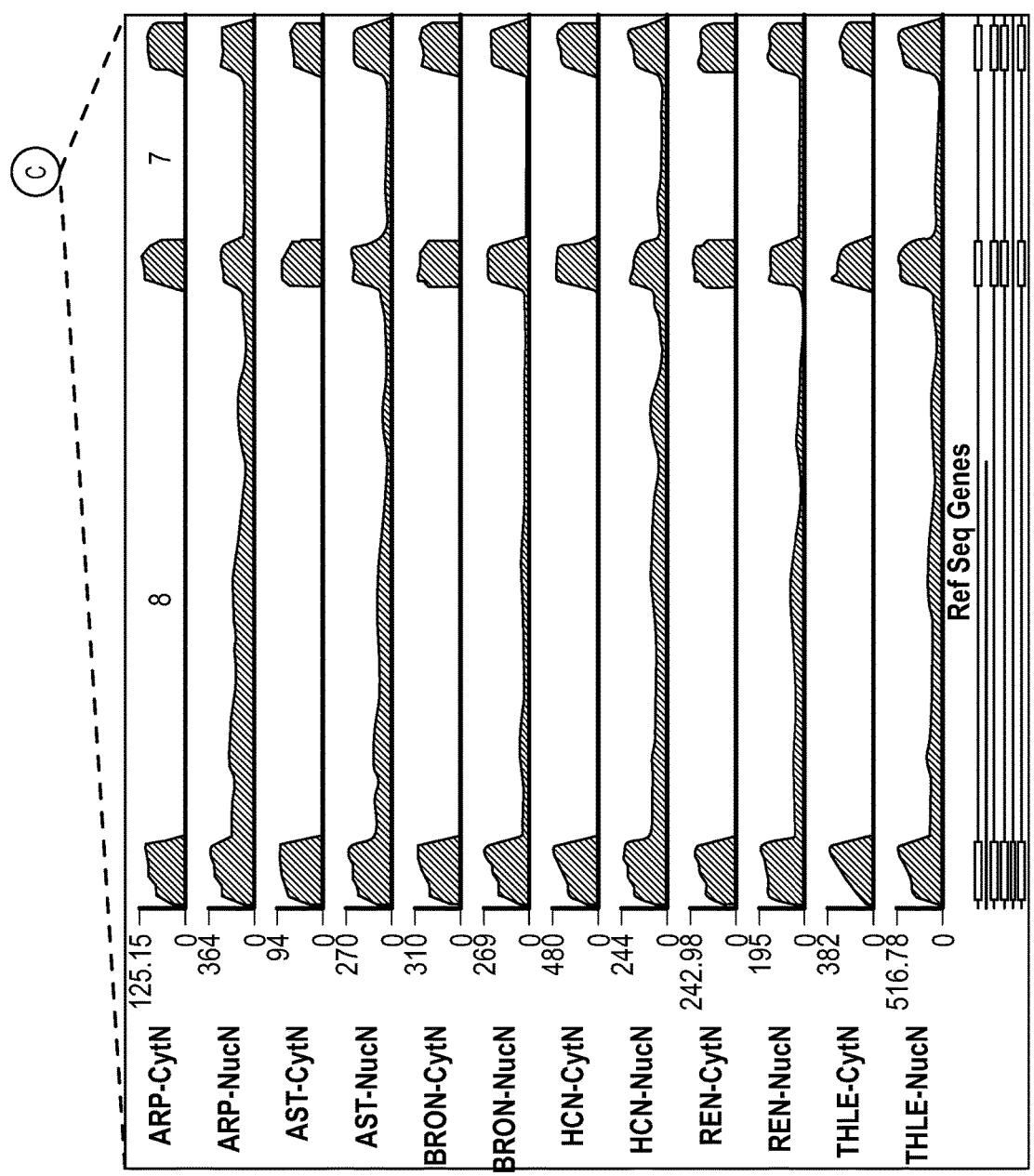

Example 31: Identification of Intron Retention Events in IKBKAP Transcripts by RNAseq Using Next Generation Sequencing We performed whole transcriptome shotgun sequencing using next generation sequencing to reveal a snapshot of transcripts produced by the IKBKAP gene to identify intron-retention events. For this purpose, we isolated polyA+RNA from nuclear and cytoplasmic fractions of ARPE-19, AST, human bronchial epithelial (BRON), HCN, REN, and THLE-3 cells and constructed cDNA libraries using Illumina's TruSeq Stranded mRNA library Prep Kit. The libraries were pair-end sequenced resulting in 100-nucleotide reads that were mapped to the human genome (February 2009, GRCh37/hg19 assembly). The sequencing results for IKBKAP are shown in FIG. 37. Briefly, FIG. 37 shows the mapped reads visualized using the UCSC genome browser and the coverage and number of reads can be inferred by the peak signals. The height of the peaks indicates the level of expression given by the density of the reads in a particular region. A schematic representation of all IKBKAP isoforms (drawn to scale) is provided by the UCSC genome browser (below the read signals), so that peaks can be matched to IKBKAP exonic and intronic regions. Based on this display, we identified 2 introns (7 and 8, indicated by arrows) that have high read density in the nuclear fraction of all cells sequenced, but has no reads in the cytoplasmic fraction of these cells (as shown for both introns in the bottom diagram of FIG. 37). This indicates that introns 7 and 8 are retained and that the intron-7 and intron-8 containing transcript remain in the nucleus. This suggests that the retained intron-containing (RIC) IKBKAP pre-mRNAs are non-productive, as they are not exported out to the cytoplasm.

Figure 38:
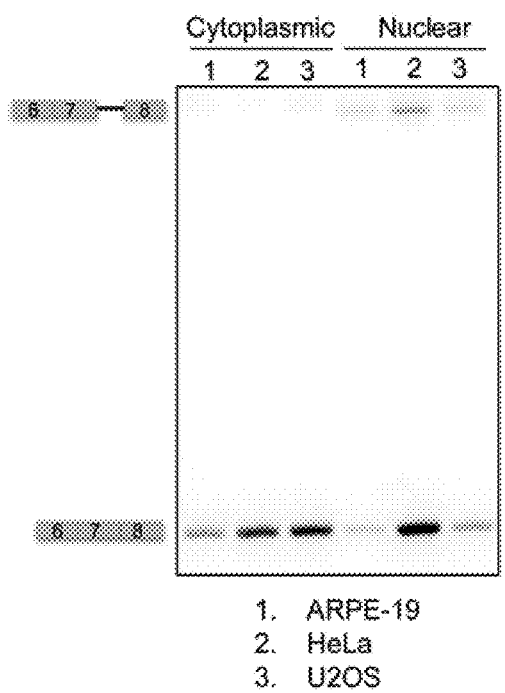
FIG. 38 shows IKBKAP intron 7 retention levels in ARPE-19, HeLa and U2OS cell lines respectively, as described in Example 32. Nuclear and cytoplasmic RNA fractions were extracted from ARPE-19, Hela and U2OS cells and their corresponding radioactive RT-PCR products were separated on a 5% polyacrylamide gel. The numbered rectangles denote exons, and intervening lines denote introns. Results show a band corresponding to the intron-7 retained product in the nuclear fractions of the three cell lines that is absent from the corresponding cytoplasmic fractions. Quantification of the bands indicated that approximately 35% of IKBKAP transcripts contain intron 7 and that this product is retained in the nucleus. Once again, the radioactive RT-PCR results validated the bioinformatic predictions. A summary of the quantification of IKBKAP intron-7 retention calculated as percent intron retention (PIR) relative to the total transcript (intron-7 retained and correctly spliced) from radioactive RT-PCR, as well as RNAseq experiment results is shown on the table on the right.

Example 32: Validation of Intron Retention Events Identified by RNAseq Analysis of IKBKAP Validation of the intron 7-retention event in the IKBKAP (familial dysautonomia) gene was performed using the methods described herein (FIG. 38). Briefly, nuclear and cytoplasmic RNA extracts from ARPE-19, HeLa, and U2OS cells were used to perform radioactive reverse transcriptase PCR (RT-PCR) as described in Example 1. In this example, intron retention was assessed using primers positioned in exon 6 and exon 8 leading to the amplification of both intron-7 containing transcript and correctly spliced transcript. The products were run in a 5% polyacrylamide gel and visualized by phosphorimaging. Intron 7 retention levels were calculated as percent intron retention (PIR) of the intensity of the band corresponding to the intron-7 containing product over total transcript (intron-containing plus correctly spliced). Quantification of the bands indicated that approximately 35% of IKBKAP transcripts contain intron 7 and that this product is retained in the nucleus. Moreover, the radioactive RT-PCR results validated the bioinformatic

Example 33: Design of ASO-Walk Targeting Intron 7 and 8 of IKBKAP

Figure 39:
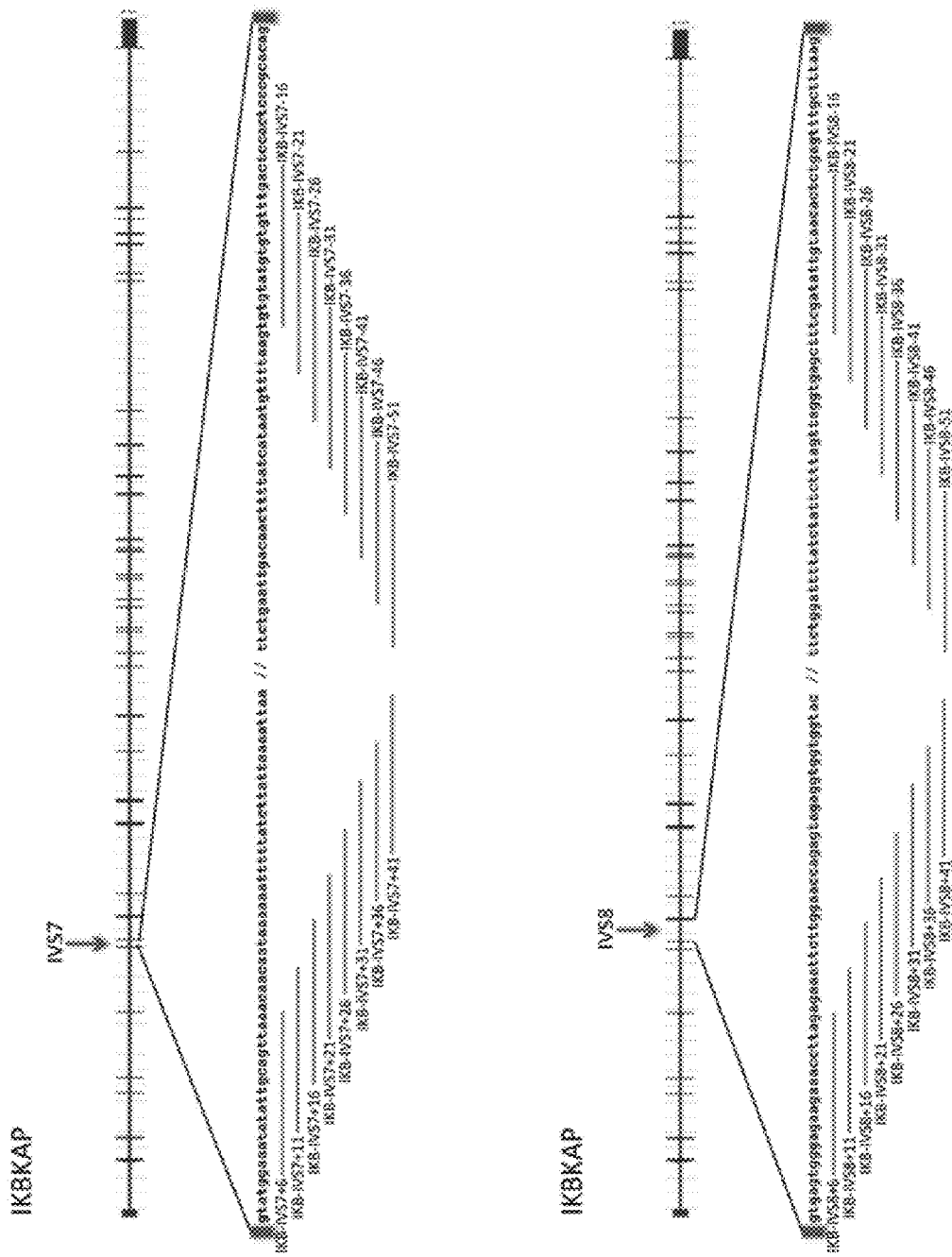
FIG. 39 shows a graphic representation of the ASO walks performed for IKBKAP IVS7 (top) and IVS8 (bottom) targeting sequences immediately downstream of the 5' splice site or upstream of the 3' splice site using 2'-O-Me ASOs, PS backbone, as described in Example 33. ASOs were designed to cover these regions by shifting 5 nucleotides at a time. IKBKAP exon-intron structure is drawn to scale. The figure discloses SEQ ID NOS 400-403, respectively, in order of appearance.

An ASO walk was designed to target intron 7 (top panel) or intron 8 (bottom panel) using the method described herein (FIG. 39). A region immediately downstream of intron 7 or 8 5' splice site spanning nucleotides +6 to +58 and a region immediately upstream of intron 7 or 8 3' splice site spanning nucleotides −16 to −68 of the intron were targeted with 2'-O-Me RNA, PS backbone, 18-mer ASOs shifted by 5-nucleotide intervals (FIG. 39; Table 8, SEQ ID NOS: 329 to 360). These target regions were selected based on the knowledge that intronic regulatory elements concentrate in sequences adjacent to splice sites.

Figure 40:
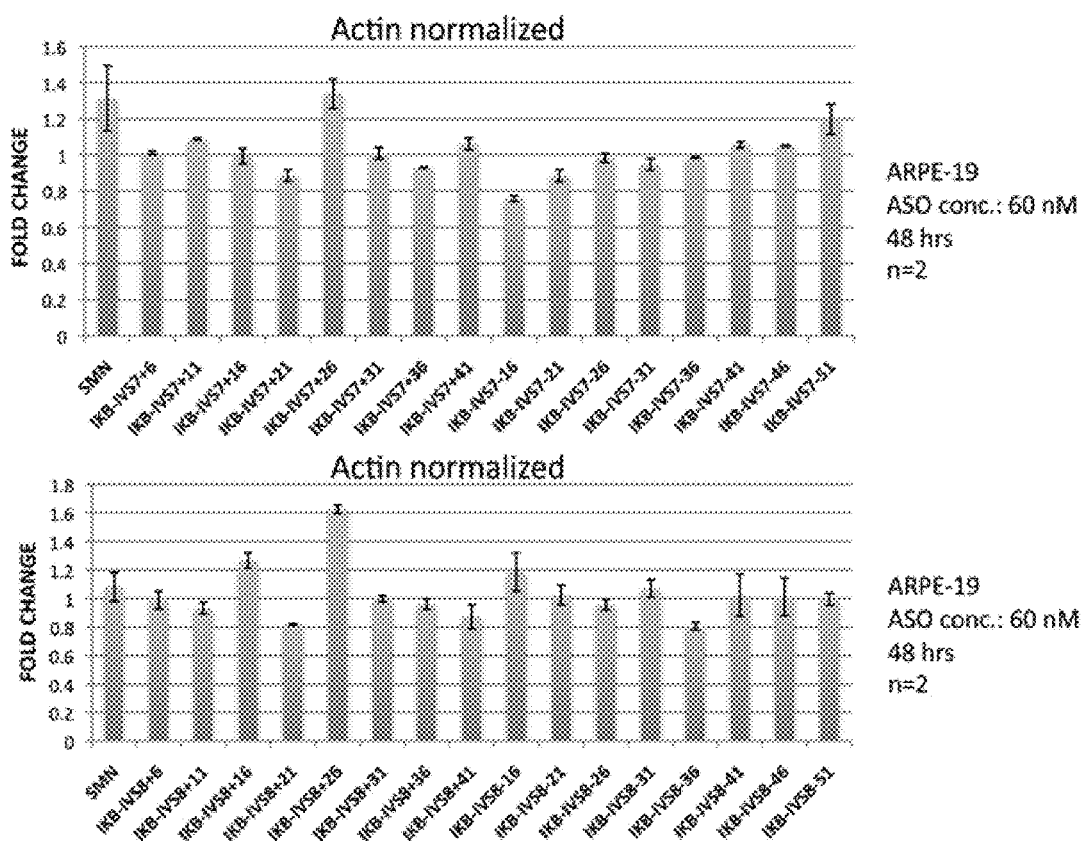
FIG. 40 demonstrates an increase in IKBKAP gene expression level achieved via specific ASO targeting of introns 7 (top) and 8 (bottom) as shown in FIG. 39, as described in Example 34. Cytoplasmic RNA was extracted from ARPE-19 cells mock-treated, SMN-control ASO-treated or treated with each ASOs at a concentration of 60 nM. RT-qPCR was performed to measure IKBKAP expression levels and ct values from IKBKAP were normalized to the corresponding ct values of the Beta actin product. Fold change was plotted relative to mock-treated products.

Example 34: Improved Splicing Efficiency Via ASO-Targeting of IKBKAP Intron 7 and 8 Increases Transcript Levels To determine whether we can achieve an increase in IKBKAP expression by improving splicing efficiency of IKBKAP introns 7 or 8 using ASOs, we used the method described herein (FIG. 40). To this end, ARPE-19 cells were mock-transfected, or transfected with each of the targeting ASOs described in FIG. 39 and Table 8, SEQ ID NOS: 329 to 360, or a non-targeting SMN-ASO control, independently, using RNAiMAX (RiM) (Invitrogen) delivery reagents. Experiments were performed using 60 nM ASOs (as indicated in FIG. 40) for 48 hrs. RT-qPCR results plotted relative to normalized IKBKAP PCR product from mock-treated cells show that the IVS7+26 targeting ASO (top graph) and the IVS8+26 and −16 (bottom graph) targeting ASOs increase IKBKAP transcript level compared to the mock-transfected or non-targeting ASO (FIG. 40). This analysis indicates that these ASOs increase IKBKAP transcript level nearly 1.2-1.6 fold (FIG. 40). These results indicate that improving the splicing efficiency of rate limiting introns in the IKBKAP gene using ASOs leads to an increase in gene expression.

Example 35: Dose Response Effect of ASOs Targeting IKBKAP Introns 7 and 8

Figure 41:
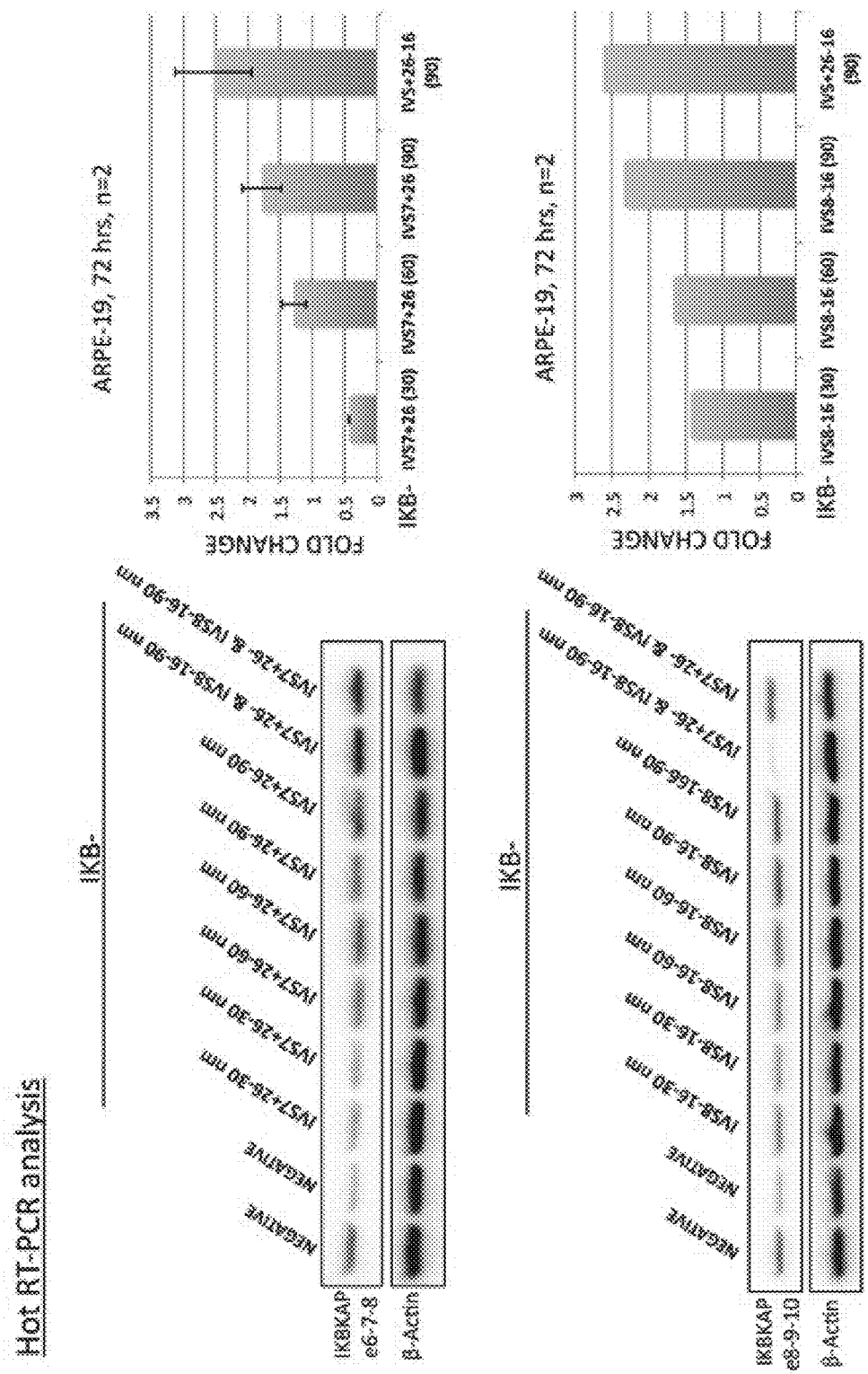
FIG. 41 indicates an increase in IKBKAP transcript level in a dose-dependent manner in cells treated with IKB-IVS7+26 or IKB-IVS8–16 ASOs at the indicated concentrations or a combination of both ASOs at 45 nM each (total 90 nM), as described in Example 35. Radioactive RT-PCR products corresponding to exons 6-8 (IKB-IVS7+26, top) or exons 8-10 (IKB-IVS8–16, bottom) using cytoplasmic RNA from ARPE-19 cells were separated on a 5% polyacrylamide gel. The expression of IKBKAP was quantified by measuring the band intensity and the values were normalized to that of Beta-actin. Fold changes from two biological replicates were plotted relative to the product of mock-treated cells and shown in the bar graphs to the right of each representative gel.

To determine a dose-response effect of the IVS7+26 and IVS8−16 ASOs, we used the method described herein (FIG. 41). ARPE-19 cells were mock-transfected, or transfected with the IVS7+26 or IVS8−16 ASOs, or a non-targeting SMN-ASO control, independently, at increasing concentrations, or a combination of both ASOs at 45 nM each (total 90 nM) using RNAiMAX (RiM) (Invitrogen) delivery reagents for 72 hrs (FIG. 41). Radioactive RT-PCR results show that the IVS7+26 or the IVS8−16 targeting ASOs increase IKBKAP transcript level compared to the mock-transfected or non-targeting ASO in a dose-dependent manner (FIG. 41). Intensities of the bands corresponding to the IKBKAP PCR products from targeting-ASO-transfected cells were normalized to Beta actin and plotted relative to the normalized IKBKAP PCR product from mock-treated cells. Results of this analysis indicate the IVS7+26 and the IVS8−16 targeting ASOs, and their combination, increase IKBKAP transcript level in a dose-dependent manner 2.0-2.5 fold (FIG. 40). These results confirm that improving the splicing efficiency of rate limiting introns in the IKBKAP gene using ASOs leads to an increase in gene expression.

Figure 42:
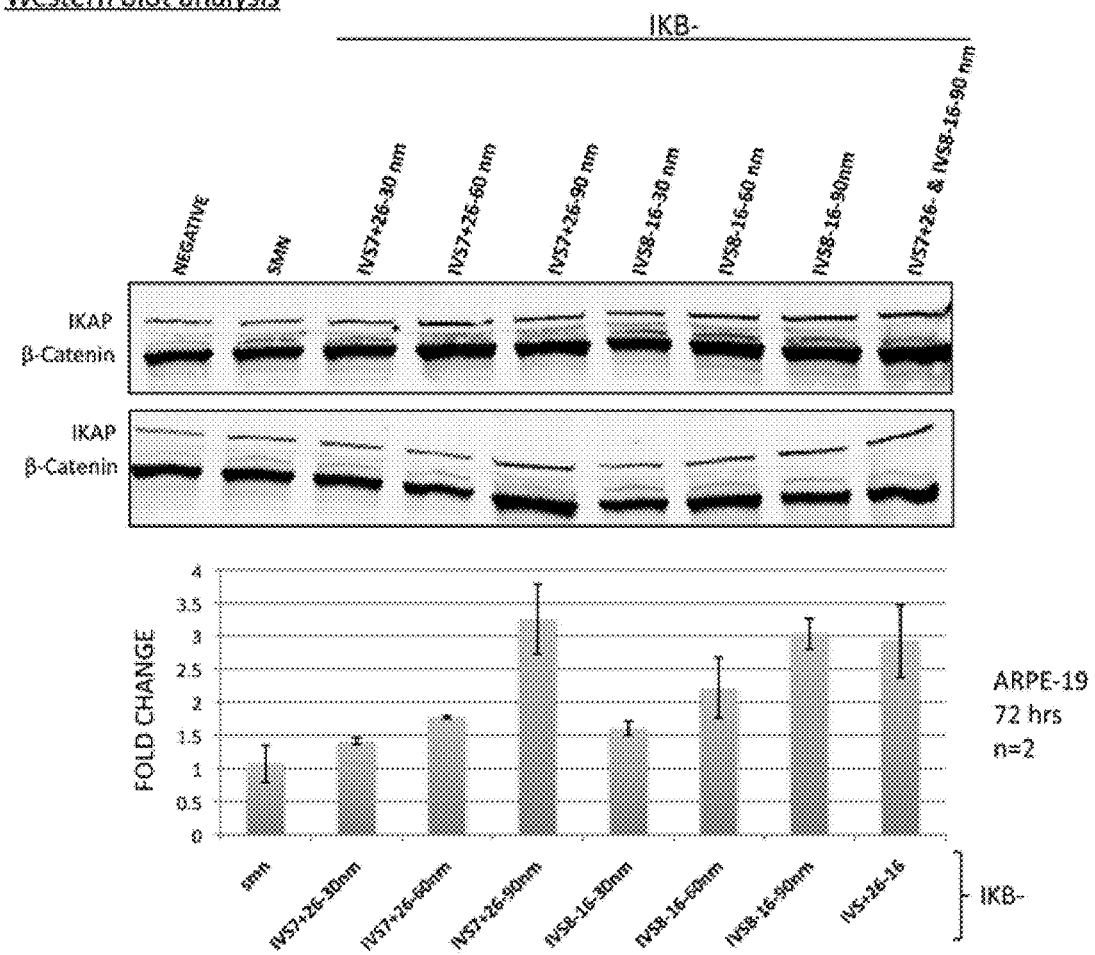
FIG. 42 shows a dose-dependent increase in IKAP protein levels in in ARPE19 cells treated with IKB-IVS7+26 or IKB-IVS8–16 ASOs at the indicated concentrations or a combination of both ASOs at 45 nM each (total 90 nM), as described in Example 36. Protein lysates from ARPE-19 cells were extracted and separated on a 4-20% SDS-polyacrylamide gel. Antibodies against IKAP and Beta catenin were used to detect the separated protein products. The intensity of the IKAP protein bands was normalized to the intensity of the Beta catenin bands, and the fold change for two biological replicates was computed relative to the mock-treated cells and plotted in the bar graph below.

Example 36: Improved Splicing Efficiency Via ASO-Targeting of IKBKAP Introns 7 or 8 Increases Protein Levels In order to detect an increase in protein production upon targeting IKBKAP intron 7 or 8 with the IVS7+26 ASO or the IVS8−16 ASO, respectively, we used the method described herein (FIG. 42). ARPE-19 cells were mock-transfected, or transfected with the IVS7+26 ASO or the IVS8−16 ASO, or a non-targeting SMN-ASO control, independently, at increasing concentrations, or a combination of both ASOs at 45 nM each (total 90 nM) using RNAiMAX (RiM) (Invitrogen) delivery reagents for 72 hrs (FIG. 42). Briefly, protein extracts from ARPE-19 treated cells were run on a 4-20% SDS-polyacrylamide gel, and transferred to a nitrocellulose membrane. To evidence an increase in protein production, an anti-IKAP antibody or anti-Beta catenin antibody was used to detect IKAP and Beta catenin as a loading control, respectively. FIG. 42 shows western blot results indicating that IKAP is increased in a dose dependent manner upon treatment with the IVS7+26 ASO or the IVS8−16 ASO, or a combination of both ASOs. Intensities of the bands corresponding to the IKAP protein from targeting-ASO-transfected cells were normalized to endogenous Beta catenin and plotted relative to the normalized IKAP protein band from mock-treated cells. Results of this analysis indicate that the targeting ASOs IVS7+26 and IVS8−16 increase IKAP protein level approximately 3 fold (FIG. 42). These results demonstrate that promoting splicing efficiency by using ASOs targeted to a region downstream of the 5' splice site of IKBKAP intron 7 or a region upstream of the 3' splice site of IKBKAP intron 8, leads to an increase in target protein production as depicted in FIG. 2.

TABLE 11

PRPF31 Target Sequences

| SEQ ID NO | REGION | TARGET SEQUENCE |
|---|---|---|
| 1 | exon 10 | UGGGCUACGAACUGAAGGAUGAGAUCGAGCGCAAAUUCG ACAAGUGGCAGGAGCCGCCGCCUGUGAAGCAGGUGAAGC CGCUGCCUGCGCCCCUGGAUGGACAGCGGAAGAAGCGAG GCGGCCG |
| 2 | intron 10 | gggcccuggggguccgguaggcauggggucauggaggg gagaagccggcguccuccucccagccgacucccuggcgc cgccca |
| 3 | exon 11 | UACCGCAAGAUGAAGGAGCGGCUGGGGCUGACGGAGAUC CGGAAGCAGGCCAACCGUAUGAGCUUCGGA |
| 4 | exon 12 | UCGAGGAGGACGCCUACCAGGAGGACCUGGGAUUCAGCC UGGGCCACCUGGGCAAGUCGGGCAGUGGGCGUGUGCGGC AGACACAGGUAAACGAGGCCACCAAGGCCAGGAUCUCCA AGACGCUG |
| 5 | intron 12 | ggccagacccaggugggggcuggggaccgagggacacaag guggggggagcccagaucgcagccucc |
| 6 | exon 13 | GGACCCUGCAGAAGCAGAGCGUCGUAUAUGGCGGGAAGU CCACCAUCCGCGACCGCUCCUCGGGCACGGCCUCCAGCG UGGCCUUCACCCCACUC |

TABLE 12

RB1 Target Sequences

| SEQ ID NO | REGION | TARGET SEQUENCE |
|---|---|---|
| 7 | exon 24 | AUCUUAGUAUCAAUUGGUGAAUCAUUC |
| 8 | intron 24 | tattttctttctatgaaatataatagtatgcattgtaagtataaaagaaattaaagctttctataatttgaatttccaaatgcagttattcaaacacctcatccaggcatattgcatagaattttatgagatatatatatctcagatttactttcaaatcaagtttaatctcaaatcatactcctaattggtgaacttcaaaacttttctaaatatccacttgagattatataatacatatatacatttgtgtatatacatacatatacgtgagctgttttttgctcacaacatttctatcaccaaatgtgtgagattttttttctcacccaaatctattcttcaactctctggtgttctacaattcaattcaattctgacactaattcccagagtcagcatcagactccacaggttcaagggctcagtcccacaaaatggtctcactgcagacaccagtcacaagtgtcaggtccccaggctacaccacacttccgtctgacttgaatacgaagttgggggttccgatagtgcctcttccttacagtttgatccactgccagaactactcacaaaactctggaaaatattctacttactattatcagttcatcataaaagatacaaatgaacagccagatgaagaaatatatatagggtgaggtccagaagagtccctagcacaggggcttctgtccctggggagttggggtgcaccaccttcctagcacttagacatgtttaccaactccaaagatctcccaaccttattgttgagggttttatgggggtttcattatataggcataattgattaactcaatttccaaccccctcccctccctggatagagggtggggctgaaagttccaagcttctactcaagacttggtctttctggcaaccagcttccatcctaaattagctaggtacccaccaagtatcacctcattagaacaaaagatggtcccatcacccttatcacacatgaaattcgaaggttttaggagctctgtcccaggaaccagggacaaagaccaaatatctttcaatgataccatgtatgtatgtacataacctcacaggaatctttataaaacaattttgaaattcactcattatgagtgtgatttgaaatgagatactccaaaatgtaagcccgatatccaaatgtcaccagcctgtccctgcctactggtctccttccatacatatgcacttttttgcttgtccttcctctcagacttctaggatattctttttctggtacactgattaggaattgtttgcatgagatcctgcctcagtgaaagtggcagagcttcattctaggagatccaagggaaagctttgctttgaaacatttattctaggctgcaaatccacaacccctagttggccttccattaaagtcactaattcagcagtcccatattcaatatgcattactgttaatatgttgcaccatctccattccctgagagcttatattttaatttttaaattttatttttagagacagtgtctcactctgtcacctacttattataacctcaaactcctcggcccaagcagtcctctcaccttagcctcccaagttgccaggactacaggcatgcaccaccatgtccagctaattttaaatttttgtagagacagggttttctatgttggccagattggtattgaactcctggcttccacgatacccgtctcagcctcccaaagaactgggattacagatgtgagccactgcacctggccagagagcttatattcttataggaatgggaagactgcctatgttatgtgttgctacataatacattaccccccaaacttagtgacttaaaacaaacgcttattatctccatttctgtgggtcaataatctaggcatgacttagctgggccagagtttctccaaagtctgtgatcaaggtgtcagttgggctgggcctgcagtcatctcaaggctccactagaggagcattcactggcagacttattcaaatggctgttggctgatcctcgatggctattggcccctctattggtttcttgcccttgggcccctccatagtactgcttgctattcacaacatggcagcttgctttgcccagagcagggactctgagggaggcagggaaataaagagcaagagagaggtcacagtcttattgtaatctaattctggaaatgacagcccattacttttggcatattattttggttagaagcaagacaacagtagatctagcccacacacgaggggaggaggatcacacaaggaggtgaataccaggaggtggggtcattgggagccatctgagaggctgccaccacactgcctcaagtaactagggagaggtaaaagtttatatgccagatgaccaaatattaaaatgtgtgttacaaatagttcacgatgggctcagctgtcagactttacaaaggagctatgggaccttataaggacagttggaactggctaggtatcacatagtggtcttcaaacattttttgcttgccataacctctaaaataattgggaaaaagttgaatgtacttccatatcttaaagctgataatttaaaatattatacatttaatagcagcacgggatttagttttgttaaattgtatatgtgctccaaatagatttaccatcaaaacctgttttgaatttaatattgggagaattcgctagtttaattttttggaaaataaagtataattggcaaagctaatcctcactgttgaatctatccgtcaaatcagtataatttctatcagaaagtctatatgacttgtcaacataatacccataaagtgaatcaaaaattattattcattgaacacatcatctcttatcaaattcttgtgaccttccttctggttgtataatagcctaaaaaacaaaaaaaggacaaaagcaagtttccagaaagctgttctgacttgcctacttctgaaaagtagtcctgtatggtgggttctgaaaatgaggaaccaggacttgcagagtaggcagttgctggaggaagaatgtgagctgcatgggaaaagacagggdatttacaaagagtgggtgtttaattgggdatggaattaggtagttattctgattttttagattttttcatatctttatttggtccaatgaagcagaaatttaaatgaagttattaccttttgcctgattttttgacacacctcaaactataacttgaggttgctaactatgaaacactggcatttaatgatttaaagtaaagaa |

TABLE 12-continued

RB1 Target Sequences

| SEQ ID NO | REGION | TARGET SEQUENCE |
|---|---|---|
| 9 | exon 25 | CUUCUGAGAAGUUCCAGAAAAUAAAUCAGAUGGUAUGUAACAGCGACCG UGUGCUCAAAAGAAGUGCUGAAGGAAGCAACCCUCCUAAACCACUGAAA AAACUACGCUUUGAUAUUGAAGGAUCAGAUGAAGCAGAUGG |

TABLE 13

HBB Target Sequences

| SEQ ID NO | REGION | TARGET SEQUENCE |
|---|---|---|
| 10 | exon 1 | AUGGUGCAUCUGACUCCUGAGGAGAAGUCUGCCGUUACUGCCCUGUGGG GCAAGGUGAACGUGGAUGAAGUUGGUGGUGAGGCCCUGGG |
| 11 | intron 1 | tatcaaggttacaagacaggtttaaggagaccaatagaaactgggcatg tggagacagagaagactcttgggtttctgataggcactgactctctctg cctattggtcta |
| 12 | exon 2 | CUGCUGGUGGUCUACCCUUGGACCCAGAGGUUCUUUGAGUCCUUUGGGG AUCUGUCCACUCCUGAUGCUGUUAUGGGCAACCCUAAGGUGAAGGCUCA UGGCAAGAAAGUGCUCGGUGCCUUUAGUGAUGGCCUGGCUCACCUGGAC AACCUCAAGGGCACCUUUGCCACACUGAGUGAGCUGCACUGUGACAAGC UGCACGUGGAUCCUGAGAACUUC |

TABLE 14

HBG1/HBG2 Target Sequences

| SEQ ID NO | REGION | TARGET SEQUENCE |
|---|---|---|
| 13 | exon 1 | ACACUCGCUUCUGGAACGUCUGAGGUUAUCAAUAAGCUCCUAGUCCAGA CGCCAUGGGUCAUUUCACAGAGGAGGACAAGGCUACUAUCACAAGCCUG UGGGGCAAGGUGAAUGUGGAAGAUGCUGGAGGAGAAACCCUGGG |
| 14 | intron 1-5' | ctctggtgaccaggacaagggagggaaggaaggaccctgtgcctggcaa aagtccaggtcgcttctcaggatttgtggcaccttctgactgtcaaact gttc |
| 15 | exon 2 | CUCCUGGUUGUCUACCCAUGGACCCAGAGGUUCUUUGACAGCUUUGGCA ACCUGUCCUCUGCCUCUGCCAUCAUGGGCAACCCCAAAGUCAAGGCACA UGGCAAGAAGGUGCUGACUUCCUUGGGAGAUGCCACAAAGCACCUGGAU GAUCUCAAGGGCACCUUUGCCCAGCUGAGUGAACUGCACUGUGACAAGC UGCAUGUGGAUCCUGAGAACUUC |
| 16 | intron 2 | tccaggagatgtttcagccctgttgcctttagtctcgaggcaacttaga caacggagtattgatctgagcacagcagggtgtgagctgtttgaagata ctggggttgggggtgaagaaactgcagaggactaactgggctgagaccc agtggtaatgttttagggcctaaggagtgcctctaaaaatctagatgga caattttgactttgagaaaagagaggtggaaatgaggaaaatgactttt ctttattagattccagtagaaagaactttcatctttccctcattttttgt tgtttaaaacatctatctggaggcaggacaagtatggtcgttaaaaag atgcaggcagaaggcatatattggctcagtcaaagtggggaacttggt ggccaaacatacattgctaaggctattcctatatcagctggacacatat aaaatgctgctaatgcttcattacaaacttatatcctttaattccagat gggggcaaagtatgtccaggggtgaggaacaattgaaacatttgggctg gagtagattttgaaagtcagctctgtgtgtgtgtgtgtgtgcgcgcg cgcgtgtgtgtgtgtgtcagcgtgtgttttcttttaacgtcttcagcc tacaacatacagggttcatggtggcaagaagatagcaagatttaaatta tggccagtgactagtgcttgaagggaacaactacctgcatttaatggg aaggcaaaatctcaggctttgagggaagttaacataggcttgattctgg gtggaagcttggtgtgtagttatctggaggccaggctggagctctcagc tcactatgggttcatcttttattgtctc |

TABLE 14-continued

HBG1/HBG2 Target Sequences

| SEQ ID NO | REGION | TARGET SEQUENCE |
|---|---|---|
| 17 | exon 3 | UCCUGGGAAAUGUGCUGGUGACCGUUUUGGCAAUCCAUUUCGGCAAAGA AUUCACCCCUGAGGUGCAGGCUUCCUGGCAGAAGAUGGUGACUGCAGUG GCCAGUGCCCUGUCCUCCAGAUACCAC |

TABLE 15

CFTR Target Sequences

| SEQ ID NO | REGION | TARGET SEQUENCE |
|---|---|---|
| 18 | exon 1 | AAUUGGAAGCAAAUGACAUCACAGCAGGUCAGAGAAAAAGGGUUGAGCG GCAGGCACCCAGAGUAGUAGGUCUUUGGCAUUAGGAGCUUGAGCCCAGA CGGCCCUAGCAGGGACCCCAGCGCCCGAGAGACCAUGCAGAGGUCGCCU CUGGAAAAGGCCAGCGUUGUCUCCAAACUUUUUUU |
| 19 and 375 | intron 1 | aaggtggccaaccgagcttcggaaagacacgtgcccacgaaagaggagg gcgtgtgtatgggttgggtttggggtaaaggaataagcagttttttaaaa agatgcgctatcattcattgttttgaaagaaaatgtgggtattgtagaa taaaacagaaagcattaagaagagatggaagaatgaactgaagctgatt gaatagagagccacatctacttgcaactgaaaagttagaatctcaagac tcaagtacgctactatgcacttgttttatttcatttttctaagaaacta aaaatacttgttaataagtacctaagtatggtttattggtttttcccct tcatgccttggacacttgattgtcttcttggcacatacaggtgccatgc ctgcatatagtaagtgctcagaaaacatttcttgactgaattcagccaa caaaaattttggggtaggtagaaaatatatgcttaaagtatttattgtt atgagactggatatatctagtatttgtcacaggtaaatgattcttcaaa aattgaaagcaaatttgttgaaatatttattttgaaaaaagttacttca caagctataaattttaaaagccataggaatagataccgaagttatatcc aactgacatttaataaattgtattcatagcctaatgtgatgagccacag aagcttgcaaactttaatgagattttttaaaatagcatctaagttcgga atcttaggcaaagtgttgttagatgtagcacttcatatttgaagtgttc tttggatattgcatctactttgttcctgttattatactggtgtgaatga atgaataggtactgctctctcttgggacattacttgacacataattacc caatgaataagcatactgaggtatcaaaaaagtcaaatatgttataaat agctcatatatgtgtgtaggggggaaggaattttagctttcacatctctc ttatgtttagttctctgcat........ccaaataaggtctgaatgaca caaattttagaactctccagagaaaagaaagatgctgagggaaaaagca taggtttgggactcactaaatcccagttcaattcctttcttaataaat atattcaattttacctgagaaagctctcgtgctctcgaatttatttag aaatttctctttgtacatgattgatttcacaatccttcttctgcctcct cttctactttcttcttctagattttcctatctttatgaagattattct gccttatcctcaacagttagaaacaatatttttgaaaatcactacggta tcctgcatagtgatttcccatgccaactttactaatttccattataaat tattatttattgatgcctagagggcagatgagtgtagctgctatggagt gaggagacaaaacataagaaagttatgatcctaccctcaggtaatgatt cagacatgataattaagtcaacaaattgatagaaactaatcactaactc tctggctatagtcattctttcaatgaatagctcattactgagtatgcat gctacagtaacaaaattatataaggctgttgattaaatgttgattaagt gcatgtcttattcagagttttttatatttgaaatggaagaggctggac ttcagtaatttgctataaactgctagtatatgattatttgggggcagtt atttttaaagaataatttaaatatggaatgtttagcagtttgttttt ccctgggaaaaaccatactattattccctcccaatccctttgacaaagt gacagtcacattagttcagagatattgatgttttatacaggtgtagcct gtaagagatgaagcctggtatttatagaaattgacttattttattctca tatttacatgtgcataattttccatgccagaaaagttgaatagtatc agattccaaatctgtatggagaccaaatcaagtgaatatctgttcctc |
| 20 | exon 2 | UGGACCAGACCAAUUUUGAGGAAAGGAUACAGACAGCGCCUGGAAUUGU CAGACAUAUACCAAAUCCCUUCUGUUGAUUCUGCUGACAAUCUAUCUGA AAAAUUGGA |
| 21 and 376 | intron 2 | ttcatgtacattgtttagttgaagagagaaattcatattattaattatt tagagaagagaaagcaaacatattataagtttaattcttatatttaaaa ataggagccaagtatggtggctaatgcctgtaatcccaactatttggga ggccaagatgagaggattgcttgagaccaggagtttgataccagcctgg gcaacatagcaagatgttatctctacacaaaatcaaaaagttagctggg aatggtagtgcatgcttgtattcccagctactcaggaggctgaagcagg aggggttacttgagcccaggagtttgaggttgcagtgagctatgattgtg |

TABLE 15-continued

CFTR Target Sequences

| SEQ ID NO | REGION | TARGET SEQUENCE |
|---|---|---|
| | | ccactgcactccagcttgggtgacacagcaaaaccctctctctctaaaa
aaaaaaaaaaaaggaacatctcattttcacactgaaatgttgactgaa
atcattaaacaataaaatcataaaagaaaaataatcagtttcctaagaa
atgattttttttcctgaaaaatacacatttggtttcagagaatttgtct
tattagagaccatgagatggattttgtgaaaactaaagtaacaccatta
tgaagtaaatcgtgtatatttgctttcaaaacctttatatttgaataca
aatgtactccctgggaagtcttaaggtaatggctactggttatcaaaca
aatgtaaaaattgtatattttgagtacctgttacatgccaggtagaat
atctcctctcagccactctgagtggaaagcatcattatctctattttac
agaaaagcaaactgaggctcagagagataatatactttgccagttaatg
aatgatggagccatgattccagctgaggtctgtattgccttgctctcta
ggaatggtagtccccccataaagaatctctcagtttcctttccaatca
aaaggttaggatccttttgattgccagtgacagaaacccaatttactag
cttaagtaaataaaaggaac......gcccgccttggcctcccaaagtg
ttgggattagtggcgtgagccactgccccggcctattactccttagag
tgatttagagccatgtttacttatggtaacttgacagtaatgggaataa
ccactgatgaaacgtaaagcctttgtctaattgtttacctagttcttcc
ttgtggttcatgaaattttcatctctgtacagtttgaaaattaagatg
ataatatttagagatattttattcctttgtgaagagaaaaaaggctttc
attaacagaaatcagtggcaataacttaatasatacaatcagctggtgt
tcctatagtatttaaaagaaaacagaaagtttactagatttcagccagt
tttcagactatttaatgtctattcttactataatagaaaatatataatt
tgatcttgttctcattttcaaagacctttaatacatgattttagtagt
tgaaaatgaagtttaatgatagtttatgcctctacttttaaaaacaaag
tctaacagatttttctcatgttaaatcacagaaaaagccacctgacatt
ttaacttgttttgatttgacagtgaaatcttataaatctgccacagtt
ctaaaccaataaagatcaaggtataagggaaaaatgtagaatgtttgtg
tgtttattttttccaccttgttctacagcaatgagcattcgtaaa
agccttactttatttgtccaccctttcattgttttttagaagcccaac
acttttctttaacacatacaatgtggccttttcatgaaatcaattccct
gcacagtgatatatggcagagcattgaattctgccaaatatctggctga
gtgtttggtgttgtatggtctccatgagattttgtctctataatacttg
ggttaatctccttggatatacttgtgtgaatcaaactatgttaagggaa
ataggacaactaaaatatttgcacatgcaacttattggtcccactt |
| 22 | exon 3 | GAAUGGGAUAGAGAGCUGGCUUCAAAGAAAAAUCCUAAACUCAUUAAUG
CCCUUCGGCGAUGUUUUUUCUGGAGAUUUAUGUUCUAUGGAAUCUUUUU
AUAUUUA |
| 23 and 377 | intron 3 | gatctcatttgtacattcattatgtatcacataactatattcattttg
tgattatgaaaagactacgaaatctggtgaataggtgtaaaaatataaa
ggatgaatccaactccaaacactaagaaaccacctaaaactctagtaag
gataagtaaaaatcctttggaactaaaatgtcctggaacacgggtggca
atttacaatctcaatgggctcagcaaaataaattgcttgcttaaaaaat
tattttctgttatgattccaaatcacattatcttactagtacatgagat
tactggtgcctttattttgctgtattcaacaggagagtgtcaggagaca
atgtcagcagaattaggtcaaatgcagctaattacatatatgaatgttt
gtaatattttgaaatcatatctgcatggtgaattgtttcaaagaaaaac
actaaaaatttaaagtatagcagctttaaatactaaataaataatacta
aaaatttaaagttctcttgcaatatattttcttaatatcttacatctca
tcagtgtgaaaagttgcacatctgaaaatccaggctttgtggtgtttaa
gtgccttgtatgttcccagttgctgtccaatgtgactctgatttatta
ttttctacatcatgaaagcattatttgaatccttggttgtaacctataa
aaggagacagattcaagacttgtttaatcttcttgttaaagctgtgcac
aatatttgctttgggcgtttacttatcatatggattgacttgtgttta
tattggtctttatgcctcagggagttaaacagtgtctcccagagaaatg
ccatttgtgttacattgcttgaaaaatttcagttcatacaccccatga
aaaatacatttaaaacttatcttaacaaagatgagtacacttaggccca
gaatgttctctaatgctcttgataatttcctagaagaaatttttctgac
ttttgaaataatagatccat.....atttcctctcagggttaccctctg
atccctattttactaaatcgttataaaacaaaatgaggaattatgtgtc
cttcccttttgaagccaatgtaacaagatgggtaagaattagacctcct
gagttcaaaatccctggattcagatctattcctgtatattcaggagaag
tggtaataaattcgatggacaatttggtttagtagtcgattgaggaccc
tgatgaggtatatttggaaaacataacttccgctctctctcattgact
cacgggcctttgaggagtccaggagtcattggaatctggcctgaggttg
aggctgctggcaaaactccttccccaaagtccattcctattgctgactg
agaagggactagcattggaagtggctgattttaaataccgctagtgctg
gtgtgctcctccctcccattcccagctctgcttttgtgtagttgccttga
gaagctaagttcattctgaaaataatgccattgcacaaaacacttttga
aagttctagtttgaaattacatcaggtcacttggtctgtgtggcctcag
tttcttcatctgccatgtgaaaataataatgcctactctgtagcaaaga
aagtctctatagtaaacaaaaaaaagcctactctgatactgaaagttg
ttatgaaaaataaaaaagggaaatgctttagaaactgttaagtgctatg |

TABLE 15-continued

CFTR Target Sequences

| SEQ ID NO | REGION | TARGET SEQUENCE |
|---|---|---|
| | | tagatgttactaattaacaaaccatttcagaaactatacttttttatttt<br>atggccactattcactgtttaacttaaaatacctcatatgtaaacttgt<br>ctcccactgttgctataacaaatcccaagtcttatttcaaagtaccaag<br>atattgaaaatagtgctaagagtttcacatatggtatgaccctctatat<br>aaactcattttaagtctcctctaaagatgaaaagtcttgtgttgaaatt<br>ctcagggtattttatgagaaataaatgaaatttaatttctctgtt |
| 24 | exon 4 | AAGUCACCAAAGCAGUACAGCCUCUCUUACUGGGAAGAAUCAUAGCUUC<br>CUAUGACCCGGAUAACAAGGAGGAACGCUCUAUCGCGAUUUAUCUAGGC<br>AUAGGCUUAUGCCUUCUCUUUAUUGUGAGGACACUGCUCCUACACCCAG<br>CCAUUUUUGGCCUUCAUCACAUUGGAAUGCAGAUGAGAAUAGCUAUGUU<br>UAGUUUGAUUUAUAAG |
| 25 | intron 4 | acttccttgcacaggccccatggcacatatattctgtatcgtacatgtt<br>ttaatgtcataaattaggtagtgagctggtacaagtaagggataaatgc<br>tgaaattaatttaatatgcctattaaataaatggcaggaataattaatg<br>ctcttaattatccttgataatttaattgacttaaactgataattattga<br>gtatcttctgtaaactgcctctgttgtagttttttttttctcctaatca<br>tgttatcatttttttggaatccatggtttcctgttaagatgactcacac<br>agcctacataaaagtaattgacaaaatatcatcttatagtaaaatgcca<br>catatctttatgttcagcaagaagagtataatatatgattgttaatgat<br>aacccaaacaacaaaagatttcaccttaactggttgtcataagtagtag<br>tatccaccgccttattttgagttggattttttatcatcctatgagcccta<br>caaatttaaagttttttggaacagcacgtgcattgaacccataagaacct<br>actctgcttttctgcatgtattgtccagacaagagaccaaattgccgag<br>gcatcatttaggtgaattctaattaacatttagctaccttacaaccaca<br>attcaaggttgtttcaaaggcatgtgcttgcatcatcctgattcactac<br>catgtgttactaacttggatctgcaaagtcattataaaaagctgttttg<br>atggacttatttggatattgctttacccttcttctctcttttcttttat<br>caatgtaaaaacattatatgttaaatacttggcttttaagagcatagat<br>ctgaaatctgcctctagcaaataacccataacacttctaagatatacct<br>gcaaggtcaattgtgttgtaaaaccttgataaccatactttattgttca<br>aaaaagcctttttatgaaggcagaagttaaaaaaaaaaaacaaaaaaaac<br>agagtccacagttatcacctcagctacaatctcatcagttcacaagtac<br>cagcaaaacatgtgataagtcaacaaatgtttttatttcaatctgaacat<br>tttacgtaagtgaagactttgttagatatcatttggaatgtggaatcta<br>cacagttggcatatcagagaaggttgaattcagtttaataaatgtttat<br>agaaagtgcttgttatcataatgataatagctcaggatgtgcatgacaa<br>gcttttaagcgattgggtacactatctcatttgatcttctgcacaacta<br>ttaatggtaggtactattatccctatcttatggataagtaaactaagat<br>ttaaaaagtacagaacatggtgtgaacactgcttcaaaatttctaaaat<br>aggtaaatcacgatctctaaactggagggttgtccaaccactagggaca<br>atagagtactgatatttagtggtcagactgtaatgcgggaagagacagg<br>catgggctaaacgggtgtagagatcaaataaggggcaggttagtttgta<br>aacatgtccatatgtaacatttagcacaaatacaggatataggtgcttt<br>cagacccagctgcattgataaaaagttaggtggtattgtatctgtcttc<br>cttctcaatgttgcatatctgtgttcttgcccagtttgcttcatctct<br>ctagccacacttattggcctacaatggcatcatcaccaaagaaggcaat<br>cccatctccgtgtggctttggtttgctccctaaagtaaaccttgtgttt<br>acttttcccaggtctcatgctttcccatatctgacctgttttgtcctca<br>tggccaggatatgtgggacctttcctacaatgttccaaagtttgtaata<br>gagctcttctctgctttgttccaaattctgcaacattttactttaaata<br>atgaatttaaatacaaacaaacttgagctttgcctatacttttcaagaa<br>tgcagagataactaaattaataaaaatattcattgagtccttactgtgc<br>acacagctctatgttaagccttgtgcagaactcaaagtcactcgagatt<br>aagcctgttactaagttatgtgcaatttagctcagtggatttcccccac<br>ttcatattgctctgataatgttttggaattaactgccttgattccttct<br>tttctctgcttgtctatacactatttattattctacaccatctcaaatt<br>ctaactcctcaagaaaatccttccagatgattttttctaaccaggagttt<br>taacttccttttaactaccctattacttttctacttccttaactcatcta<br>tcatattatatttagttatttatatactaggtcgccttgaagaagggat<br>tgtgttttcataaatcttaataatccctgaggcatcaagtacagtgatt<br>tgcatttactaaatgctcaacaaatgtgagggattcacttgaaacta<br>atattagataattcccagtcaaagtgatctaatagcaaatcaattcttc<br>agttttataggcaaagtatgactctggttttccataatcataattaatt<br>tgtcaactttataattttaattaagtaaatttaattggtagataaataa<br>gtagataaaaataatttacctgcttaactacgtttcatatagcattgc<br>attttttctttgtaaaatttaagaattttgtattaataaacttttttaca<br>aaagtattaattattcagttattcatcatatacttttattgacttaaaa<br>gtaattttattcaaaagagttagtataggactacatgaaaaattcaagg<br>ccaaggcttaaatttcaaatttcactgcctttggctctatcttttaaaac<br>aaaacaaaaaactcccgcacaatatcaatgggtatttaagtataatatc<br>attctcattgtgaggagaaaaaataattatttctgcctagatgctggga<br>aataaaacaactagaagcatgccagtataatattgactgttgaaagaaa |

TABLE 15-continued

CFTR Target Sequences

| SEQ ID NO | REGION | TARGET SEQUENCE |
|---|---|---|
| | | catttatgaacctgagaagatagtaagctagatgaatagaatataatttt tcattaccttttacttaataatgaatgcataataactgaattagtcatat tataattttacttataatatatttgtattttgttgttgaaattatcta actttt |
| 26 | exon 5 | CUUUAAAGCUGUCAAGCCGUGUUCUAGAUAAAAUAAGUAUUGGACAACU UGUUAGUCUCCUUUCCAACAACCUGAACAAAUUUGAU |
| 27 | intron 5 | tacctattgatttaatcttttaggcactattgttataaattatacaact ggaaaggcggagttttcctgggtcagataatagtaattagtggttaagt cttgctcagctctagcttcccctattctggaaactaagaaaggtcaattg tatagcagagcaccattctggggtctggtagaaccacccaactcaaagg caccttagcctgttgttaataagattttttcaaaacttaattcttatcag accttgcttctttttaaaactttaaatctgttatgtactttggccagat atgatacctgagcaattcttgttctgggttgtcttatgtgaaaaataaa ttcaaggtccttgggacagataatgtgttttatttatctttgcatatcc attacttaaaacagcattggacccacagctggtacaaaattaattactg ttgaattgagcaaatatttattctaaatgtctctgtcaaatgacagagt gtggttgtgtggattaagtccctggagagagttctttgttctctcatgt tctatgctgtggttcttgctttatgcaaaaagaagtaagttacttaaaa cctggacatgatacttaagatgtccaatcttgattccactgaataaaaa tatgcttaaaaatgcactgacttgaaatttgttttttgggaaaaccgat tctatgtgtagaatgtttaagcacattgctatgtgctccatgtaatgat tacctagattttagtgtgctcagaaccacgaagtgtttgatcatataag ctccttttacttgctttctttcatatatgattgttagtttctaggggtg gaagatacaatgacacctgtttttgctgt |
| 28 | exon 6 | GACUUGCAUUGGCACAUUUCGUGUGGAUCGCUCCUUUGCAAGUGGCACU CCUCAUGGGGCUAAUCUGGGAGUUGUUACAGGCGUCUGCCUUCUGUGGA CUUGGUUUCCUGAUAGUCCUUGCCCUUUUUCAGGCUGGGCUAGGGAGAA UGAUGAUGAAGUA |
| 29 | intron 6 | aacctattttcataacttgaaagttttaaaaattatgttttcaaaaagc ccactttagtaaaaccaggactgctctatgcatagaacagtgatcttca gtgtcattaaattttttttttttttttttttgagacagagtctagat ctgtcacccaggctggagtgcagtggcacgatcttggctcactgcactg caacttctgcctcccaggctcaagcaattctcctgcctcagcctccgga gtagctgggattagaggcgcatgccaccacacccagctaattttttgtat tttagtagagacagggtttcaccaggttgcccaggctggtctcgaatgc ctgacctcaggtgatccgcccacctcggcctcccaaagtactgatatta caggcatgagctaccgcgcccggcctaaaaaatactttttaagatggtg taaatattactttctgtatcaatggtacattttttacttgtcagtctct agaatttctttataaatatgttgattcagttcatttttgtagattataa aacaggtaaaaaggataaaacatttatgtgaattaaagggaataccta attttttgtgtagagtttattagcttttactactctggttttatggatcat cacaccagagccttagttactttgtgttacagaataactaatatgagtg aatgaatgacttacacaagtcactgcttaggataaagggcttgagtttg tcagctagagtatgacagaaagtatctaagttttggagtcaaatagcac tttgtttgaatcccagattgcatgcttactagttatgtgaccttagtca agccacttcacctcactgagtctttgctttttttcatctctaaaatagag atacccaccgctcataggctgtcataagggatagagatagcatatggaa tgagtctgtacagcgtctggcacataggaggcatttaccaaacagtagt tattattttttgttaccatctcatttgataataaaataatgcccatctgtt gaataaaagaaatatgacttaaaaccttgagcagttcttaatagataat ttgacttgttttttactattagattgattgattgattga |
| 30 | exon 7 | GAUCAGAGAGCUGGGAAGAUCAGUGAAAGACUUGUGAUUACCUCAGAAA UGAUUGAAAAUAUCCAAUCUGUUAAGGCAUACUGCUGGGAAGAAGCAAU GGAAAAAAUGAUUGAAAACUUAAG |
| 31 | intron 7 | ttgttccaataatttcaatattgttagtaattctgtccttaatttttta aaaatatgtttatcatggtagacttccacctcatatttgatgtttgtga caatcaaatgattgcatttaagttctgtcaatattcatgcattagttgc acaaattcactttcatgggctgtagttttatgtagttggtccagggtgt tattttatgctgcaagtatattatactgatacgttattaaagaattcc tacatatgttcactgctgctcaatacatttatttcgttaaaacaattat caagatactgaaggctgattggtaactcacatgaactgggagagtata caattctgaaccaaatagatgattctctattattatatcttaatttatg tgttatggtatattaaacatgaaaaaaattgtatttggttagaatatgt ttgctcttccttaactcgggaatgacatagggtaatattcacagattgg gttcctataaatcctccacttgaagtgaagtcagttcaagtaatgaaag ctacctcctgagatagaatcagtacttggcacctatctctagtgttctt tcacctcatataacctttcactgattagtaaagattatatccaacaaag aaagtacagcacagactgagatatgattactgagataaatttggcaaa |

TABLE 15-continued

CFTR Target Sequences

| SEQ ID NO | REGION | TARGET SEQUENCE |
|---|---|---|
| | | atataaactacagcatttctgtagcaatgagaccatttttcttcagttg agctccatgttctacaaacttcaatcaaaaaaggttctaggagactcag tgaaagttgatacactgttcaaggaacaaataatttcagcacatgggaa tttcacagggaaaaatatactaaaaagagaggtaccattttggatggtg tcaatatgggttatgaggaattcaggctgctgagtccagtgtacaatgg aaactgagctgcaggtgtgtgattgtaacaacaaaagaaatgctgaaat attaagtcctttgccatgtaaatagaaaaagagtatttatttcccaaac attattgctcacctgtttttgttatgcctttcaagataaatccaggaaa ggaattgcattttctttccagaaaacaagttcttggggaattgttcaa ttggtagatgttgttttctcattaacaagtgagtgctccatcacactt gctgagtgctccatcacacttgctctctgcattactcctctgcctgcaa acacatatatagcaagggtgatgacaaggatatcagagggtctggtttt ctcaaactcatgataaactcatggctgggtcattcttggtgctgatttt actttgttttttgttgttattgttccctcttcctcaaaagatgaaatct atccctcttacttggaatttctctttgatatatagcgaatgtttggttg taacctgtataatctggcatgaaattgtcactcgaaaaggctagaagtg ttgacataaatatgggacagcaagagttgctcctactcaagagagcaaa tataatgttctggaagagattggcagaattcacatcaaaggagtgatta cttcagcctgggccactgttgtactggtcaaaaggctgtgcaaagctct ctgaaaatccactctttttattgctctttagtaataaagtcactttcaat tttaaaaataacaaactgatatatttttatgactcataaaatgttagca attatattatggagaatctactttctgggtgattcttacaaatgttctt ggatctatttttttttcttatagtacctattcttcccatttttctcagc tctagttaatatatttcaacaacagttcaacaaatttaacatttttata aaaagtgtttcctatcattttataaataccagcctagtccatgttattc ctttcttgttgaggagaaaggacacacattgtaaattcaaatatagac ctctactgtgctatttaatcttggtaacaactccacaaaggagatgaca tgttttccttctatagaggtagattctgtaaagttagagggaagagtga cttgcttaagatggcataagctgtaactggcagaaccaggattcaaagc caggtgggatgccaaaatcataatctgtcttcagtgtcaagttactgaa attggtaaacattagacctaaatagacggaattgcaatccgggttgggc acattaaactccattttcttcatcaatgtgctcagattacattttactt ttcaggctaaaaatggaaaaaaagagtccctcttagttctgcacttgag aatgagaatagcttttctgaattatacaaggaagaagaactaatgccca aatgccaggtacccacatgcactatgccatggcacagctgttgccccct ttcaccagagccctctctctgtatcctggttgacctttccttgggcaag agctgggtggggaggatcacaagtgactccaatttggatggcttcggga agactgggaccgagctgaaggcagtgttgtcctctgcactccctgtttt ctgtctgctggagcactgaagcctcacatatgtattaaaaaataattt ccatttgcatttcagactagaagattgaacgtatagtgtaatgtgattg caaataattatattgaaatgagacagagaggatgtagtatctactgtca taatttttcaaaacccacctgcaacttgaattaaaagaaccacttgggt ttttttttttgtttcaaacgcaaatcctggaaacctactgagactcatt cagtcagtatctctaagaggcaagcttgagactgtatatttaaaaagca tctcaggtgatttttacacatgctaaggcttaagaaccacttctctgta gcttatatgttattttcaatgttcctcaaagccaagttagaatttccaa agtgttaagaatccattagacaatcacagaattgtcttttttcctttata aatcttgcaatgtgttctcattcccatacttaattacttaaaacacca accaaccaacaagcaaaaaatgattagtctaactaatattacaagttaa taatgaagtaaaggtttaaaaataatgtcataataatgttaataacaaa ttattaattataatttaaaaataatatttataatttaaaaataatattt acaagtactacaagcaaaacactggtactttcattgttatcttttcata taaggtaactgaggcccagagagattaaataacatgcccaaggtcacac aggtcatatgatgtggagccaggttaaaaatataggcagaaagactcta gagaccatgctcagatcttccattccaagatccctgatatttgaaaaat aaaataacatcctgaatttttattgt |
| 32 | exon 8 | ACAGAACUGAAACUGACUCGGAAGGCAGCCUAUGUGAGAUACUUCAAUA GCUCAGCCUUCUUCUUCUCAGGGUUCUUUGUGGUGUUUUUAUCUGUGCU UCCCUAUGCACUAAUCAAAGGAAUCAUCCUCCGGAAAAUAUUCACCACC AUCUCAUUCUGCAUUGUUCUGCGCAUGGCGGUCACUCGGCAAUUUCCCU GGGCUGUACAAACAUGGUAUGACUCUCUUGGAGCAAUAAACAAAAUA |
| 33 | intron 8 | gtaccataatgctgcattatatactatgatttaaataatcagtcaatag atcagttctaatgaactttgcaaaaatgtgcgaaaagatagaaaaagaa atttccttcactaggaagttataaaagttgccagctaatactaggaatg ttcacccttaaacttttcctagcatttctctggacagtatgatggatgag agtggcattttatgccaaattaccttaaaatcccaataatactgatgta gctagcagctttgagaaattctaaagtttttcaagtgataagactcaatt tatacaaagctaattggataaacttgtatatgattaagaagcaaataaa tacttattatgctttttttgctgtttatttaaatatttaacccagaaaat aagtcactgtgacagaaataaaaatgagagagaagggtgagccactctt aggtagttctggcattatttaatctaggccagaggttgcaaatggtgtc ccatagaactaattttggctcctagacctgtcttatttaacctttcatt |

TABLE 15-continued

CFTR Target Sequences

| SEQ ID NO | REGION | TARGET SEQUENCE |
|---|---|---|
| | | taaaaaatttgtattggttgccagcaattaaaaatttgggagatgtctca cacacacacacacataaacacacacactcatgtgtgcagcctcttttga agaattggaataactagtcaactgcgtcctccttttccacaagctgtga cagctccctgctcacagagcacctgccctctcctgttcatcatgctctc ttctcagtcccattccttcattatatcacctatttggtcctgagactaa gtgagtttgagatctgtgatttagacaaagtggtgaatctagctctgaa tcatagtaagtagctctgggaatcatcttgtcttctgttagcccattga gagagaaatagagagagagagagagagaaagaaagaagaagaaacagat ctggggagagtcactgaatgggagcatagagacagagaaacagatctag aaaaccaaactgggagaaaatgagagaaaccaaaagagaggtagagagg agcagagaagaaaatgaagaagcaaggcaaggaccaggcttttttcatta tttcttatggccaagacttcagtatgcgtggacttaattcttccttatg ctcctaccttccctagggaaactgatttggagtctctaatagagcccct cttttagaatcacagtttgatgccttaaaactagttatataccttcaca tgcttccttaacccacagaagtgatgctaatgaggcccttaataaggag cgtgctattaagatgaagacattcatttttttctccgtccaatgttgg attaaggcacattagtgggtaattcagggttgctttgtaaattcatcac taaggttagcatgtaatagtacaaggaagaatcagttgtatgttaaatc taatgtataaaaagttttataaaatatcatatgtttagagagtatattt caaatatgatgaatcctagtgcttggcaaattaactttagaacactaat aaaattattttattaagaaataattactattttcattattaaaattcata tataagatgtagcacaatgagagtataaagtagatgtaataatgcatta atgctattctgattctataatatgttttttgct |
| 34 | exon 9 | AUUUCUUACAAAAGCAAGAAUAUAAGACAUUGGAAUAUAACUUAACGAC UACAGAAGUAGUGAUGGAGAAUGUAACAGCCUUCUGGGAG |
| 35 | intron 9 | aatttttaaaaaattgtttgctctaaacacctaactgttttcttctttg tgaatatggatttcatcctaatggcgaataaaattagaatgatgatata actggtagaactggaaggaggatcactcacttattttctagattaagaa gtagaggaatggccaggtgctcatggttgtaatcccagcactttgggag accaaggcgggtggatcacctgaggtcaggagttcaagaccagcctggc caacatggtaaaacccggtctctactaaaaatacaaaaaattaactggg catggtggcagatgctgtagtcccagctgctcgggaggctgaggcagga gaatcacttgaacctgggaggcggaggttgcagtgagctaagatcacgc cactgcactccagcctgggcaacaaggcgagactctgtctgaaaaagaa aaaaaataaaaataaaaataaaaagaagtggaggaatattaaatgcaa tataaaagctttttttattttttaagtcatacaatttgtttcacataaca gatcaggaaataatacagagatcataagttttggagctgggtttgaatc ctggctctgccatttacttctgtgtaatctaagtcaagttactgaact ttgtgggccctctggctctccatgtgtaaaatggagaatattaatattt accttgcaagtttgttgtgaagactgaaggagagaatttaggtaaaaca ttcatcagagtaccatgcacacagttgttcctcaataaacattagcttc tctgattgcaagttccagtctaaagtgctttatatataccagccaataa aaggatgcgagagagatataccagtgtattgttttctaccattttaaac ctattttcatccactgttacaaattctatcatactgctccacataaaaa atattatcaatgattttttagtctctgaagtgcaatatttgattattgag cacacctgttgaagttttagtttcttctcacttacatgggttgtgtaaa ggtaggaggtataaaaccagtgtcctaggtctaaatcttcttaatgtc atactttggattcattgatataagtaacttgagcaccagcgcttcattt tacttcattttttaaagatatagtaagagtaattcccatctgcctagca aaattgttttgtagaaaagtttgtggatcagatttattttactttgatt ttaggaatttcaagtgtcttcgtcggcatgaaggaaaaaatatgcagttt gacattttctactactttcaggtcattatttttcctactctggtgcaaaa accctcaattcctgtctcactccatctaatcaaataggtagcatgcttg agcccttactatgtgccaggcactaggataagcactttatatgttttgt cccaattaattctcacagcatttctatgacctaaataaaattaatattt tcatttcaccaataataaaatggaggcttcaaaaagtttagggacttgg ctcagctcacacaactggcaaggactgaaaatggatttagtcccaaat gtcataggctagagcccttcactaaactgttgtcttccatctggtggc atcctcttcctccagtctttgtcacctaaactctgggcaccccttgatg gcatttacttatgatggtgatgcttgttaaacttcctgtttgcgacttc aacgtccatataaatgagtcttccaatactgtacttagaacttatattt tgtagtgacttcttttaaaagctttctctcttagtcatatcctgagtttt gttagcacctggacttaccttacttttggaaatgttgcactctgaaatct ctttctcagcttggaatttcctaatcttccaactgtttgagtcttttaa ttctacatttactgcctttccatttcatcaggatttctagtctctttaa ttcttccttttgaactcctcctgatttaacctctgcttattcgaagaac aataattttattctcagctgcactctcaattcccttttccttttggt gattttctttttcctacagaacacttacttttatcagttttggagaagg aagtgctatctgggtaacagtagtgctatctgttgactctagtcaactg taagttttatacatttattgtttaaaccttatatgggtctataatcctt cttgggaaatcctttcatttgtctttaatttccttaccatttccctaa aggctattccagatttttatcacattcacaaaaattcccgtctttttctca |

TABLE 15-continued

CFTR Target Sequences

| SEQ ID NO | REGION | TARGET SEQUENCE |
|---|---|---|
| | | ggatctgttcaccccagtagatagccttgtctcccacaatacatggag
aaaatagaggccaccgtcatatttgaatgtttccaacttctctcttcac
ctttggaattatcttttcttcttttgtgtctaagagaaagatgtatac
ttcttcttaccttgtctgaactactctattttgcttcatcttctcaga
acaggggaccagcaattattcttcctccagaagcttcaacatcttttgt
caactgactccttctcatgtttaaatattttcaagttaaacaatttctt
tcctgacttcgctcacgcaacctcatgcccaaaaccttatcactcttc
ttccctttgctgtcaaggctgttctcacttcttcacttttttgtggactt
ctccccactacaacatagattctgctatcaccaatctattaaaactgtt
atactcttgtggaatttatcatttaatttagcttcagtgaaccgttctt
tccagattattttggcctcagaccatgacttctaagtctgccgtgcttg
ccacttaagtgatgatgggccagtgggtccccacctaggcctctgtgtt
agtctgttttcatgttgctgataaagacatacccaagaatgggcaattt
acagaagaaagggggtttgagggactcacagttccatgtgactggggagg
cctcacaatcatggtggatgatgaaaggcatgtctcacatggaggcaga
taagagcatagaacttgtgcagggaaacttccctttattaaaccaccag
gtcttgtgagacttcttcactatcacgagaataggatgggcaagaccct
cccccatgattcaattatctcccactgggtccctcccacaacacatggg
aattatgggagctataattcaagatgagatttgggtgaggacatagcca
aaccatatcagcctccttctggcttttatgttctccgtgggtgacctc
tctcaggctcaagtgataaccaatgtgctgatgactctcaaatgcgcat
ctctggcttcagtttcttccttgaacttcatacatatgtttccaaattt
cctgcgtgtacctcaaggttcttgttcatcacttcccaagcttcataaa
cgcactcattttagtgtattctctgtctcctttgatagcatccctgaga
ggcaagtccctggtgagttatatacaactcctccttgctccaaacctg
agagtaagtaacattcctattaacatattaggaagctgaggcttagaca
gtttaagtaactcaagcatggttacacaactagctagggcagagctaaa
atgtcaggctaggcttctgtgactccaaagcccttctcacttagcata
tcatcacttattttttttttaatcacatatatgattttttttttcttta
agagatagaatcttgctctatcacgtgggctggagtgcagtggcacaat
catagctcactgtaaccttgaacttgggctcaagtgatcctcctgcctt
agcctactgagtagctagggctacagacacacaccaccatgcctagcta
atttttatttatttatttttttagagacagagtctcactctgtca
cccaggctggagtgcagtggtgcgatcttggctcactgaacctctgct
gcccgggttcaagcgattctcctgcctcagcctcctgagtagctgggat
tacaggtgcctgccactgtgcccagctaattttgtatttagtagag
acggggttcaccatcttggccaggcttgtcttgaactcctgacctcgt
gatccactcgcctcggcctcccaaagtgctgggattacaggtgtgagcc
accacgcctggccacctacctaatttttaatttttttgtagagacaggg
tctcactacgttgcccaggctggtcttgaactcctgttctcaaacaatc
ctcctgcctcggacaccccaagtgcagggattacaggcatgagtcattg
cagctgacctgtatatatgattttagtatatgtaaatatacatattta
ttaaatgtaaatataaatataaatgtgtggagtgatatccattgaaatg
ttaaacatagttctcagtggtacaactacaggtgatttctcttttctta
tttctggttttctgtgttttccaaatttcttgaaatgtgtcttctgtaa
tcagaaataaaagttattagtaacaacagtcttccactggtacaagtgc
ttattggataaaagtcccacttctaagcatgatactcacaacttttagg
ttaatagcctttgtcaccttgccatatacatctgatccagccactcaca
ccattcctgagatatattttgttcctttgtgcctaaatcattgtgcatg
cagatccatcttcctggaacacctataaccatttcttagtcctgtgaaa
tcctacttacatccttcatagcctagcatgtatgtcatttatttggtca
agggtgagttggttgttctcttgaatgtactgccatatgacgtggtgtg
atttcaattgtagcaccaagctcattgcaatattaattcgtttgtcatt
ctcccatgtaggatgtttgaagtagtttctaacacagagattatactca
ataaatatttattagataaataaatgaataagggaataacaaatgcctt
tgtctcatttttaaaatactttcattgttagctacccatataataaaaaa
ctaaaagcagtagttttcaagcatgattgtttatgtatgcctaaaaga
attttgaaaacctatgtacccctgacacacttttaagttaacttataaa
ttttttcaacatagttttaagtggtggcaaatgatgtagtttcttgtgta
ttttaaactgcttaagtatgctatacatggatttcttcaaaaccctgaa
gctgcagtttcagtgcattcaatttatggaaaagaaattaatttataaa
attggttcttattgtcaagtcaatcagctaaatataacttgctttctgt
caggaaaagtctgactttaaaatacagataagtaataactattattaat
taattaaattattaaaattaaaataattaaataatttgttaattaaaat
gccttattcccctacttatttctgcaatttgactctaagaatagataggg
acatgtagattgccttaggtttgaaatctgggtgaaataagatactgcc
tccttcagtatttctgcctttgcttttatgggagcctctttcaagaaaa
agtcattctctcatggtccctttgtttgagtcccagaggttttcctact
ccagaaagtgcaacgtagtgagactagtactatactcccttgcatggta
agtgagaaggctgtctgtataaaatgagggaaggactcatgagagggaa
gtaggtcaggagaaatgataggttctcaggcaggttaattttaggaaag
agtgaatagagtcccttaaaacaaggtgcatctgcttcctcctgatcaa
tctttaggactgttttactttgatttgaagaccactatgctaaagcttcc
cacgggggcaatagtgaggcaaggaattttttaaaagggaattacttctt |

TABLE 15-continued

CFTR Target Sequences

| SEQ ID NO | REGION | TARGET SEQUENCE |
|---|---|---|
| | | cgtagctacttttgtgaaatgaattcatttgaattatctggcaatctct tcatatttatattcaacaataattacttaaagaaatgctttgagcttct cagaggagggtgctaccagtgtgatggagtagaattcagatttgggtag tgactttaaagctgtgtgactttagtcatttaactgctgagtcacagtc tacagctttgaaagaggaggattataaaatctatctcatgttaatgctg aagattaaataatagtgtttatgtaccccgcttataggagaagagggtg tgtgtgtgtgtgtgtgtgtgtgtgtatgtgtatgtgtatacatgtat gtattcagtctttactgaaattaaaaaatctttaacttgataatgggca aatatcttagttttagatcatgtcctctagaaaccgtatgctatataat tatgtactataaagtaataatgtatacagtgtaatggatcatgggccat gtgcttttcaaactaattgtacataaaacaagcatctattgaaaatatc tgacaaactcatcttttattttttgatgtgtgtgtgtgtgtgtgt |
| 36 | exon 10 | GAUUUGGGGAAUUAUUUGAGAAAGCAAAACAAAACAAUAACAAUAGAAA AACUUCUAAUGGUGAUGACAGCCUCUUCUUCAGUAAUUUCUCACUUCUU GGUACUCCUGUCCUGAAAGAUAUUAAUUUCAAGAUAGAAAGAGGACAGU UGUUGGCGGUUGCUGGAUCCACUGGAGCAGGC |
| 37 and 378 | intron 10 | tcttttgttcttcactattaagaacttaatttggtgtccatgtctcttt ttttttctagtttgtagtgctggaaggtattttggagaaattcttaca tgagcattaggagaatgtatgggtgtagtgtcttgtataatagaaattg ttccactgataatttactctagttttttatttcctcatattattttcag tggcttttttcttccacatctttatattttgcaccacattcaacactgta tcttgcacatggcgagcattcaataactttattgaataaacaaatcatc catttatccattcttaaccagaacagacattttttcagagctggtcca ggaaaatcatgacttacattttgccttagtaaccacataaacaaaggt ctccattttgttaacattacaattttcagaatagatttagatttgctt atgatatattataaggaaaaattatttagtgggatagtttttgaggaa atacataggaatgttaatttattcagtggtcatcctcttctccatatcc caccctaagaacaacttaacctggcatatttggagatacatctgaaaaa atagtagattagaaagaaaaaacagcaaaaggaccaaaactttattgtc aggagaagactttgtagtgatcttcaagaatataacccattgtgtagat aatggtaaaaacttgctctcttttaactattgaggaaataaatttaaag acatgaaagaatcaaattagagatgagaaagagcttctagtattagaa tgggctaaagggcaataggtatttgcttcagaagtctataaaatggttc cttgttcccatttgattgtcattttagctgtgggtactttgtagaaatgt gagaaaaagtttagtggtctcttgaagcttttcaaaatactttctagaa ttataccgaataatctaagacaaacagaaaaagaaagagaggaaggaag aaagaaggaaatgaggaaga.....gaggctgaggcaggagaatggcgt gaacccaggaggcagaacttgcagtgagccgagatcgcgccactgcact ctagcctgggtgacagagtgagactctgtctctaaataaataaataaat aaataaataaataaataaatcagtgcttttttcttcctctgctacctcc tttccttctactcagttttagtcagtagtattatctttttcagattta tctttgtattgttaaatctgcttatgcttctattctttatttattagc tttaaatgatacctttgacttcagcttttcttaataaagcaatcagc aaatttcctttacactccacacttataccccatttcctttgtttgttta tttggttttacttctaacttttcttattgtcaggacatataacatatt taaactttgttttcaactcgaattctgccattagtttttaattttttgtt cacagttatataaatctttgttcactgatagtccttttgtactatcatc tcttaaatgactttatactccaagaaaggctcatgggaacaatattacc tgaatatgtctctattacttaatctgtacctaataatatgaaggtaatc tactttgtaggatttctgtgaagattaaataaattaatatagttaaagc acatagaacagcactcgacacagagtgagcacttggcaactgttagctg ttactaaccttttcccattcttcctccaaacctattccaactatctgaat catgtgcccttctctgtgaacctctatcataatacttgtcacactgta ttgtaattgtctcttttactttcccttgtatcttttgtgcatagcagag tacctgaaacaggaagtattttaaatattttgaatcaaatgagttaata gaatctttacaaataagaatatacacttctgcttaggatgataattgga ggcaagtgaatcctgagcgtgatttgataatgacctaataatgat |
| 38 | exon 11 | CUUCACUUCUAAUGGUGAUUAUGGGAGAACUGGAGCCUUCAGAGGGUAA AAUUAAGCACAGUGGAAGAAUUUCAUUCUGUUCUCAGUUUUCCUGGAUU AUGCCUGGCACCAUUAAAGAAAAAUAUCAUCUUUGGUGUUUCCUAUGAU AAUAUAGAUACAGAAGCGUCAUCAAAGCAUGCCAACUAGAA |
| 39 and 379 | intron 11 | aaactatgtgaaaacttttttgattatgcatatgaacccttcacactacc caaattatatatttggctccatattcaatcggttagtctacatatattt atgtttcctctatgggtaagctactgtgaatggatcaattaataaaaca catgacctatgctcttaagaagcttgcaaacacatgaaataaatgcaatt tatttttaaataatgggttcatttgatcacaataaatgcattttatga aatggtgagaattttgttcactcattagtgagacaaacgtcctcaatgg ttatttatatggcatgcatataagtgatatgtggtatctttttaaaaga taccacaaaatatgcatctttaaaaatatactccaaaaattattaagat tattttaataattttaataatactatagcctaatggaatgagcattgat |

TABLE 15-continued

CFTR Target Sequences

| SEQ ID NO | REGION | TARGET SEQUENCE |
|---|---|---|
| | | ctgccagcagagaattagaggggtaaaattgtgaagatattgtatccct
ggctttgaacaaataccatataacttctagtgactgcaattctttgatg
cagaggcaaaatgaagatgatgtcattactcatttcacaacaatattgg
agaatgagctaattatctgaaaattacatgaagtattccaagagaaacc
agtatatggatcttgtgctgttcactatgtaaattgtgtgatggtgggt
tcagtagttattgctgtaaatgttagggcagggaatatgttactatgaa
gtttattgacagtatactccaaatagtgtttgtgattcaaaagcaatat
ctttgatagttggcatttgcaattcctttatataatctttatgaaaaa
aattgcagagaaagtaaaatgtagcttaaaatacagtatccaaaaaaat
ggaaaagggcaaaccgtggattagatagaaatggcaattcttataaaaa
gggttgcatgcttacatgaatggctttccatgtatatactcagtcattc
aacagtttttttttttagagc.....gaggaggtggaaacgaatgtacaa
ggatgggaggagaaaaggagagagactttttttttttttaaggcgagag
tttactacctatctaactcttcgcattcttgaagtctcagaccaaatcc
catcggtttgaaagcctctagggtattctatctattgtatacttctgtt
atgtacaaaattaatttgccaattaattgtgaactgttttataaactat
cttaaaatggttagttaaatctttgggatagtatttagctttctccagg
attatgacttaccttctaaattagacatacaatgcctaggagtcaagga
ctatttgcataaattccagtcttcttttacaatgcctagaatgattgt
taccacagaaatattcattacctgggagaaaggatgacaggaggggcag
aatgaatggagagaggtcgtgagaatgaggtgctgaggatggacgagga
agaaagctgttttagttgggaggataggtgacagaagcatggaaaggaa
ttgccttggacccatggaagcccagtgaagatacttagatcctgcaggg
gtgtgaataatgttcttttagtttctcttcttaggaggtttgttcattt
tgggagatttcttttgaaaagagtgaacttaaattggagaaaagtacat
tttagtatgttgataacatttgaatttgtaaaatggacctatggatgat
ctacacatatttatatacccataaatatacacatatttttaattttggt
attttataattattatttaatgatcattcatgacattttaaaaattaca
gaaaaatttacatctaaaatttcagcaatgttgttttttgaccaactaaa
taaattgcatttgaaataatggagatgcaatgttcaaaatttcaactgt
ggttaaagcaatagtgtgatatatgattacattagaaggaagatgtgcc
tttcaaattcagattgagcatactaaaagtgactctctaattttc |
| 40 | exon 12 | ACAUCUCCAAGUUUGCAGAGAAAGACAAUAUAGUUCUUGGAGAAGGUGG
AAUCACACUGAGUGGAGGUCAACGAGCAAGAAUUUCUUUAGC |
| 41 | intron 12 | taactaattattggtctagcaagcatttgctgtaaatgtcattcatgta
aaaaaattacagacatttctctattgctttatattctgtttctggaatt
gaaaaaatcctggggttttatggctagtgggttaagaatcacatttaag
aactataaataatggtatagtatccagatttggtagagattatggttac
tcagaatctgtgcccgtatcttggtgtcagtgtatttgtttgcctcata
gtatagtttactacaaatggaaaactctaggattctgcataatactgga
cagagaagatgtaaatatctgttagttccatcatagaccctgccactcc
aatgtacacaccagctttaggcttcttggtatagataaacatacattt
caaaattttttcatcataattttcataacaaaataggaaggcaaatgatg
tcacttggcttaaaatctataatatttaaaataaacaggacaaatgcat
taacattgttgggggaggaggtcccttagtagaaacactcttggtccaa
gcattttaaagctgtcaaagagatgtaaatatagataatgtatgtcaag
gagagagctttgtggttaaactgtaactttcagtttaaacaattattgg
tgactctgatgtcaaatgtttctcaagctttatctgaacaaaattcttc
tcactttgttgccaaagtcgttaacaagaaatcacattgactcattgat
gttttggctcctttcccttactttctgttgctttccaaaagctgagaca
ggaaactaaccctaactgagcacctgcaattgcctggtagtattctagt
catgtgtgtactttttgtgtgtatgtaatcccttacagctctgcaaagt
aagaattgttctccctgctttacagaagagatcataagataattgaggc
tgttagatgttaacttgccaaaagccatacaggaaatggtagagtcac
agtttgaaccaggtccttttgattcttttacattaaaccatgctttgatc
ttggaaatacactgtaaggcaataaatcaatagatacggataattcaca
ggcttctaaataaatggaagttgattgttttatctgtgagccaaagta
agacttattctaagaattccacaaatttagataagatagagtatatggc
ttctagacatccaacatagaactgagtttgtgttatcagtttaagattt
ggttttgctgtaaggtgcacacactttgaggaactaaaaataattgtct
gttcttattctgatcagaatgtgtaatgtgttgtccagttttggatgat
gaatttcttatttctaatctcataagaaacttgtcatagatgtgaggga
gagaattaagaacagagtgtgggaagaaactgtgtacattttgatggg
atccattatgtagctcttgcatactgtcttcaaaaataagttacactat
aaaggttgttttagacttttaaagttttgccattggttttttaaaaaat
ttttaaattggctttaaaaatttcttaattgtgtgctgaatacaatttt
ctttattacagaagtaccaacaattacatgtataaacagagaatcctat
gtacttgagatataagtaaggttactatcaatcacacctgaaaaattta
aatgttatgaagaaattatctcatttctattaatatgggaactgtgtct
tcatctttattactgttctaaggtcaactcaatgtagattttacttgct
tatggtttcatatttagctaaatagtaaaataatatgggatatacatt
tgttgtgacttactcatactttccttatttggaacttttatgaatatga |

TABLE 15-continued

CFTR Target Sequences

| SEQ ID NO | REGION | TARGET SEQUENCE |
|---|---|---|
| | | tatagagactgaaactacaaggaacaaaatgcaatatcaattatacagt<br>tgtggcagcactgctatcaatttgttgatagtggttaacacttagaaaa<br>acattttaaaaataatttcacataagtaatgtaatttattagctgtctc<br>tgacattttacagtttggaatagtttattttcttttggtgtcctcacc<br>aaaacccaacatcttcaagggcaggaactgtataattttttgccattgta<br>ttttgagcacatagcatggtacttgcctctaaatagatactattgttaa<br>aatattttttaaggtaatattttaaagtgtatgctatggtacagttcag<br>tttgtgacttttgctagtttatgccacttacagttagcaaaatcacttc<br>agcagttcttggaatgttgtgaaaagtgataaaaatcttctgcaactta<br>ttcctttattcctcatttaaaataatctaccatagtaaaaacatgtata<br>aaagtgctacttctgcaccacttttgagaatagtgttatttcagtgaat<br>cgatgtggtgaccatattgtaatgcatgtagtgaactgtttaaggcaaa<br>tcatctacactagatgaccaggaaatagagaggaaatgtaatttaattt |
| 42 | exon 13 | GCAGUAUACAAAGAUGCUGAUUUGUAUUUAUUAGACUCUCCUUUUGGAU<br>ACCUAGAUGUUUUAACAGAAAAAGAAAUAUUUGA |
| 43 | intron 13 | ttctttgaatacctttacttataatgctcatgctaaaataaaagaaagac<br>agactgtcccatcatagattgcattttacctcttgagaaatatgttcac<br>cattgttggtatggcagaatgtagcatggtattaactcaaatctgatct<br>gccctactgggccaggattcaagattacttccattaaaaccttttctca<br>ccgcctcatgctaaaccagtttctctcattgctatactgttatagcaat<br>tgctatctatgtagttttttgcagtatcattgccttgtgatatatattac<br>tttaattattattatacttaacattttatttacttttttgtgttagtat<br>tttattctgtcttctccttagatagtaaccttcttaagaaaatatatat<br>gctaagtgttttactggtttaatatgcttagactactcatctacctcaa<br>tacttccttggagatctcctcctcagtcacacagagctcaggacttata<br>tttccttggaactcctgttagggtccaatgtacatgaaattccctagac<br>agacagacagtcagttatatggcttgatttcaaagtttcaaaatgattt<br>aatggactatcaagtagtttattaggagaacagttattatactcttcta<br>aaaataaagactttaagcaataaagatgtatatgtatataaaatggctg<br>ggttattcctagaagtaccttcttagaatttagttaaatttaatatcc<br>aagatactatcttttcaaccctgagattgtgaaaagtaacttctatcaa<br>tataaactttactacatttgtattgtgttagtgtgttacagtataatct<br>agaacaatgtgtctttctatatgatatatgacattttaatgcctaaaaa<br>aactgatatgtcttagatgattctagtcaggatttacttctagaataga<br>ttaaaattctatttgaggagagtcaaattaattatcgaattctcagttg<br>ttattattgctgttttattttagtgaaacagattagtcttaatgtaaa<br>cacttgagaaataaattgatggtcaacctaaaatgtaaaaaagaaatta<br>atagaaaatttaaagagcaacaaagctctgacatttaaaagaaatgaag<br>tacaaatctctagggaccttaaagatcatctaataatttcctcattttc<br>tagataaaataaactgagagaccccgaggataaatgatttgctcaaagtc<br>aaatatctacttaatataggaaatttaatttcattctcagtctgttaac<br>atgcaacttttcaatatagcatgttatttcatgctatcagaattcacaa<br>ggtaccaatttaattactacagagtacttatagaatcatttaaaatata<br>ataaaattgtatgatagagattatatgcaataaaacattaacaaaatgc<br>taaaatacgagacatattgcaataaagtatttataaaaattgatatttat<br>atgt |
| 44 | exon 14 | UGUGUCUGUAAACUGAUGGCUAACAAAACUAGGAUUUUGGUCACUUCUA<br>AAAUGGAACAUUUAAAGAAAGCUGACAAAAUAUUAAUUUUGCAUGAAGG<br>UAGCAGCUAUUUUUAUGGGACAUUUUCAGAACUCCAAAAUCUACAGCCA<br>GACUUUAGCUCAAAACUCAUGGGAUGUGAUUCUUUCGACCAAUUUAGUG<br>CAGAAAGAAGAAAUUCAAUCCUAACUGAGACCUUACACCGUUUCUCAUU<br>AGAAGGAGAUGCUCCUGUCUCCUGGACAGAAACAAAAAAACAAUCUUUU<br>AAACAGACUGGAGAGUUUGGGGAAAAAAGGAAGAAUUCUAUUCUCAAUC<br>CAAUCAACUCUAUACGAAAAUUUUCCAUUGUGCAAAAGACUCCCUUACA<br>AAUGAAUGGCAUCGAAGAGGAUUCUGAUGAGCCUUUAGAGAGAAGGCUG<br>UCCUUAGUACCAGAUUCUGAGCAGGGAGAGGCGAUACUGCCUCGCAUCA<br>GCGUGAUCAGCACUGGCCCCACGCUUCAGGCACGAAGGAGGCAGUCUGU<br>CCUGAACCUGAUGACACACUCAGUUAACCAAGGUCAGAACAUUCACCGA<br>AAGACAACAGCAUCCACACGAAAAGUGUCACUGGCCCCUCAGGCAAACU<br>UGACUGAACUGGAUAUAUAUUCAAGAAGGUUAUCUCAAGAAACUGGCUU<br>GGAAAUAAGUGAAGAAAUUAACGAAGAAGACUUA |
| 45 | intron 14 | tatacatcgcttgggggtatttcaccccacagaatgcaattgagtagaa<br>tgcaatatgtagcatgtaacaaaatttactaaaatcataggattaggat<br>aaggtgtatcttaaaactcagaaagtatgaagttcattaattatacaag<br>caacgttaaaatgtaaaataacaaatgatttcttttttgcaatggacata<br>tctcttcccataaaatgggaaaggatttagttttttggtcctctactaag<br>ccagtgataactgtgactataagttagaaagcatttgctttattaccat<br>cttgaaccctctgtgggaagaggtgcagtataaataactgtataaataa<br>atagtagctttcattatttatagctcgcaaaataatctgtatggaagta<br>gcatatataaggtatataaacatttagcctcttgataggactaactcac |

TABLE 15-continued

CFTR Target Sequences

| SEQ ID NO | REGION | TARGET SEQUENCE |
|---|---|---|
|  |  | attctggtttgtatatcagtcttgcctgaatttagctagtgtgggcttt ttttatcttgtgagtttgctttatacattgggtttctgaaaagatttc ttttagagaatgtatataagcttaacatgtactagtgccaatcttcaga cagaaattttgttctattaggttttaagaataaaagcattttattttta aaacaggaaataatataaaaggagagttttttgttgttttagtagaaaa cttaatgccttggatgaaatgagccatgggcagggttgtaatgaattga tatgtttaatagtatagatcatttgtgaataatatgacctttgacaaga cacaagccattaacatctgtaggcagaagtttccttctttgtaaaatga gggaataaaatagatccctaaagtgtgtaattttagtatttctaaactt tatgaaggtttcctaaatgataattcatctatatagtgttttttgtgt gtttgtttgtttgtttgagatggagtctcgctctgtcacctaggc tggagtgcaatggtgcaacctcggctcactgcaacctctgcctcctggg ttcaagctaatctcctgcctcagcctcctgagtagctgagattacaggc atgcaccaccatgccgagctaattttgtatttttagtagagaaggggt ttcatcatgttgaccaggctggtcttgaactcctgaccttgtgatccac ccacctcagcctcccaaagtgctggtattacaggcgtgtgccaccacgt ccagcctgagccactgcgcccagcccatctatagtttaatatcaatc taaatgaatttctcagtcctgagcctaaaaatttagttgtaaagaatga tatccttgactaataatagtttctattaatggattgcatctagtgctag gtggcatatatttagtccccacaactaccctggaaggtatttaaaattt ttcacatttgcagataaggaaactaaagttcagagttcggcaacatgct tgaattcaagcagctcctaggatgttaatggtggaggttgggttcaaat ccagatctgtctgactcaaaaaatgcatactcctaaccagtgcactata tcccaattccataggagcccttctttgtgattcatagcactttcccatg agttttgttgattttgtgagaaacaaaactctttttcctttggactgtc tggaatctctcttttcaaatttttgaaatgtatttctatgccaaaaga caaagatttctagaggaatatgcctaggatgagaattatgtaatttaaa tcacagctggaaagagagaaagtcctaagttactaagaaatgttcaaac acaaatgagctttcagtctattggaagacctttatagctagaagtatac tgaactgtacttgtccatggaccctgaagaaacaggtaaatcaaaga gagttctgggaaacttcatttagatggtatcattcatttgataaaaggt atgccactgttaagccttaatggtaaaattgtccaataataatacagt tatataatcagtgatacatttttagaattttgaaaaattacgatgtttc tcatttttaataaagctgtgttgctccagtagacattattctggctata gaatgacatcatacatggcatttataatgatttatatttgttaaaatac acttagattcaagtaatactattcttttatttcatatattaaaaataa aaccacaatggtggcatgaaactgtactgtcttattgtaatagccat |
| 46 | exon 15 | AGUGCUUUUUGAUGAUAUGGAGAGCAUACCAGCAGUGACUACAUGGAA CACAUACCUUCGAUAUAUUACUGUCCACAAGAGCUUAAUUUUUGUGCUA AUUUGGUGCUUAGUAAUUUUUCUGGCA |
| 47 and 380 | intron 15 | aatgttctattgtaaagtattactggatttaaagttaaattaagatagt ttggggatgtatacatatatatgcacacacataaatatgtatatataca catgtatacatgtataagtatgcatatatacacacatatatcactatat gtatatatgtatatattacatatatttgtgattttacagtatataatgg tatagattcatatagttcttagcttctgaaaaatcaacaagtagaacca ctactgatattttattatttcatattacatataaaatatatttaaatac aaatataagaagagttttttaatagatttttaataataaaggttaagaga ttcgaaagctcaaagtagaaggcttttatttggattgaaattaaacaat tagaatcactgttgatattttattatttcatattacatataaaatatat ttaaatataaagataagagttttaatagattttataataaatgttaag agattaaaaaactgaaaatagaaggcttttatttggattgaaattaaag gccaggcatggtggttcatgcctgtaatcccagaatttaggagactga gtgggaggattgcttgagcccaggggtcaagaccagcctgggcaacac agtgagacaccgtatctacaaaataattaaaaaattagctgggcatggt ggtgtgtgcctgtatgctaccattaactaaggaggctgaggtgggagaa tcgcttgagcctgggaggtcaaggctgccctgaactgtgattgtgccat tgcattccagcctgggtgccagagagagaccctatctctaaataaataa ataagtaaataaataaacagcaacaacaaaaacactcaaagcaaatctg tactaaattttgaattcattctgagaggtgacagcatgctggcagtcct ggcagccctcgctcactctcagggcctccttgaccttgacgcccactct ggctgtgcgtgaggagccct.....tagaacagagcacagatgatctaa atataaaagaactacaaaaatcacagttgtttaaaaaggttttttgtt tgtttatatatggtgcagaacatttgttccttagccaaatgtttccacc ttgagaaagctatagagattctatgtagtcctagtaccaataatatgtt ttaacctgaatgtaccttatctttattcataaactgtgacttttacac tgctgaaacttttttttttaagacaatctcactctgtcgtccagtctgg agtgcagcagtggtgtgatcttggctcactgcaacctctacctctgtg ttcaagcaattctggtgcctcggccacctgagtagttgggattcacaggt gtacaccaccaggcctggctaatagttttttgatatttctagtagagatg agttttgccacattggccaggctggcctgaaactcctggcctcaagtga tctgcctgccttggcctcccaaagtgttggtattacaagtgtgagccac tgtgcctggcctgaaactcataattcatttccattaatattaatctcac |

TABLE 15-continued

CFTR Target Sequences

| SEQ ID NO | REGION | TARGET SEQUENCE |
|---|---|---|
| | | cttttccaataattaattgatttcacaagtattagtcccctataatcat tgaatggctaataaaattatttatagcaaacagattaattatctgccag cagtctgagattagtttctttaaaaaatgtttattatttaaaacattca gctgtgatcttggctttcttgtgaggttcaatagtttctattgagtaaa ggagagaaatggcagagaatttacttcagtgaaatttgaattccattaa cttaatgtggtctcatcacaaataatagtacttagaacacctagtacag ctgctggacccaggaacacaaagcaaaggaagatgaaattgtgtgtacc ttgatattggtacacacatcaaatggtgtgatgtgaatttagatgtggg catgggaggaataggtgaagatgttagaaaaaaaatcaactgtgt |
| 48 | exon 16 | UGGCUGCUUCUUUGGUUGUGCUGUGGCUCCUUGG |
| 49 | intron 16 | tattccatgtcctattgtgtagattgtgttttatttctgttgattaaat attgtaatccactatgtttgtatgtattgtaatccacttgttcattt ctcccaagcattatggtagtggaaagataaggtttttgtttaaatgat gaccattagttgggtgaggtgacacattcctgtagtcctagctcctcca caggctgacgcaggaggatcacttgagcccaggagttcagggctgtagt gttgtatcattgtgagtagccaccgcactccagcctggacaatatagtg agatcctatatctaaaataaaataaaataaaatgaataaattgtgagca tgtgcagctcctgcagttttctaaagaatatagttctgttcagtttctgt gaaacacaataaaaatatttgaaataacattacatatttagggttttct tcaaattttttaatttaataaagaacaactcaatctctatcaatagtga gaaaacatatctattttcttgcaataatagtatgattttgaggttaagg gtgcatgctcttctaatgcaaaatattgtatttatttagactcaagttt agttccatttacatgtattggaaattcagtaagtaactttggctgccaa ataacgatttc |
| 50 | exon 17 | ACUCCUCUUCAAGACAAAGGGAAUAGUACUCAUAGUAGAAAUAACAGCU AUGCAGUGAUUAUCACCAGCACCAGUUCGUAUUAUGUGUUUUACAUUUA CGUGGGAGUAGCCGACACUUUGCUUGCUAUGGGAUUCUUCAGAGGUCUA CCACUGGUGCAUACUCUAAUCACAGUGUCGAAAAUUUUACACCACAAAA UGUUACAUUCUGUUCUUCAAGCACCUAUGUCAACCCUCAACACGUUGAA AG |
| 51 | intron 17 | ttactaggtctaagaaatgaaactgctgatccaccatcaataggcctg tggttttgttggttttctaatggcagtgctggcttttgcacagaggcat gtgccctttgttgaacctccatttgactggcatgcacatgtctcagata ttataggttatcatatattgttgctcctaatatttctgtgttagataat tagagtagcttggtttgtaagaatgtgatgttggtgggactgtagcaga acaagaaggcccttatgggtcagtcatacctctcttttcaaatatttgg tctagctctcttctgggcatcttgttgccaatatatagtattgctcaaa agggcaggagatttgaagtgatcaaggaaaatatattttttctattgat taagtcttttgatggggtagaataatctaatttcatgtaactgctcaaa gttatatggtaggggatcccaaatgtattttaaaactattttatatc atcatatttgaagtaatagaaagtcagagtagcagaataaaggtactaa aaattttaaaaactaataaggtactttgaaagaaatcaattatgttgat tcctcattaaacaaatttgcacttaaagactgaggttaataaggatttc cccaagttttttcatagcaacctgtgagcactttctctgttgaggcatt tatggtatgaaaagatgagtaaggcacagttcttgccctggagaaggtc acaggtgagaggaggagtigacacagaaacattgatataaagcaagga ataaattccaagactaaaattttcagaaatctaaaaaactcaagataag aaaaacccattatattttctgggtaacaaaatttcagtgttattaacat gtaggaagatcttgatatttattctgaagcccatgtgtgttgctgaaat attgccgcatttgcatatactcatcaccatcctctgttttggagctaag aattttagactcaagatgtctaattaagttgatccattgattttatttt ttatggaaatctgagacccacagaaggcaggggatttgcccacatttct agaagagtcagacatgagcgatgaggcacagtggaaagaacatgagcat tgcctgagctctgagttggcgctataagagcagtgatcatgggcaagtg actcttctgagccttggcctcctcacctgttaagtgaagaaaagaatat ttcagaagatctttgtgagaatgaaacaaggcaatttacttgcctgcta catagccaatgggaaatcaatataagttccccgtggttccttctgtgg ggttttgttcccacagagggtgcactggccattccacttcttcttttcc aagctcctcattcccttaacgctgttcatagttggttccaaaccatt gaaatataataagcaccaggatggttttttcttttccaccaaagcaaatt tcattttctaaacactgttttataaatatcaatggctattttttcaattt ttgattatcatgaaaatatacaaatatgtttaattaaatatgctaaaga atgtattaataaatatgtattaaataattcctacatataaggccttttt gcttggggtatgggtgatacaaaataaatgtggcatgaacccactgacc tctagcaatttataacctagaaaaagagttatgatatgtttataagttc ctgtgatataagacatgcatatagtcattataacagaggtgcaaacaag atgtatcaagtatgtccagaggaggaagagattaatcccagctggagga aacactgatgctttcttgcagcaggggcatttgagttgagaaagggagg aaacatagattttgacaatgagagctgaggggaaggggtttcaggtgg agggaaccgcatgtggaaagcaggaggtaggaaagtgtagagtgtgtt |

TABLE 15-continued

CFTR Target Sequences

| SEQ ID NO | REGION | TARGET SEQUENCE |
|---|---|---|
|  |  | taaagaatagaccagtttggctgaaacaggatatttgagcagaggaagc<br>ttgtactaggtaggtgggttgaggccaaattatgcaaggcattaaatat<br>taaactaggaattttggactttatcctgcagtttatgggggtaaatga<br>taagattcaatatcactttatttgtacagtattatgttacattttatct<br>aattgtttgtttaattcctgtctagacaatgaattcctcaagggcaagg<br>agcatggcttattcacctcagtaatttcagtgcctagcattgtgcctgg<br>tacaaagtggacacttgtatataaccttttttaattgaagcaacaagtt<br>gtcaaccttacaaatgtgaatccgtgattcagatgacaggttgaaatgt<br>agattgtctgcgaagagggcagaaagagagtatgacaaaggaggacaag<br>acagtggggcaggcagggagagagagcagccagggtttcggtagaggta<br>tgtcaaaaaggtatggaagtcagaggagaaggagaccccctatgttatag<br>aatacaaatggaagggaaatgatgacaacagtaagttgtcattaaatgc<br>aaggttgcaaaagtaagattgtaaagcaggatgagtacccacctattcc<br>tgacataatttatagtaaaagctatttcagagaaattggtcgttacttg<br>aatcttacaagaatctgaaactttttaaaaaggtttaaaagtaaaagaca<br>ataacttgaacacataattatttagaatgtttggaaagaaacaaaaatt<br>tctaagtctatctgattctatttgctaattcttatttgggttctgaatg<br>cgtctactgtgatccaaacttagtattgaatatattgatatatctttaa<br>aaaattagtgttttttgaggaatttgtca |
| 52 | exon 18 | UGGGAUUCUUAAUAGAUUCUCCAAAGAUAUAGCAAUUUUGGAUGACCUU<br>CUGCCUCUUACCAUAUUUGACUUCAUC |
| 53 | intron 18 | taaaaataagtaccgttaagtatgtctgtattattaaaaaaacaataac<br>aaaagcaaatgtgattttgttttcattttttatttgattgagggttgaa<br>gtcctgtctattgcattaattttgtaattatccaaagccttcaaaatag<br>acataagtttagtaaattcaataataagtcagaactgcttacctggccc<br>aaacctgaggcaatcccacatttagatgtaatagctgtctacttgggag<br>tgatttgagaggcacaaaggaccatctttcccaaaatcactggccacaa<br>agtgtgacattttggcattggcatcactatttgatggaagccaacctcc<br>ccccaaaaggcctgtattagaatgaagatggattccctgggtgggttac<br>acttgaaactagcctcacccatgaacactttggcacagattagctagcc<br>cattcccccacagtaaggaccataaggaagggacagaagcaaagataag<br>ttttagaacaaaagagaggggaaagaaaaaatctagggttttatgaggg<br>ctgtccctgagtgatagatgtgaataggcctccagggcaggctggctca<br>gaggctgactcttttgggttggggtgactgattggtggtgaggatggaga<br>agaaaaggggagtggaggaggtgaaagtgaccttgggacattaggtctc<br>cataagtgacaggatttaaggagtgttgtaagctgtggttgttggacca<br>ggtttaagcacagcttcctgagcttcctgactggtttaggtcaagctcc<br>agagagcaaatgccacagtctcagtgatctccttggagaaacagttgga<br>ataggatgttgccatgttgggatgagtcattgtccgctcttgctcttt<br>ccctacccctgcaaaataataatactgtatttgattgaacatataaaac<br>aaaagaaggattatcacataagtatgtatatataaccaacattggcagg<br>tgcagaaaaaccagactgtcagtttgcctcatctgaaatgattgacaca<br>aacaaatatatttactgtcccaagtgaactttggcattttggatatcct<br>tcagttgttctgtttaaagatataacttagaagcagctgatggaatatt<br>taaatccatgcgttgaattcatgcattcaaagaaacatgtcctgagtca<br>ctaaatgctgacatttgtttttcatgttaagagtgtaaataactggtcc<br>caaatataatattattacatcagataaaaactggaatgtgaacctctta<br>acttgattgtgaaagtatttgccaatggtgcctcttgataattatttga<br>ggctcacttcagaactcctctggaagggttaattttaaatagtcattt<br>tataaattaacattttgacatatgtgatggctctcaaattttttctt<br>tatgccagtttgaatcatttctgctcaattttttttttttaattgggatg<br>gagtctcactctgttgcccaggctggagtgcagtgatgcaatcttggct<br>gactgcaacctccacctcctcggttcaagcgattctctcgcatcagcct<br>ccagagtagctgggattacaggcgcgcaccaccatgcctggataattt<br>tgtattattactagagatgggtttcaccacgttggccaggctggtctt<br>gaactcctgaactcctgacctcaagtgatccacctgcctcagcctctta<br>aagagctggaattataggtgtgagccactgcaccaggccctgttcaact<br>tttaatgctaagattcatttgttgttgtttcacaagtgattaggcagag<br>gtcttttatattaatttacccatttttatttgtaagagagtctcatatta<br>aggaagcataatatatgacaatccaaatacagtacaaatttggttaatt<br>ttgattttgttaaataattaatcacagggtccttcaaattgtgagctc<br>ctctggttatacttatgttttacctctggttatacttaatttcaaacaa<br>atgaaatttcattctattcatgatatttcagaagcagatctgttgcaca<br>aaataaagcatacctataaatttctttttttaaaaaaaagtctctgtt<br>cactctattttctattattttttctcttttaaaatttgaattttattgt<br>ggcaagtccacttaacatgagatttaccctcttaacagatttttatgtg<br>taaaatacaatattgttcaccatgggtaaatgttgcacagcagatctct<br>ggaacttattcattttgcactactgaaattttataccgtgttgattagta<br>tctcccatttccctctctcccctgtcctgttacccatggttctgttct<br>ttgcttctttgagtttgagtattttgatacctcatgtaatcttcattct<br>attttctaactttgacaatgttctgacaaatttgctttccggattggag<br>cactgtatagtgaaaattgaaaatcttggttattttctacagattccca |

TABLE 15-continued

CFTR Target Sequences

| SEQ ID NO | REGION | TARGET SEQUENCE |
|---|---|---|
| | | ctattttaccttgagcagacacttatcttgaagggtctcagatttgtca cttgtagaatggggaatataaacctgataatggtcccttcagttctaa agttatatcagttgaaaatacatgtgtcacttatggtaacgggtagaga actggctcactgaacagcatatggatattataaagtggttttttttaat cctttctgcagacagttactttatactttattcaaatggattattgtga agtacatgttagcggactttgtaccttttaaaaatgtatgtatttggtg taatgtagaaatatagaaatttattaagtatgatttatttcaatgttaa gcatgagaaaatatgctccgaaaggttagatagcttgcctaaatgacaa gcttgtatttcaagcagaactttctgaatcaaaagactccaagacgaat gcccagcttttcaaaaactgtctaaccaaaataaatcctaagattcacct tcatactaaaattatttaaaaatagtttattttaaattaatattcactt aaaatgtatttatcatgcaatactttaaagtgtctgggaaatgaaaata tccaaagatcaaagaacaccatgttttcaaacttcaaaaatgttatcag tgacctaaacaattttaaaattttcatagagcctatgaaaaatgtact tgcaaatggctactttctgactaggaatagaatggggagagtatttagt ccaacaatgatagactggattaagaaaatgtggcacatatacaccatgg aacactatgcagccataaaaaatgatgagttcatgtccttgtagggac atggatgaaattggaaaacatcattctcagtaaactatcgcaagaacaa aaaaccaaacaccgcatattctcactcataggtgggaattgaacaatga gatcacatggacacaggaaggggaatatcacactctgggactgttgtg gggtggggggaggggaggggatagcactgggagatatacctaatgcta gatgacgagttagtgggtgcagtgcaccagcatggcacatgtatacata tgtaactaacctgcacaatgtgcacatgtaccctaaaacttaaagtata ataaaaaaataaaaaaaagtttgaggtgtttaaagtatgcaaaaaaaa aaaagaaataaatcactgacacactttgtccactttgcaatgtgaaaa tgtttactcaccaacatgttt |
| 54 | exon 19 | UGUUAUUAAUUGUGAUUGGAGCUAUAGCAGUUGUCGCAGUUUUACAACC CUACAUCUUUGUUGCAACAGUGCCAGUGAUAGUGGCUUUUAUUAUGUUG AGAGCAUAUUUCCUCCAAACCUCACAGCAACUCAAACAACUGGAAUCUG |
| 55 | intron 19 | acagtgaatgtgcgatactcatcttgtaaaaaagctataagagctattt gagattctttattgttaatctacttaaaaaaaattctgcttttaaactt ttacatcatataacaataattttttttctacatgcatgtgtatataaaag gaaactatattacaaagtacacatggatttttttctaattaatgacc atgtgacttcattttggttttaaaataggtatatagaatcttaccacag ttggtgtacaggacattcatttataataaacttatatcagtcaaattaa acaaggatagtgctgctattactaaaggtttctctgggttcccaaatga tacttgaccaaatttgtccctttggcttgttgtcttcagacacccttc ttcatgtgttggagctgccatttcgtgtgcccccaaactctacttgagc tgttagggaatcacattttgcagtgacagccttagtgtgggtgcatttt caggcaatacttttcagtatatttctgctttgtagattattagctaaa tcaagtcacataaacttccttaatttagatacttgaaaaattgtctta aaagaaaatttttttagtaagaattaatttagaattagccagaaaactc ccagtggtagccaagaaagaggaataaatattggtggtaattttttaag ttcccatctctggtagccaagtaaaaaaagagggtaactcattaataaa ataacaaatcatatctattcaaagaatggcaccagtgtgaaaaaaagct ttttaaccaatgacatttgtgatatgattattctaatttagtcttttc aggtacaagatattatgaaattacattttgtgtttatgttatttgcaat gttttctat |
| 56 | exon 20 | CAGGAGUCCAAUUUUCACUCAUCUUGUUACAAGCUUAAAAGGACUAUGG ACACUUCGUGCCUUCGGACGGCAGCCUUACUUUGAAACUCUGUUCCACA AAGCUCUGAAUUUACAUACUGCCAACUGGUUCUUGUACCUGUCAACACU GCGCUGGUUCCAAAUGAGAAUAGAAAUGAUUUUUGUCAUCUUCUUCAUU GCUGUUACCUUCAUUUCCAUUUUAACAA |
| 57 | intron 20 | atgaactcattaactttagctaagcatttaagtaaaaaattttcaatga ataaaatgctgcattctataggttatcaattttgatatctttagagtt tagtaattaacaaatttgttggtttattattgaacaagtgatttctttg aatttccattgttttattgttaaacaaataatttccttgaaatcggata tatatatatatatgtatatatatatatatatatatatatatacatat atatatatagtattatccctgttttcacagttttaaaaaccgatgcaca cagattgtcagatagcaattctgtgattgaagggaaatatgtcacctc ttcatactcatattggtgaagggtcctagcttcaaaattaatagattcc taaagaggggaaatgaaacatccgcatttacacacacacacacacacac acacacagagttcctcttgtcggtaagttttgtttttttaaatctcta ctagataaatttgttatctaattgtgagttttacacaaagaaaaactg tcacagaaaagaaagacagtgtcacattttcaaaagaaaaagaagaaa agaaagtgccatgttttcaaatacaaatgttctggattgatttagga tctttagtgaaaacaaagtatttcataataagtaaaataaaaatctat gtaggtaaatttgtttctctaatttaagaatttgaatttctgagtattt atgataagtgttgaaataacttcttatatgtgacagtgaatactggcag agcaaatgccaaatcaatgccaaatctgtaggatcatttgatttgtagga |

TABLE 15-continued

CFTR Target Sequences

| SEQ ID NO | REGION | TARGET SEQUENCE |
|---|---|---|
| | | acagaattctactcaaaccgaaagcaggcatttgctggagttacagaaa
ggcctcatggaacaccgagaaggtggtgccattcgactcttaaagaagc
tgcaacaggcacaagagagtcagctgcagctcttcttcttgagtctata
tctgtcctgggtccattccttttgtggttgcttcattcctttctctct
ctgaagactggttttctggtctaccagggctatgccacattgacttta
tgtagtgtctccattctggcctcctgaatttacaggagagttcctctgt
acaaactcaaagtcctggagagaacagaaaacagcttccttttggctca
ggggtccaactgcagtctactctgctgctatgaggatagtggggttcacc
acctttgttgttctctcagctagggcagtgggaaatgactctatgaaag
gaatatacatgggcaggcaaatgtactaatcctcatcagtactgtaatt
ttaagcaactttaaaaaattcttttaagttatttgaaaataagatcaaa
gaaggctgaattacataaatgaagatttgttaacaattaattcaaacca
atataacacatgctataacatggttgagtgtgattgagtcttgatttat
taggggcaataatcaaaacatttaacaatcattatagtacagaacttac
caatcaaatcagatgctcagccgagtggatgttggccacccagctatt
attatccctggctcaattggtcttcagctgtgttaacttgcaaacatta
attaactatctaagcccctcattttcctcaagtgtaaatagacacaata
atattacctattccataggtgtggggtgaatagtaaatgtaataatttg
tccaaaacacttagtatagtgcctggtccatggtaaatactaaataaat
gttatctgacttattattaaaattttatcttctcagcttaaccttcaga
acagtaatatattggggtctagataaatcttgcctatatgaaaataatt
taatactacatgcagatatatgctgtgtatattatgccttctgttagag
gaattgcagaaacaaaaatttcaattaataataagatgaattatttctc
ccaattgtagaatcttttgacaattttatcatgcattacagatgtaaga
actcttgattgggacttgatagtctaactttataataatttaagaacat
tcctcttagagaatttctatggccataatactgaacacatgaattttaa
ttagctgtcctcttagccctaaaaaaaaaattactgtaatttaacact
taagtgttgttcttcccaggtacagtaatcttttttttttttttttttt
tttttgcatagagggtaatcttttctctttccaaatggcagaactgtt
agttttctgactgtccggtgaaattctaagtccacttacttcccaatag
catgcaattagcaaaggtcctccttgcaaaggcacagaacacacctaaa
catcttgcagatgctgtttggacactcttcccctgcttttggtctcttt
gtaaagcagctcatctggatacaggatctcttttccccattgcccattc
taatatatgttaccgttattacttatagaataatagtagaagagacaaa
tatggtacctacccattaccaacaacacctccaataccagtaacatttt
ttaaaaagggcaacacttttcctaatattcaatcgctctttgatttaaaa
tcctggttgaatacttactatatgcagagcattattctattagtagatg
ctgtgatgaactgagatttaaaaattgttaaaattagcataaaattgaa
atgtaaatttaatgtgatatgtgccctaggagaagtgtgaataaagtcg
ttcacagaagagagaaataacatgaggttcatttacgtct |
| 58 | exon 21 | AGAAGGAGAAGGAAGAGUUGGUAUUAUCCUGACUUUAGCCAUGAAUAUC
AUGAGUACAUUGCAGUGGGCUGUAAACUCCAGCAUAGAUGUGGAUAGC |
| 59 and 381 | intron 21 | tcttatcatcttttaacttttatgaaaaaaattcagacaagtaacaaa
gtatgagtaatagcatgaggaagaactatataccgtatattgagcttaa
gaaataaaacattacagataaattgagggtcactgtgtatctgtcatta
aatccttatctcttctttccttctcatagatagccactatgaagatcta
atactgcagtgagcattcttccacctgtttccttattcaggatttcta
ggagaaataccctaggggttgtattgctgggtcataggattcacccatgc
ttaactgagtggtgccaaattgtcctcaagtctgttgtactgatatata
tccccatcaagagagtacaagaattctcatagctatgtatcttcaacaa
cacttggtgtctggtagatgtgaagtgattactaaaaatataggggagc
tgcatacataattattggcttttgctgttctcttacattaatttcttat
tcatgttgattactcatttgtcacctagtttttcttccttaattaaat
tgtaggaatttatgaattatggattgatcatcagctctatacatttcaa
acataatccctcagtcagtggcttggcttatagagtcttttgatgaaaa
gaagcttttaagttaataaagttcaatttattgtcttttcctttatgt
tttgtgctttggtatcttgattaagaactccttccttatattgggttc
tcaaatttagcagcataacattttcatactattatttaaatttttttca
cattatttagtgatagcacctttcttattcctaaagtgtttatcattgc
cttctgtctttctgcttgataaatattgccacacatttgtatactttat
tagtgtgtacaaagaccacatttagttgtgttatttctcttgttttgg
ttttctagaatgcagagccattaatattatagtaatgcttatgtgctaa
taccatatcaggggcacaaa.....aaataagagcagtaaaattgtgtc
taatcagctactaatatctgggaaggattgagccacaggatcaaagatg
gtatcttttaaaaatagaagttgagtgaattcggtcttcaaattctttc
tttttattcatttatttttactcattagtatattcattcctttat
tcatgtattgttcaaatatatattgggtacttattatatgccaagttgt
ttttaaaatcacattccaaattcccgtaagtcataattattcagagatg
tatgtttttttaaaaaaaattgaacacctttaaaaattatcaagtcct
tttatttctgtatgcattaaagataaactttactaaatgttacatgaat
agatttataaagcagataaatatttaatttcaaatataacccttatatg
caattatattttccttagcactaaaaatgaatatttaagtaaatttatat |

TABLE 15-continued

CFTR Target Sequences

| SEQ ID NO | REGION | TARGET SEQUENCE |
|---|---|---|
| | | taaaagtgtaattatttaactgcagatgtatgccaatgacttaaattgt<br>ttaaagattatagcaaagttgtttaaaattgtctaatcatgaagagttc<br>acttaaccacctggttgacacataaaattatagttagttactaaggtag<br>ttcgagagaaagagaagaatcttcagtagtggttttgaggtgtggtaca<br>ttttattataatataccggttatacagcattgtgcagtgctgctcatag<br>tagaaataaattttctctttgatgtcatctattcccttgtgtggcttac<br>ataactgagaattaggtgatcacaaaaataaacaggcctataacagagcc<br>catttatataagtcctggttatttctcttcagttaaacttttaattata<br>tccaattatttcctgttagttcattgaaaagcccgacaaataaccaagt<br>gacaaatagcaagtgttgcattttacaagttatttttaggaagcatca<br>aactaattgtgaaattgtctgccattcttaaaaacaaaaatgttg |
| 60 | exon 22 | UGCGAUCUGUGAGCCGAGUCUUUAAGUUCAUUGACAUGCCAACAGAAGG<br>UAAACCUACCAAGUCAACCAAACCAUACAAGAAUGGCCAACUCUCGAAA<br>GUUAUGAUUAUUGAGAAUUCACACGUGAAGAAAGAUGACAUCUGGCCCU<br>CAGGGGGCCAAAUGACUGUCAAAGAUCUCACAGCAAAAUACACAGAAGG<br>UGGAAAUGCCAUAUUAGAGAACAUUUCCUUCUCAAUAAGUCCUGGCCAG |
| 61 and 382 | intron 22 | atttgaacactgcttgctttgttagactgtgttcagtaagtgaatccca<br>gtagcctgaagcaatgtgttagcagaatctatttgtaacattattattg<br>tacagtagaatcaatattaaacacacatgttttattatatggagtcatt<br>atttttaatatgaaatttaatttgcagagtcctgaacctatataatggg<br>tttattttaaatgtgattgtacttgcagaatatctaattaattgctagg<br>ttaataactaaagaagccattaaataaatcaaaattgtaacatgttta<br>gatttcccatcttgaaaatgtcttccaaaaatatcttattgctgactcc<br>atctattgtcttaaattttatctaagttccattctgccaaacaagtgat<br>actttttttctagcttttttcagtttgtttgtttgttttctttgaag<br>ttttaattcagacatagattatttttcccagttatttactatatttat<br>taagcatgagtaattgacattattttgaaatccttcttatggatcccag<br>cactgggctgaacacatagaaggaacttaatatatactgatttctggaa<br>ttgattcttggagacagggatggtcattatccatatacttcaggctcca<br>taaacatatttcttaattgccttcaaatccctattctggactgctctat<br>aaatctagacaagagtattatatattttgattgatattttttagataaa<br>ataaaagggagctgaaaactgaattgcaaactgaatttaaaactttat<br>ctctctgtggttaattgcaaacacagatacaaaaatatagagagagata<br>cagttagtaaagatgttaggtcaccgttactaacactgacatagaaaca<br>gttttgctcatgagtttcagaatatatgagtttgattttgcccatggat<br>tttagaatatttgataaacatttaatgcattgtacaaattctgtgaaaa<br>catatatataggatgtgcga.....aacaaaactgtccttcactacaga<br>ttgaaaagcattatactaaaagaccatttgctcagttatagtatataaa<br>ggccaaatgacttaaaaacaaattatgtaaggagaaggaaacaaccatt<br>tattcagtgccactaactgtcagccagttttttcagtggtcagttaatg<br>actgcagtagtgttctaccttgctcaaagcaccctcctcaagttctggc<br>atctaagctgacatcagaacacagagttggggctctctgtgggtcacct<br>ctagcacttgatctcctcatgcagtgcatggtgctctcacgtctatgct<br>atgttcttatggtctttaggtaacaagaataattttctttcttttcctt<br>actatacattttgcttctgaaattcccttctcgccaatccaggtgaat<br>gtcagaatgtgatttgacaactgtccaaagtactcattcactgaggagt<br>ggtaaggccttcgcccaacctgccttctctgggaatatactgctgcctg<br>aacatatcattgtttattgccaggcttgaacttcaccaaattaatttat<br>tagggtcaacatctaaatattagaactatttcagattaattttttaagtc<br>gtatccactttgggtactagatcaaattgcaggtctctgcttctggctt<br>gagcctatgtttagagatgatgtgcatgaagacactcttgcttttcct<br>ttatgcaaaatgggcattttcaatctttttgtcattagtaaaggtcagt<br>gataaaggaagtctgcatcaggggtccaattccttatggccagtttctc<br>tattctgttccaaggttgtttgtctccatatcaacattggtcaggat<br>tgaaagtgtgcaacaaggtttgaatgaataagtgaaaatcttccactgg<br>tgacaggataaaatattccaatggttttattgaagtacaatactgaat<br>tatgtttatggcatggtacctatatgtcacagaagtgatcccatc |
| 62 | exon 23 | UGGGCCUCUUGGGAAGAACUGGAUCAGGGAAGAGUACUUUGUUAUCAGC<br>UUUUUUGAGACUACUGAACACUGAAGGAGAAAUCCAGAUCGAUGGUGUG<br>UCUGGGGAUUCAAUAACUUUGCAACAGUGGAGGAAAGCCUUUGGAGUGA<br>UACCA |
| 63 and 383 | intron 23 | caaaaggacttagccagaaaaaaggcaactaaattatattttttactgc<br>tatttgatacttgtactcaagaaattcatattactctgcaaaatatatt<br>tgttatgcattgctgtctttttctccagtgcagttttctcataggcag<br>aaaagatgtctctaaaagtttggaattctcaaattctggttattgaaat<br>gttcatagctttgatagtgttttcagaagaccaaatttacagtgggag<br>cctgggcttttgtttttaacagctctttttgttcctgcttcagtgg<br>cctgacctccaagttagcaatcgccaggttgagaaatgctttgcgagac<br>ataacagatgctcctgaaataacaaacacttggaatcatgaggtagtgg<br>aattgaaaatagaaagtgtagtgattgttttttgttatttggatgggat |

TABLE 15-continued

CFTR Target Sequences

| SEQ ID NO | REGION | TARGET SEQUENCE |
|---|---|---|
| | | gaacaatgtcagattagtctgtaactatttttttttaatgtcactctga<br>tttggtcacaaaggatctctagtctcattgccttagtatcattctacga<br>attagaatgtgttactgtgtaagagcacttcttgtatatgagagaaata<br>gcaacagttccagtttaaagtgatataaatggaaaccaagaaatgtctt<br>tactgggaccaaatctggacagcatttactgtattttgctggtatttt<br>ctctagtctttccgggtatattcacatttaatgatcacttttctccctt<br>tgtgctaatggacactgaatccattccactaccatagttcttgctaata<br>ctactctacttttttacacaaaattaaaatgccaggagcacctccaggta<br>gactgactataaatctagactgaaaaaaaagcttgtatttcttaacaga<br>ttaccttgtggaacatttgctcctttcaactaatgaggcactaaatatt<br>gtaactgctcaactggtgcttttaatttatttgtctagactttgtcatg<br>ttgccagaagctttatcctg.....ttgacttgacttgtgtggttcctt<br>gtggaccagatggccactaaatattctcatttcaaggcaattggtaaaa<br>actacacttcaagaaatttcattcttaattcccttagtggatgttatt<br>aaccaaaggcaaaagaaaaaaagggtaaaaaaaatattctaaatgttaa<br>tatcaaaaatattattttcaattcacccaggcacagagaactaagtat<br>tattattgctattgcaccggcattccccaatgagacagtgattttcttt<br>taagacattttaaataatataggcagaattaagtagacggtgatctgg<br>taagtagatgtttcagggtaacagctgtgcaatgctccatgcagggaat<br>tagattgtcattttattccttaccaggaacatacattcagttaaacaat<br>tatttgacttctgctcttccactgatttctaagttgaggctctctcttg<br>tgcctgtctgatcagataagtagagttgtgccttggtttatagatgaga<br>taaatgtgtatttgaataagcataagttaaagaaattttaaaatccctt<br>aggaagctaggcttatcagagaaatccaaggaaatacattaacaaacta<br>ggaatttgttctaacaggttaattataactcataaacttattgggtttt<br>tttaccttttaattttatattacatttgcttataataaggaatattgct<br>aggaataaaattttttaatattctacaattaacaattatctcaatttct<br>ttattctaaagacattgggattagaaaaatgttcacaagggactccaaa<br>tattgctgtagtatttgtttcttaaaagaatgatacaaagcagacatga<br>taaaatattaaaatttgagagaacttgatggtaagtacatgggtgttc<br>ttatttaaaataattttctacttgaaatattttacaatacaataagg<br>gaaaaataaaaagttatttaagttattcatactttcttcttcttt |
| 64 | exon 24 | AAGUAUUUAUUUUUCUGGAACAUUUAGAAAAAACUUGGAUCCCUAUGA<br>ACAGUGGAGUGAUCAAGAAAUAUGGAAAGUUGCAGAU |
| 65 and 384 | intron 24 | gctgctaactgaaatgattttgaaaggggtaactcataccaacacaaat<br>ggctgatatagctgacatcattctacacactttgtgtgcatgtatgtgt<br>gtgcacaactttaaaatggagtaccctaacatacctggagcaacaggta<br>cttttgactggacctaccctaactgaaatgattttgaaagaggtaact<br>cataccaacacaaatggttgatatggctaagatcattctacacactttg<br>tgtgcatgtatttctgtgcacaacttcaaaatggagtaccctaaaatac<br>ctggcgcgacaagtacttttgactgagcctacttctctcctcactggta<br>tggctccaaccatcaggcccctatcttggtccatttaggctgctaaaata<br>aaataccaaagactgagctgcttataagcaatctttggaggctgagaag<br>tcaaagatcaaggtgccagcaggtttgctgtctcgtgagagcatacttc<br>ctggttcattgatggtgctttcttgctgtgtcctcacataatggaaagg<br>gcaagacctctctggtgtctcttttacaatggcactaatcccatcatga<br>gggctttgttctcatgacctaatcacctcccacatgtcctacattctaa<br>tactatcaccttgggggttaggatttttaacatatgaatttgaggagtg<br>gcgggggggacacaaatatttagaccatagcatttcactcctgacctcc<br>aaagttcatgtcttcttcacatgcaaaatacattcattccatcccaata<br>gcccccaaagtcttaacttgttccagcatcaacttacaaggctaaagtc<br>caaggtttcatctaaatatcagctaaatcagcacaaacagctaaatcag<br>gtagagtgggacttaaggtgtgattcctctttaggcagattgctctcca<br>actatgaaattgtgaaatcaaacctattatgtactttcaaaataaaatg<br>gtgaaacaggcacaggctag.....ataagattcttctgagccattat<br>ctcattctatattacagtcaggtggagcccatcttacctcctcatacta<br>aattctagacttctcaagggcaggagacaatcatctgtatatctctttg<br>gccttcatacactcaggagtacttgccaaaaataaacatttaatgcaca<br>ttttatttgaataattgataagatccaatacttcaataacttttgtcatat<br>ttttatagaatgggtttctatatctcatttgcattttcaaactttactt<br>ttactgtctagctttaaaaaaaaagcctttgactctaatacagccctca<br>tattctaccccaatatctaagaggctttatatctcctagtgttgtacca<br>ctattttaactccagtattttttacttcatagttttacctatttgttac<br>agttagttttttatgaattcaagagatgaatagcaattttccatatgtaa<br>tttaaaaaaccccacagttgactattttatgctatcttttgtcctcagt<br>catgacagagtagaagatgggaggtagcaccaaggatgatgtcatacct<br>ccatccttatgctacattctatcttctgtctacataagatgtcatact<br>agagggcatatctgcaatgtatacatattatcttttccagcatgcattc<br>agttgtgttggaataatttatgtacacctttataaacgctgagcctcac<br>aagagccatgtgccacgtattgttttcttactacttttgggatacctg<br>gcacgtaatagacactcattgaaagtttcctaatgaatgaagtacaaag<br>ataaaacaagttatagactgattcttttgagctgtcaaggttgtaaata |

TABLE 15-continued

CFTR Target Sequences

| SEQ ID NO | REGION | TARGET SEQUENCE |
|---|---|---|
| | | gacttttgctcaatcaattcaaatggtggcaggtagtgggggtagaggg attggtatgaaaaacataagctttcagaactcctgtgtttattttaga atgtcaactgcttgagtgttttttaactctgtggtatctgaactat |
| 66 | exon 25 | UUGGGCUCAGAUCUGUGAUAGAACAGUUUCCUGGGAAGCUUGACUUUGU CCUUGUGGAUGGGGGCUGUGUCCUAAGCCAUGGCCACAAGCAGUUGAUG UGCUUGGCUAGAUCUGUUCUCAGUAAGGCGAAGAUCUUGCUGCUUGAUG AACCCAGUGCUCAUUUGGAUCC |
| 67 | intron 25 | tttcagatgttctgttacttaatagcacagtgggaacagaatcattatg cctgcttcatggtgacacatatttctattaggctgtcatgtctgcgtgt gggggtctcccccaagatatgaaataattgcccagtggaaatgagcata aatgcatatttccttgctaagagtcttgtgttttcttccgaagatagtt tttagtttcatacaaactcttccccttgtcaacacatgatgaagcttt taaatacatgggcctaatctgatccttatgatttgcctttgtatcccat ttataccataagcatgtttatagccccaaataaagaagtactggtgatt ctacataatgaaaaatgtactcatttattaaagtttctttgaaatattt gtcctgtttatttatggatacttagagtctaccccatggttgaaaagct gattgtggctaacgctatatcaacattatgtgaaaagaacttaaagaaa taagtaatttaaagagataatagaacaatagacatattatcaaggtaaa tacagatcattactgttctgtgatattatgtgtggtatt |
| 68 | exon 26 | ACAUACCAAAUAAUUAGAAGAACUCUAAAACAAGCAUUUGCUGAUUGCA CAGUAAUUCUCUGUGAACACAGGAUAGAAGCAAUGCUGGAAUGCCAACA AUUU |
| 69 | intron 26 | tctttataactttacttaagatctcattgcccttgtaattcttgataac aatctcacatgtgatagttcctgcaaattgcaacaatgtacaagttctt ttcaaaaatatgtatcatacagccatccagctttactcaaaatagctgc acaagttttcactttgatctgagccatgtggtgaggttgaaatatagt aaatctaaaatggcagcatattactaagttatgtttataaataggatat atatactttttgagccctttatttggggaccaagtcatacaaaatactc tactgtttaagattttaaaaaaggtccctgtgattcttcaataactaa atgtcccatggatgtggtctgggacaggcctagttgtcttacagtctga tttatggtattaatgacaaagttgagaggcacatttcatttttctagcc atgatttgggttcaggtagtaccttctcaaccaccttctcactgttct taaaaaaactgtcacatggccaggcacagtggcttacatctgtaatccc aatactttgggaggctgaggtggggggattacttgaggccaggaattca agaccagcccaggcaacatagtgagccccatctgtctttattaaaaca aaacaaaactgtcacagcttctttcaagtgatgtttacaaattccctat ggtttagtcacaaggaagttctgaggatgatgtatcacgtcatttctgt tcaggcttttgagcctcctggaggtaaatggtttccttactgaaggctt gttattaccatgattatcactaagcttgaagtaacaaattaggggggca gactcacaacctcttgccctgccatggacaagttcaagaatctaagtaa agtcctctattgtctgatcttggatttgctcaacctgaacaagccaagg aggtgtattaaactcaggcacatcctgaccaatttggaattcttaagct tcagatcactgtggaagaggctcaactctttatggtgctgtagacttac gctcattttctaggtaattttataagggacctaatattttgttttcaaag caacttcagttctactaaacctccctgaagaatcttccagctgctgagt agaaaatcacaactaatttcacagatggtagaacctccttagagcaaaa ggacacagcagttaaatgtgacatacctgattgttcaaaatgcaaggct ctggacattgcattctttgacttttattttcctttgagcctgtgccagt ttctgtccctgctctggtctgacctgccttctgtcccagatctcactaa |
| 70 | exon 27 | UCAUAGAAGAGAACAAAGUGCGGCAGUACGAUUCCAUCCAGAAACUGCU GAACGAGAGGAGCCUCUUCCGGCAAGCCAUCAGCCCCUCCGACAGGGUG AAGCUCUUCCCCACCGGAACUCAAGCAAGUGCAAGUCUAAGCCCCAGA UUGCUGCUCUGAAAGAGGAGACAGAAGAAGAGGUGCAAGAUACAAGGCU U |

TABLE 16

ADAMTS13 Target Sequences

| SEQ ID NO | REGION | TARGET SEQUENCE |
|---|---|---|
| 71 | exon 25 | GCUCUGUUCCUGUGGGGAUGGCAUCCAGCGCCGGCGUGACACCUGCCU CGGACCCCAGGCCCAGGCGCCUGUGCCAGCUGAUUUCUGCCAGCACUUG CCCAAGCCGGUGACUGUGCGUGGCUGCUGGGCUGGGCCCUGUGUGGGAC |

TABLE 16-continued

ADAMTS13 Target Sequences

| SEQ ID NO | REGION | TARGET SEQUENCE |
|---|---|---|
| | | AGGGUACGCCCAGCCUGGUGCCCCACGAAGAAGCCGCUGCUCCAGGACG GACCACAGCCCACCCCUGCUGGUGCCUCCCUGGAGUGGUCCCAGGCCCGG GGCCUGCUCUUCUCCCCGGCUCCCCAGCCUCGGCGGCUCCUGCCCGGGC CCCAGGAAAACUCAGUGCAGU |
| 72 | intron 25 | guccuguccuccuuccugucaggcagcugcugcaggaggggugggcaaa ggcaucuuccucuggggaaggacuggcacaagcacuugguccugggguug ugugccugggaggccgggaucagggcuggcccucuuucucccuggcaaa gcaaaaccucccuuuuacuacuaucaaggggaaguaacuugaagguagg aacccagcuugugagccccuagccucugggcugcucugcaugugcccc cucuugcuggaucaucugguagcagcccugugcccugagggugaugcuc ugaccuaugcagccccccucccugccugagaaggcuuccagcuggggcc uuggaggacaggguccaccccuaccuccuggucuccuuccucagcuugg aagccccggagccugcccugcugggaaucggggaagcacugcuuaccug ucuc |
| 73 | exon 26 | UGCCUGUGGCAGGCAGCACCUUGAGCCAACAGGAACCAUUGACAUGCGA GGCCCAGGGCAGGCAGACUGUGCAGUGGCCAUUGGGCGGCCCCUCGGGG AGGUGGUGACCCUCCGCGUCCUUGAGAGUUCUCUCAACUGCAGUG |
| 74 | exon 27 | GGACAUGUUGCUGCUUUGGGGCCGGCUCACCUGGAGGAAGAUGUGCAGG AAGCUGUUGGACAUGACUUUCAGCUCCAAGACCAACACGCUGGUGGUGA GGCAGCGCUGCGGGCGGCCAGGAGGUGGGGUGCUGCUGCGGUAUGGGAG CCAGCUUGCUCCUGAAACCUUCUACA |
| 75 | intron 27 | gccaggccuucuccaccucccuggggugcuccaguccuggcagggaggc ugggugggugcugcuggggauggggccagucccagugggcagugggaa gauacggagggaacugacugagauggaaggaacuggggguuggccagugu cagucugcacgugccagggaggggucacaggaugaaugcuauaucccuc cuuuuuggaccgugcagcaagauggacggaugugggacauggucccaca uccucagucaguccccucaggccucugcccccacaccuccaccugccccgccc ccaccccuccagccuuucaagggcuuuuagggguuuugguggaagccacug uccucagcccuguuucagugcacguguaagcagacaugcuuguaca ugcaugugcacccacaagcacaccucaggcagaggaugccaccucaggg acuccagccuugcccguggccccccugauauccucugauagccccucucg guugucuggggggcuugcccucuccaacagcccgagcuggccgaagu uggcuucccuagcugguuccagaggguuccucggcuccccccaggugucug gggcuuaguggcaacagggcuuagccucugcagagaccuagucgccg ccuccuugcccagaccugcccgggcagagagccgugugugucccag ugcacaggcgcugcuggcccugccaaaaggccacaagcccacugucac cguucacauugccuucucgcuucccgcccagcccgcccacacaggcau cugccuugaaagaggugcaggaggguacaggcaggugggggcuccaguga gcucugaggaacagcaguggccgccaugggguggagccuaucuuguugc caguuucagaguguuaaacacuuugcacguguggacaucauugagcccuaa agaccacucugcucagugcaugccauuguuuccuucaguuacagaggag ggaaccagagcccagaacauuuagccuuugccaaaagucacugggccag gaagugguagaggugggguucagcaggauuugccugggaaccccaauau ugaccacagugccaugcugcccugcacgcguccccuggcugugaguugcuc cuggccucuggcaccaccggucugucuggguuccuaugucccu |
| 76 | exon 28 | AUGUGACAUGCAGCUCUUUGGGCCCUGGGGUGAAAUCGUGAGCCCCUCG CUGAGUCCAGCCACGAGUAAUGCAGGGGGCUGCCGGCUCUUCAUUAAUG UGGCUCCGCACGCACGGAUUGCCAUCCAUGCCCUGGCCACCAACAUGGG CGCUGGGACCGAGGGAGCCAAUGCCAGCUACAUC |

TABLE 17

TSC1 Target Sequences

| SEQ ID NO | REGION | TARGET SEQUENCE |
|---|---|---|
| 77 | exon 5 | ACCUCUUGGACAGGAUUAACGAAUAUGUGGGCAAAGCCGCCACUCGUUU AUCCAUCCUCUCGUUACUGGGUCAUGUCAUAAGACUGCAGCCAUCUUGG AAGCAUAAGCUCUCUCAAGCACCUCUUUUGCCUUCUUUACUAAAAUGUC UC |
| 78 | intron 5 | auguuuguaaggauuugaaugaaaugguuuuaugaguauaguuucugaa auuuuaggcaacuuaaagcaaggaagcuagauuuuaacuuuuagaguuu aaaaccuucuaggcauuuggcuuuucucaaauagaauguugucccagagu |

TABLE 17-continued

TSC1 Target Sequences

| SEQ ID NO | REGION | TARGET SEQUENCE |
|---|---|---|
| | | ugguacuuaguaaguucucaaauacaucacuaugacuauugaauaccuu guccaugcaaguauggaaaaauuucgaucagaugggUucaauguuacau uauuccaaaccucuugauuucgucaucguuuagccuucccucauuuaaa aacauccuggauuaucuuuugggaaucccuguuucuaaauuaucuuuua gcuaauagaaaaaauggcuuaaaguuucuguuaaccauuuaggaguaugg ucugguugcagcuauaauuaagacuuuguugauguaaauucuacuaagu ugcauucuauuuuuugcacuaaauuuagugcauuuuucuauauagggag ucaaaaucuaaauagaacuuuaugguuuuaguuuuaacaguggcgugca gccauacucagggUuauuuguuuaaucuguuuuaguuccuggacuuguu uucuaucuauaaaauaagaaaaugugguuaauauuaacugccuguaccu cacagagacaugaaaauauccaauaguauuuguuccaggauggcaguac cauuggauucaucugcuacagcaccaugcaaauugauuuuugugucugc caagaagggUaacucuuuuauuaucccuagaggugggUcccaaggaguc acauuggcagggUauuauaaaacaugcauuuaauucagaaaaaauagg aacaguuuaacaacuuaaguguuuuuaaacaaauggauugaugagaau auaaucuaauuaauggauuggugagaauauaaucuaaauggauugauga gaauauaaucuaaauggauuggugagaauauaaucuaaauggauugaug agaauauaaucuaauuugaggcacaucauuuaguucagauugcaaaac acuuaucuuuccaaaagaguacguuuguuaaucauggauaagucuuc aguuagacuguuaggaaaaugaaaucagggcuaguucuuucugcugaga aucauuauauagucucauauauucucaauucuccuaccaauauauuauu cuuacuggauaucuuccguaaugaaaggcuugaugcuugauguaaaaau caaaauauauuuaaaacuuuauuccagacucauagauuccuauucuaa uaggaauaauggaugucuuaaccuacauaguagucuuuugauuaauauc uuguuucauaaaucugaauuucaucuaccuggcaaacauucaugauuua auuaugggUcaggugagcugcuguagcuagcuagucagagcugauugag uauccauugggUguuaagugucuucaguuagccugaaguuauuuauuug acuuaauauuuaaacuguaggcgugcugaaaggUuuccauauauauaua uuuuaauuuacuggUcucuaaauacugcuuugaagugagccuuuaaguu gacuuguuagugcuauaugaauuuucccuucaauuauacuucuguugua guucuuuaaaaaauaguaaguuacuugucaaugugcaguuuuuuuuuu uuuaauuaacaaaaaguaaguaucuuaggauuuugguugaaugaaugaa cagagcagugcuccugugUuuuguugaaaagcagcccuuuuguuuca uccaacugcuaucaauagggcauccuaaggcugcaggacuugggUgucc ccaagucaaguuugaacucgucucccggaugccuuugcauaggUgUgUu guaaauguccucacugacucauuacaguagaguuggggcucaaguguuc uguugagucuguuugaauguuaucccuucaguaauccuuagggauaggg aaaugaguacgugagucaacuugugauuugugaauucucucaguguuuag agccucuucaugUacuguacaaugccgauccuggUgccagugccugaca gacguuuccuguuuga |
| 79 | exon 6 | UGGACACUGACGUCGUUGUCCUCACAACAGGCGUCUUGGUGUUGAUAAC CAUGCUACCAAUGAUUCCACAGUCUGGGAAACAGCAUCUUCUUGAUUUC UUUGACAUUUUUGGCCGUCUGUCAUCAUGGUGCCUGAAGAAAC |
| 80 | exon 10 | GUGUGCUACUUCUACCCCUUACUCCACGUCUCGGCUGAUGUUGUUAAAU AUGCCAGGGCAGCUACCUCAGACUCUGAGUUCCCCAUCGACACGGCUGA UAACUGAACCACCA |
| 81 | intron 10 | gugucaacuagugUgccugcucucuccucugcuuucggugaagcugac ccuuugggUcagauuuaguaugugguuggguaaaaauuucacacugcucau uucaggagucacuuuuaaggauccaugauauuagcaaagaaaguuacug uugccucuuuagauucaucuugaagucuugauuuacaaaaugcaacuugu uucuugauacgcuuuuaauaagaugccuuuuucuagaugaaaaagcuaa auuuaagcugaacacuggccauggauauaaaccucguggaugacuuagc auuccuuugccacugcugaugUacu |
| 82 | exon 11 | CUACUCUUUGGAGCCCAUCUAUGGUUUGUGGUAUGACCACUCCUCCAAC UUCUCCUGGAAAUGUCCCACCUGAUCUGUCACACCCUUACAGUAAAGUC UUUGGUACAA |
| 83 | intron 11 | uaugucuuagguuggauuugauuaguuggUuuuuggccugccuuuaaugg caggaggagcucucuuuuagaucuaagggaccacuugcuguugUaaacu uguuuuugacacuuauugcaaaucccuggggcuuucagaauguguaaag ugaaccuaaaaacaaaaagagagagacugaucuagauccccagaaagu uaacucuagcagcuuuauuuauaguaauaguuauaggcugaaaaaaaau cggcaguuuuucuaauaguugggcucaguguucauauaugUuucu |
| 84 | exon 12 | AGGUGGAAAAGGAACUCCUCUGGGAACCCCAGCAACCUCUCCUCCUCCA GCCCCACUCUGUCAUUCGGAUGACUACGUGCACAUUUCACUCCCCCAGG CCACAGUCACACCCCCAGG |

TABLE 18

IMPDH1 Target Sequences

| SEQ ID NO | REGION | TARGET SEQUENCE |
|---|---|---|
| 85 | exon 14 | GAUGAUGGGCUCCCUGCUGGCCGCCACUACGGAGGCCCCUGGCGAGUAC UUCUUCUCAGACGGGGUGCGGCUCAAGAAGUACCGGGGCAUGGGCUCAC UGGAUGCCAUGGAGAAGAGCAGCAGCAGCCAGAAACGAUACUU |
| 86 | intron 14 | cugacccugggccccaccugggcagaucagcccacaacccuucagggcc cgcucaugccaccgacuuccccagauggcagccaguccccauaugugg uucuggaaacugaggcacagggcuuaaguagcagacccaggaucuguccc cugggccaucugacucagcccagugaggggugccuggggaccuuccu gggcgguaucccguuuuugcccuuaagagguggggugggguccucugag cuucaagcugcugggcucagucuu |
| 87 | exon 15 | GAGGGGGAUAAAGUGAAGAUCGCGCAGGGUGUCUCGGGCUCCAUCCAGG ACAAAGGAUCCAUUCAGAAGUUCGUGCCCUACCUCAUAGCAGGCAUCCA ACACGGCUGCCAGGAUAUCGGGCCCGCAGCCUGUCUGUCCU |

TABLE 19

PKD1 Target Sequences

| SEQ ID NO | REGION | TARGET SEQUENCE |
|---|---|---|
| 88 | exon 32 | AGGCCUUUGUUGGACAGAUGAAGAGUGACUUGUUUCUGGAUGAUUCUAA |
| 89 | intron 32 | uucccuagagaaaccucgagcccuggugcaggucacugugucuggggug ccgggggugugcgggcugcguguccuugcugggugucuguggcuccaug uggucacaccaccgggagcagguuugcucggaagcccaggguguccgu gcgugacuggacggggguggggcugugugugugacacaucccccugguacc uugcugac |
| 90 | exon 33 | CUGGUGUGCUGGCCCUCCGGCGAGGGAACGCUCAGUUGGCCGGACCUGC UCAGUGACCCGUCCAUUGUGGGUAGCAAUCUGCGGCAGCUGGCACGGGG CCAGGCGGGCCAUGGGCUGGGCCCAGAGGAGGACGGCUUCUCCCUGGCC AGCCCCUACUCGCCUGCCAAAUCCUUCUCAGCAU |
| 91 | intron 33 | cuggggugagaggaggggggcucugaagcucacccuugcagcugggccca cccuaugc |
| 92 | exon 34 | UGAAGACCUGAUCCAGCAGGUCCUUGCCGAGGGGGUCAGCAGCCCAGCC CCUACCCAAGACACCCACAUGGAAACGGACCUGCUCAGCAG |
| 93 | exon 37 | UCUUGCUGGAAGCCCUGUACUUCUCACUGGUGGCCAAGCGGCUGCACCC GGAUGAAGAUGACACCCUGGUAGAGAGCCCGGCUGUGACGCCUGUGAGC GCACGUGUGCCCCGCGUACGGCCACCCCACGGCUUUGCACUCUUCCUGG CCAAGGAAGAAGCCCGCAAGGUCAAGAGGCUACAUGGCAUGCUG |
| 94 | intron 37 | ccugggugcggccugugccccugccaccuccgucucuugcucucccaccu cccacccaugcacgcaggacacuccuguccccuuuccucaccucagaa ggcccuuaggggguucaaugcucugcagccuuugcccggucucccuccua ccccacgccccccacuugcugccccaguccccugccagggcccagucca augcccacuccugccuggcccugaaggcccuaagcaccacugcagugg ccugugugucugccccaguggggguuccgggcagggugugugcugcca uuacccuggccagguagagucuuggggcgccccugccagcucaccuuc cugcagccacaccugccgcagccauggcuccagccguugccaaagcccu gcugucacugugggcuggggcaggcugaccacagggc |
| 95 | exon 38 | GCCUCCUGGUGUACAUGCUUUUUCUGCUGGUGACCCUGCUGGCCAGCUA UGGGGAUGCCUCAUGCCAUGGGCACGCCUACCGUCUGCAAAGCGCCAUC AAGCAGGAGCUGCACAGCCGGGCCUUCCUGGCCAUCAC |
| 96 | intron 38 | ggcauccggugcacuggucugucuucugggcuuuaguuuugccuuuagu ccagccagacccuaggggacauguggacauguguagauaccuuuguggc ugcuagaacuggaggugcugcuggcaucaguaggcagagggggagg gacacagguccguguscuugcagugcacaggacgggcccaugacagacaa cugucugcccccagaacaucccscaggauaaggcugagaagcccaggucua gccguggccagcagggcagugggagccaugucccugggucucuggugg ccgcucacucgaggcgggcaugggcaguagggggcuggagcguguga |

TABLE 19-continued

PKD1 Target Sequences

| SEQ ID NO | REGION | TARGET SEQUENCE |
|---|---|---|
| 97 | exon 39 | UCUGAGGAGCUCUGGCCAUGGAUGGCCCACGUGCUGCUGCCCUACGUCC ACGGGAACCAGUCCAGCCCAGAGCUGGGGCCCCCACGGCUGCGGCAGGU GCGGCUGCAGG |

TABLE 20

IKBKAP Target Sequences

| SEQ ID NO | REGION | TARGET SEQUENCE |
|---|---|---|
| 98 | exon 7 | AUGAGUCUGCUUUGCCCUGGGAUGACCAUAGACCACAAGUUACCUGGCG GGGGAUGGACAGUUUUUUGCUGUGAGUGUUGUUUGCCCAGAAA |
| 99 | intron 7 | gaaauauauugcaguuaaacaacaauaaaaaauuuuuaucuuauuaaaa uuaaggaaaauuuucuuucuuuugcuuugaguagggauauuaauuauaca uaugaggcaaggaugugcugcuuuaaaugugaaaugagguuagaguuaa gaauuagaagaguccuuugaggccauuuggucccauccuccuaccuggug gacacaaauuuguaacaaaauuaaucuaauuggcuauguaaaaccaugg caguuuuuauuuguaaggaaggguguuugaauaguucugaauugacaacu uuuaucauaauguuuuaagugguguaugugguguuugac |
| 100 | exon 8 | GGCUCGGAAGGUCAGAGUGUGGAACCGAGAGUUUGCUUUGCAGUCAACC AGUGAGCCUGUGGCAGGACUGGGACCAGCCCUGGCUUG |
| 101 | intron 8 | ugggagaagaaaccuuagagaaauucuuggaaccagaguagagguggug guacacauggauacagaugauacagaugauuugaaucacaaaaggauu uuuacguuucuucauuugguuauaaggcuguaucuaucuuuguuucuuc uuuuuuuuuuucuuauucccugaagucugaauucaacucgaauaguag auuuuacgcuucuucacagauuucauuguuccaaggccgcauauauuuu gcauuccuaacucuuaaaaaggcugugguuuuaaggcaggguauauauga agccauugucagagcagaaaauuggugguuuagaagggaaggcccaguuu gcaaggcucugugggggaaagguugcuuuugugggaaauuaggggaagaag ccuccuuccuuggcacaaaauuccuacagcagaggaucugcuugccaag gagcaugcaggcuggauucagacccugcucuuccuuccauucuccucc uuggcccaguacccuugugcagguuacaauuugccugucauaugugcu gccugauuuuagauagaagauguaucuccucuguuucggugauaucugu uguaugugaccucuuguuucccaccaguaucugaaugguauuauauga uagagcagaagagaaaugcaauuugaauuaaaaaacccuagagacaaauaug aauaagaugaggcaauuaagaugauuuucaacauuugggugagucuuaaa aaagaccuacuggagcauagaauauuugcugaaguuguauaauggaagg agaaauagauuuugauuuuuaggacauuauccuggaauggguuuagaua acuuauauauuuuuuaaagucauccaaaugcaauguaaaauaugaauguuu ugugggcaaauggagccucugguaaaacaggaaaaggcacucuuuccu cugggcaaguacaguccccacaguggggaugaaccgcucgccgagagacaa gggacacaugggauuuaaaacuuccuuggauaaagauauucauuaauuc guucauucauucauucauguuuugcuggaaaaaaaacucuucuggauuuu aucuauucuuuaguuaaggugagcuuucgauauuguaacacuc |
| 102 | exon 9 | CCCUCAGGCAGUUUGAUUGCAUCUACACAAGAUAAACCCAACCAGCAGG AUAUUGUGUUUUUUGAGAAAAAUGGACUCCUUCAUGGACACUUUACACU UCCCUUCCUUAAAGAUGAGGUU |

---

What is claimed is:

1. A method of treating a subject to increase expression of a target protein or a target functional RNA by cells of the subject, the method comprising contacting the cells of the subject with an antisense oligomer, wherein the cells have a retained-intron-containing pre-mRNA (RIC pre-mRNA), wherein the RIC pre-mRNA comprises a retained intron, an exon flanking a 5' splice site of the retained intron, and an exon flanking a 3' splice site of the retained intron, and wherein the RIC pre-mRNA encodes the target protein or the target functional RNA;

wherein the antisense oligomer binds to a targeted region of the RIC pre-mRNA; wherein the targeted region of the RIC pre-mRNA is in the retained intron within a region +6 relative to the 5' splice site of the retained intron to −16 relative to the 3' splice site of the retained intron;

whereby the retained intron is constitutively spliced from the RIC pre-mRNA encoding the target protein or the target functional RNA, thereby increasing a level of mRNA encoding the target protein or the target functional RNA and increasing expression of the target protein or the target functional RNA by the cells of the subject; wherein the cells of the subject produce the target protein or the target functional RNA in a form that is fully-functional compared to a corresponding wild-type protein or wild-type RNA;

wherein the subject has a condition caused by a deficient amount or activity of the target protein or a deficient amount or activity of the target functional RNA; and wherein the deficient amount or activity of the target protein or the target functional RNA is caused by haploinsufficiency of the target protein or the target functional RNA.

2. The method of claim 1, wherein the targeted region of the RIC pre-mRNA is in the retained intron within:

a region +6 to +100 relative to the 5' splice site of the retained intron.

3. The method of claim 1, wherein the target protein produced is a full-length protein, or a wild-type protein.

4. The method of claim 1, wherein a total amount of the mRNA encoding the target protein or the target functional RNA produced in the cell contacted with the antisense oligomer is increased at least about 1.1-fold compared to a total amount of the mRNA encoding the target protein or the target functional RNA produced in a control cell.

5. The method of claim 1, wherein a total amount of the target protein produced by the cell contacted with the antisense oligomer is increased at least about 1.1-fold compared to a total amount of the target protein produced by a control cell.

6. The method of claim 1, wherein the antisense oligomer comprises a backbone modification comprising a phosphorothioate linkage or a phosphorodiamidate linkage.

7. The method of claim 1, wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety.

8. The method of claim 1, wherein the antisense oligomer comprises a modified sugar moiety.

9. The method of claim 1, wherein the antisense oligomer consists of from 8 to 50 nucleobases.

10. The method of claim 1, wherein the antisense oligomer comprises a sequence with at least 80% complementary to the targeted region of the RIC pre-mRNA that encodes the target protein or the target functional RNA.

11. The method of claim 1, wherein the condition is a disease or disorder.

12. The method of claim 11, wherein the disease or disorder is selected from the group consisting of thrombotic thrombocytopenic purpura, tuberous sclerosis complex, polycystic kidney disease, familial dysautonomia, retinitis pigmentosa type 10, retinitis pigmentosa type 11, cystic fibrosis, retinoblastoma, beta thalassemia, and sickle cell disease.

13. The method of claim 11, wherein the target protein or the target functional RNA and the RIC pre-mRNA are encoded by a gene selected from the group consisting of ADAMTS13, TSC1, PKD1, IKBKAP, IMPDH1, PRPF31, CFTR, RB1, HBG1, HBG2, and HBB.

14. The method of claim 1, wherein the targeted region of the RIC pre-mRNA comprises a sequence selected from the group consisting of SEQ ID NOS: 1-102 and 375-384.

15. The method of claim 1, wherein the subject is a human.

16. The method of claim 1, wherein the subject is a non-human animal.

17. The method of claim 1, wherein the cells are contacted with the antisense oligomer ex vivo.

18. The method of claim 1, wherein the antisense oligomer is administered to the subject by intravitreal injection, intrathecal injection, intraperitoneal injection, subcutaneous injection, intravenous injection, subretinal injection, intracerebroventricular injection, intramuscular injection, topical application, or implantation.

19. The method of claim 1, wherein nucleotides that are −3e to −1e of the exon flanking the 5' splice site and +1 to +6 of the retained intron are identical to nucleotides at corresponding positions of a corresponding wild-type sequence.

20. The method of claim 1, wherein nucleotides that are −15 to −1 of the retained intron and +1e of the exon flanking the 3' splice site are identical to nucleotides at corresponding positions of a corresponding wild-type sequence.

21. The method of claim 1, wherein the antisense oligomer comprises a sequence selected from the group consisting of SEQ ID NOs: 103-374 and 385-390.

22. The method of claim 1, wherein the targeted region of the RIC pre-mRNA is in the retained intron within the region −16 to −100 relative to the 3' splice site of the retained intron.

23. A method of treating a subject to increase expression of a target protein or a target functional RNA by cells of the subject, the method comprising contacting the cells of the subject with an antisense oligomer, wherein the cells have a retained-intron-containing pre-mRNA (RIC pre-mRNA), wherein the RIC pre-mRNA comprises a retained intron, an exon flanking a 5' splice site of the retained intron, and an exon flanking a 3' splice site of the retained intron, and wherein the RIC pre-mRNA encodes the target protein or the target functional RNA;

wherein the antisense oligomer binds to a targeted region of the RIC pre-mRNA; wherein the targeted region of the RIC pre-mRNA is in the retained intron within a region +6 relative to the 5' splice site of the retained intron to −16 relative to the 3' splice site of the retained intron;

whereby the retained intron is constitutively spliced from the RIC pre-mRNA encoding the target protein or the target functional RNA, thereby increasing a level of mRNA encoding the target protein or the target functional RNA and increasing expression of the target protein or the target functional RNA by the cells of the subject; wherein the cells of the subject produce the target protein or the target functional RNA in a form that is fully-functional compared to a corresponding wild-type protein or wild-type RNA;

wherein the subject has a condition caused by a deficient amount or activity of the target protein or a deficient amount or activity of the target functional RNA; wherein the condition is a disease or disorder; and wherein the disease or disorder is selected from the group consisting of thrombotic thrombocytopenic purpura, tuberous sclerosis complex, polycystic kidney disease, familial dysautonomia, retinitis pigmentosa type 10, retinitis pigmentosa type 11, cystic fibrosis, retinoblastoma, beta thalassemia, and sickle cell disease.

24. A method of treating a subject to increase expression of a target protein or a target functional RNA by cells of the subject, the method comprising contacting the cells of the subject with an antisense oligomer, wherein the cells have a retained-intron-containing pre-mRNA (RIC pre-mRNA), wherein the RIC pre-mRNA comprises a retained intron, an exon flanking a 5' splice site of the retained intron, and an exon flanking a 3' splice site of the retained intron, and wherein the RIC pre-mRNA encodes the target protein or the target functional RNA;

wherein the antisense oligomer binds to a targeted region of the RIC pre-mRNA; wherein the targeted region of the RIC pre-mRNA is in the retained intron within a region +6 relative to the 5' splice site of the retained intron to −16 relative to the 3' splice site of the retained intron;

whereby the retained intron is constitutively spliced from the RIC pre-mRNA encoding the target protein or the target functional RNA, thereby increasing a level of mRNA encoding the target protein or the target functional RNA and increasing expression of the target protein or the target functional RNA by the cells of the subject; wherein the cells of the subject produce the target protein or the target functional RNA in a form that is fully-functional compared to a corresponding wild-type protein or wild-type RNA;

wherein the subject has a condition caused by a deficient amount or activity of the target protein or a deficient amount or activity of the target functional RNA; wherein the condition is a disease or disorder; and wherein the target protein or the target functional RNA and the RIC pre-mRNA are encoded by a gene selected from the group consisting of ADAMTS13, TSC1, PKD1, IKBKAP, IMPDH1, PRPF31, CFTR, RB1, HBG1, HBG2, and HBB.

25. A method of treating a subject to increase expression of a target protein or a target functional RNA by cells of the subject, the method comprising contacting the cells of the subject with an antisense oligomer, wherein the cells have a retained-intron-containing pre-mRNA (RIC pre-mRNA), wherein the RIC pre-mRNA comprises a retained intron, an exon flanking a 5' splice site of the retained intron, and an exon flanking a 3' splice site of the retained intron, and wherein the RIC pre-mRNA encodes the target protein or the target functional RNA;

wherein the antisense oligomer binds to a targeted region of the RIC pre-mRNA comprising a sequence selected from the group consisting of SEQ ID NOS: 1-102 and 375-384; wherein the targeted region of the RIC pre-mRNA is in the retained intron within a region +6 relative to the 5' splice site of the retained intron to −16 relative to the 3' splice site of the retained intron; and whereby the retained intron is constitutively spliced from the RIC pre-mRNA encoding the target protein or the target functional RNA, thereby increasing a level of mRNA encoding the target protein or the target functional RNA and increasing expression of the target protein or the target functional RNA by the cells of the subject; wherein the cells of the subject produce the target protein or the target functional RNA in a form that is fully-functional compared to a corresponding wild-type protein or wild-type RNA.

26. A method of treating a subject to increase expression of a target protein or a target functional RNA by cells of the subject, the method comprising contacting the cells of the subject with an antisense oligomer, wherein the cells have a retained-intron-containing pre-mRNA (RIC pre-mRNA), wherein the RIC pre-mRNA comprises a retained intron, an exon flanking a 5' splice site of the retained intron, and an exon flanking a 3' splice site of the retained intron, and wherein the RIC pre-mRNA encodes the target protein or the target functional RNA;

wherein the antisense oligomer binds to a targeted region of the RIC pre-mRNA; wherein the targeted region of the RIC pre-mRNA is in the retained intron within a region +6 relative to the 5' splice site of the retained intron to −16 relative to the 3' splice site of the retained intron; wherein the antisense oligomer comprises a sequence selected from the group consisting of SEQ ID NOs: 103-374 and 385-390; and whereby the retained intron is constitutively spliced from the RIC pre-mRNA encoding the target protein or the target functional RNA, thereby increasing a level of mRNA encoding the target protein or the target functional RNA and increasing expression of the target protein or the target functional RNA by the cells of the subject; wherein the cells of the subject produce the target protein or the target functional RNA in a form that is fully-functional compared to a corresponding wild-type protein or wild-type RNA.

27. The method of any one of the claims 23-26, wherein the targeted region of the RIC pre-mRNA is in the retained intron within:

a region +6 to +100 relative to the 5' splice site of the retained intron.

28. The method of any one of the claims 23-26, wherein the target protein produced is a full-length protein, or a wild-type protein.

29. The method of any one of the claims 23-26, wherein a total amount of the mRNA encoding the target protein or the target functional RNA produced in the cell contacted with the antisense oligomer is increased at least about 1.1-fold compared to a total amount of the mRNA encoding the target protein or the target functional RNA produced in a control cell.

30. The method of any one of the claims 23-26, wherein a total amount of the target protein produced by the cell contacted with the antisense oligomer is increased at least about 1.1-fold compared to a total amount of the target protein produced by a control cell.

31. The method of any one of the claims 23-26, wherein the antisense oligomer comprises a backbone modification comprising a phosphorothioate linkage or a phosphorodiamidate linkage.

32. The method of any one of the claims 23-26, wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety.

33. The method of any one of the claims 23-26, wherein the antisense oligomer comprises a modified sugar moiety.

34. The method of any one of the claims 23-26, wherein the antisense oligomer consists of from 8 to 50 nucleobases.

35. The method of any one of the claims 23-26, wherein the antisense oligomer comprises a sequence with at least 80% complementary to the targeted region of the RIC pre-mRNA that encodes the target protein or the target functional RNA.

36. The method of any one of the claims 23-26, wherein the subject is a human.

37. The method of any one of the claims 23-26, wherein the subject is a non-human animal.

38. The method of any one of the claims 23-26, wherein the cells are contacted with the antisense oligomer ex vivo.

39. The method of any one of the claims 23-26, wherein the antisense oligomer is administered to the subject by intravitreal injection, intrathecal injection, intraperitoneal injection, subcutaneous injection, intravenous injection, subretinal injection, intracerebroventricular injection, intramuscular injection, topical application, or implantation.

40. The method of any one of the claims 23-26, wherein nucleotides that are −3e to −1e of the exon flanking the 5' splice site and +1 to +6 of the retained intron are identical to nucleotides at corresponding positions of a corresponding wild-type sequence.

41. The method of any one of the claims 23-26, wherein nucleotides that are −15 to −1 of the retained intron and +1e of the exon flanking the 3' splice site are identical to nucleotides at corresponding positions of a corresponding wild-type sequence.

42. The method of any one of the claims 23-26, wherein the targeted region of the RIC pre-mRNA is in the retained intron within a region −16 to −100 relative to the 3' splice site of the retained intron.

* * * * *